(12) United States Patent
Fink et al.

(10) Patent No.: US 11,660,311 B2
(45) Date of Patent: May 30, 2023

(54) CYCLIC DINUCLEOTIDES AS ANTICANCER AGENTS

(71) Applicant: BRISTOL-MYERS SQUIBB COMPANY, Princeton, NJ (US)

(72) Inventors: Brian E. Fink, Yardley, PA (US); Dharmpal S. Dodd, Monmouth Junction, NJ (US); Yufen Zhao, Pennington, NJ (US); Lan-Ying Qin, Plainsboro, NJ (US); Zheming Ruan, Dayton, NJ (US); Lalgudi S. Harikrishnan, Skillman, NJ (US); Muthoni G. Kamau, Lawrenceville, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 385 days.

(21) Appl. No.: 16/754,301

(22) PCT Filed: Oct. 9, 2018

(86) PCT No.: PCT/US2018/054944
§ 371 (c)(1),
(2) Date: Apr. 7, 2020

(87) PCT Pub. No.: WO2019/074887
PCT Pub. Date: Apr. 18, 2019

(65) Prior Publication Data
US 2022/0117995 A1    Apr. 21, 2022

Related U.S. Application Data

(60) Provisional application No. 62/570,386, filed on Oct. 10, 2017.

(51) Int. Cl.
*C07H 21/04* (2006.01)
*A61K 31/7084* (2006.01)
*A61K 39/395* (2006.01)

(52) U.S. Cl.
CPC ...... *A61K 31/7084* (2013.01); *A61K 39/3955* (2013.01); *C07H 21/04* (2013.01)

(58) Field of Classification Search
None
See application file for complete search history.

(56) References Cited

FOREIGN PATENT DOCUMENTS

| WO | WO2017027646 A1 | 2/2017 |
|---|---|---|
| WO | WO2017123657 A1 | 7/2017 |
| WO | WO2017161349 A1 | 9/2017 |
| WO | WO2018198084 A1 | 11/2018 |
| WO | 2019046496 A1 | 3/2019 |
| WO | 2019046498 A1 | 3/2019 |
| WO | 2019046500 A1 | 3/2019 |
| WO | 2019079261 A1 | 4/2019 |
| WO | 2019173587 A1 | 9/2019 |

OTHER PUBLICATIONS

Zhou et al., RSC Advances, Jan. 17, 2017, 7(9), 5421-5426. (Year: 2017).*
U.S. Pat. No. 8,338,604, Grant Date: Dec. 25, 2012, Granted.
U.S. Appl. No. 16/641,679, filed Feb. 25, 2020, Filed.
U.S. Appl. No. 16/642,440, filed Feb. 27, 2020, Filed.
Smietana, Michael, et al., "Solid-Phase Synthesis and Screening of Macrocyclic Nucleotide-Hybrid Compounds Targeted to Hepatitis CNS5B", Chem. Eur. J. 2004, vol. 10, pp. 173-181.

* cited by examiner

*Primary Examiner* — Traviss C McIntosh, III
(74) *Attorney, Agent, or Firm* — Elliott Korsen

(57) ABSTRACT

The present invention is directed to compounds of the formula (I), wherein all substituents are defined herein, as well as pharmaceutically acceptable compositions comprising compounds of the invention and methods of using said compositions in the treatment of various disorders.

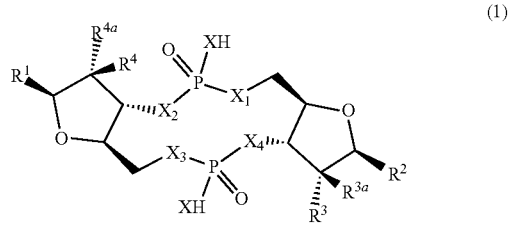

(I)

17 Claims, No Drawings
Specification includes a Sequence Listing.

SEQUENCE LISTING

```
<160> NUMBER OF SEQ ID NOS: 2

<210> SEQ ID NO 1
<211> LENGTH: 210
<212> TYPE: PRT
<213> ORGANISM: Artificial Sequence
<220> FEATURE:
<223> OTHER INFORMATION: Homosapien

<400> SEQUENCE: 1

Met Gly Ser Ser His His His His His His Ser Ser Gly Glu Thr Val
1               5                   10                  15

Arg Phe Gln Gly His Met Ser Val Ala His Gly Leu Ala Trp Ser Tyr
            20                  25                  30

Tyr Ile Gly Tyr Leu Arg Leu Ile Leu Pro Glu Leu Gln Ala Arg Ile
        35                  40                  45

Arg Thr Tyr Asn Gln His Tyr Asn Asn Leu Leu Arg Gly Ala Val Ser
    50                  55                  60

Gln Arg Leu Tyr Ile Leu Leu Pro Leu Asp Cys Gly Val Pro Asp Asn
65                  70                  75                  80

Leu Ser Met Ala Asp Pro Asn Ile Arg Phe Leu Asp Lys Leu Pro Gln
                85                  90                  95

Gln Thr Gly Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
        115                 120                 125

Glu Tyr Ala Thr Pro Leu Gln Thr Leu Phe Ala Met Ser Gln Tyr Ser
    130                 135                 140
```

```
Gln Ala Gly Phe Ser Arg Glu Asp Arg Leu Glu Gln Ala Lys Leu Phe
145                 150                 155                 160

Cys Arg Thr Leu Glu Asp Ile Leu Ala Asp Ala Pro Glu Ser Gln Asn
            165                 170                 175

Asn Cys Arg Leu Ile Ala Tyr Gln Glu Pro Ala Asp Asp Ser Ser Phe
            180                 185                 190

Ser Leu Ser Gln Glu Val Leu Arg His Leu Arg Gln Glu Glu Lys Glu
            195                 200                 205

Glu Val
    210

<210> SEQ ID NO 2
<211> LENGTH: 210
<212> TYPE: PRT
<213> ORGANISM: Artificial Sequence
<220> FEATURE:
<223> OTHER INFORMATION: Homosapien

<400> SEQUENCE: 2

Met Gly Ser Ser His His His His His His Ser Ser Gly Glu Thr Val
1               5                   10                  15

Arg Phe Gln Gly His Met Ser Val Ala His Gly Leu Ala Trp Ser Tyr
            20                  25                  30

Tyr Ile Gly Tyr Leu Arg Leu Ile Leu Pro Glu Leu Gln Ala Arg Ile
            35                  40                  45

Arg Thr Tyr Asn Gln His Tyr Asn Asn Leu Leu Arg Gly Ala Val Ser
        50                  55                  60

Gln Arg Leu Tyr Ile Leu Leu Pro Leu Asp Cys Gly Val Pro Asp Asn
65                  70                  75                  80

Leu Ser Met Ala Asp Pro Asn Ile Arg Phe Leu Asp Lys Leu Pro Gln
            85                  90                  95

Gln Thr Ala Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
            115                 120                 125

Glu Tyr Ala Thr Pro Leu Gln Thr Leu Phe Ala Met Ser Gln Tyr Ser
            130                 135                 140

Gln Ala Gly Phe Ser Arg Glu Asp Arg Leu Glu Gln Ala Lys Leu Phe
145                 150                 155                 160

Cys Gln Thr Leu Glu Asp Ile Leu Ala Asp Ala Pro Glu Ser Gln Asn
            165                 170                 175

Asn Cys Arg Leu Ile Ala Tyr Gln Glu Pro Ala Asp Asp Ser Ser Phe
            180                 185                 190

Ser Leu Ser Gln Glu Val Leu Arg His Leu Arg Gln Glu Glu Lys Glu
            195                 200                 205

Glu Val
    210
```

CYCLIC DINUCLEOTIDES AS ANTICANCER AGENTS

CROSS-REFERENCE TO RELATED APPLICATIONS

This application is a national phase application under 35 U.S.C. § 371 of International Patent Application No. PCT/US2018/054944, filed Oct. 9, 2018, which claims priority to U.S. Provisional Application Ser. No. 62/570,386 filed Oct. 10, 2017, the contents of which are specifically incorporated fully herein by reference.

FIELD OF THE INVENTION

The invention provides novel compounds, pharmaceutical compositions comprising the compounds, and methods of using them, for example, for the treatment or prophylaxis of certain cancers and to their use in therapy.

BACKGROUND OF THE INVENTION

Immunotherapy is a rapidly expanding area of medical treatment in which a patient's immune system is deliberately activated, suppressed or otherwise modulated for a positive therapeutic effect. Immunotherapy agents include such things as cells, antigens, antibodies, nucleic acids, proteins, peptides, naturally occurring ligands and synthetically prepared molecules. Cytokines are small glycoprotein molecules known for their role in causing immune response through complex signaling networks. Cytokines have been explored as immunotherapy agents but their direct administration is hampered by many factors including their short half-life in blood which can only be compensated with frequent and often high doses. One highly promising approach is cytokine induction in which the patient is treated with an immunomodulatory agent that triggers the production of one or more therapeutically beneficial cytokines in their body.

One agent in the production of cytokines is the adaptor protein STING (STimulator of INterferon Genes; also known as MPYS, TMEM173, MITA and ERIS). STING is an intracellular receptor situated on the endoplasmic reticulum. The binding to STING by an agonist activates a signaling pathway culminating in the induction of Type I IFNs, which are secreted and protect the secreting and nearby cells. STING can be activated by two different pathways, each involving a different type of cyclic dinucleotide ("CDN") agonist. In the first pathway, the agonist is an exogenous CDN used by bacterial pathogens as a second messenger (Burdette et al. 2013). In the second pathway the enzyme cyclic GMP-AMP synthase (cGAS) detects cytosolic DNA and, in response, synthesizes a CDN that functions as an endogenous STING agonist (Ablasser et al. 2013; Gao et al. 2013; Sun et al. 2013).

Activation of STING results in up-regulation of IRF3 and NF-κB pathways leading to induction of Interferon-β and other cytokines. STING is crucial for responses to cytosolic DNA of pathogen or host origin.

Two exogenous bacterial STING agonist CDNs are 3'3'-cGAMP and c-GMP. The endogenous STING agonist CDN made by cGAS is 2'3'-cGAMP. The bacterial CDNs are characterized by two 3'5' phosphodiester bridges, while the cGAS-produced CDN is characterized by one 2'5' and one 3'5' phosphodiester bridge. As a shorthand, the former CDNs are referred to as 3'3' CDNs and the latter as 2'3' CDNs. For historical reasons, 3'3' CDNs also are referred to as the "canonical" form and 2'3' CDNs are referred to as the "non-canonical" form.

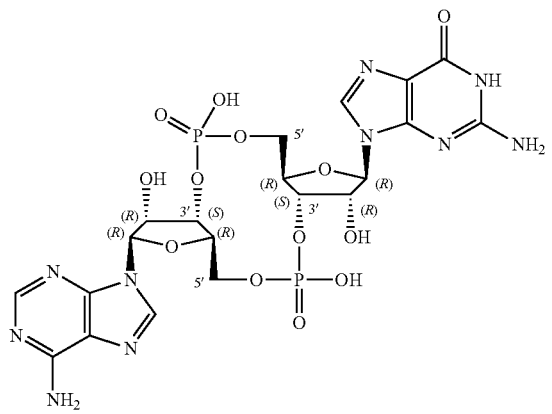

3'3'-cGAMP

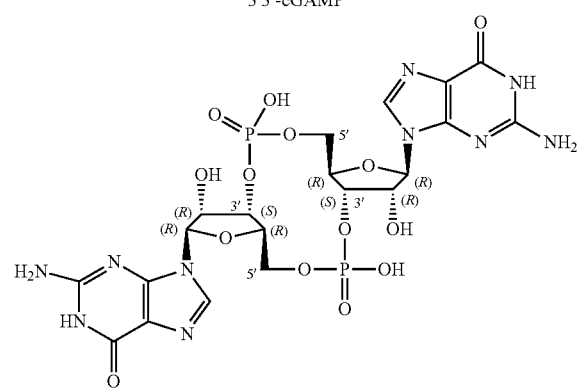

c-di-GMP

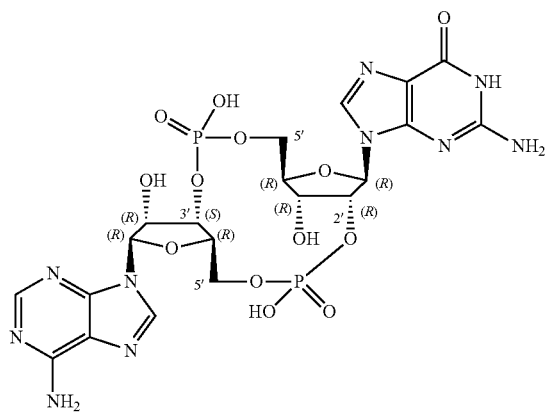

2'3'-cGAMP

In addition to protecting an organism against pathogen infection, STING activation has also been reported to be beneficial in the treatment of inflammatory diseases and, in an area of particular current interest, cancer. Administration of a synthetic CDN in combination with the cancer vaccine STINGVAX demonstrated enhanced antitumor efficacy in multiple therapeutic models (Fu et al. 2015). Administration of STING agonists alone has been reported to show potent antitumor immune efficacy in a mouse model (Corrales et al. 2015a). For reviews on the role of STING in infection, inflammation, and/or cancer, see Ahn et al. 2015; Corrales et al. 2015b and 2016; and Barber 2015.

The present invention, therefore, provides novel cyclic dinucleotides which may be useful for the treatment of cancer.

SUMMARY OF THE INVENTION

There is provided a compound of formula (I)

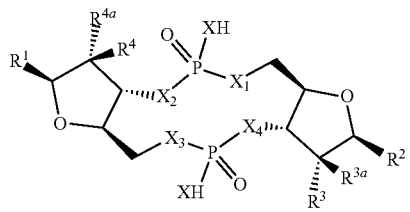

(1)

wherein
each X is independently O or S;
$X_1$, $X_2$, $X_3$ and $X_4$ are each independently O or NH;
$R^1$ and $R^2$ are independently

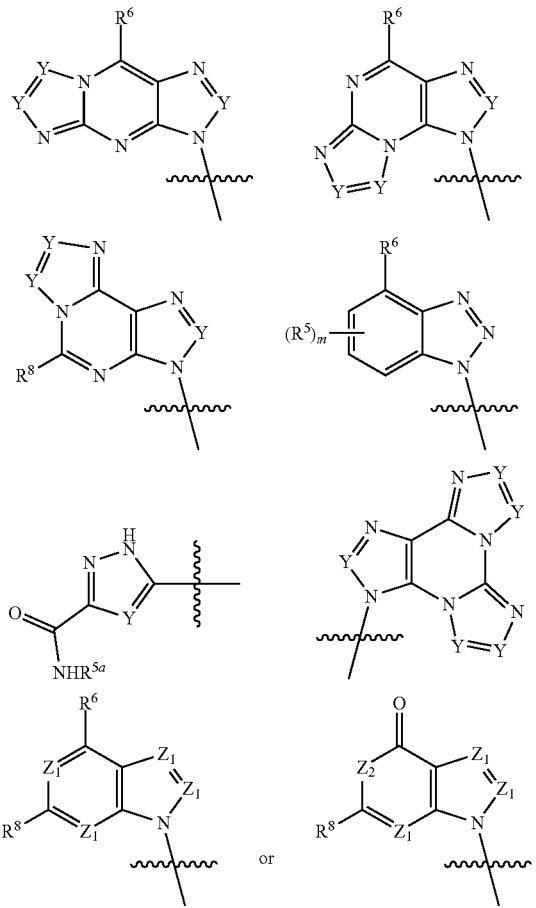

with the proviso that one of $R^1$ and $R^2$ must be

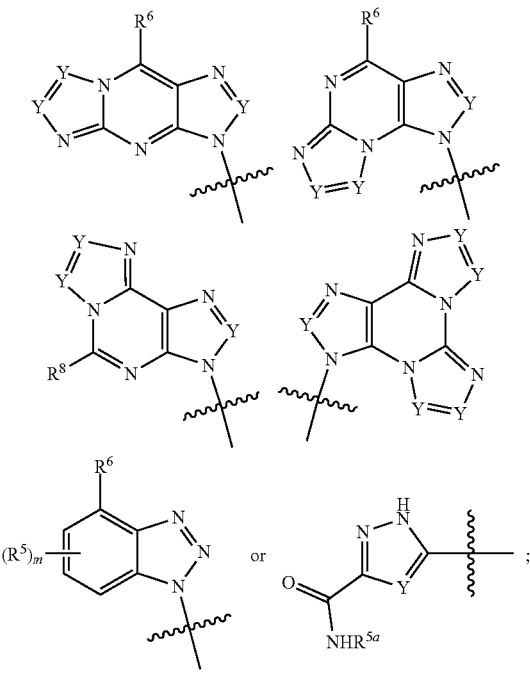

Z is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl substituted with 0-6 $R^5$;
$R^3$ and $R^4$ are independently H, $CH_3$, halogen, $NH_2$ or OH;
$R^{3a}$ and $R^{4a}$ are independently H, $CH_3$, halogen, $NH_2$ or OH; or
$R^3$ and $R^{3a}$ or $R^4$ and $R^{4a}$ may independently be taken together to form a 3-4 membered carbocycle; or
$R^3$ and $R^{3a}$ or $R^4$ and $R^{4a}$ may independently be taken together to form a C=$CH_2$ substituent;
$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a method of treating cancer which comprises administering to a subject in need thereof a therapeutically effective amount of an activator of STING (of Formula I).

DETAILED DESCRIPTION OF THE INVENTION

In a first aspect of the invention, there is provided a compound of formula (I)

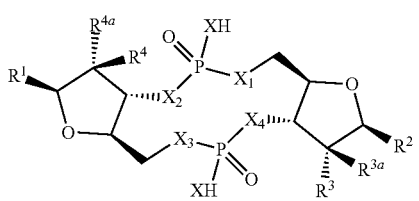

(I)

wherein each X is independently O or S;

X$_1$, X$_2$, X$_3$ and X$_4$ are each independently O or NH;

R$^1$ and R$^2$ are independently

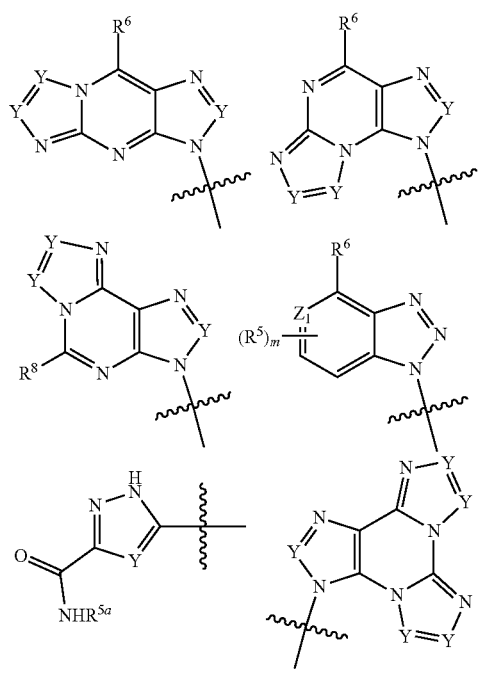

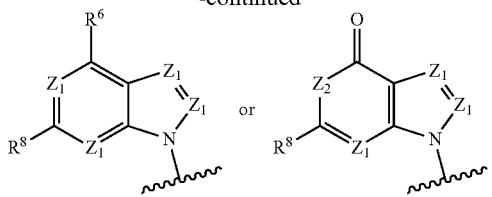

with the proviso that one of R$^1$ and R$^2$ must be

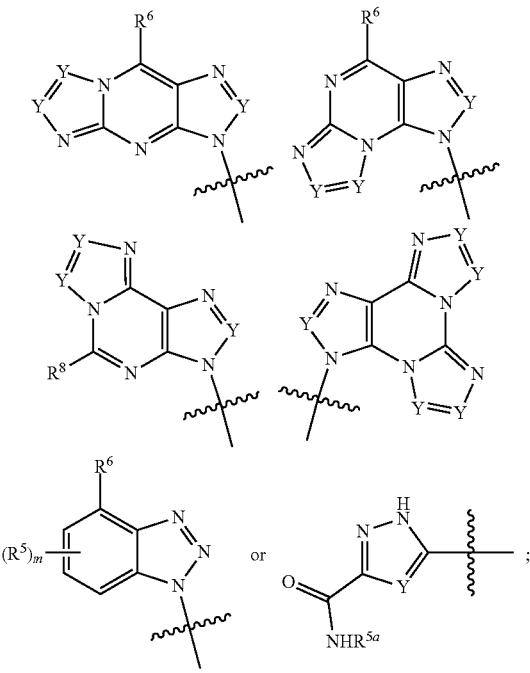

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ and R$^4$ are independently H, CH$_3$, halogen, NH$_2$ or OH;

R$^{3a}$ and R$^{4a}$ are independently H, CH$_3$, halogen, NH$_2$ or OH; or

R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

or a pharmaceutically acceptable salt, tautomer or stereoisomer thereof.

In a second aspect of the invention, there is provided a compound of formula (I)

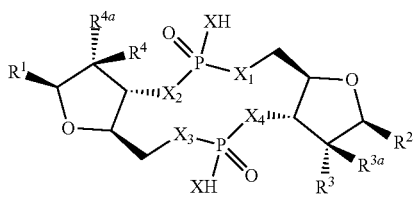
(I)

wherein

X is S;

$X_1$, $X_2$, $X_3$ and $X_4$ are each independently O or NH;

$R^1$ and $R^2$ are independently

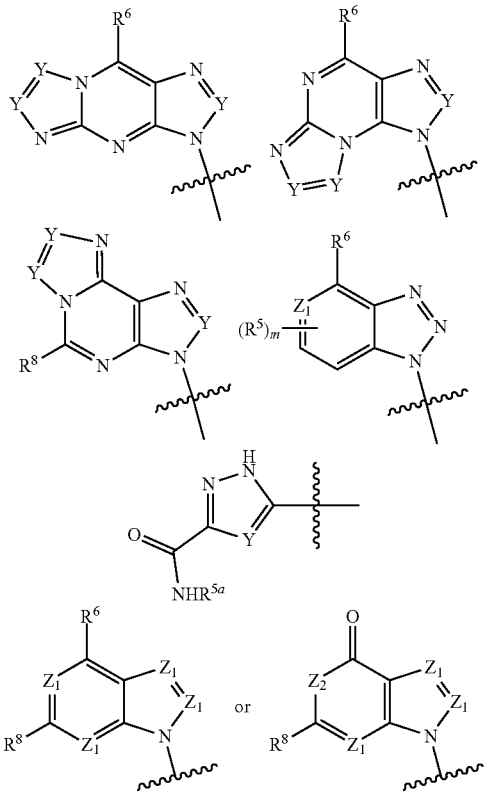

with the proviso that one of $R^1$ and $R^2$ must be

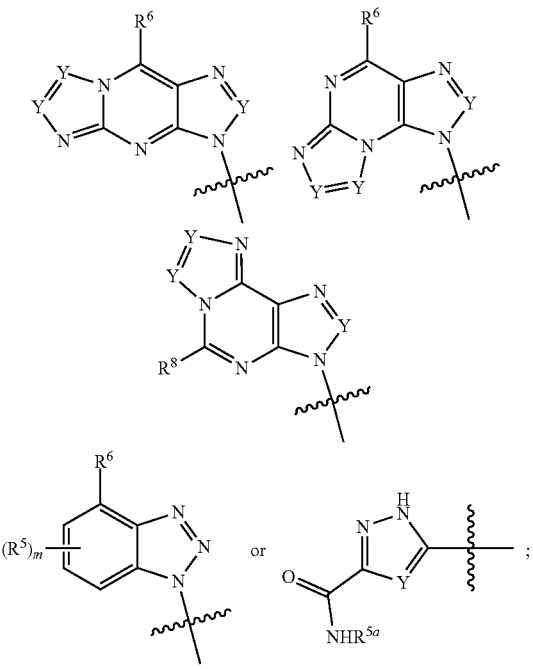

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

or a pharmaceutically acceptable salt, tautomer or stereoisomer thereof.

In a third aspect of the invention, there is provided a compound of formula (I) wherein

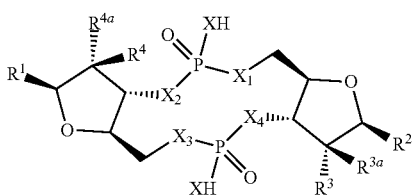
(I)

wherein

X is O;

X$_1$, X$_2$, X$_3$ and X$_4$ are each independently O or NH;

R$^1$ and R$^2$ are independently

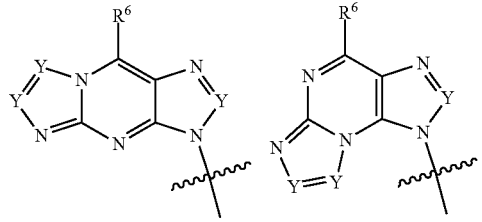

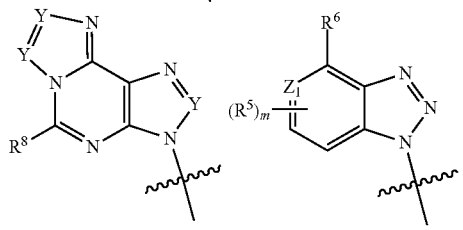

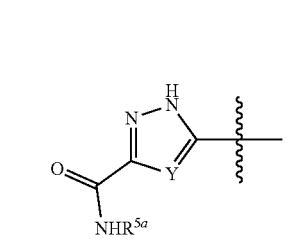

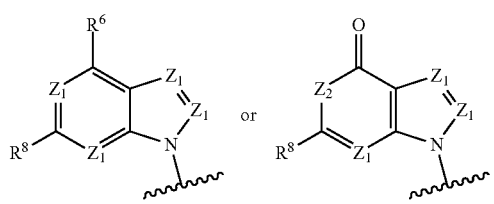

with the proviso that one of R$^1$ and R$^2$ must be

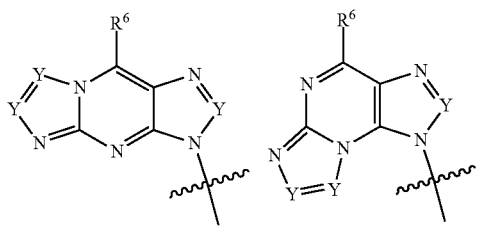

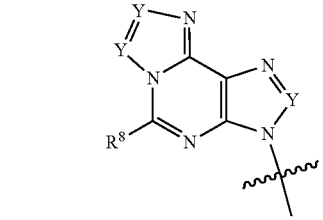

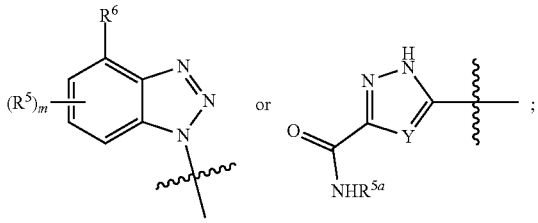

Z$^1$ is N or CR$^a$;

Z$^2$ is NR$^b$.

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ and R$^4$ are independently H, CH$_3$, halogen, NH$_2$ or OH;

R$^{3a}$ and R$^{4a}$ are independently H, CH$_3$, halogen, NH$_2$ or OH; or

R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

or a pharmaceutically acceptable salt, tautomer or stereoisomer thereof.

In a 4th aspect of the invention, there is provided a compound of the formula

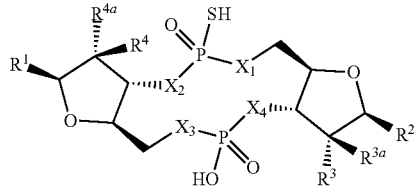

wherein $X_1$, $X_2$, $X_3$ and $X_4$ are each independently O or NH;

$R^1$ and $R^2$ are independently

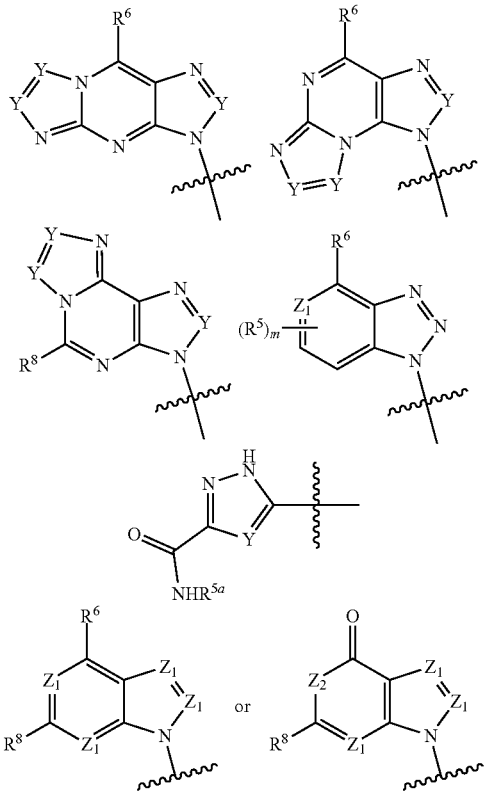

with the proviso that one of $R^1$ and $R^2$ must be

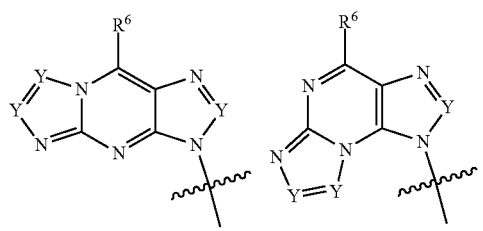

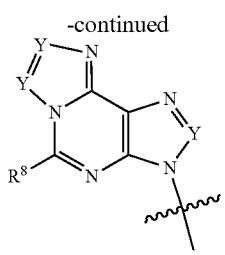

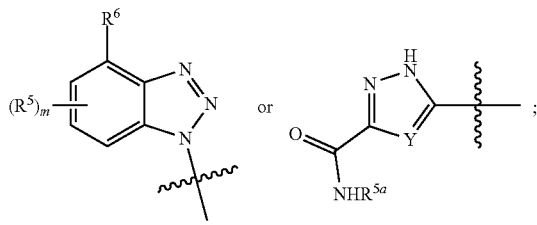

$Z^1$ is N or CR$^a$.

$Z^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ and R$^4$ are independently H, CH$_3$, halogen, NH$_2$ or OH;

R$^{3a}$ and R$^{4a}$ are independently H, CH$_3$, halogen, NH$_2$ or OH; or

R$^3$ and R$^{3a}$ or R$^4$ and R$^{4a}$ may independently be taken together to form a 3-4 membered carbocycle; or R$^3$ and R$^{3a}$ or R$^4$ and R$^{4a}$ may independently be taken together to form a C=CH$_2$ substituent;

R$^5$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

or a pharmaceutically acceptable salt, tautomer or stereoisomer thereof.

In a 5th aspect of the invention, there is provided a compound of the formula

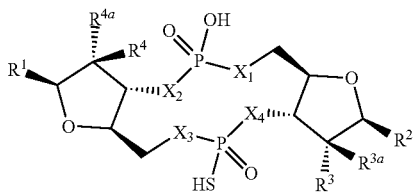

wherein $X_1$, $X_2$, $X_3$ and $X_4$ are each independently O or NH;

$R^1$ and $R^2$ are independently

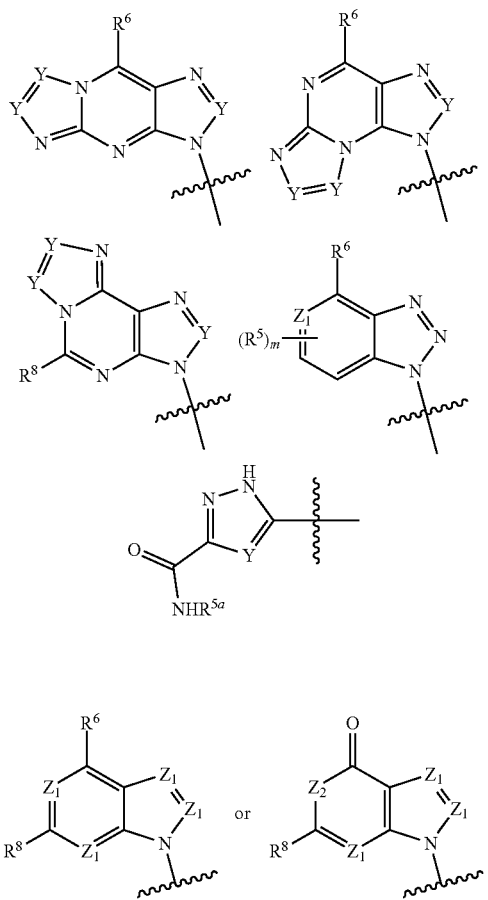

with the proviso that one of $R^1$ and $R^2$ must be

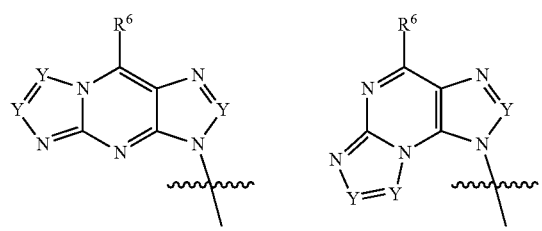

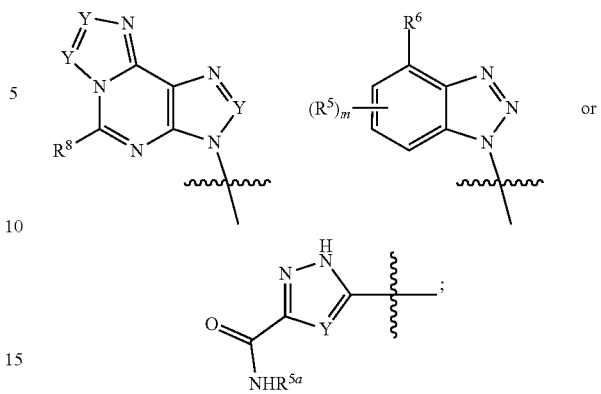

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 6th aspect of the invention, there is provided a compound of the formula

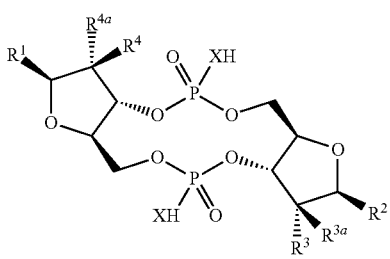

wherein
each X is independently O or S;
R¹ and R² are independently

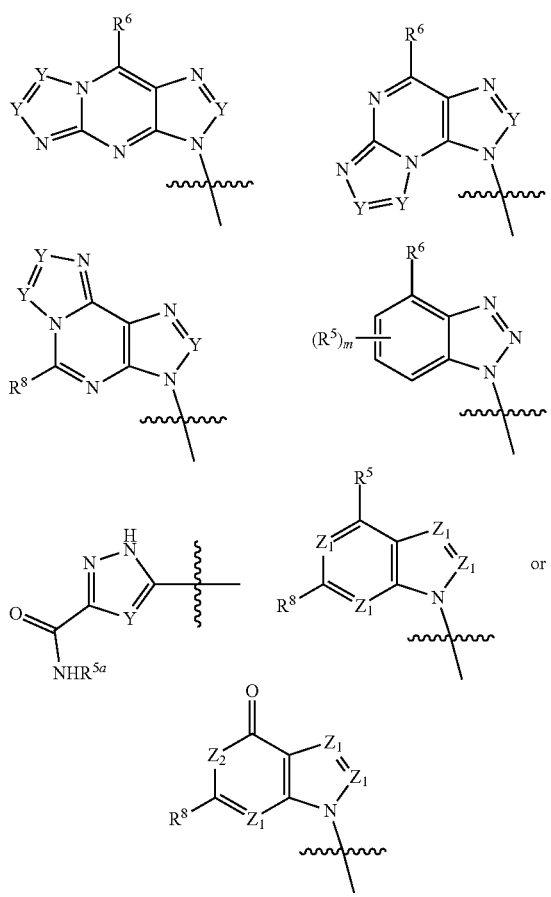

with the proviso that one of R¹ and R² must be

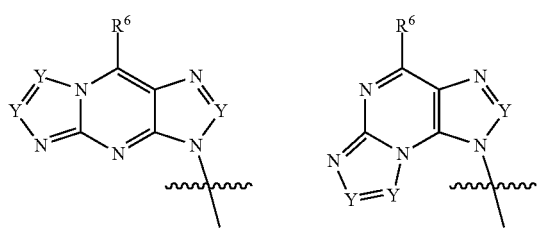

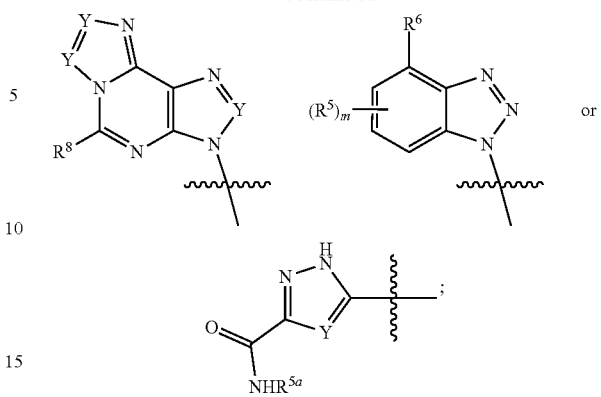

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

or a pharmaceutically acceptable salt, tautomer or stereoisomer thereof.

In a 7th aspect of the invention, there is provided a compound of the formula

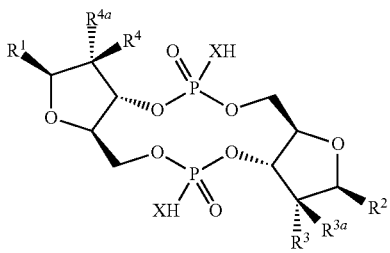

wherein

X is S;

R¹ and R² are independently

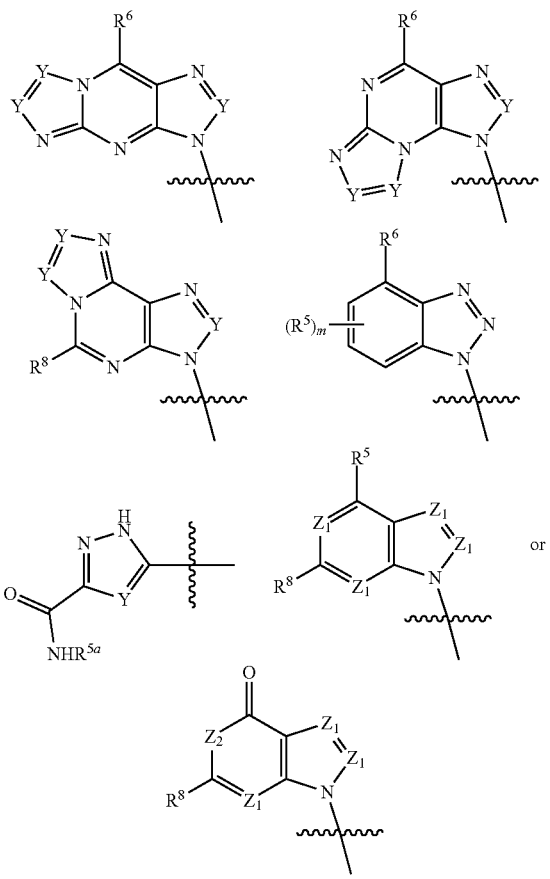

with the proviso that one of R¹ and R² must be

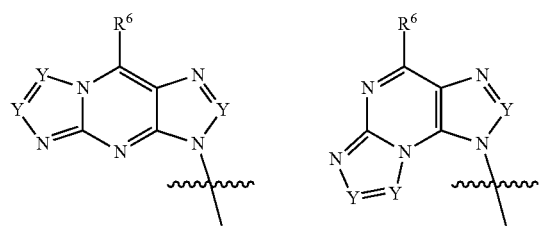

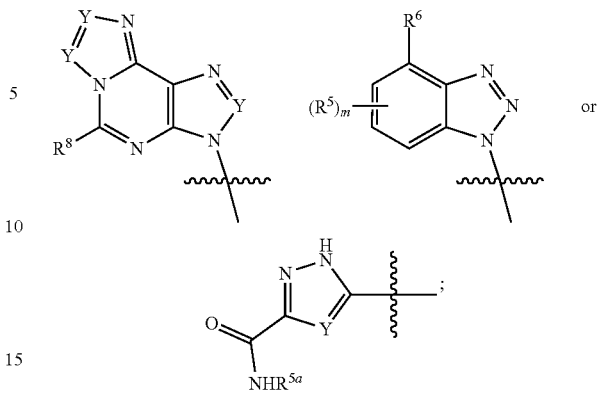

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COOR$^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COOR$^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COOR$^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COOR$^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

or a pharmaceutically acceptable salt, tautomer or stereoisomer thereof.

In an 8th aspect of the invention, there is provided a compound of the formula

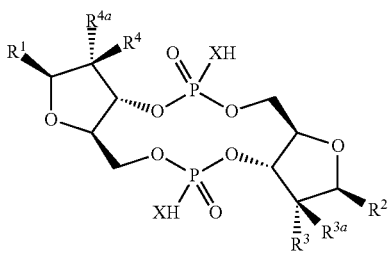

wherein
X is O;
R¹ and R² are independently

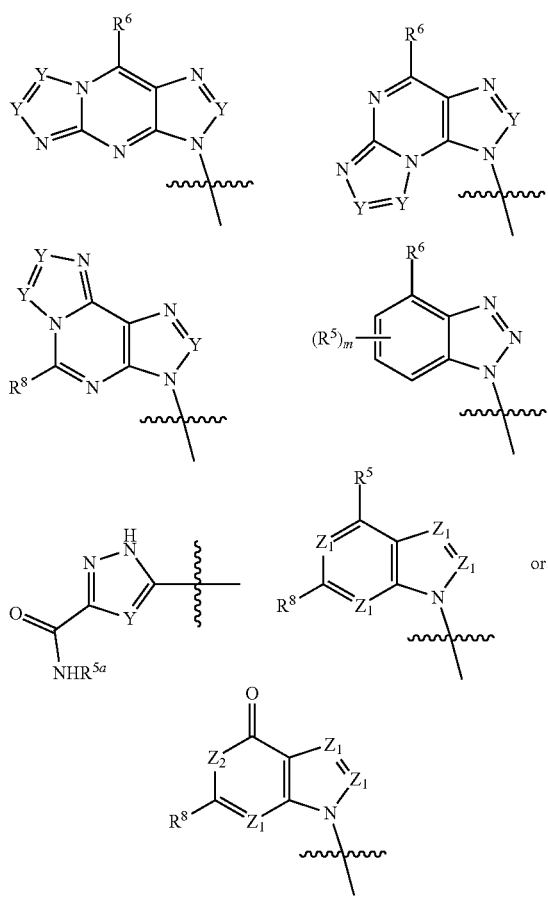

with the proviso that one of R¹ and R² must be

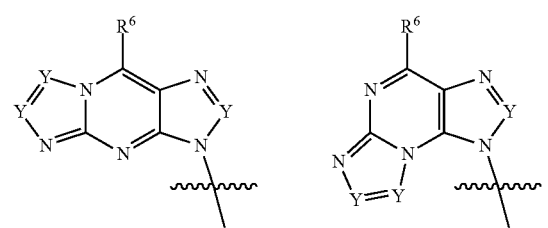

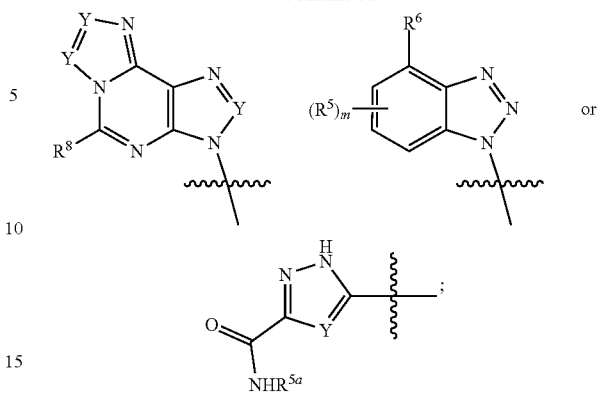

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 9th aspect of the invention, there is provided a compound of the formula

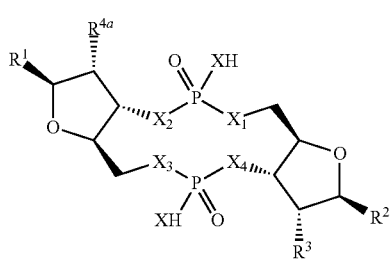

wherein
each X is independently O or S;
$X^1$, $X^2$, $X^3$ and $X^4$ are each independently O or NH;
$R^1$ and $R^2$ are independently

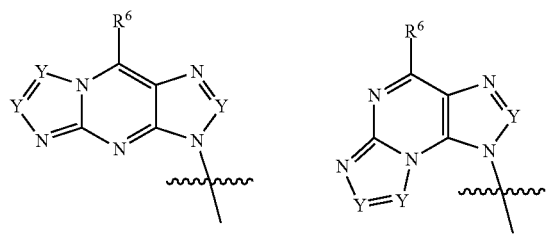

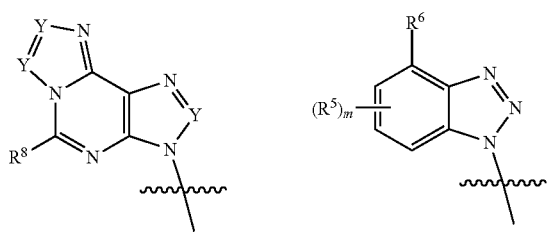

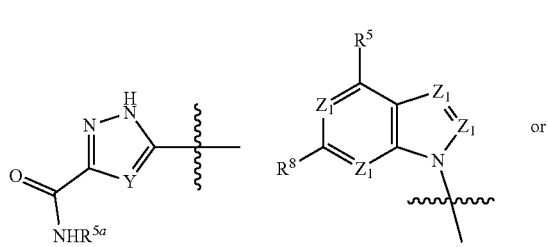

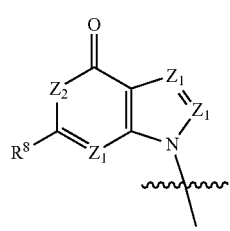

with the proviso that one of $R^1$ and $R^2$ must be

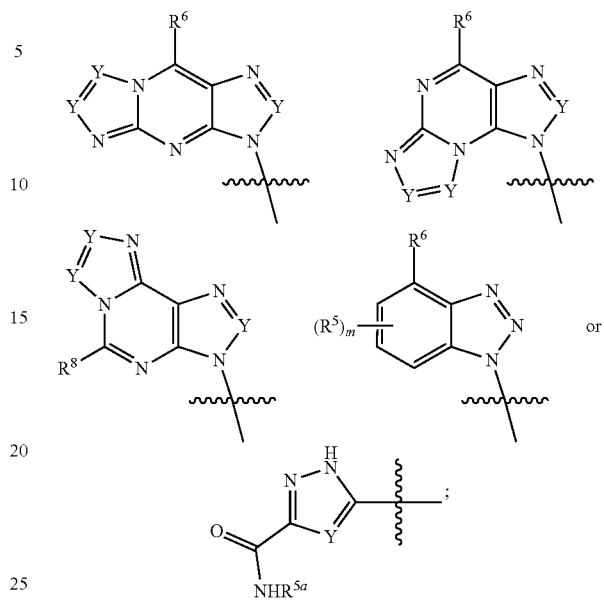

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^{4a}$ are independently H, $CH_3$, halogen, $NH_2$ or OH;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 10th aspect of the invention, there is provided a compound of the formula

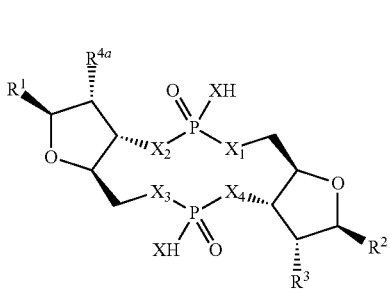

wherein
X is S;
$X^1$, $X^2$, $X^3$ and $X^4$ are each independently O or NH;
$R^1$ and $R^2$ are independently

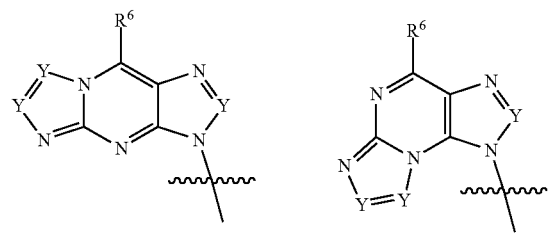

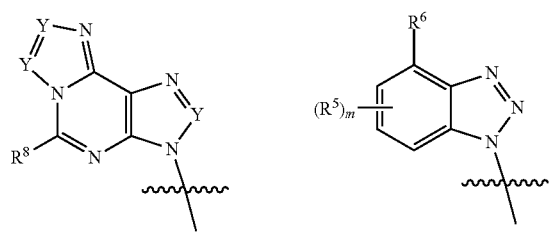

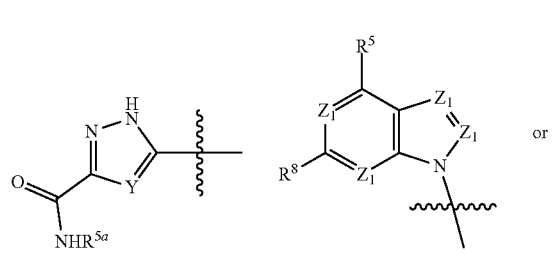

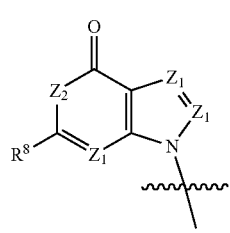

with the proviso that one of $R^1$ and $R^2$ must be

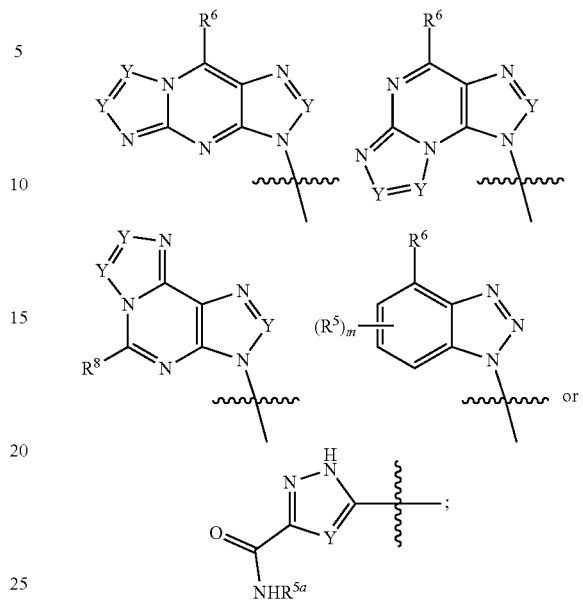

$Z^1$ is N or $CR^a$.
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^3$ and $R^{4a}$ are independently H, $CH_3$, halogen, $NH_2$ or OH;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

or a pharmaceutically acceptable salt, tautomer or stereoisomer thereof.

In an 11th aspect of the invention, there is provided a compound of the formula

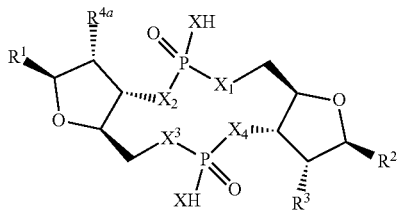

wherein

X is O;

$X^1$, $X^2$, $X^3$ and $X^4$ are each independently O or NH;

$R^1$ and $R^2$ are independently

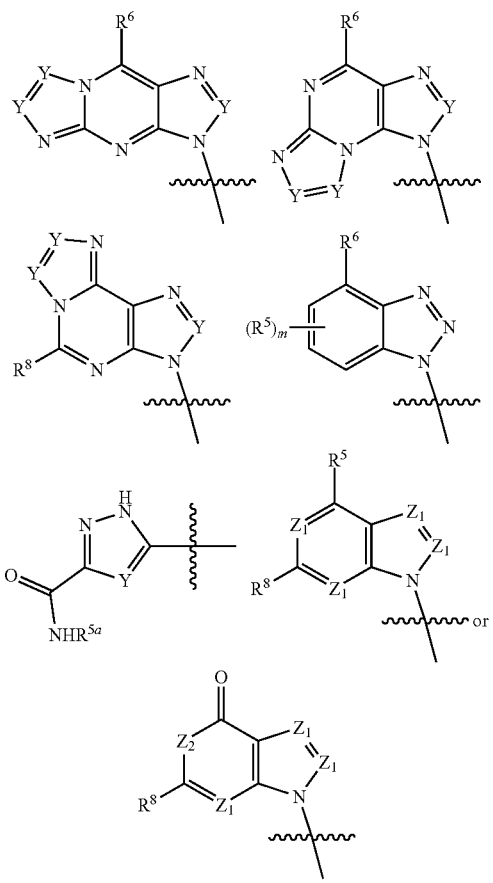

with the proviso that one of $R^1$ and $R^2$ must be

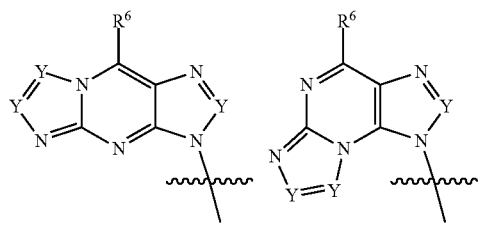

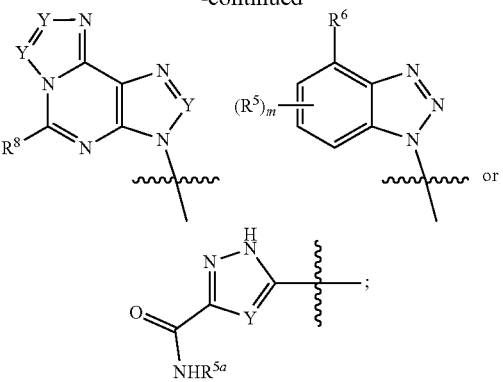

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^{4a}$ are independently H, $CH_3$, halogen, $NH_2$ or OH;

$R^5$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

Y is $CR^5$ or N;

or a pharmaceutically acceptable salt, tautomer or stereoisomer thereof.

In a 12th aspect of the invention, there is provided a compound of the formula

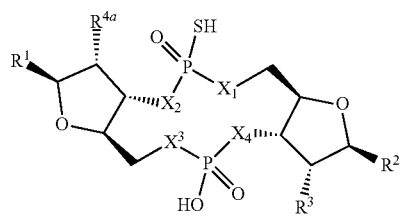

wherein

X$^1$, X$^2$, X$^3$ and X$^4$ are each independently O or NH;

R$^1$ and R$^2$ are independently

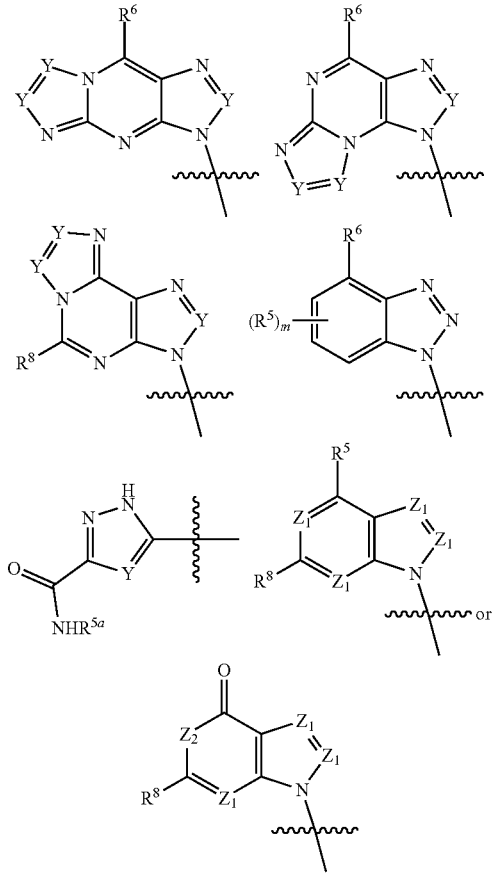

with the proviso that one of R$^1$ and R$^2$ must be

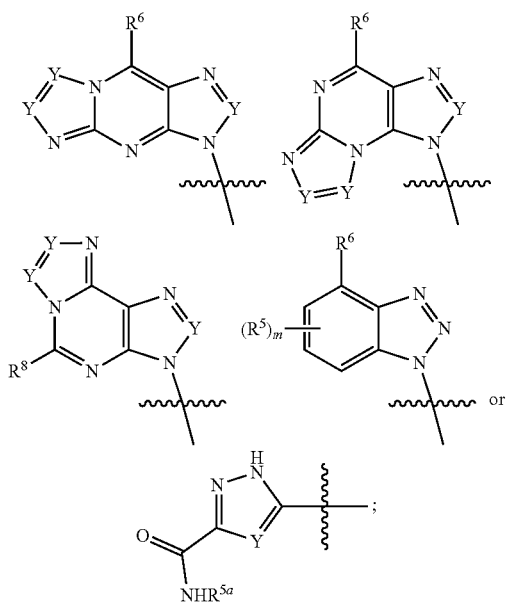

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl substituted with 0-6 R$^5$;

R$^3$ and R$^{4a}$ are independently H, CH$_3$, halogen, NH$_2$ or OH;

R$^5$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl substituted with 0-6 R$^5$;

R$^6$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

or a pharmaceutically acceptable salt, tautomer or stereoisomer thereof.

In a 13$^{th}$ aspect of the invention, there is provided a compound of the formula

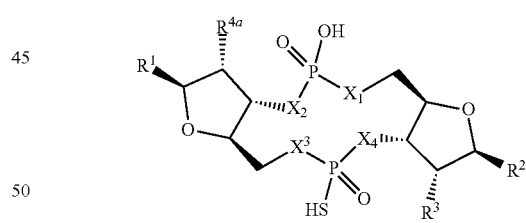

wherein

X$^1$, X$^2$, X$^3$ and X$^4$ are each independently O or NH;

R$^1$ and R$^2$ are independently

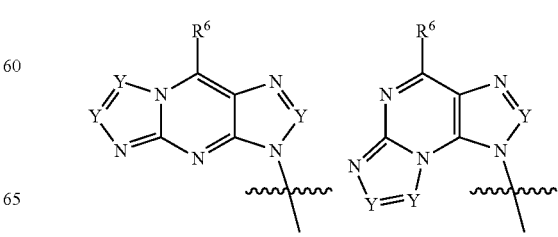

-continued

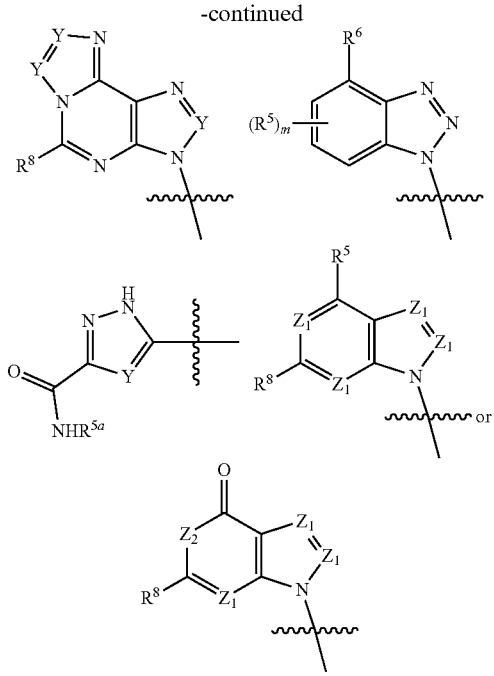

with the proviso that one of R¹ and R² must be

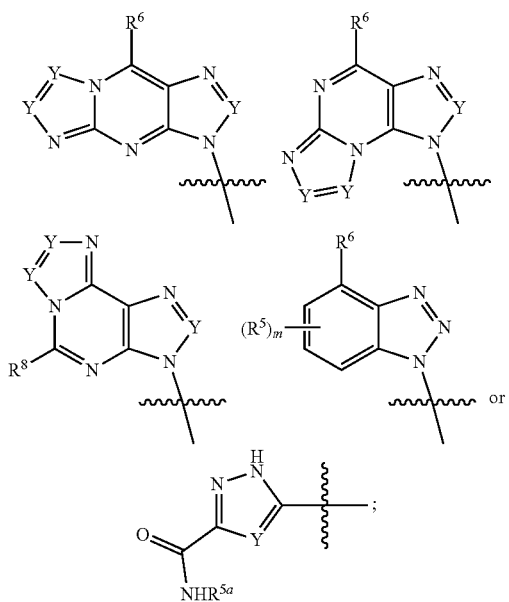

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^{4a}$ are independently H, $CH_3$, halogen, $NH_2$ or OH;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 14$^{th}$ aspect of the invention, there is provided a compound of the formula

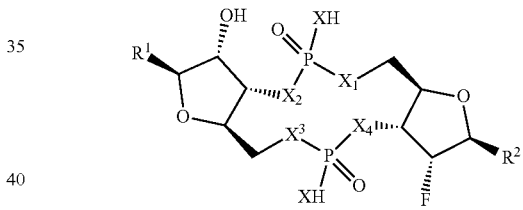

wherein

X is S;

$X^1$, $X^2$, $X^3$ and $X^4$ are each independently O or NH;

$R^1$ and $R^2$ are independently

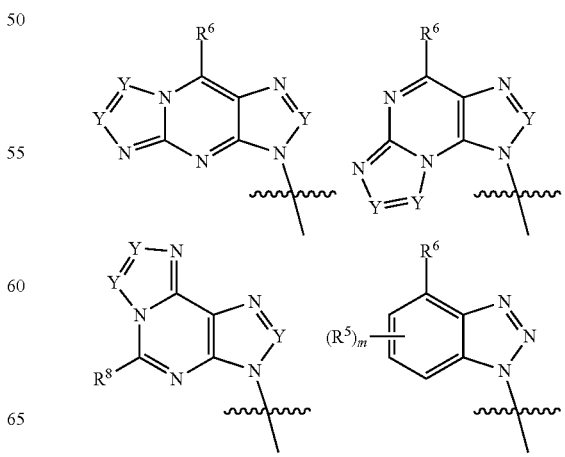

-continued

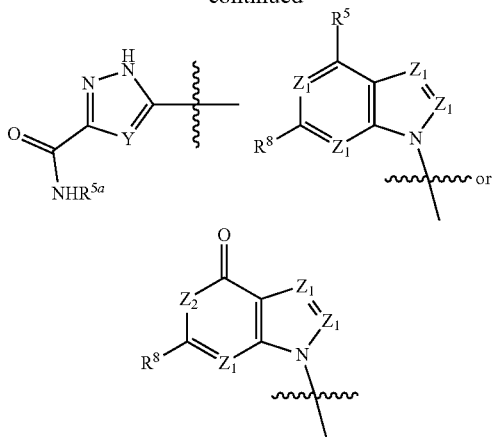

with the proviso that one of $R^1$ and $R^2$ must be

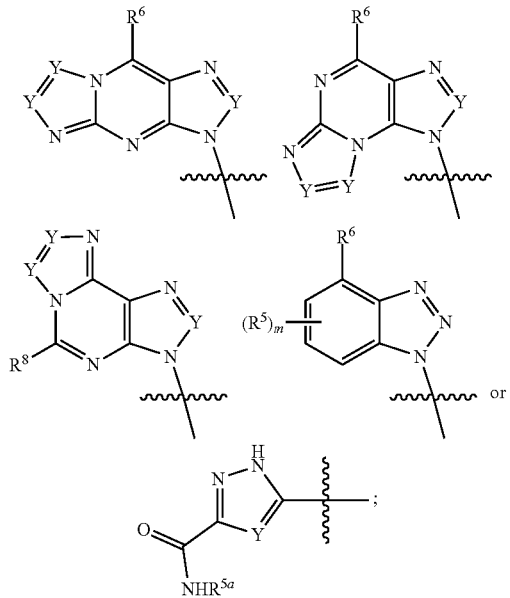

$Z^1$ is N or $CR^a$.
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl substituted with 0-6 $R^5$;
$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
Y is $CR^5$ or N;
or a pharmaceutically acceptable salt, tautomer or stereoisomer thereof.

In a 15th aspect of the invention, there is provided a compound of the formula

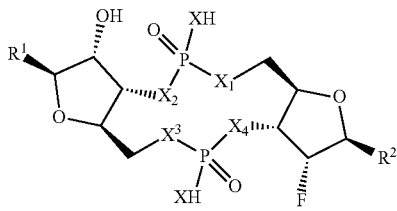

wherein
X is O;
$X_5$, $X^2$, $X^3$ and $X^4$ are each independently O or NH;
$R^1$ and $R^2$ are independently

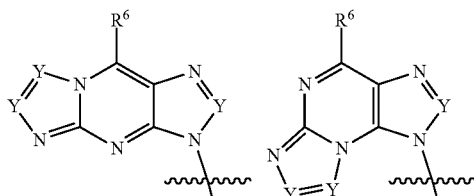

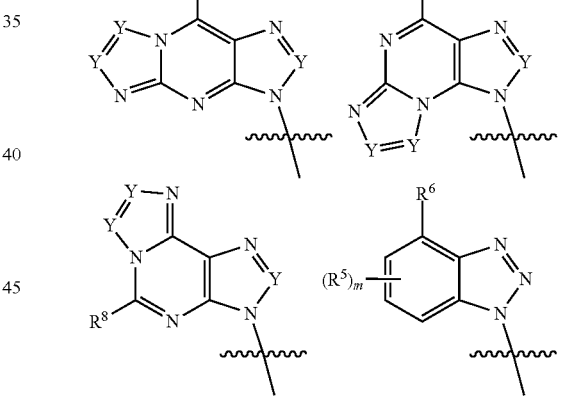

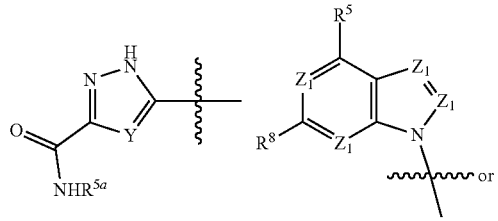

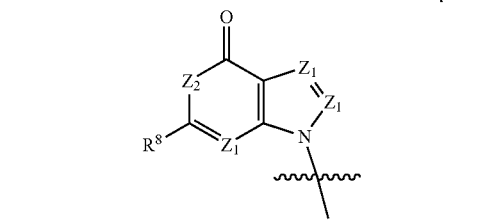

with the proviso that one of $R^1$ and $R^2$ must be

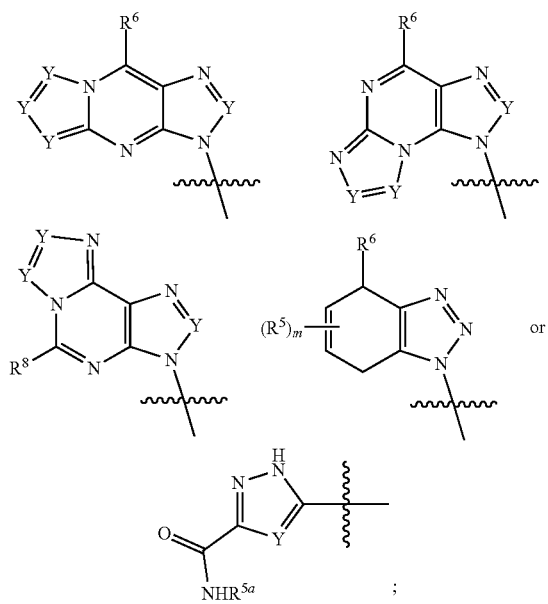

$Z$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 16$^{th}$ aspect of the invention, there is provided a compound of the formula

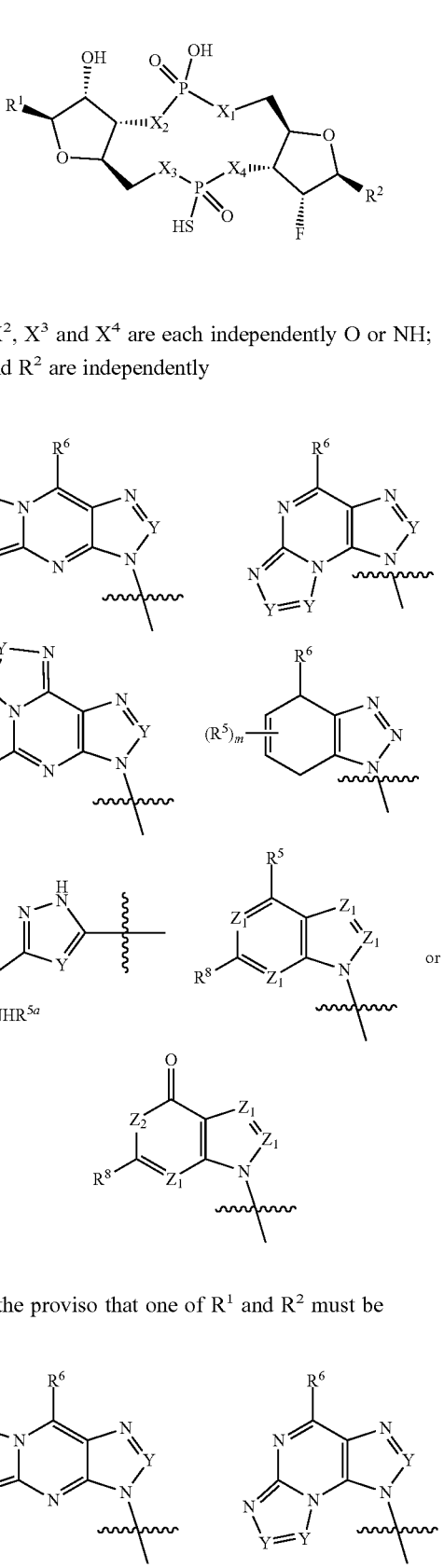

wherein $X^1$, $X^2$, $X^3$ and $X^4$ are each independently O or NH;

$R^1$ and $R^2$ are independently with the proviso that one of $R^1$ and $R^2$ must be -continued

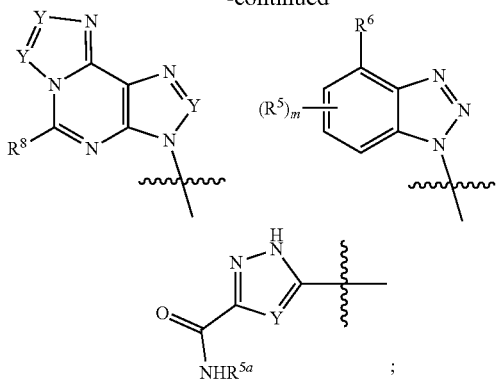

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

or a pharmaceutically acceptable salt, tautomer or stereoisomer thereof.

In a 17th aspect of the invention, there is provided a compound of the formula

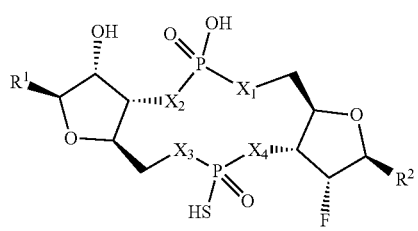

(I)

wherein $X^1$, $X^2$, $X^3$ and $X^4$ are each independently O or NH;

$R^1$ and $R^2$ are independently

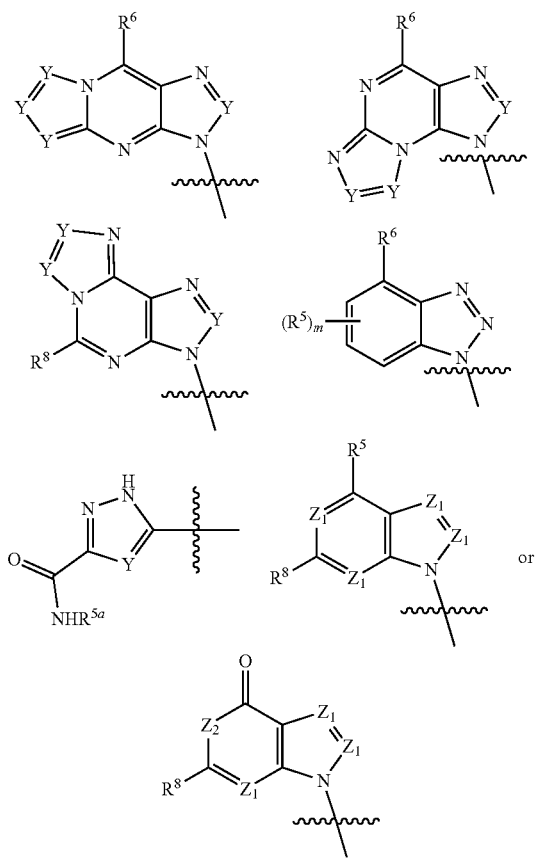

with the proviso that one of $R^1$ and $R^2$ must be

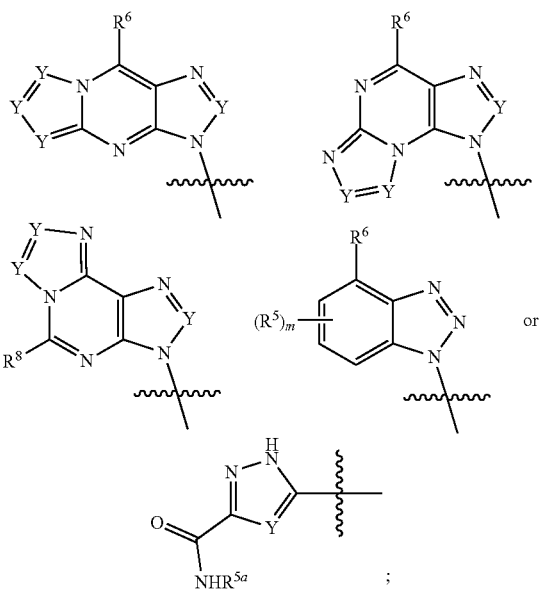

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In an 18th aspect of the invention, there is provided a compound of the formula wherein $Z^1$ is N or $CR^a$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 19th aspect of the invention, there is provided a compound of the formula wherein $Z^1$ is N or $CR^a$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 20th aspect of the invention, there is provided a compound of the formula

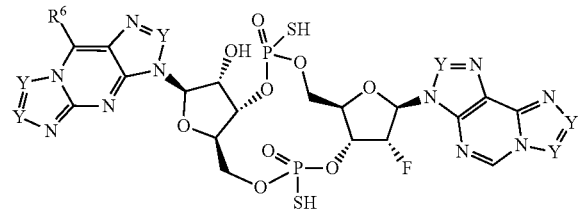

wherein $R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 21st aspect of the invention, there is provided a compound of the formula

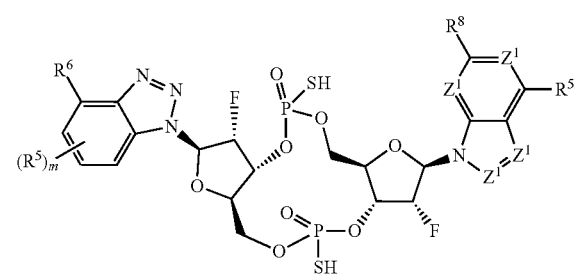

wherein $Z^1$ is N or $CR^a$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 22nd aspect of the invention, there is provided a compound of the formula

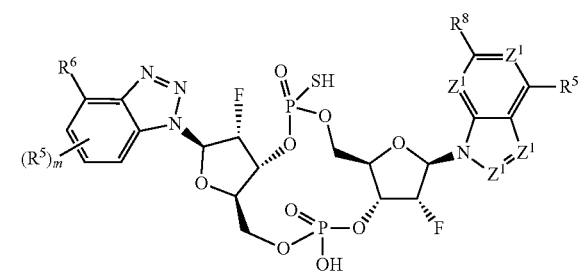

wherein $Z^1$ is N or $CR^a$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

In a 23rd aspect of the invention, there is provided a compound of the formula

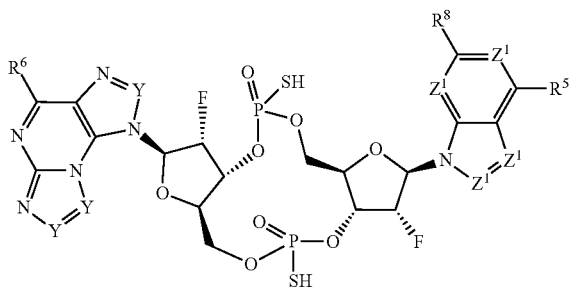

or a pharmaceutically acceptable salt, tautomer or stereoisomer thereof.

In a 24th aspect of the invention, there is provided a compound of the formula

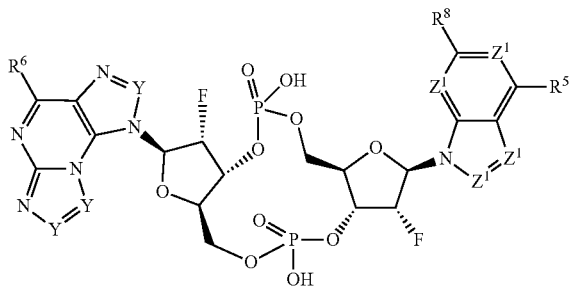

or a pharmaceutically acceptable salt, tautomer or stereoisomer thereof.

In a 25th aspect of the invention, there is provided a compound of the formula

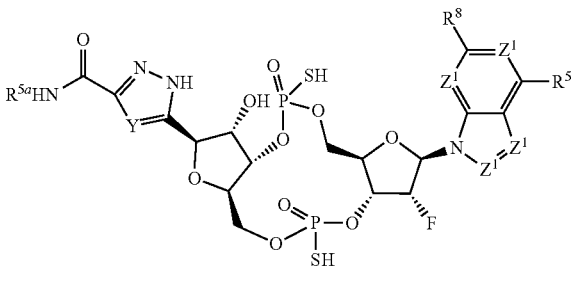

or a pharmaceutically acceptable salt, tautomer or stereoisomer thereof.

In another aspect of the invention, there are provided compounds of the formula

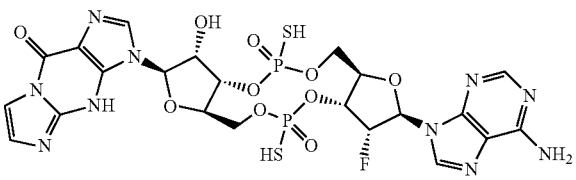

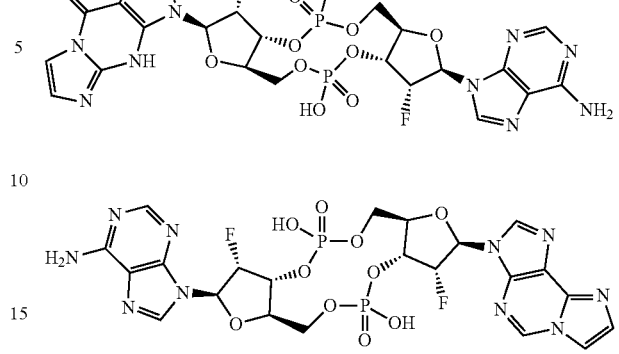

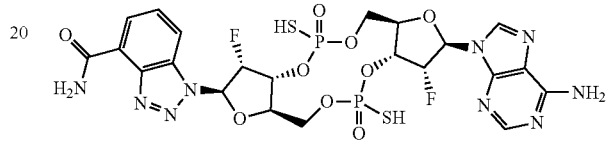

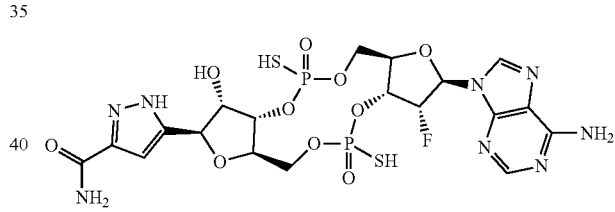

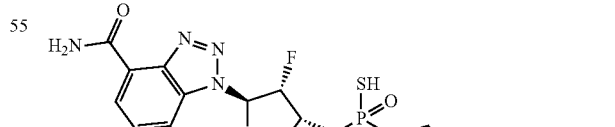

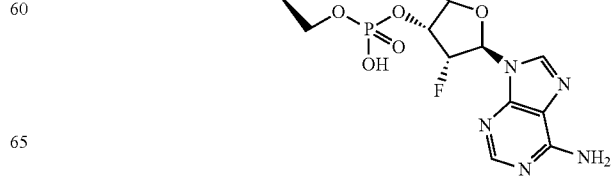

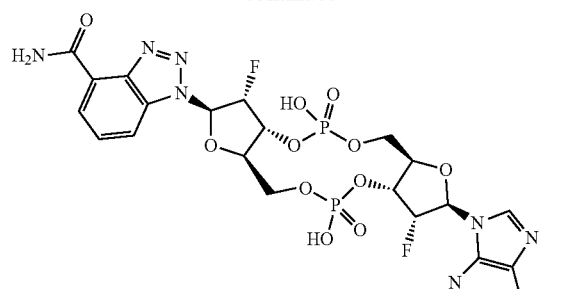
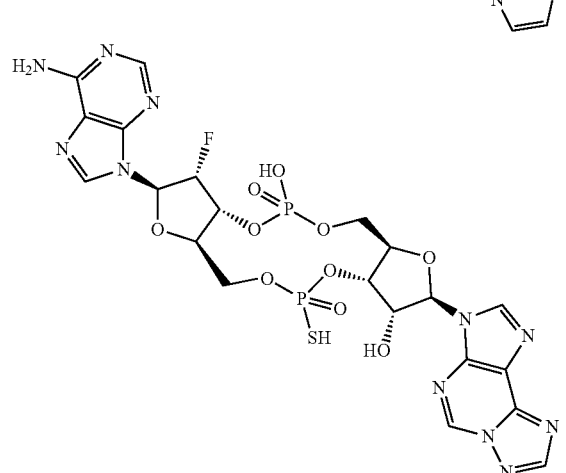
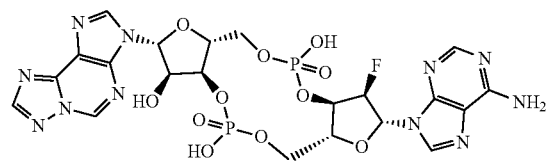
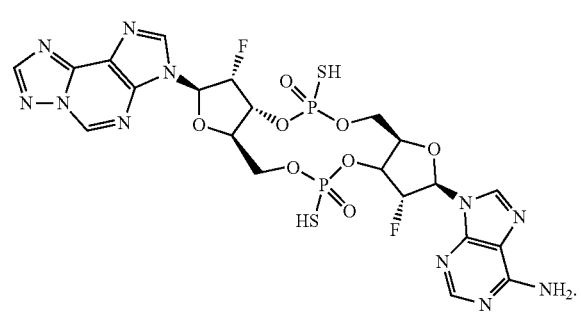
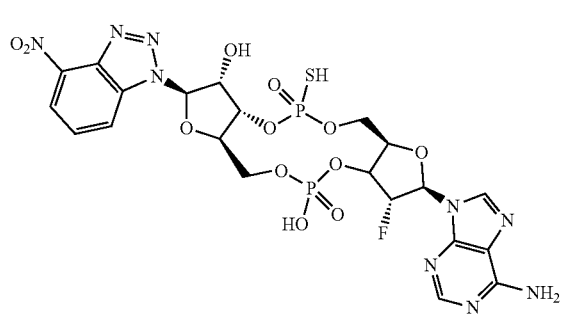
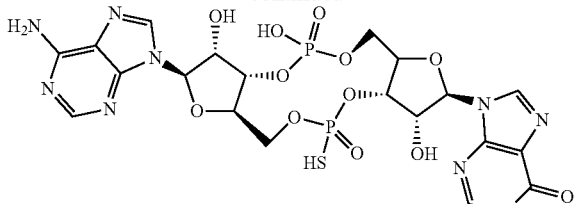
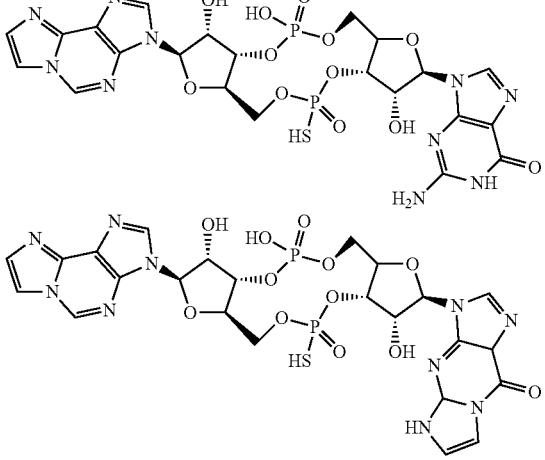
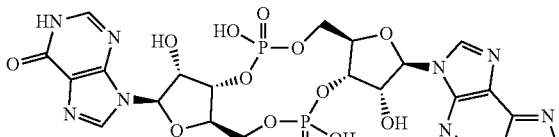
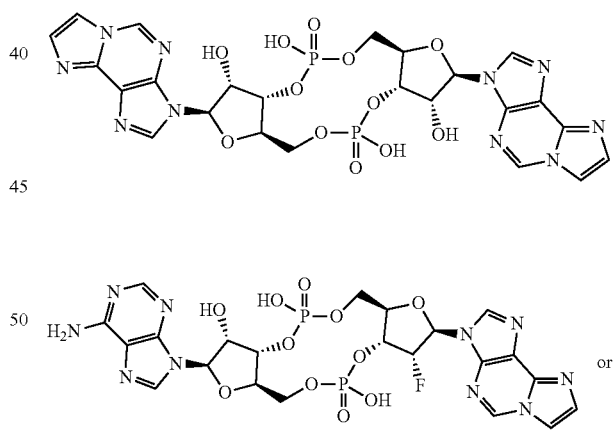
or a pharmaceutically acceptable salt, tautomer or stereoisomer thereof.

In another aspect of the invention, there are provided compounds of the formula
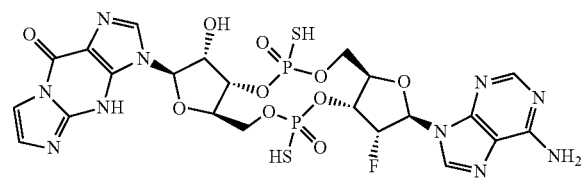
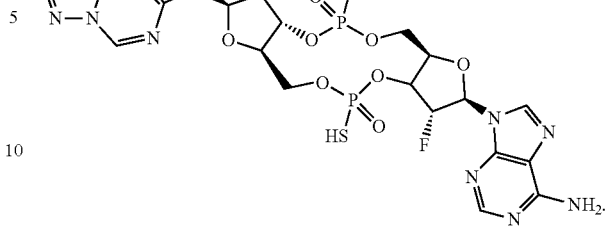
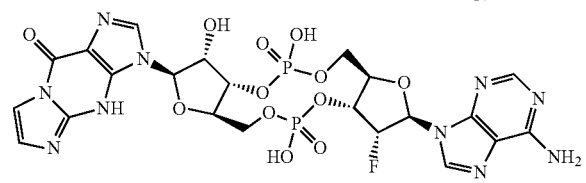
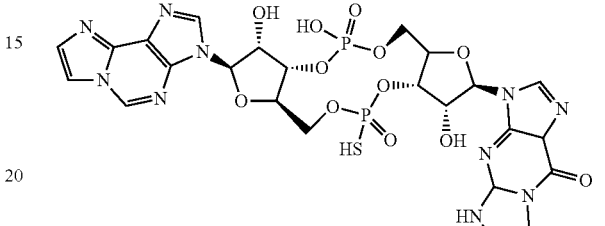
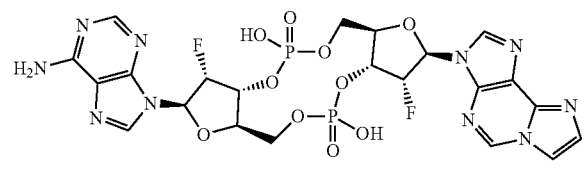
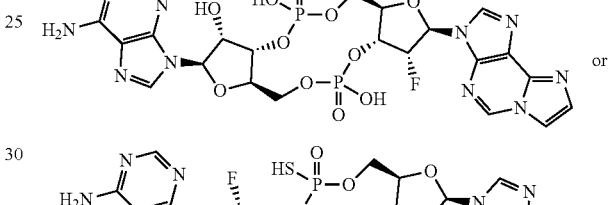
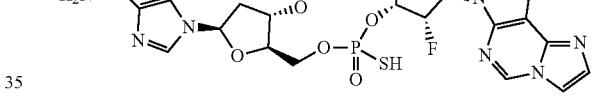
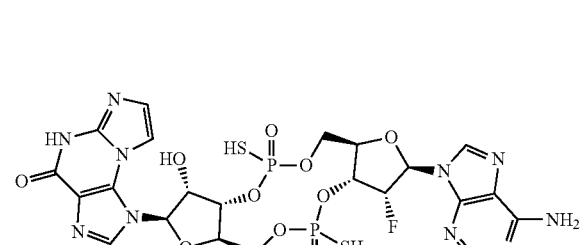
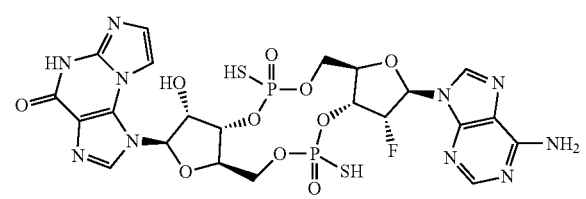
or
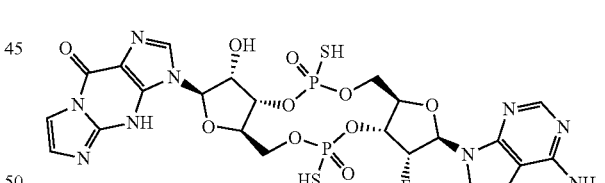
or a pharmaceutically acceptable salt, tautomer or stereoisomer thereof.
In another aspect of the invention, there is provided a compound of the formula
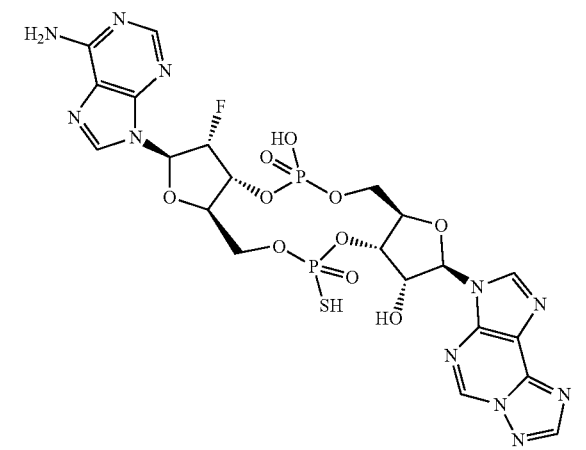
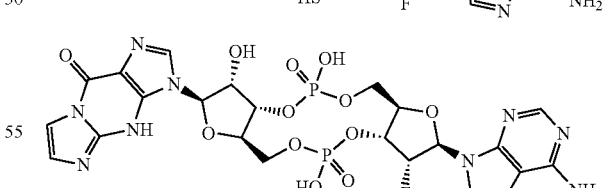
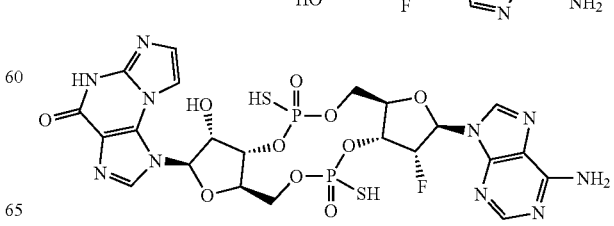

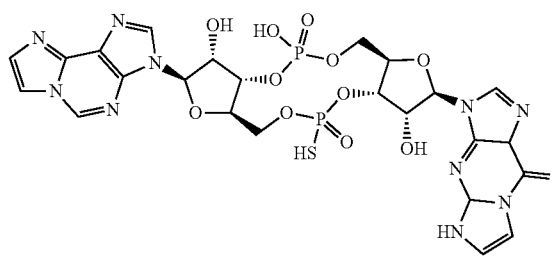

or a pharmaceutically acceptable salt, tautomer or stereoisomer thereof.

In another aspect of the invention, there is provided a compound of the formula

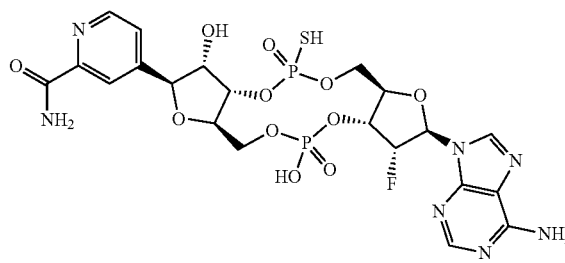

or a pharmaceutically acceptable salt, tautomer or stereoisomer thereof.

In another aspect of the invention, there is provided a compound of the formula

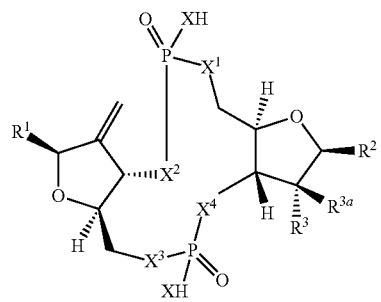

wherein each X is independently O or S;

$R^1$ and $R^2$ are independently

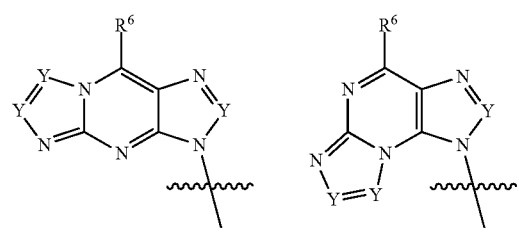

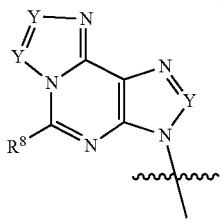 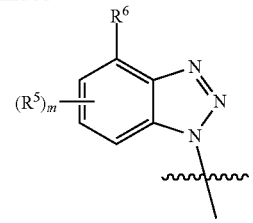

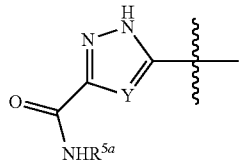 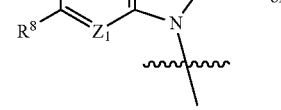 or

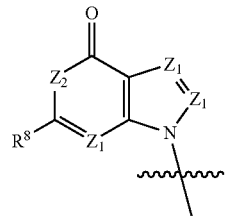

with the proviso that one of $R^1$ and $R^2$ must be

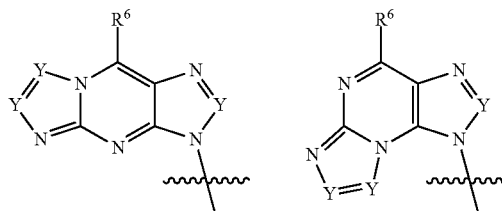

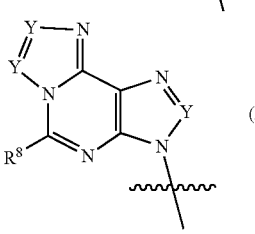 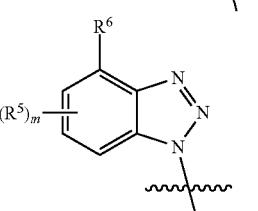 or

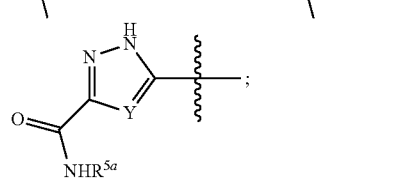 ;

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)R$^{a1}$, —OC(O)NR$^{a1}R^{a1}$, —NR$^{a1}R^{a1}$, —NR$^{a1}$C(O)R$^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2NR^{a1}R^{a1}$, —S(O)R$^{a1}$, —S(O)NR$^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

Y is $CR^5$ or N;

or a pharmaceutically acceptable salt, tautomer or stereoisomer thereof.

In another aspect of the invention, there is provided a compound of the formula

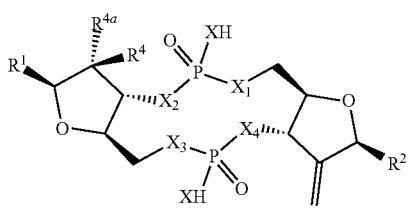

wherein each X is independently O or S;

$R^1$ and $R^2$ are independently

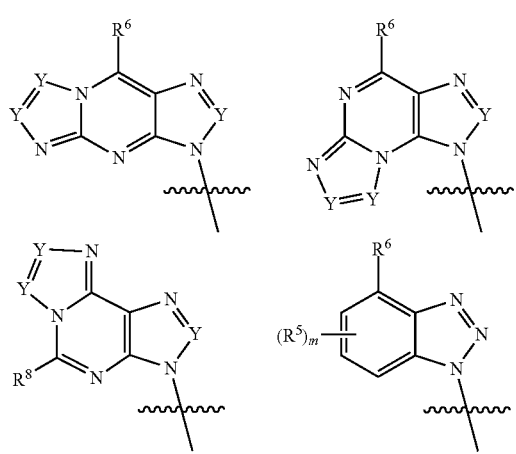

-continued

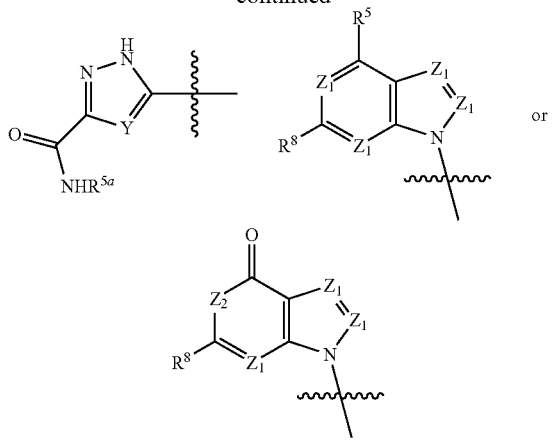

with the proviso that one of $R^1$ and $R^2$ must be

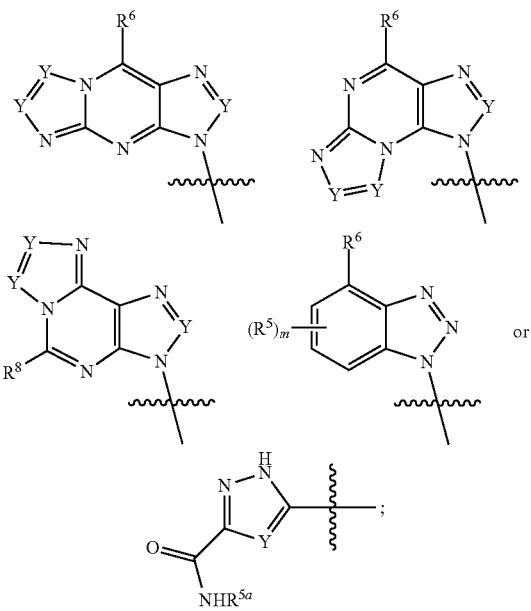

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H or $C_{1-3}$ alkyl substituted with 0-6 $R^5$;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl substituted with 0-6 $R^5$, CN, $NO_2$, OH, $OR^{a1}$, $SR^{a1}$, $-C(O)NR^{a1}R^{a1}$, $-COOR^{a1}$, $-OC$ (O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, NO$_2$, OH, O$R^{a1}$, S$R^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, NO$_2$, OH, O$R^{a1}$, S$R^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound which is (1S,6R,8R,9R,10R,15R,17R,18R)-8-(6-amino-9H-purin-9-yl)-9-fluoro-18-hydroxy-17-{9-oxo-3H,4H,9H-imidazo[1,2-a]purin-3-yl}-3,12-disulfanyl-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-3,12,18-trihydroxy-17-{9-oxo-3H,4H,9H-imidazo[1,2-a]purin-3-yl}-2,4,7,11,13,16-hexaoxa-3$\lambda^5$,12$\lambda^5$-diphosphatricyclo[13.3.0.0$^{6,10}$]octadecane-3,12-dione, (1R,6R,8R,9R,10R,15R,17R,18R)-8-(6-amino-9H-purin-9-yl)-9,18-difluoro-3,12-dihydroxy-17-{3H-imidazo[2,1-f]purin-3-yl}-2,4,7,11,13,16-hexaoxa-3$\lambda^5$,12$\lambda^5$-diphosphatricyclo[13.3.0.0$^{6,10}$]octadecane-3,12-dione, 1-[(1R,6R,8R,9R,10R,15R,17R,18R)-17-(6-amino-9H-purin-9-yl)-9,18-difluoro-3,12-dioxo-3,12-disulfanyl-2,4,7,11,13,16-hexaoxa-3$\lambda^5$,12$\lambda^5$-diphosphatricyclo[13.3.0.0$^{6,10}$]octadecan-8-yl]-1H-1,2,3-benzotriazole-4-carboxamide, (1S,6R,8R,9R,10R,15R,17R,18R)-8-(6-amino-9H-purin-9-yl)-9-fluoro-18-hydroxy-17-{4-oxo-1H,4H,5H-imidazo[2,1-b]purin-1-yl}-3,12-disulfanyl-2,4,7,11,13,16-hexaoxa-3$\lambda^5$,12$\lambda^5$-diphosphatricyclo[13.3.0.0$^{6,10}$]octadecane-3,12-dione, 5-[(1R,6R,8S,9S,10S,15R,17R,18R)-17-(6-amino-9H-purin-9-yl)-18-fluoro-9-hydroxy-3,12-dioxo-3,12-disulfanyl-2,4,7,11,13,16-hexaoxa-3$\lambda^5$,12$\lambda^5$-diphosphatricyclo[13.3.0.0$^{6,10}$]octadecan-8-yl]-1H-pyrazole-3-carboxamide, 1-[(1R,6R,8R,9R,10R,15R,17R,18R)-17-(6-amino-9H-purin-9-yl)-9,18-difluoro-3,12-dihydroxy-3,12-dioxo-2,4,7,11,13,16-hexaoxa-3$\lambda^5$,12$\lambda^5$-diphosphatricyclo[13.3.0.0$^{6,10}$]octadecan-8-yl]-1H-1,2,3-benzotriazole-4-carboxamide, 1-[(1R,6R,8R,9R,10R,15R,17R,18R)-17-(6-amino-9H-purin-9-yl)-9,18-difluoro-3,12-dihydroxy-3-oxo-12-sulfanylidene-2,4,7,11,13,16-hexaoxa-3$\lambda^5$,12$\lambda^5$-diphosphatricyclo[13.3.0.0$^{6,10}$]octadecan-8-yl]-1H-1,2,3-benzotriazole-4-carboxamide, 1-[(1R,6R,8R,9R,10R,15R,17R,18R)-9,18-difluoro-3,12-dihydroxy-17-{3H-imidazo[2,1-f]purin-3-yl}-3,12-dioxo-2,4,7,11,13,16-hexaoxa-3$\lambda^5$,12$\lambda^5$-diphosphatricyclo[13.3.0.0$^{6,10}$]octadecan-8-yl]-1H-1,2,3-benzotriazole-4-carboxamide, (1S,6R,8R,9R,10R,15R,17R,18R)-8-(6-amino-9H-purin-9-yl)-9-fluoro-12,18-dihydroxy-3-sulfanyl-17-{3H-[1,2,4]triazolo[3,2-f]purin-3-yl}-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-3,12,18-trihydroxy-17-{3H-[1,2,4]triazolo[3,2-f]purin-3-yl}-2,4,7,11,13,16-hexaoxa-3$\lambda^5$,12$\lambda^5$-diphosphatricyclo[13.3.0.0$^{6,10}$]octadecane-3,12-dione, 12 (1R,6R,8R,9R,10R,15R,17R,18R)-8-(6-amino-9H-purin-9-yl)-9,18-difluoro-3,12-disulfanyl-17-{3H-[1,2,4]triazolo[3,2-f]purin-3-yl}-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-12,18-dihydroxy-17-(4-nitro-1H-1,2,3-benzotriazol-1-yl)-3-sulfanyl-2,4,7,11,13,16-hexaoxa-3$\lambda^5$,12$\lambda^5$-diphosphatricyclo[13.3.0.0$^{6,10}$]octadecane-3,12-dione, (1S,8R,9R,10S,15R,17R,18R)-8-(2-amino-6-oxo-6,9-dihydro-1H-purin-9-yl)-17-(6-amino-9H-purin-9-yl)-3,9,18-trihydroxy-12-sulfanyl-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10S,15R,17R,18R)-8-(2-amino-6-oxo-6,9-dihydro-1H-purin-9-yl)-3,9,18-trihydroxy-17-{3H-imidazo[2,1-f]purin-3-yl}-12-sulfanyl-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10S,15R,17R,18R)-3,9,18-trihydroxy-17-{3H-imidazo[2,1-f]purin-3-yl}-8-{9-oxo-3H,4aH,5H,9H,9aH-imidazo[1,2-a]purin-3-yl}-12-sulfanyl-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10S,15R,17R,18R)-3,9,12,18-tetrahydroxy-8-{3H-imidazo[2,1-f]purin-3-yl}-17-(6-oxo-6,9-dihydro-1H-purin-9-yl)-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10S,15R,17R,18R)-3,9,12,18-tetrahydroxy-8,17-bis({3H-imidazo[2,1-f]purin-3-yl})-2,4,7,11,13,16-hexaoxa-3$\lambda^5$,12$\lambda^5$-diphosphatricyclo[13.3.0.0$^{6,10}$]octadecane-3,12-dione, (1R,6R,8R,9R,10S,15R,17R,18R)-8-(6-amino-9H-purin-9-yl)-18-fluoro-3,9,12-trihydroxy-17-{3H-imidazo[2,1-f]purin-3-yl}-2,4,7,11,13,16-hexaoxa-3$\lambda^5$,12$\lambda^5$-diphosphatricyclo[13.3.0.0$^{6,10}$]octadecane-3,12-dione, or (1R,6R,8R,9R,10R,15R,17R,18R)-8-(6-amino-9H-purin-9-yl)-9,18-difluoro-17-{3H-imidazo[2,1-f]purin-3-yl}-3,12-disulfanyl-2,4,7,11,13,16-hexaoxa-3$\lambda^5$,12$\lambda^5$-diphosphatricyclo[13.3.0.0$^{6,10}$]octadecane-3,12-dione, or a pharmaceutically acceptable salt thereof.

In another aspect, there is provided a compound which is (1S,6R,8R,9R,10R,15R,17R,18R)-8-(6-amino-9H-purin-9-yl)-9-fluoro-18-hydroxy-17-{9-oxo-3H,4H,9H-imidazo[1,2-a]purin-3-yl}-3,12-disulfanyl-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-3,12,18-trihydroxy-17-{9-oxo-3H,4H,9H-imidazo[1,2-a]purin-3-yl}-2,4,7,11,13,16-hexaoxa-3$\lambda^5$,12$\lambda^5$-diphosphatricyclo[13.3.0.0$^{6,10}$]octadecane-3,12-dione, (1R,6R,8R,9R,10R,15R,17R,18R)-8-(6-amino-9H-purin-9-yl)-9,18-difluoro-3,12-dihydroxy-17-{3H-imidazo[2,1-f]purin-3-yl}-2,4,7,11,13,16-hexaoxa-3λ$^5$,12λ$^5$-diphosphatricyclo[13.3.0.0$^{6,10}$]octadecane-3,12-dione, 1-[(1R,6R,8R,9R,10R,15R,17R,18R)-17-(6-amino-9H-purin-9-yl)-9,18-difluoro-3,12-dioxo-3,12-disulfanyl-2,4,7,11,13,16-hexaoxa-3λ$^5$,12λ$^5$-diphosphatricyclo[13.3.0.0$^{6,10}$]octadecan-8-yl]-1H-1,2,3-benzotriazole-4-carboxamide, (1S,6R,8R,9R,10R,15R,17R,18R)-8-(6-amino-9H-purin-9-yl)-9-fluoro-18-hydroxy-17-{4-oxo-1H,4H,5H-imidazo[2,1-b]purin-1-yl}-3,12-disulfanyl-2,4,7,11,13,16-hexaoxa-3λ$^5$,12λ$^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-12,18-dihydroxy-3-sulfanyl-17-{3H-[1,2,4]triazolo[3,2-f]purin-3-yl}-2,4,7,11,13,16-hexaoxa-3λ$^5$,12λ$^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-3,12,18-trihydroxy-17-{3H-[1,2,4]triazolo[3,2-f]purin-3-yl}-2,4,7,11,13,16-hexaoxa-3λ$^5$,12λ$^5$-diphosphatricyclo[13.3.0.0$^{6,10}$]octadecane-3,12-dione, 12 (1R,6R,8R,9R,10R,15R,17R,18R)-8-(6-amino-9H-purin-9-yl)-9,18-difluoro-3,12-disulfanyl-17-{3H-[1,2,4]triazolo[3,2-f]purin-3-yl}-2,4,7,11,13,16-hexaoxa-3λ$^5$,12λ$^5$-diphosphatricyclo[13.3.0.0$^{6,10}$]octadecane-3,12-dione, (1S,6R,8R,9R,10S,15R,17R,18R)-3,9,18-trihydroxy-17-{3H-imidazo[2,1-f]purin-3-yl}-8-{9-oxo-3H,4aH,5H,9H,9aH-imidazo[1,2-a]purin-3-yl}-12-sulfanyl-2,4,7,11,13,16-hexaoxa-3λ$^5$,12λ$^5$-diphosphatricyclo[13.3.0.0$^{6,10}$]octadecane-3,12-dione, (1R,6R,8R,9R,10S,15R,17R,18R)-8-(6-amino-9H-purin-9-yl)-18-fluoro-3,9,12-trihydroxy-17-{3H-imidazo[2,1-f]purin-3-yl}-2,4,7,11,13,16-hexaoxa-3λ$^5$,12λ$^5$-diphosphatricyclo[13.3.0.0$^{6,10}$]octadecane-3,12-dione, or (1R,6R,8R,9R,10R,15R,17R,18R)-8-(6-amino-9H-purin-9-yl)-9,18-difluoro-17-{3H-imidazo[2,1-f]purin-3-yl}-3,12-disulfanyl-2,4,7,11,13,16-hexaoxa-3λ$^5$,12λ$^5$-diphosphatricyclo[13.3.0.0$^{6,10}$]octadecane-3,12-dione, or a pharmaceutically acceptable salt thereof.

In another aspect, there is provided a compound which is (1S,6R,8R,9R,10R,15R,17R,18R)-8-(6-amino-9H-purin-9-yl)-9-fluoro-18-hydroxy-17-{9-oxo-3H,4H,9H-imidazo[1,2-a]purin-3-yl}-3,12-disulfanyl-2,4,7,11,13,16-hexaoxa-3λ$^5$,12λ$^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-3,12,18-trihydroxy-17-{9-oxo-3H,4H,9H-imidazo[1,2-a]purin-3-yl}-2,4,7,11,13,16-hexaoxa-3λ$^5$,12λ$^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-18-hydroxy-17-{4-oxo-1H,4H,5H-imidazo[2,1-b]purin-1-yl}-3,12-disulfanyl-2,4,7,11,13,16-hexaoxa-3λ$^5$,12λ$^5$-diphosphatricyclo[13.3.0.0$^{6,10}$]octadecane-3,12-dione, or (1S,6R,8R,9R,10S,15R,17R,18R)-3,9,18-trihydroxy-17-{3H-imidazo[2,1-f]purin-3-yl}-8-{9-oxo-3H,4aH,5H,9H,9aH-imidazo[1,2-a]purin-3-yl}-12-sulfanyl-2,4,7,11,13,16-hexaoxa-3λ$^5$,12λ$^5$-diphosphatricyclo[13.3.0.0$^{6,10}$]octadecane-3,12-dione, or a pharmaceutically acceptable salt thereof.

OTHER EMBODIMENTS OF THE INVENTION

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers In another embodiment, the invention provides a method for the treatment and/or prophylaxis of various types of cancer, including without limitation, small cell lung cancer, non-small cell lung cancer, colorectal cancer, melanoma, renal cell carcinoma, head and neck cancer, Hodgkin's lymphoma or bladder cancer.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The cyclic dinucleotides of the invention induce Type I interferons and/or pro-inflammatory cytokines in vitro in human cells, animal cells and human blood. The cytokine-inducting activity of these CDNs requires the presence of STING, as confirmed by in vitro experiments in human or animal cells.

The CDNs of the invention are agonists of the receptor STING.

The term "agonist" refers to any substance that activates a biologic receptor in vitro or in vivo to provoke a physiological response.

"STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein that in humans is encoded by the gene TMEM173. Activation of STING by cyclic dinucleotides (CDN) leads to activation of the IRF3 and NF-κB pathways and consequently, to induction of Type I interferons and of pro-inflammatory cytokines, respectively.

Another object of the present invention is the cyclic dinucleotides of Formula (I), for use in a therapeutic treatment in humans or animals. In particular, the compounds of the present invention may be used for therapeutic or diagnostic applications in human or animal health.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "antagonist" refers to any substance that inhibits, counteracts, downregulates, and/or desensitizes a biologic receptor in vitro or in vivo to provoke a physiological response.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both.

"Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the cyclic dinucleotide of Formula (I) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of infection or disease in that human or animal, and/or to modulate the immune system of that human or animal to achieve some other therapeutic benefit.

In one particular embodiment, the cyclic dinucleotides of the present invention can be used for cytokine induction immunotherapy of immunosuppressed individuals.

In this example, a cyclic dinucleotide of Formula (I) would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof a cyclic dinucleotide of Formula (I) or a pharmaceutically acceptable salt or prodrug thereof.

In another embodiment, the cyclic dinucleotides of the present invention can be used for cytokine induction immunotherapy in combination with chemotherapy. In this example, a cyclic dinucleotide of Formula (I) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The present invention thus discloses a method for treating cancer, said method comprising administering to a patient in need thereof: a chemotherapeutic agent; and
a cyclic dinucleotide of Formula (I) or a pharmaceutically acceptable salt or prodrug thereof.

Another object of the present invention is the cyclic dinucleotides of Formula (I) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: small cell lung cancer, non-small cell lung cancer, colorectal cancer, melanoma, renal cell carcinoma, head and neck cancer, Hodgkin's lymphoma or bladder cancer.

The present invention thus discloses a method for treating a bacterial infection, a viral infection or a cancer, said method comprising administering to a patient in need thereof a cyclic dinucleotide of Formula (I) or a pharmaceutically acceptable salt or prodrug thereof.

Another object of the present invention is the cyclic dinucleotides of Formula (I) for use in the treatment of a pathology that may be alleviated by the induction of an immune response via the STING pathway.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colorectal cancers, blood cancers, lung cancers and bone cancers. Examples of such cancer types include neuroblastoma, intestinal carcinoma such as rectal carcinoma, colon carcinomas, familiar adenomatous polyposis carcinoma and hereditary non-polyposis colorectal cancer, esophageal carcinoma, labial carcinoma, larynx carcinoma, nasopharyngeal cancers, oral cavity cancers, salivary gland carcinoma, peritoneal cancers, soft tissue sarcoma, urothelial cancers, sweat gland carcinoma, gastric carcinoma, adenocarcinoma, medullary thyroid carcinoma, papillary thyroid carcinoma, renal carcinoma, kidney parenchymal carcinoma, ovarian carcinoma, cervical carcinoma, uterine corpus carcinoma, endometrial carcinoma, pancreatic carcinoma, prostate carcinoma, testis carcinoma, breast cancers including HER2 Negative, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, multiple myeloma, seminoma, osteosarcoma, chondrosarcoma, anal canal cancers, adrenal cortex carcinoma, chordoma, fallopian tube cancer, gastrointestinal stromal tumors, myeloproliferative diseases, mesothelioma, biliary tract cancers, Ewing sarcoma and other rare tumor types.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergistic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTOR, Lymphotoxin α 1β2, FAS, FASL, RELT, DR6, TROY, NGFR.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. The PD-1 antibody can be selected from Opdivo (nivolumab), Keytruda (pembrolizumab), PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHRI210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In one aspect,

In another aspect, the immuno-oncology agent is a PD-L1 antagonist, such as an antagonistic PD-L1 antibody. The PD-L1 antibody can be selected from Tecentriq (atezolizumab), durvalumab, avelumab, STI-1014 (Sorrento; see WO2013/181634), or CX-072 (CytomX; see WO2016/149201).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intratumoral, intravenous or epidural injection as, for example, a sterile solution or suspension, or sustained release formulation; (3) topical application, for example, as a cream, ointment, or a controlled release patch or spray applied to the skin; or intratumorally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the present invention include those suitable for oral, intratumoral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous, intratumoral or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol ⟜ is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

Additionally, the phosphorothioate group can be drawn as either

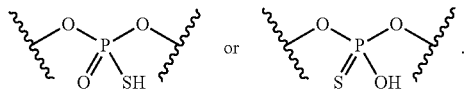 [SMILES: *OP(=O)(S)O* ; *OP(O)(=S)O*]

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, CF$_3$, CF$_2$CF$_3$, CN, halogen, haloalkyl, NO$_2$, sulfone, sulfoxide, ester, sulfonamide, carboxamide, alkoxy, alkoxyether, alkenyl, alkynyl, OH, C(O)alkyl, CO$_2$H, phenyl, heteroaryl, —O-phenyl, and —O— heteroaryl. Preferred examples of EWG include, but are not limited to, CF$_3$, CF$_2$CF$_3$, CN, halogen, SO$_2$(C$_{1-4}$ alkyl), CONH(C$_{1-4}$ alkyl), CON(C$_{1-4}$ alkyl)$_2$, and heteroaryl. More preferred examples of EWG include, but are not limited to, CF$_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4$^{th}$ Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, CD3 denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 2007).

Compounds of Formula (I) may be prepared by reference to the methods illustrated in the following Scheme. As shown therein, the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

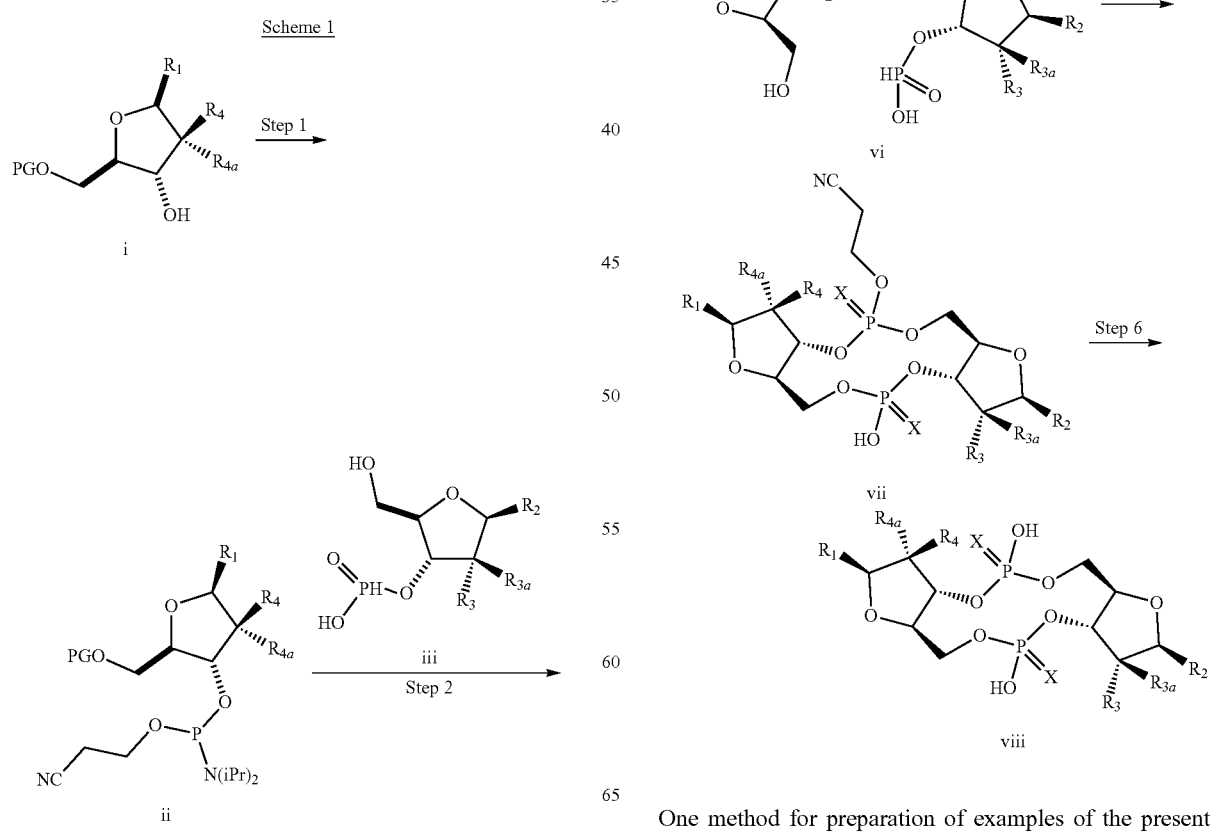

One method for preparation of examples of the present disclosure is described in Scheme 1. The method starts from a ribo-nucleoside (i), wherein the nucleobase ($R^1$ or $R^2$) is appropriately protected, such as with a benzoyl group, and the 5'-hydroxy group is appropriately protected (PG), such as with a DMTr ether, and the 3'-position is a free hydroxyl group. In step 1, the hydroxyl group may be converted to a phosphoramidite functionality through treatment with an appropriate reagent, such as 2-cyanoethyl N,N,N',N'-tetraisopropylphosphorodiamidite in the presence of 1H-imidazole-4,5-dicarbonitrile to afford compounds of formula (ii). In step 2, treatment with appropriate reagents, such as pyridine and an H-phosphonate (iii) in an appropriate solvent such as pyridine or acetonitrile affords compounds of formula (iv), which may typically be used without isolation in step 3. Oxidation or sulfurization with, for example t-butyl hydroperoxide or DDTT provides compounds of formula (v). Subsequent removal of the 5'-OH protecting group in step 4, under acidic conditions (for example when PG=DMTr) affords compounds of formula vi. Treatment of compounds vi with an appropriate cyclization reagent in step 5, such as DMOCP, followed again by sulfurization with DDTT or oxidation with t-butyl hydroperoxide provides compounds of formula vii. Compounds of formula (I) may be prepared in step 6 or subsequent steps by removal of any remaining protecting group using methods known to one skilled in the art.

An alternative method for the preparation of compounds of formula I is described in Scheme 2.

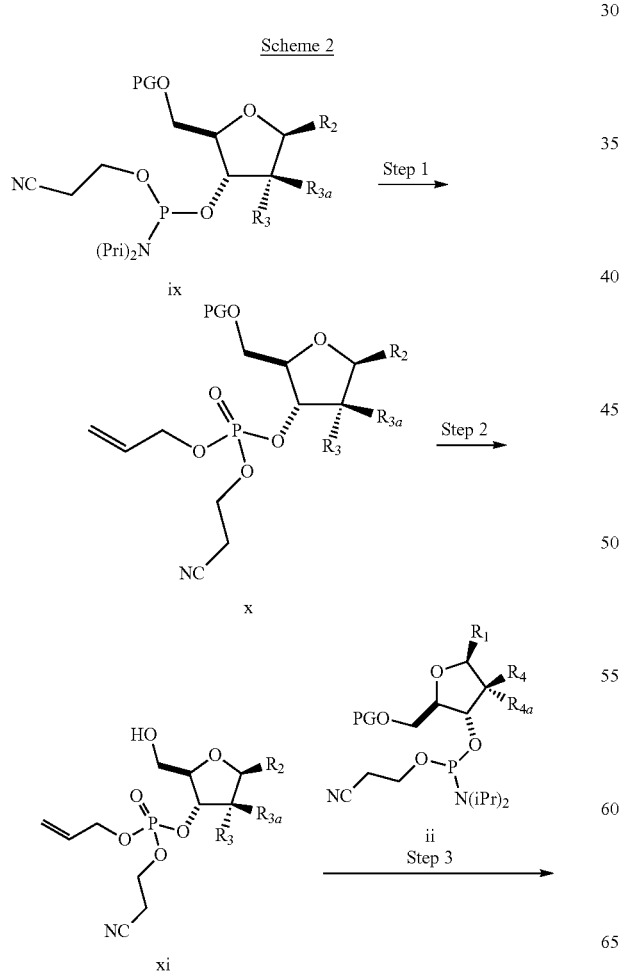

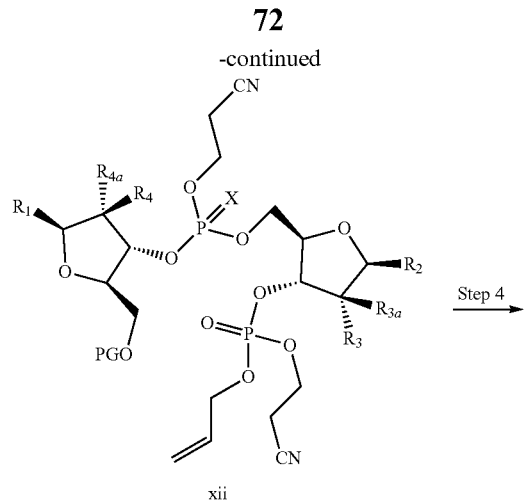

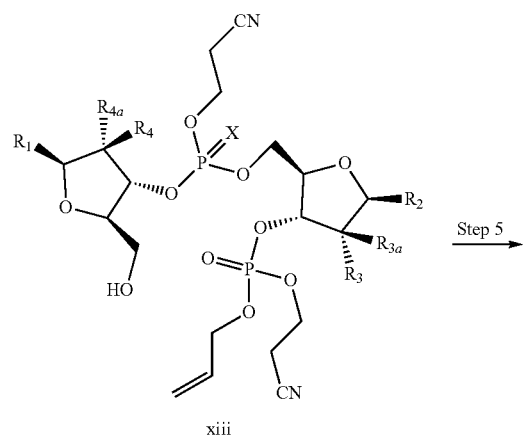

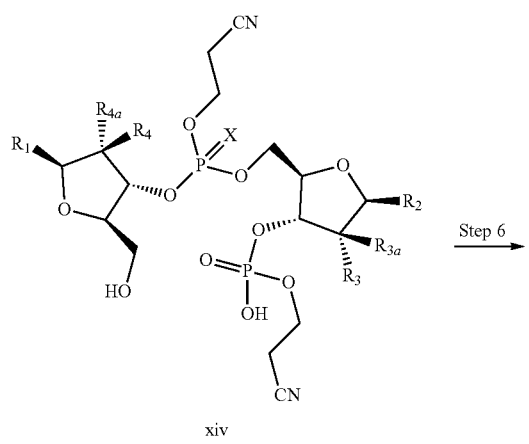

-continued

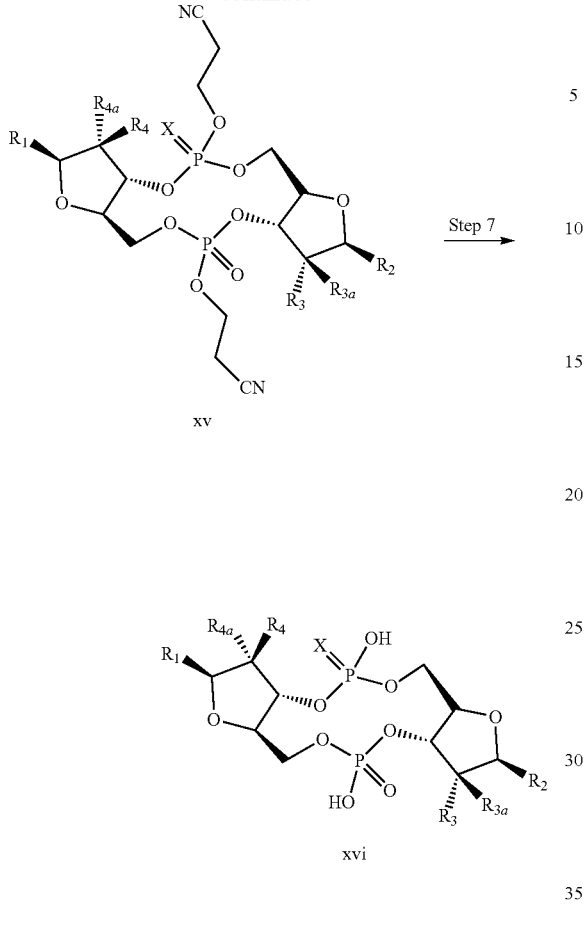

xv

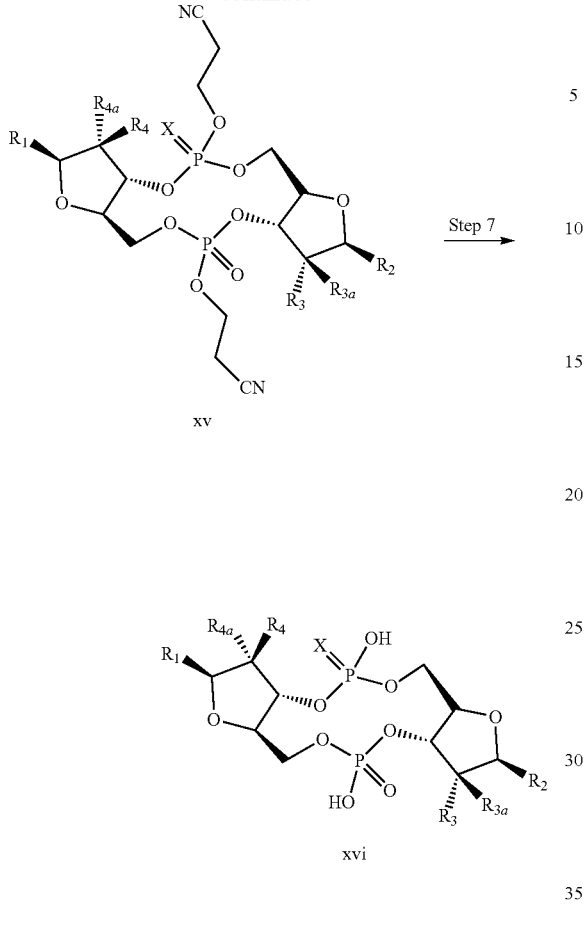

xvi

The sequence starts from a modified ribo-nucleoside (ix), wherein the nucleobase (R¹ or R²) is appropriately protected, such as with a benzoyl group, and the 5'-hydroxy group is appropriately protected (PG), such as with a DMTr ether, and the 3'-position is a phosphoramidite functionality. In step 1, treatment with prop-2-en-1-ol, followed by immediate oxidation (x=O), for example, with 2-butanone peroxide, affords the phosphodiester (x). Subsequent removal of the 5'-OH protecting group in step 2, under acidic conditions (PG=DMTr) affords compounds of formula xi. The resulting compound of formula xi may be reacted with a fully protected 3'-phosphoramidite (ii) in step 3 followed by oxidation, for example, with 2-butanone peroxide to provide compounds of formula xii (X=O) or may be treated, for example with DDTT, to provide additional compounds of formula xii (X=S). Removal of the 5'-protecting group from the second ribo-nucleoside in step 4, under acidic conditions (PG=DMTr) provides compounds of formula xiii. Removal of the allyl protecting group with an appropriate reagent in step 5, such as NaI or Pd(PPh₃)₄, provides compounds of formula xiv. Treatment of compounds xiv with an appropriate cyclization reagent in step 6, such as 1-(mesitylsulfonyl)-3-nitro-TH-1,2,4-triazole, provides compounds of formula xv. Compounds of formula xv may be treated with an appropriate reagent, such as t-butylamine, to remove the 2-cyanoethyl groups and provides compounds of formula xvi, Additional steps to remove remaining protecting groups may be necessary. For example, treatment with NH₄OH/MeOH to remove alkyl or phenyl carbonyl groups and treatment with fluoride ion where silyl protecting groups have been employed affords compounds of formula (I).

Alternatively, an additional method for the preparation of compounds of Formula (I) is shown in Scheme 3.

Scheme 3

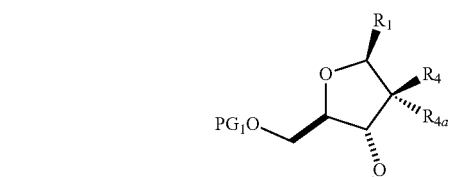

xv

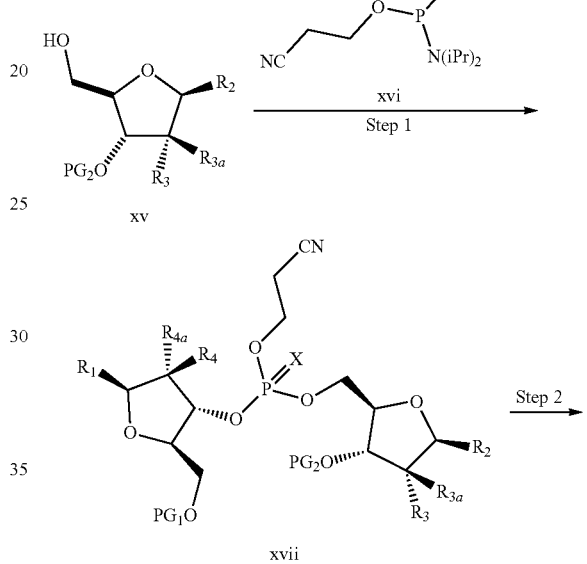

xvii

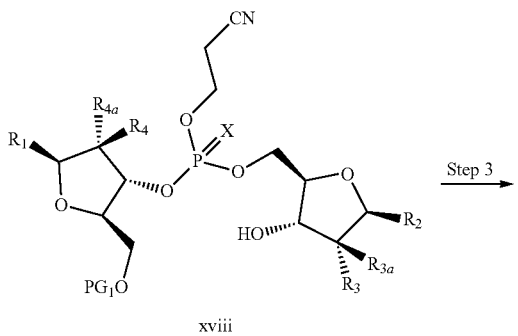

xviii

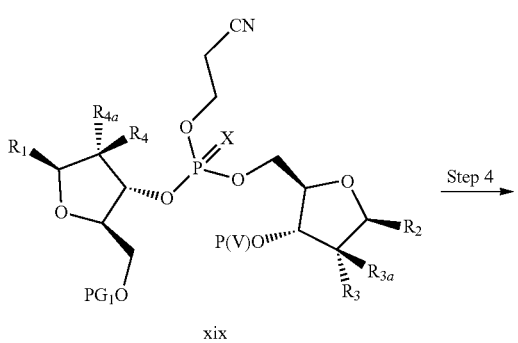

xix

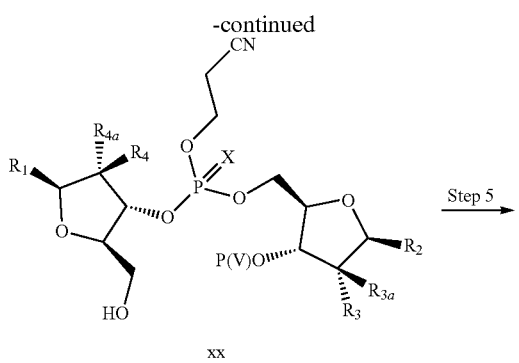

xx

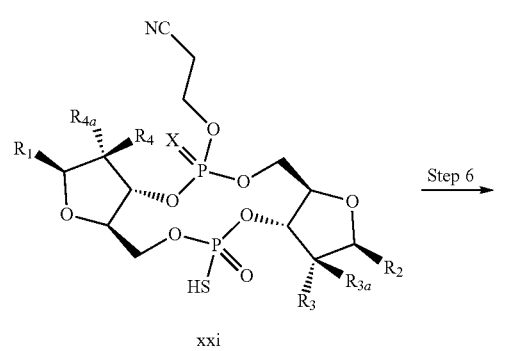

xxi

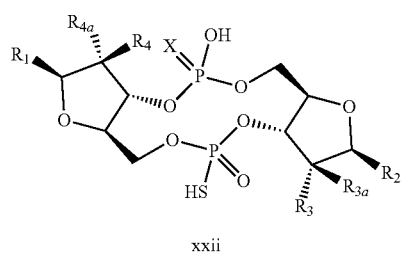

xxii

The method starts from an appropriately substituted natural or modified nucleoside (xv), wherein the nucleobase (R²) is appropriately protected, such as with a benzoyl group. In Step 1, reaction of xv with an appropriately protected substituted or modified nucleoside (xvi) containing a 3'-phosphoramidite functionality, followed by oxidation with, for example, 2-butanone peroxide provides compounds of formula xvii (X=O) or, for example with DDTT, provides additional compounds of formula xvii (X=S). In step 2, deprotection of the 3'-OH may be effected by one skilled in the art. For example, when PG₂=an ester, treatment with hydrazine affords compounds of general formula xviii. Reaction of compounds of formula xviii with an appropriate organophosphorus (V) reagent, for example one of those listed in Table 1, in an appropriate solvent (such as acetonitrile or dimethylformamide), with an appropriate base (for example DBU) affords compounds of formula xix in step 3. Removal of the 5'OH protecting group for example, with 2,2-dichloroacetic acid (PG1=DMTr) in step 4 affords compounds of formula xx. In step 5, treatment of compound xx, in an appropriate solvent (for example acetonitrile or dimethylformamide) in the presence of a base (for example DBU) affords compounds of formula xxi. In Step 6, any remaining protecting groups may be removed under conditions known to one skilled in the art to afford compounds of formula xxii.

Alternatively, an additional method for the preparation of examples of the present disclosure is described in Scheme 4.

Scheme 4

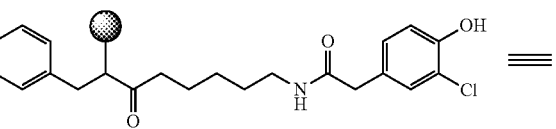

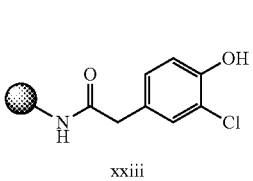

xxiii

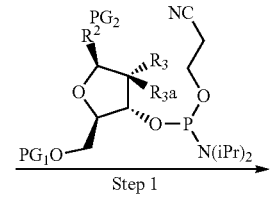

Step 1

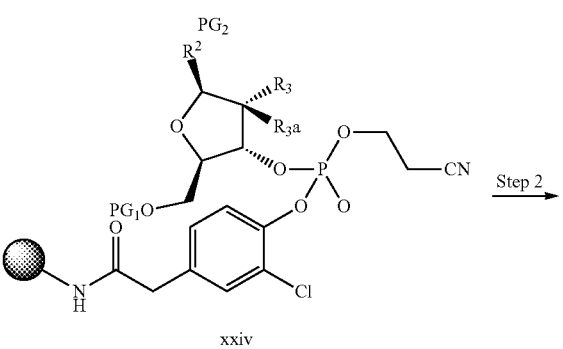

xxiv

Step 2

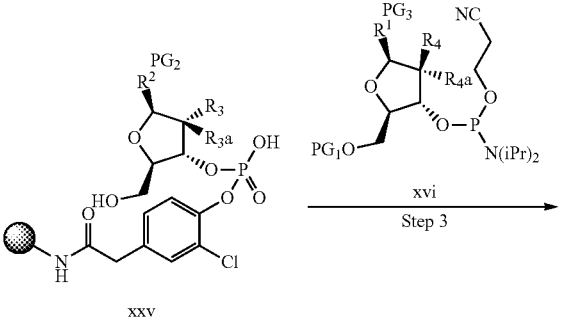

xxv

Step 3

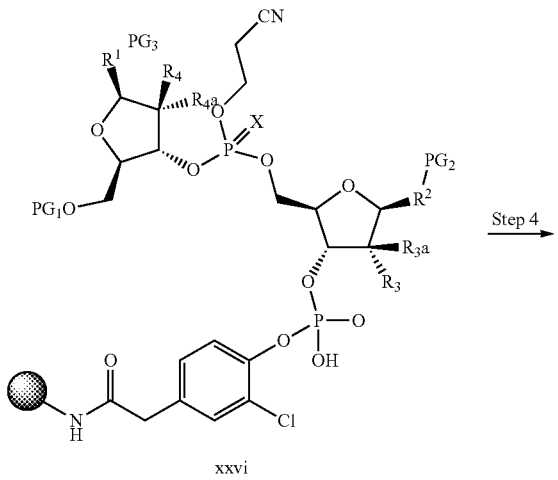

xxvi

Step 4

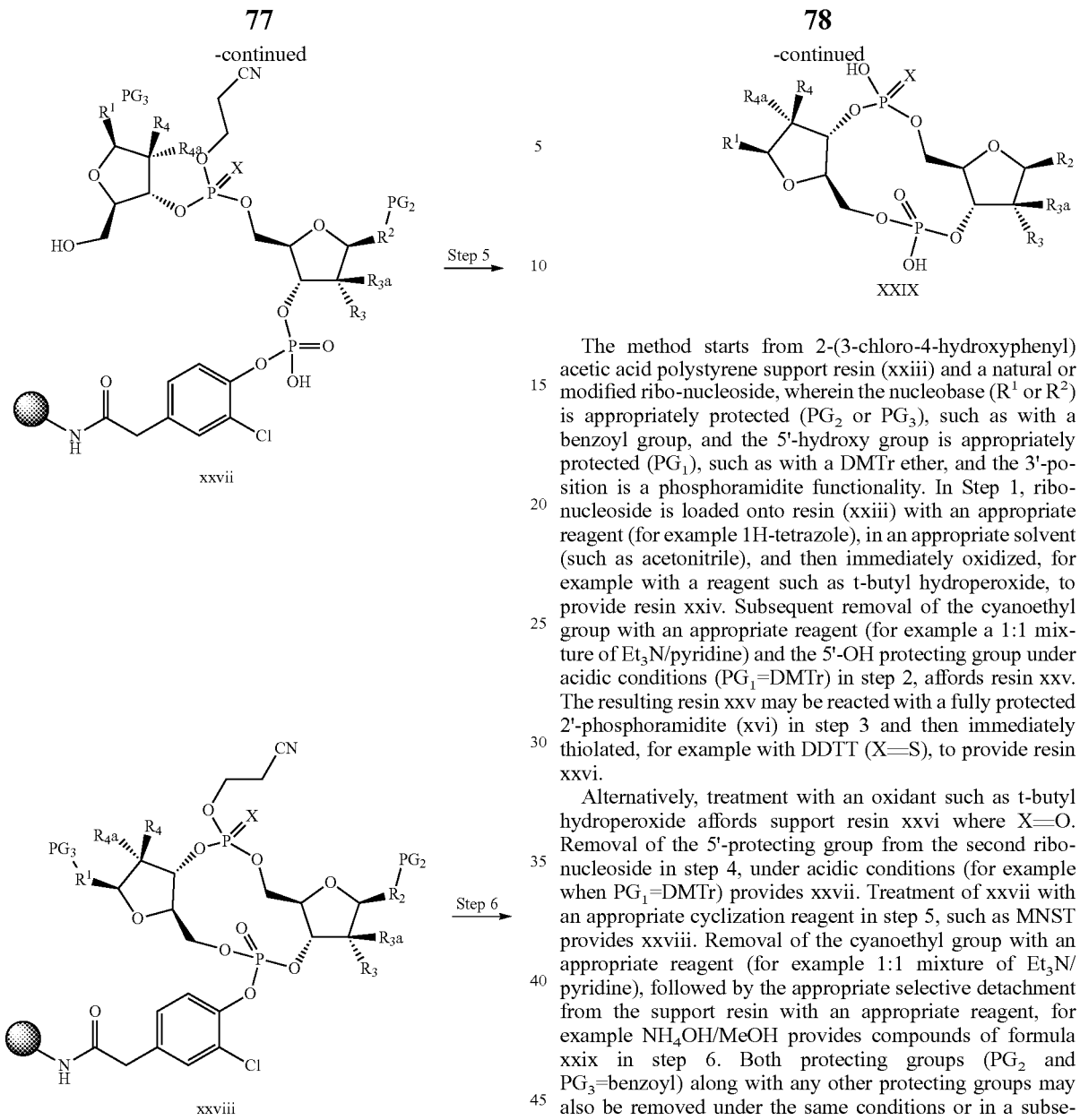

The method starts from 2-(3-chloro-4-hydroxyphenyl) acetic acid polystyrene support resin (xxiii) and a natural or modified ribo-nucleoside, wherein the nucleobase ($R^1$ or $R^2$) is appropriately protected ($PG_2$ or $PG_3$), such as with a benzoyl group, and the 5'-hydroxy group is appropriately protected ($PG_1$), such as with a DMTr ether, and the 3'-position is a phosphoramidite functionality. In Step 1, ribo-nucleoside is loaded onto resin (xxiii) with an appropriate reagent (for example 1H-tetrazole), in an appropriate solvent (such as acetonitrile), and then immediately oxidized, for example with a reagent such as t-butyl hydroperoxide, to provide resin xxiv. Subsequent removal of the cyanoethyl group with an appropriate reagent (for example a 1:1 mixture of $Et_3N$/pyridine) and the 5'-OH protecting group under acidic conditions ($PG_1$=DMTr) in step 2, affords resin xxv. The resulting resin xxv may be reacted with a fully protected 2'-phosphoramidite (xvi) in step 3 and then immediately thiolated, for example with DDTT (X=S), to provide resin xxvi.

Alternatively, treatment with an oxidant such as t-butyl hydroperoxide affords support resin xxvi where X=O. Removal of the 5'-protecting group from the second ribo-nucleoside in step 4, under acidic conditions (for example when $PG_1$=DMTr) provides xxvii. Treatment of xxvii with an appropriate cyclization reagent in step 5, such as MNST provides xxviii. Removal of the cyanoethyl group with an appropriate reagent (for example 1:1 mixture of $Et_3N$/pyridine), followed by the appropriate selective detachment from the support resin with an appropriate reagent, for example $NH_4OH$/MeOH provides compounds of formula xxix in step 6. Both protecting groups ($PG_2$ and $PG_3$=benzoyl) along with any other protecting groups may also be removed under the same conditions or in a subsequent step, through appropriate selection of reagents known to those skilled in the art.

TABLE 1

Organophosphorus Reagents and Corresponding —P(V) groups

TABLE 1-continued

Organophosphorus Reagents and Corresponding —P(V) groups

Organophosphorus (V) Reagent        —P(V)

Reagent-2

Reagents-3

Reagent-4

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

The following abbreviations may be used in the example section below and elsewhere herein:

| Abbreviation | Full Name |
| --- | --- |
| Ac | acetyl |
| ACN | acetonitrile |
| aq. | aqueous |
| DBU | 1,8-diazabicyclo[5.4.0]undec-7-ene |
| DCM | dichloromethane |
| DDTT | ((dimethylamino-methylidene)amino)-3H-1,2,4-dithiazoline-3-thione |
| DMA | dimethylacetamide |
| DMF | dimethylformamide |
| DMSO | dimethylsulfoxide |
| DMOCP | 2-chloro-5,5-dimethyl-1,3,2-dioxaphosphorinane 2-oxide |
| DMTr | 4,4'-dimethoxytrityl |
| EtOAc | ethyl acetate |
| Et$_3$N or TEA | triethylamine |
| EtOH | ethanol |
| HPLC | high-performance liquid chromatography |
| iPr | isopropyl |
| MeOH | methanol |
| min | minute(s) |
| RT | room temperature |
| satd., sat., or sat'd | saturated |
| SEM | 2-(trimethylsilyl)ethoxymethyl |
| TBS, or TBDMS | t-Butyldimethylsilyl |
| TFA | trifluoroacetic acid |
| TMOF | trimethyl orthoformate |
| t$_R$ | retention time |

Preparation of Intermediate I-1: (2R,3R,4R,5R)-5-(6-benzamido-9H-purin-9-yl)-4-fluoro-2-(hydroxymethyl)tetrahydrofuran-3-yl hydrogen phosphonate

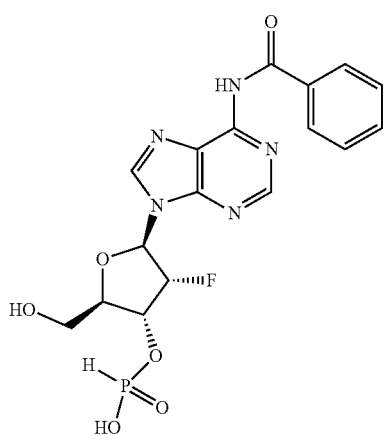

I-1

A solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl 2-cyanoethyl diisopropylphosphoramidite (Sigma-Aldrich, 2 g, 2.3 mmol) in ACN (5 mL) was treated with water (0.05 mL, 2.7 mmol), followed by pyridine trifluoroacetate (0.53 g, 2.7 mmol) The colorless solution was stirred for 10 min. and then concentrated in vacuo to afford a light pink foam. The resulting solid was dissolved in MeCN (5 mL) and concentrate to dryness. The resulting material was again dissolved in MeCN (5 mL). A solution of DBU (2.75 mL, 18.3 mmol) in ACN (6 mL) and nitromethane (1 mL, 18.3 mmol.) was prepared. To this DBU solution was added the ACN solution from above in one portion and the mixture was stirred for 20 min. The reaction was then poured into a 15 wt % aqueous solution of $KH_2PO_4$ (25 mL) and 2-MeTHF (20 mL) and agitated. The aqueous layer was extracted with 2-MeTHF (20 mL) and the combined organic layers were washed with a 15 wt % aqueous solution of $KH_2PO_4$ (2×20 mL), then a solution of brine (20 mL). The organic layer was dried over sodium sulfate, filtered and concentrated in vacuo. The resulting gel was dried by azeotropic distillation with 2-MeTHF (30-40 mL/g total, charged in 8-10 mL amounts). The crude material was then dissolved in DCM (20 mL). Methanol (1 mL) was added, followed by 2,2-dichloroacetic acid (0.8 mL, 10.8 mmol). The reaction was stirred for 3 h. To this mixture was added pyridine (2 mL, 27 mmol.) and then the mixture was concentrated in vacuo to a gel-like residue. Dimethoxy ethane (10 mL) was added and a white solid precipitated. The solids were collected by filtration and re-suspended in DME (2.5 mL/g) and agitated carefully with a spatula on the filter. The solids were again filtered and the process was repeated two more times to afford Intermediate I-1 as a white powder. (1 g, 72%).

Example 1

(1S,6R,8R,9R,10R,15R,17R,18R)-8-(6-amino-9H-purin-9-yl)-9-fluoro-18-hydroxy-17-{9-oxo-3H,4H,9H-imidazo[1,2-a]purin-3-yl}-3,12-disulfanyl-2,4,7,11,13,16-hexaoxa-3λ$^5$,12λ$^5$-diphosphatricyclo[13.3.0.0$^{6,10}$]octadecane-3,12-dione

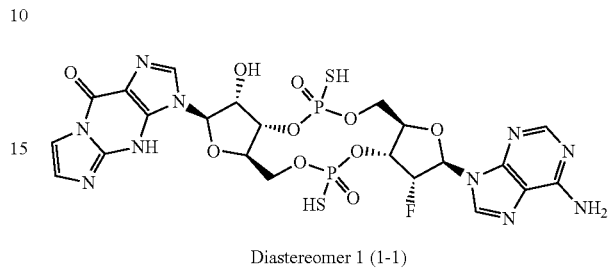

Diastereomer 1 (1-1)
Diastereomer 2 (1-2)

Preparation of Intermediate 1A

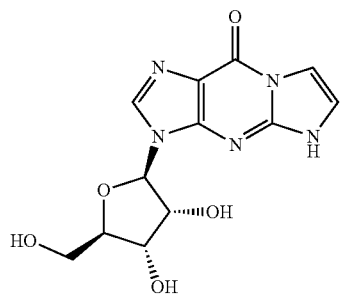

1A

To a solution containing (2R,3R,4S,5R)-2-(2-amino-6-chloro-9H-purin-9-yl)-5-(hydroxymethyl)tetrahydrofuran-3,4-diol (10 g, 33.1 mmol) in AcOH/NH$_4$OAc buffer (4.5 pH) (100 mL) and EtOH (100 mL) was added 2-bromoacetaldehyde (80 mL, 104 mmol). The reaction was heated for 48 h at 37° C. The filtrate was then neutralized to pH ~7 with solid ammonium bicarbonate and the resulting solid was collected by filtration and the solid was rinsed with acetonitrile. The filtrate was concentrated to ~½ volume on a rotary evaporator and then treated with acetonitrile (~100 mL) and a second crop of product was collected and rinsed with additional acetonitrile to give Intermediate 1A (5 g, 16.27 mmol, 49.1% yield), m/z (308, M+H). $^1$H NMR (400 MHz, DMSO-d$_6$) δ 8.15 (m, 1H), 7.63 (m, 1H), 7.42 (d, J=2.5 Hz, 1H), 5.83 (d, J=5.8 Hz, 1H), 5.42 (br d, J=5.8 Hz, 1H), 5.21-5.07 (m, 2H), 4.50 (q, J=5.3 Hz, 1H), 4.14 (br d, J=3.9 Hz, 1H), 3.92 (q, J=3.8 Hz, 1H), 3.73-3.62 (m, 1H), 3.60-3.49 (m, 1H).

Preparation of Intermediate 1B

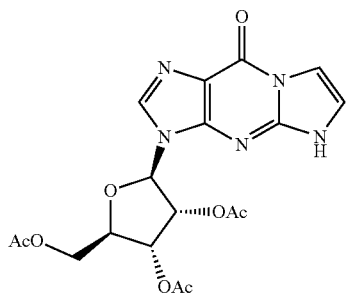

A solution of Intermediate 1A (4.5 g, 14.65 mmol) dissolved in pyridine (50 mL) was azeotroped on the rotary evaporator to dryness and then re-dissolved in pyridine (50 mL) and treated dropwise with acetic anhydride (13.82 mL, 146 mmol). The reaction was stirred for 20 h and then treated with MeOH (10 mL) and concentrated. The material was taken up in DCM (100 mL) and washed with 1.5 N $K_2HPO_4$ aq. solution (1×50 mL), dried ($Na_2SO_4$), filtered and concentrated. The crude product was dissolved in a small amount of DCM and charged to a 40 g ISCO silica gel column and purified using a Teledyne ISCO system, eluting over a 15 min gradient with 1%-10% DCM (0.1% TEA)/MeOH to give Intermediate 1B (3.1 g, 7.15 mmol, 48.8% yield), m/z (434, M+H). $^1$H NMR (400 MHz, DMSO-$d_6$) δ 12.58-12.53 (m, 1H), 8.15 (s, 1H), 7.65 (t, J=2.2 Hz, 1H), 7.47 (t, J=2.5 Hz, 1H), 6.14 (d, J=5.9 Hz, 1H), 5.92 (t, J=6.0 Hz, 1H), 5.54 (dd, J=5.9, 4.4 Hz, 1H), 4.46-4.26 (m, 3H), 2.16-2.11 (m, 3H), 2.04 (d, J=2.4 Hz, 6H).

Preparation of Intermediate 1C

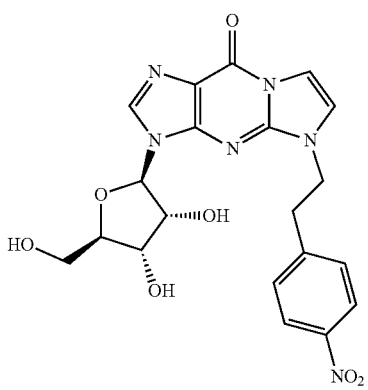

To a solution containing Intermediate 1B (2.5 g, 5.77 mmol), 2-(4-nitrophenyl)ethan-1-ol (1.543 g, 9.23 mmol) and triphenylphosphine (2.270 g, 8.65 mmol) in THF (50 mL) was added dropwise, DIAD (1.682 mL, 8.65 mmol). The reaction was stirred at room temperature for 20 h and then concentrated in vacuo. The crude product was dissolved in a small amount of DCM and charged to a 80 g ISCO silica gel column and purified using a Teledyne ISCO system, eluting over a 30 min gradient with 5%-100% DCM/EtOAc to give (2R,3R,4R,5R)-2-(acetoxymethyl)-5-(5-(4-nitrophenethyl)-9-oxo-5,9-dihydro-3H-imidazo[1,2-a]purin-3-yl)tetrahydrofuran-3,4-diyl diacetate, m/z (583, M+H). The crude (2R,3R,4R,5R)-2-(acetoxymethyl)-5-(5-(4-nitrophenethyl)-9-oxo-5,9-dihydro-3H-imidazo[1,2-a]purin-3-yl)tetrahydrofuran-3,4-diyl diacetate was re-dissolved in 7 N ammonia in MeOH (50 mL) and stirred for 20 h. The reaction was then concentrated to ~½ volume and treated with diethylether ~50 mL. The resulting solid was collected by filtration and rinsed with diethylether and dried to give Intermediate 1C (2.5 g, 5.48 mmol, 95% yield), m/z (457, M+H). $^1$H NMR (400 MHz, DMSO-$d_6$) δ 8.16-8.10 (m, 3H), 7.66-7.63 (m, 1H), 7.53-7.48 (m, 1H), 7.46-7.43 (m, 1H), 5.86-5.82 (m, 1H), 5.44-5.39 (m, 1H), 5.24-5.20 (m, 1H), 5.06-5.01 (m, 1H), 4.63-4.56 (m, 1H), 4.45-4.39 (m, 2H), 4.22-4.17 (m, 1H), 3.98-3.93 (m, 1H), 3.72-3.65 (m, 1H), 3.63-3.55 (m, 1H), 3.33-3.27 (m, 2H).

Preparation of Intermediate 1D

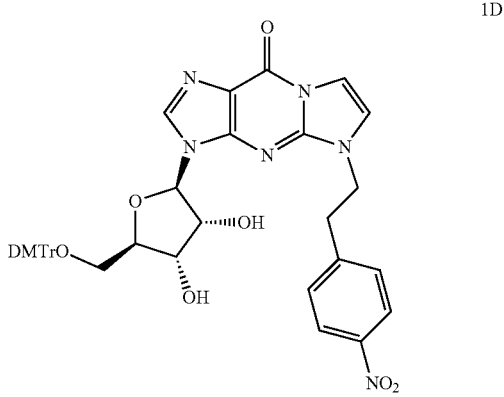

A solution containing Intermediate 1C (2.5 g, 5.48 mmol) in pyridine (40 mL) was concentrated to a thick oil. The oil was azeotroped a second time with additional pyridine (40 mL). The resulting viscous oil was re-dissolved in pyridine (30 mL) under a nitrogen atmosphere and 4,4'-(chloro(phenyl)methylene)bis(methoxybenzene) (2.227 g, 6.57 mmol) was added in small portions. The reaction was stirred for 20 h, and then concentrated on the rotary evaporator. The resulting residue was diluted with DCM (100 mL) and washed with sat. aq. $NaHCO_3$ solution (25 mL) and sat. aq. NaCl solution, then dried ($Na_2SO_4$), filtered and concentrated. The crude product was dissolved in a small amount of DCM and charged to a 40 g ISCO silica gel column and purified using a Teledyne ISCO system, eluting over a 20 min gradient with 5%-100% DCM/EtOAc (DCM containing 0.25% TEA) to give Intermediate 1D (1.95 g, 2.57 mmol, 46.9% yield), m/z (759, M+H). $^1$H NMR (400 MHz, DMSO-$d_6$) δ 8.13-8.06 (m, 3H), 7.68-7.62 (m, 1H), 7.45-7.39 (m, 3H), 7.35-7.29 (m, 2H), 7.21-7.12 (m, 7H), 6.72 (dd, J=16.5, 8.9 Hz, 4H), 5.92 (d, J=4.3 Hz, 1H), 5.55 (d, J=5.6 Hz, 1H), 5.23 (d, J=6.1 Hz, 1H), 4.68 (q, J=5.2 Hz, 1H), 4.40 (q, J=5.6 Hz, 1H), 4.33-4.14 (m, 2H), 4.10-4.04 (m, 1H), 3.69 (s, 3H), 3.68-3.66 (m, 3H), 3.32-3.26 (m, 1H), 3.22-3.13 (m, 3H).

Preparation of Intermediate 1E

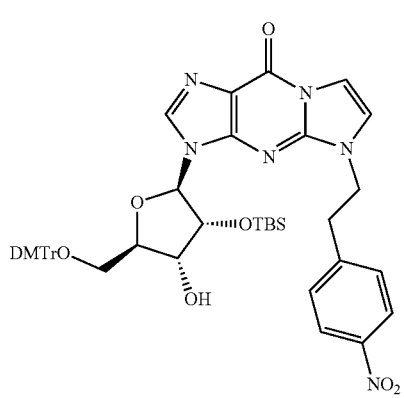

To a solution containing Intermediate 1D (1.43 g, 1.885 mmol) in DMF (10 mL) was added imidazole (0.642 g, 9.42 mmol) followed by the addition of TBS-Cl (0.312 g, 2.073 mmol). The reaction was stirred for 12 h. The reaction was then diluted with ethyl acetate (150 mL), washed with water (1×50 mL), aq. 10% LiCl solution (2×50 mL) and finally with sat. aq. NaCl solution (50 mL). The organic layer was dried (Na$_2$SO$_4$), filtered and concentrated. The crude product was dissolved in a small amount of DCM and charged to a 220 g ISCO silica gel column that had been equilibrated with DCM (0.25% TEA) and purified using a Teledyne ISCO system, eluting over a 30 min. gradient with 0%-50% ethylacetate/DCM (0.25% TEA) to afford the desired Intermediate 1E. $^1$H NMR (400 MHz, DMSO-d$_6$) δ 8.36-8.32 (m, 1H), 8.17-8.13 (m, 2H), 8.06 (d, J=1.6 Hz, 1H), 7.67-7.60 (m, 2H), 7.50 (d, J=1.6 Hz, 1H), 7.17-7.05 (m, 5H), 7.05-6.97 (m, 4H), 6.70 (br d, J=8.9 Hz, 2H), 6.69-6.65 (m, 2H), 6.31 (d, J=2.7 Hz, 1H), 5.75-5.74 (m, 1H), 5.30 (d, J=7.0 Hz, 1H), 4.93-4.89 (m, 1H), 4.82-4.69 (m, 2H), 4.35 (br d, J=4.8 Hz, 1H), 4.22-4.17 (m, 1H), 3.70 (s, 3H), 3.69 (s, 3H), 3.32-3.24 (m, 2H), 3.00 (dd, J=10.8, 3.8 Hz, 1H), 0.81 (s, 9H), 0.06 (s, 3H), 0.01 (s, 3H).

Preparation of Intermediate 1F

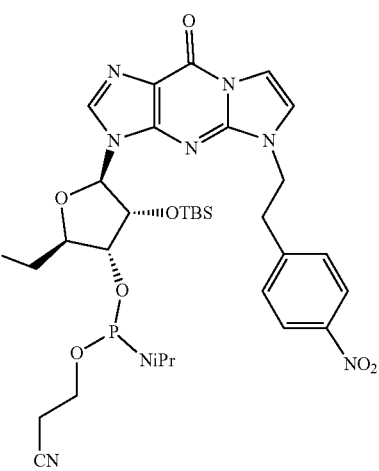

To a solution containing Intermediate 1F (950 mg, 1.0 mmol) in DCM (12 mL) was added 2-cyanoethyl N,N,N', N'-tetraisopropylphosphorodiamidite (0.717 mL, 2.176 mmol). The reaction was stirred for 20 h, then diluted with additional DCM (100 mL) and washed with sat. aq. NaHCO$_3$ solution (10 mL) and sat. aq. NaCl solution (10 mL), dried (Na$_2$SO$_4$), filtered and concentrated. The crude product was dissolved in a small amount of DCM and charged to a 40 g column and purified using a Teledyne ISCO system, eluting over a 20 min gradient with 0%-50% EtOAc/DCM (0.25% TEA) to afford Intermediate 1F (950 mg, 0.885 mmol, 81% yield) as a mixture of diastereomers that ionizes as m/z (990/991 hydrolysis of diisopropylamine).

Preparation of Intermediate 1G

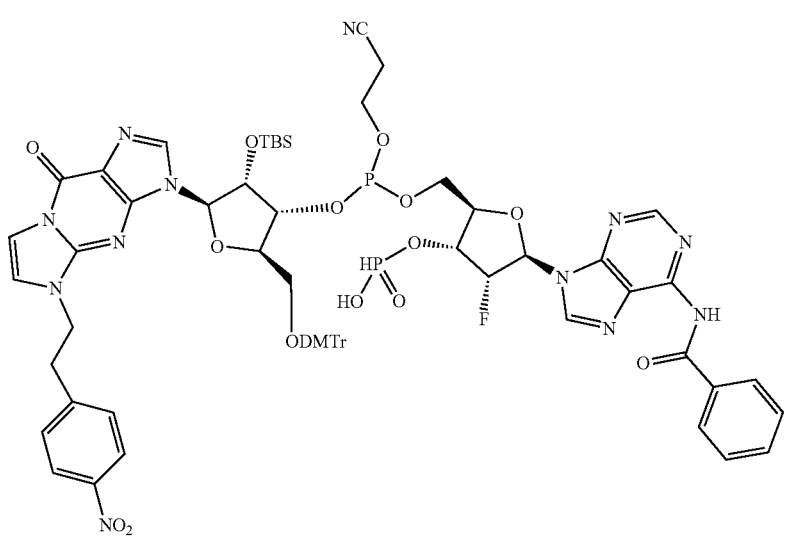

Compound Intermediate 1F (950 mg, 0.885 mmol) was dissolved in acetonitrile (10 mL). This solution was concentrated in vacuo (35° C. water bath) to a thick oil. The oil obtained was azeotroped a second time with additional acetonitrile (10 mL) to afford a thick oil. To this oil was added a third portion of acetonitrile (5 mL) and this solution was allowed to sit under a nitrogen atmosphere. A second 25 mL round-bottomed flask was charged with Intermediate I-1 (445 mg, 1.018 mmol)) and a small stir bar. To this solid was added pyridine (15 mL) and this solution was concentrated in vacuo (35° C. water bath). The procedure was repeated once more with additional pyridine (10 mL). Then, pyridine trifluoroacetate (188 mg, 0.974 mmol) was added, and this solution was azeotroped again with additional pyridine (10 mL) and concentrated to a solid. Acetonitrile (10 mL) was added to the solid under a nitrogen atmosphere to form a slightly cloudy freely stirring heterogeneous mixture. This mixture was stirred, as the previously prepared solution of Intermediate 1F was added via syringe. The resulting mixture was stirred and occasionally sonicated for 4 h to provide a solution of crude Intermediate 1G, m/z (1357, M+-cyanoethyl), which was used directly in subsequent steps.

Preparation of Intermediate 1H

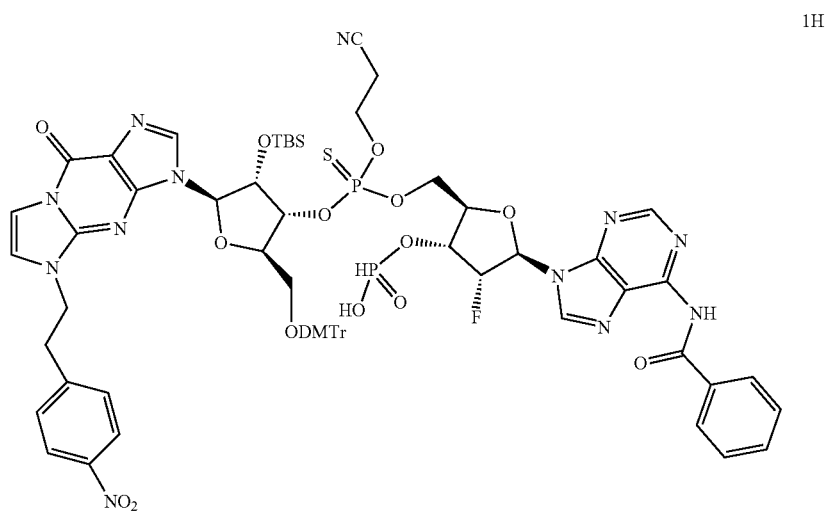

1H

The crude solution of Intermediate 1G (17 mL) was then treated with (E)-N,N-dimethyl-N'-(3-thioxo-3H-1,2,4-dithiazol-5-yl)formimidamide (227 mg, 1.106 mmol) and stirred an additional 25 minutes. The yellow solution was concentrated in vacuo (36° C. water bath) to give an oil. The residue was dissolved in a minimal amount of MeOH/DCM (5 mL, 1/1) and ~3 g of celite was added. The free flowing mixture was concentrated to dryness on the rotary evaporator to adsorb the crude product mixture and transferred to an empty ISCO cartridge and purified on an ISCO reverse phase chromatography system using a RediSep C18, 150 g Gold column using the following conditions: Flow Rate: 40 mL/min solvent A: water (95%)/ACN (5%) with ammonium acetate (0.05%) as additive and solvent B acetonitrile (95%)/water with 0.05% ammonium acetate as additive. Elution gradient of 0% B, hold for 2 column volume to 100% B over 14 column volumes afforded Intermediate 1H (600 mg, 0.416 mmol), m/z (1441.8, M+H).

Preparation of Intermediate 1I

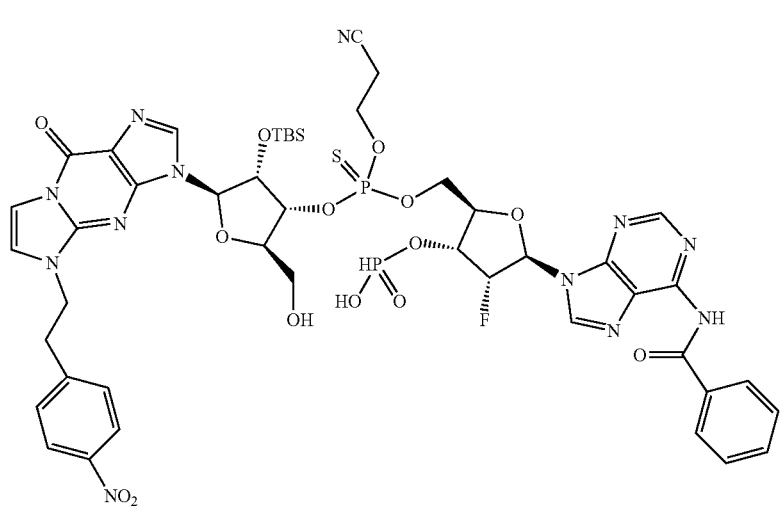

1I

Intermediate 1H (650 mg, 0.451 mmol) was dissolved in a mixture of DCM (6 mL)/MeOH (2 mL) and treated dropwise with 2,2-dichloroacetic acid (0.179 mL, 2.255 mmol). The reaction was stirred for 4 h and then quenched with pyridine (0.750 mL, 9.5 mmol). The mixture was then concentrated on the rotary evaporator. The residue was dissolved in MeOH (~2 mL) and loaded onto a pre-equilibrated ISCO 50 g HP Gold C-18 column and eluted with Solvent A: 95% water/5% ACN (0.01M ammonium acetate additive), Solvent B: 95% ACN/5% water (0.05% ammonium acetate additive) with an elution gradient of 0% B for 3 column volumes to 60% B over 15 column volumes to give Intermediate 1I (300 mg, 0.263 mmol, 58.4% yield), m/z 1139 (M+H), as a diastereomeric mixture of two major diastereomers.

Preparation of Intermediates 1J and 1K

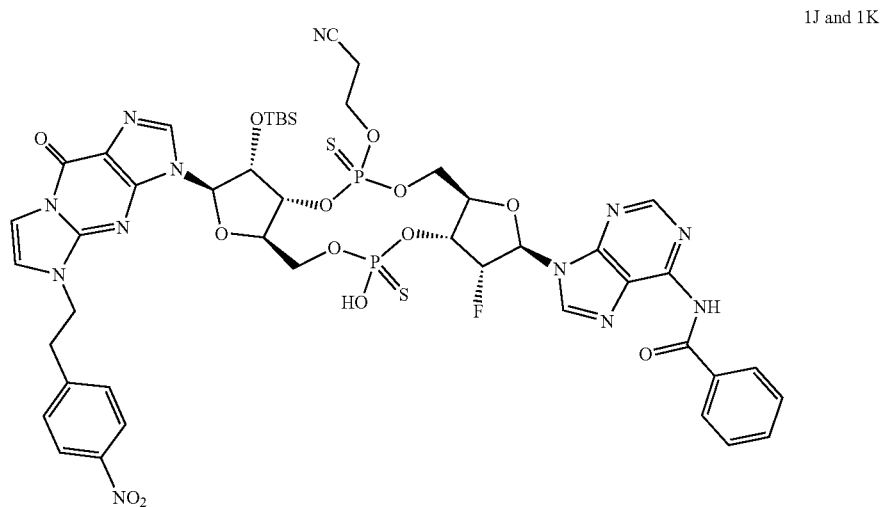 [SMILES: CC(C)(C)[Si](C)(C)O[C@@H]1[C@@H]2OP(=S)(OCCC#N)OC[C@H]3O[C@@H](n4cnc5c(NC(=O)c6ccccc6)ncnc54)[C@H](F)[C@@H]3OP(O)(=S)OC[C@H]2O[C@H]1n1cnc2c(=O)n3ccn(CCc4ccc([N+](=O)[O-])cc4)c3nc21]

1J and 1K

The mixture of diastereomers 1I (300 mg, 0.263 mmol) was dissolved in anhydrous pyridine (20 mL). This solution was concentrated in vacuo (35° C. water bath) to a thick oil. The oil obtained was azeotroped a second time with additional anhydrous pyridine (20 mL) resulting in a thick oil. To this oil was added a third portion of anhydrous pyridine (10 mL) and this solution was allowed to sit under a nitrogen atmosphere. In a separate 50 mL flask was dissolved 2-chloro-5,5-dimethyl-1,3,2-dioxaphosphinane 2-oxide (146 mg, 0.790 mmol) in anhydrous pyridine (10 mL), under a nitrogen atmosphere. The solution was cooled to −5° C. in an ice/NaCl bath. To this cooled solution was added dropwise, over a 30 minute period, the pyridine solution of 1I, using a syringe. The reaction was stirred for an additional 30 min, and then warmed to 25° C. over 20 min. Solid (E)-N,N-dimethyl-N'-(3-thioxo-3H-1,2,4-dithiazol-5-yl)formimidamide (81 mg, 0.395 mmol) was added and the mixture was stirred for an additional 30 min. The reaction was then treated with water (0.20 mL) and concentrated in vacuo. The residue was dissolved in acetonitrile (3 mL) and purified on a reverse phase C-18, 50 g HP Gold ISCO column using solvent A 95% water/5% ACN (0.01M NH$_4$OAc additive) and solvent B 95% ACN/5% water (0.01M NH$_4$OAc additive). Gradient: 0% B hold for 3 column volumes to 50% B over 10 column volumes. Fractions containing two major diastereomers were collected, and lyophilized to give diastereomer 1J (faster eluting fractions), and diastereomer 1K (slower eluting fractions) (~100 mg each), m/z (1153, M+H).

Preparation of Intermediate 1L and 1M

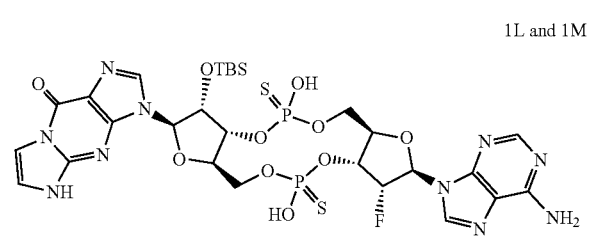 [SMILES: CC(C)(C)[Si](C)(C)O[C@@H]1[C@@H]2OP(O)(=S)OC[C@H]3O[C@@H](n4cnc5c(N)ncnc54)[C@H](F)[C@@H]3OP(O)(=S)OC[C@H]2O[C@H]1n1cnc2c(=O)n3cc[nH]c3nc21]

1L and 1M

A vial containing nitromethane (0.070 mL, 1.301 mmol) in pyridine (1.5 mL) was treated with DBU (0.131 mL, 0.867 mmol) and stirred for 10 min. To this DBU solution was added a solution containing Intermediate 1J (100 mg, 0.087 mmol) dissolved in pyridine (1 mL). The reaction was stirred for 10 h at 30° C. and then concentrated to a viscous oil. The oil was dissolved in a 7 N ammonia in MeOH solution (2 mL, 14 mmol) and heated in a sealed vial at 35° C. for 12 h. The reaction was then concentrated to dryness. The residue was dissolved in a minimal amount of MeOH and purified on reverse phase C-18, 50 g HP Gold ISCO column using solvent A 95% water/5% ACN (0.01 M NH$_4$OAc additive) and solvent B 95% ACN/5% water (0.01M NH$_4$OAc additive). Gradient: 0% B hold for 3 column volumes to 50% B over 10 column volumes. Fractions containing the desired compound were collected and lyophilized to afford Intermediate 1L (45 mg, 0.053 mmol, 61.3% yield), m/z (847, M+H).

Using the same protocol, but starting with the slower eluting isomer Intermediate 1K (100 mg, 0.087 mmol), afforded Intermediate 1M (40 mg, 55% yield), m/z (847, M+H).

Example 1

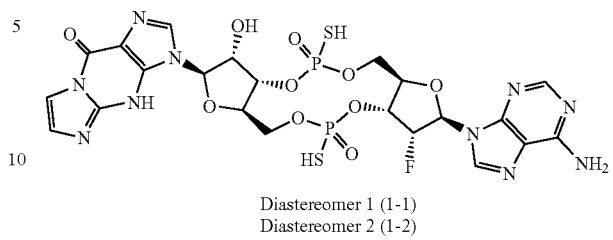

Diastereomer 1 (1-1)
Diastereomer 2 (1-2)

To a solution containing Intermediate 1L (90 mg, 0.106 mmol) in a mixture of acetonitrile (1 mL)/pyridine (0.5 mL) was added triethylamine trihydrofluoride (0.5 mL, 3 mmol). The reaction was heated at 35° C. for 20 h and then filtered through a 0.45 micron nylon syringe filter and purified. The crude material was purified via preparative LC/MS with the following conditions: Column: Agilent Bonus RP, 21.2×200 mm, 5-μm particles; Mobile Phase A: 5:95 acetonitrile:water with 20-mM ammonium acetate; Mobile Phase B: 95:5 acetonitrile:water with 20-mM ammonium acetate; Gradient: 0-60% B over 20 minutes, then a 4-minute hold at 100% B; Flow: 20 mL/min. Fractions containing the desired product were combined and dried via centrifugal evaporation to give Example 1-1 (52 mg, 65% yield), m/z (733, M+H). HPLC retention Time: 2.18 min, using Agilent column Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm).

Intermediate 1M was converted to Example 1-2, using a procedure analogous to Example 1-1. HPLC retention time: 2.36 min, using Agilent column Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm. $^1$H NMR (601 MHz, DEUTERIUM OXIDE) δ 8.30 (s, 1H), 8.26 (s, 1H), 8.11 (s, 1H), 7.52 (d, J=2.6 Hz, 1H), 7.27 (d, J=2.6 Hz, 1H), 6.40 (d, J=16.2 Hz, 1H), 6.02 (s, 1H), 5.58 (dd, J=51.1, 4.1 Hz, 1H), 5.22-5.09 (m, 1H), 5.03 (td, J=8.9, 4.8 Hz, 1H), 4.60-4.45 (m, 4H), 4.07-4.02 (br m, 2H).

Example 2

(1S,6R,8R,9R,10R,15R,17R,18R)-8-(6-amino-9H-purin-9-yl)-9-fluoro-3,12,18-trihydroxy-17-{9-oxo-3H,4H,9H-imidazo[1,2-a]purin-3-yl}-2,4,7,11,13,16-hexaoxa-3λ$^5$,12λ$^5$-diphosphatricyclo[13.3.0.0$^{6,10}$]octadecane-3,12-dione

2

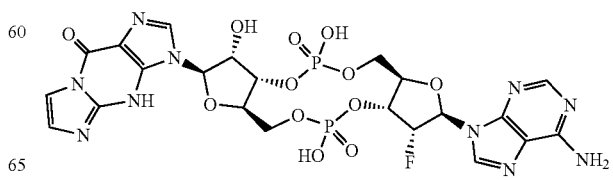

Preparation of Intermediate 2A

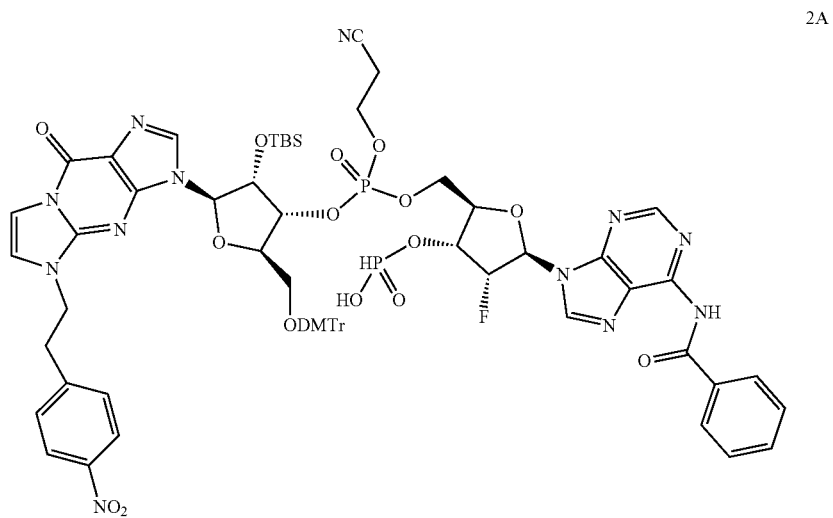

The crude solution of Intermediate 1G (5 mL) in acetonitrile/DMF, freshly prepared according to procedure outlined above, was treated with 2-hydroperoxy-2-methylpropane (0.109 mL, 0.600 mmol) and stirred for 30 min. The reaction was quenched with sodium bisulfite [(100 mg, dissolved in water (0.100 mL)] and concentrated in vacuo. The residue was re-dissolved in MeOH (2 mL), and celite (2 g) was added and the mixture was concentrated to dryness. The resulting solid was transferred to an empty ISCO solid phase cartridge and purified on an ISCO C-18 HP Gold 50 g column using mobile Phase A: 5:95 acetonitrile:water with 0.01M ammonium acetate; Mobile Phase B: 95:5 acetonitrile:water with 0.01M ammonium acetate; Gradient: 0% B for 2 column volumes to 100% B over 20 columns. The appropriate fractions were combined and concentrated to give Intermediate 2A (205 mg, 0.144 mmol). m/z: (1426, M+H).

Preparation of Intermediate 2B

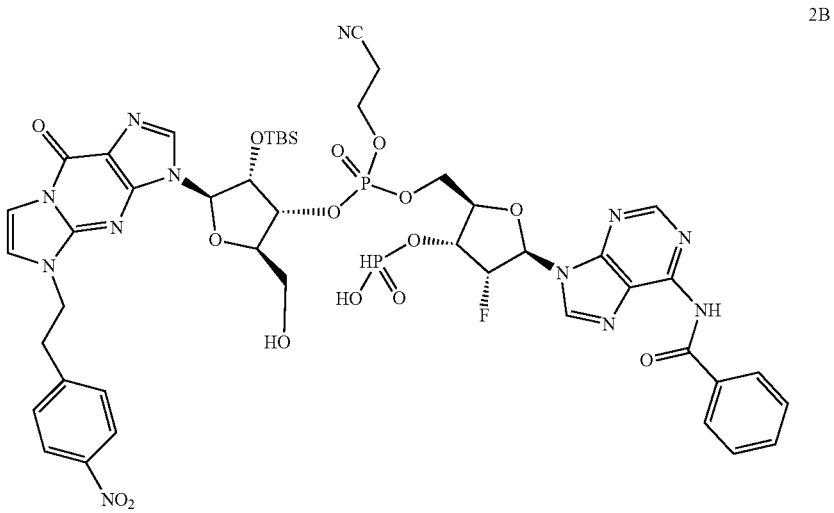

Intermediate 2A (200 mg, 0.14 mmol) was dissolved in a mixture of DCM (4 mL)/MeOH (1 mL) and treated dropwise with 2,2-dichloroacetic acid (0.050 mL, 0.60 mmol). The reaction was stirred for 4 h and then quenched with pyridine (0.1 mL, 1.4 mmol) and concentrated on the rotary evaporator. The residue was suspended in MeOH (~2 mL) and purified using an ISCO C-18 HP Gold 50 gold column using mobile Phase A: 5:95 acetonitrile:water with 0.01M ammonium acetate; Mobile Phase B: 95:5 acetonitrile:water with 0.01M ammonium acetate; Gradient: 0% B for 2 column volumes to 100% B over 20 columns. The appropriate fractions were combined and concentrated to give Intermediate 2B (100 mg, 0.089 mmol, 63.5% yield), m/z (1124, M+H).

Preparation of Intermediate 2C iodine (50 mg, 0.2 mmol). The reaction was stirred for 10 min and sodium bisulfite (50 mg, 0.5 mmol in 0.1 mL water) was added. The reaction was then concentrated to an oil using a rotary evaporator. The residue was dissolved in MeOH and purified on an ISCO C-18 HP Gold 50 g column using mobile Phase A: 5:95 acetonitrile:water with 0.01M ammonium acetate; Mobile Phase B: 95:5 acetonitrile:water with 0.01M ammonium acetate; Gradient: 0% B for 2 column volumes to 100% B over 15 column volumes. The fractions were combined and lyophilized to give Intermediate 2C (77 mg, 0.07 mmol, 52% yield), m/z (1122, M+H).

Preparation of Intermediate 2D

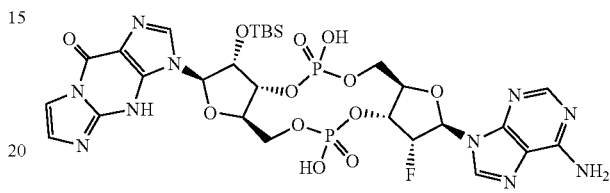

2D

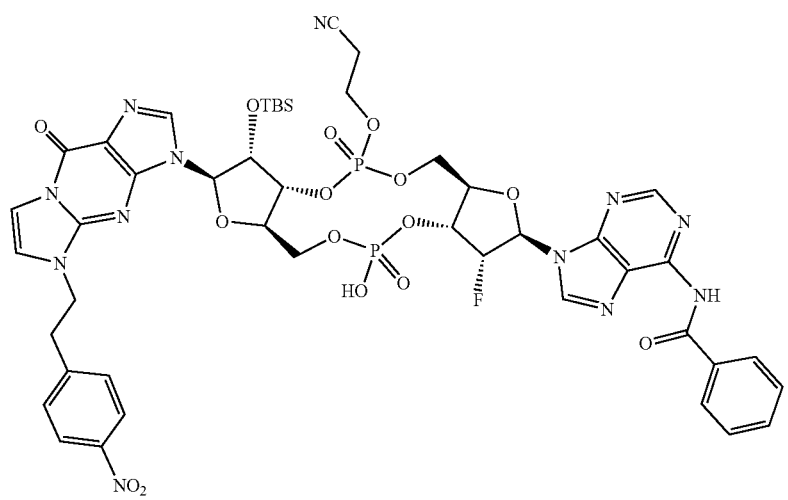

2C

Intermediate 2B (150 mg, 0.134 mmol) was dissolved in anhydrous pyridine (10 mL). This solution was concentrated in vacuo (35° C. water bath) to a thick oil. The oil obtained was azeotroped a second time with additional anhydrous pyridine (10 mL) and concentrated to a thick oil. To this oil was added a third portion of anhydrous pyridine (10 mL) and this solution was allowed to sit under a nitrogen atmosphere. In another vessel was dissolved 2-chloro-5,5-dimethyl-1,3,2-dioxaphosphinane 2-oxide (74.0 mg, 0.401 mmol) in dry pyridine (5 mL) under a nitrogen atmosphere and cooled to −5° C. To the cooled solution was added the pyridine solution of Intermediate 2B via syringe over 30 min. The reaction was stirred for an additional 30 min at −5° C. The ice bath was removed and the reaction was allowed to warmed to room temperature over 10 min. The reaction was then cooled back to −5° C. and treated with water (0.060 mL, 3.4 mmol) followed immediately by the addition of solid Intermediate 2C (77 mg, 0.07 mmol) was dissolved in pyridine (0.5 mL) and added to a pre-generated solution containing DBU (0.2 mL, 1.4 mmol) and nitromethane (0.1 mL, 2 mmol) in pyridine (1 mL). The reaction was stirred for 16 h at 35° C. and then concentrated in vacuo to an oil. The residue was suspended in 7 N ammonia in MeOH (2.5 mL, 18 mmol) and heated at 35° C. in a sealed vial for 6 h. The reaction was then concentrated in vacuo and purified using an ISCO C-18 HP Gold 50 g column using mobile Phase A: 5:95 acetonitrile:water with 0.01M ammonium acetate; Mobile Phase B: 95:5 acetonitrile:water with 0.01M ammonium acetate; Gradient: 0% B for 2 column volumes to 50% B over 15 column volumes. The appropriate fractions were combined and concentrated to give Intermediate 2D (45 mg), m/z (815, M+H).

Example 2

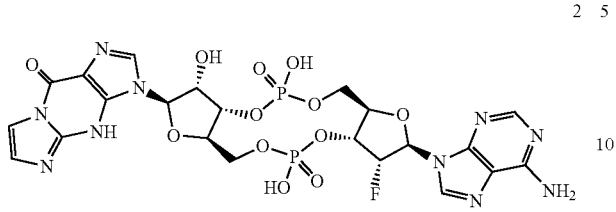

In a vial was dissolved Intermediate 2D (45 mg, 0.06 mmol) in pyridine (1 mL) and triethylamine trihydrofluoride (0.15 mL) was added and the mixture was stirred at 35° C. for 16 h. The reaction was concentrated and re-dissolved in water (2 mL) and the crude material was purified via preparative LC/MS with the following conditions: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-40% B over 20 minutes, then a 4-minute hold at 100% B; Flow: 20 mL/min. Fractions containing the desired product were combined and dried via centrifugal evaporation to afford Example 2. (27 mg, 42%), m/z (701, M+H). HPLC retention Time: 1.87 min using column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm). $^1$H NMR (400 MHz, DEUTERIUM OXIDE) δ 8.17 (bs, 2H), 8.00-7.95 (m, 1H), 7.46-7.41 (d, J=2.5 Hz, 1H), 7.18 (d, J=2.5 Hz, 1H), 6.33-6.30 (d, J=15.8 Hz, 1H), 5.94-5.88 (m, 1H), 5.64-5.45 (m, 1H), 5.04-4.97 (m, 1H), 4.96-4.90 (m, 1H), 4.90-4.82 (m, 1H), 4.53-4.33 (m, 4H), 4.10-4.01 (m, 2H).

Example 3

(1R,6R,8R,9R,10R,15R,17R,18R)-8-(6-amino-9H-purin-9-yl)-9,18-difluoro-3,12-dihydroxy-17-{3H-imidazo[2,1-f]purin-3-yl}-2,4,7,11,13,16-hexaoxa-3λ$^5$,12λ$^5$-diphosphatricyclo[13.3.0.0$^{6,10}$]octadecane-3,12-dione

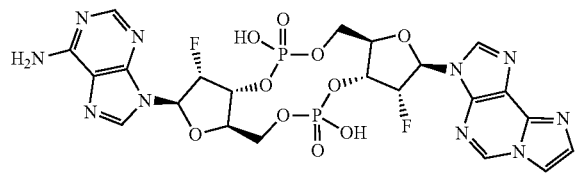

Preparation of Intermediate 3A

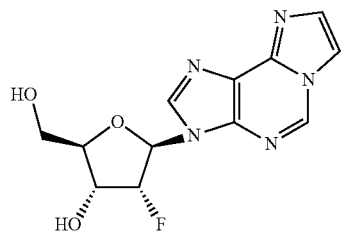

(2R,3R,4R,5R)-5-(6-amino-9H-purin-9-yl)-4-fluoro-2-(hydroxymethyl) tetrahydrofuran-3-ol (3 g, 11.14 mmol) was dissolved in NaOAc buffer (pH=4.5) (100 mL) and 50% 2-chloroacetaldehyde (30 mL, 11.14 mmol) in water was added and the mixture was stirred at room temperature overnight. The resulting mixture was concentrated and the residue was loaded onto celite and purified by silica column chromatography (80 g column, MeOH/DCM=5-20%) to give Intermediate 3A. HPLC: Retention time=0.37 min (H$_2$O/ACN with 0.05% TFA, Waters Acquity HPLC BEH C18, 2.1×50 mm, 1.7-μm particles, gradient=2 min, wavelength=220 nm); MS (ES): m/z=294 [M+H]$^+$.

Preparation of Intermediate 3B

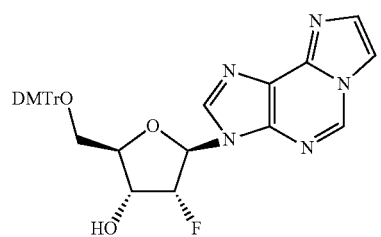

Intermediate 3A (3.5 g, 11.93 mmol) was azeotroped with pyridine two times, and the resulting residue was dissolved in pyridine (100 mL). To this solution was added a catalytic amount of DMAP and 4,4'-(chloro(phenyl)methylene)bis (methoxybenzene) (5.26 g, 15.52 mmol). The mixture was stirred at room temperature for 3.5 h, and then MeOH (5 mL) was added, and stirring continued for 30 min. The reaction mixture was then concentrated to dryness. The residue was dissolved in DCM, washed with sat. aq. NaHCO$_3$, and concentrated. The residue was purified by silica gel column chromatography (80 g column, eluted with EtOAc/DCM 0-100% 25 min, then 0-10% MeOH/DCM, 25 min) to give Intermediate 3B (5.9 g, 9.82 mmol, 82% yield). HPLC: retention time=0.84 min (H$_2$O/ACN with 0.05% TFA, Waters Acquity HPLC BEH C18, 2.1×50 mm, 1.7-μm particles, gradient=2 min, wavelength=220 nm); MS (ES): m/z=596 [M+H]$^+$.

Preparation of Intermediate 3C

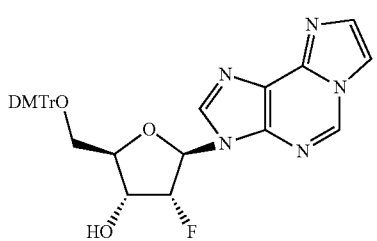

3C

To a solution of Intermediate 3B (5.9 g, 9.86 mmol) in pyridine (50 mL) was added diphenyl phosphonate (11.3 mL, 59.0 mmol). The reaction was stirred for 45 min. and then water (3 mL) and Et$_3$N (3 mL) were added, and the reaction mixture was stirred for 15 min. The solution was concentrated, and the residue was partitioned between DCM (200 mL, with 1% Et$_3$N) and 5% NaHCO$_3$ (150 mL). The organic layer was washed with 5% NaHCO$_3$ two more times and then concentrated. The residue was purified by silica gel column chromatography (80 g column, MeOH/DCM with 0.5% Et$_3$N=0-40%) to give Intermediate 3C (6.5 g, 100% yield). HPLC: RT=0.73 min (H$_2$O/ACN with 0.05% TFA, Waters Acquity HPLC BEH C18, 2.1×50 mm, 1.7-µm particles, gradient=2 min, wavelength=220 nm); MS (ES): m/z=660 [M+H]$^+$.

Preparation of Intermediate 3D

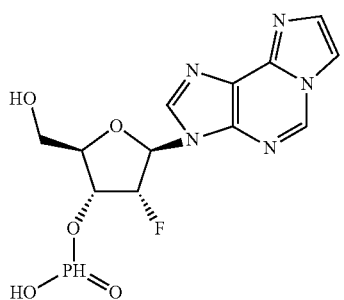

3D

To a solution of Intermediate 3C (2 g, 1.668 mmol) in DCM (50 mL) was added water (0.300 mL, 16.68 mmol), followed by 2,2-dichloroacetic acid (1.935 g, 15.01 mmol). The reaction was stirred for 15 min, and then triethylsilane (10 mL) was added, and stirring continued for 1 h. To the reaction mixture was added pyridine (20 mL), and it was then concentrated to dryness and used directly in the next step.

Preparation of Intermediate 3E

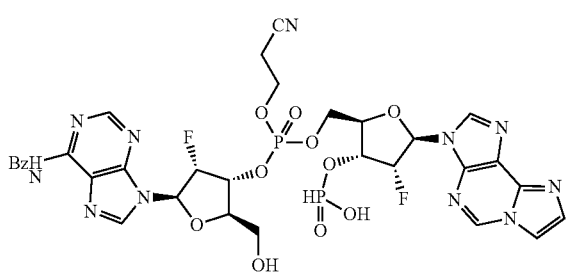

3E (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (1.75 g, 2.002 mmol) was co-evaporated with ACN (2×20 mL), dissolved in acetonitrile (20 mL) and concentrated to approximately 4 mL. Molecular sieves were added to the solution. In a separate flask, Intermediate 3D (0.60 g, 1.67 mmol) was co-evaporated with ACN (2×20 mL). The residue was again taken up in acetonitrile (20 mL) and concentrated to approximately 10 mL of solution. The above dried solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite was added via cannula to the mixture of Intermediate 3D. The reaction mixture was stirred for 10 min, and then 5.5M tert-butyl hydroperoxide in decane (0.485 mL, 5.01 mmol) was added and the resulting mixture was stirred for 30 min. The reaction was then cooled to 0° C. and treated with a solution of sodium thiosulfate (1.055 g, 6.67 mmol) in H$_2$O (4 mL). The resulting mixture was then concentrated, and the residue was dissolved in DCM (50 mL) and treated with water (0.300 mL, 16.68 mmol), and then 2,2-dichloroacetic acid (1.935 g, 15.01 mmol) was added. The reaction was stirred for 15 min, and then pyridine (20 mL) was added and the resulting mixture was concentrated. The crude product was purified by C18 reverse phase preparative HPLC (150 g column, eluted with 0-95% ACN in aqueous NH$_4$OAc). The desired fractions were combined and lyophilized to give Intermediate 3E. HPLC: retention time=0.68 min (H$_2$O/ACN with 0.05% TFA, Waters Acquity HPLC BEH C18, 2.1×50 mm, 1.7-µm particles, gradient=2 min, wavelength=220 nm); MS (ES): m/z=846 [M+H]$^+$.

Preparation of Intermediate 3F

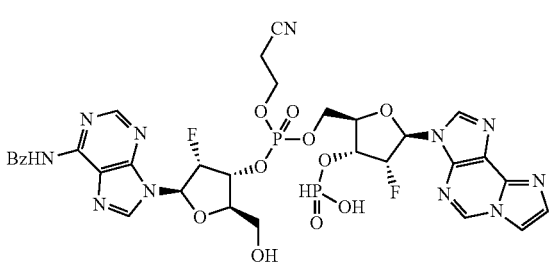

3F

Intermediate 3E (50 mg, 0.058 mmol) was co-evaporated with pyridine (30 mL) two times. The residue was taken up again in pyridine (30 mL) and concentrated to approximately 15 mL. To this solution was added 2-chloro-5,5-dimethyl-1,3,2-dioxaphosphorinane 2-oxide (53.4 mg, 0.289 mmol). The reaction was stirred for 8 min and then water (0.037 mL, 2.026 mmol) was added, immediately followed by iodine (44.1 mg, 0.17 mmol). The resulting mixture was stirred for 30 min, and then quenched with a solution of sodium bisulfite (30.1 mg, 0.289 mmol) in water (3 mL), and then concentrated. The residue was purified by reverse phase (C-18) chromatography and eluted with 0-50% ACN in aq. NH$_4$OAc to give Intermediate 3F. HPLC: retention time=0.52 min (H$_2$O/ACN with 0.05% TFA, Waters Acquity HPLC BEH C18, 2.1×50 mm, 1.7-μm particles, gradient=2 min, wavelength=220 nm); MS (ES): m/z=844 [M+H]$^+$.

Example 3

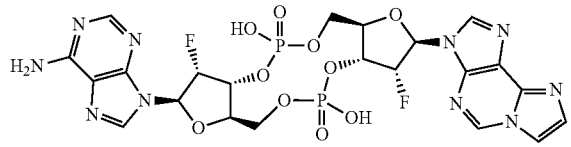

Intermediate 3F (53 mg, 0.062 mmol) was treated with 33% MeNH$_2$ in EtOH. The reaction was stirred for 3.5 h and then concentrated. The crude material was purified via preparative LC/MS with the following conditions: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-40% B over 20 minutes, then a 4-minute hold at 100% B; Flow: 20 mL/min. Fractions containing the desired product were combined and dried to give Example 3. HPLC: Retention time=1.997 min (Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm)) MS (ES): m/z=687[M+H]$^+$.

Example 4

1-[(1R,6R,8R,9R,10R,15R,17R,18R)-17-(6-amino-9H-purin-9-yl)-9,18-difluoro-3,12-dioxo-3,12-disulfanyl-2,4,7,11,13,16-hexaoxa-3λ$^5$,12λ$^5$-diphosphatricyclo[13.3.0.0$^{6,10}$]octadecan-8-yl]-1H-1,2,3-benzotriazole-4-carboxamide

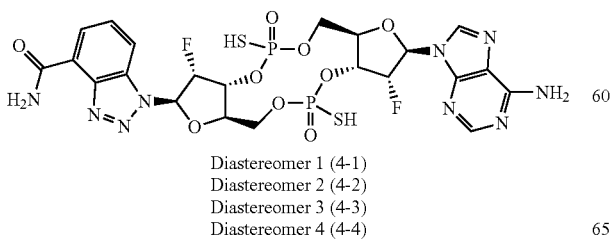

Diastereomer 1 (4-1)
Diastereomer 2 (4-2)
Diastereomer 3 (4-3)
Diastereomer 4 (4-4)

Preparation of Intermediate 4A

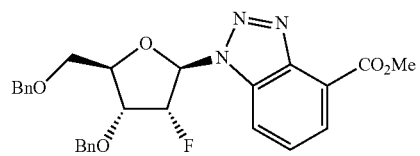

4A (3R,4R,5R)-4-(benzyloxy)-5-(benzyloxymethyl)-3-fluorotetrahydrofuran-2-yl acetate (*Journal of the American Chemical Society*, 2005, 127, 10879) (2.1 g, 5.64 mmol) andmethyl 1H-benzo[d][1,2,3]triazole-7-carboxylate (1.0 g, 5.64 mmol) were suspended in acetonitrile (30 mL) under a nitrogen atmosphere at room temperature, and then perchlorostannane (0.661 mL, 5.64 mmol) was added dropwise. The reaction was stirred for 16 h. The mixture was made basic with sat. aq. NaHCO$_3$ and then extracted with EtOAc (30 mL×3). The combined organic layers were washed with brine, dried over Na$_2$SO$_4$, and then concentrated. The residue was purified on a silica column (40 g), 0-60% EtOAc/hex to give Intermediate 4A (2.2 g, 4.48 mmol, 79% yield). $^1$H NMR (499 MHz, CHLOROFORM-d) δ 8.06 (dd, J=7.3, 0.9 Hz, 1H), 7.93-7.83 (m, 1H), 7.46 (dd, J=8.2, 7.3 Hz, 1H), 7.41-7.26 (m, 5H), 7.24-7.12 (m, 3H), 7.09-6.96 (m, 2H), 6.59-6.47 (m, 1H), 5.97-5.74 (m, 1H), 4.79 (d, J=11.6 Hz, 1H), 4.67 (d, J=11.9 Hz, 2H), 4.55-4.47 (m, 1H), 4.29 (d, J=4.6 Hz, 2H), 4.08 (s, 3H), 3.70-3.58 (m, 1H), 3.53-3.41 (m, 1H). MS (ES): m/z=492.3[M+H]$^+$.

Preparation of Intermediate 4B

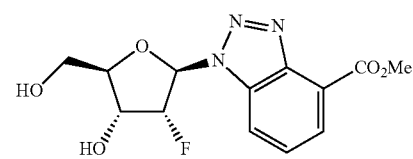

4B

To Intermediate 4A (2.5 g, 5.09 mmol) in DCM (30 mL) cooled to −78° C. was added trichloroborane (40.7 mL, 40.7 mmol) dropwise. The reaction was stirred at this temperature for 4 h, and then additional trichloroborane (2 eq.) was added. After an additional 2 h, the reaction was quenched carefully with aq. NaHCO$_3$ at low temperature. The resulting mixture was extracted with DCM (3×30 mL), the combined organic layers were washed with brine, dried over Na$_2$SO$_4$, filtered and then concentrated to dryness. The residue was purified on an ISCO column eluting with 0-10% MeOH/DCM to give Intermediate 4B (1.0 g, 3.21 mmol, 63.2% yield). MS (ES): m/z=312.1[M+H]$^+$.

Preparation of Intermediate 4C

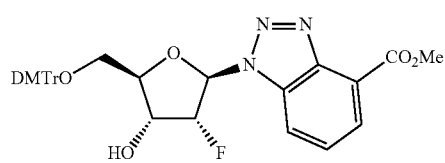

4C

To Intermediate 4B (1 g, 3.21 mmol) in DCM (20 mL) and pyridine (2 mL) was added 4,4'-(chloro(phenyl)methylene)bis(methoxybenzene) (1.31 g, 3.9 mmol). The reaction was stirred at room temperature for 4 h. The mixture was then diluted with DCM (60 mL) and washed with water (50 mL). The organic layer was washed with brine, dried over $Na_2SO_4$, and then concentrated to dryness. The residue was purified on an ISCO column (24 g), eluting with 0-100% EtOAc/hexanes to afford Intermediate 4C (1.96 g, 3.19 mmol, 99% yield). MS (ES): m/z=614.2[M+H]$^+$.

Preparation of Intermediate 4D

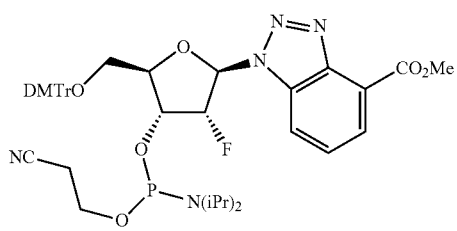

4D

To a solution of Intermediate 4C (1.96 g, 3.19 mmol) in anhydrous DCM (20 mL) was added a 1.0 M solution of 1H-imidazole-4,5-dicarbonitrile (2.24 mL, 2.24 mmol) in acetonitrile, followed by the dropwise addition of 3-((bis(diisopropylamino)phosphanyl)oxy) propanenitrile (1.16 g, 3.83 mmol). The mixture was stirred at room temperature for 6 h. The mixture was then diluted with DCM (30 mL), washed with sat. aq. $NaHCO_3$, dried over $Na_2SO_4$, and then filtered and concentrated to dryness. The residue was purified on an ISCO column (40 g) eluting with 0-60% EtOAc/hexane (w/ 0.5% $Et_3N$) to give Intermediate 4D (2.2 g, 2.70 mmol, 85% yield) as a mixture of diastereomers. MS (ES): m/z=814.3 [M+H]$^+$.

Preparation of Intermediate 4E

Intermediate 4D (732 mg, 0.90 mmol) was dissolved in acetonitrile (4.0 mL). This solution was concentrated in vacuo (90 mbar, 32° C. water bath) to dryness and this process was repeated two times. Then 4 Å molecular sieves (100 mg) were added, followed by acetonitrile (2.0 mL). This solution was capped and set aside under a nitrogen atmosphere. In a separate flask, Intermediate I-1 (492 mg, 0.90 mmol) was suspended in pyridine (4.0 mL). This suspension was concentrated in vacuo (20 mbar, 32° C. water bath). Then, pyridine 2,2,2-trifluoroacetate (261 mg, 1.350 mmol) and a small stir bar were added, and the mixture was azeotroped two additional times with pyridine (4.0 mL). On the final azeotrope, the solution was homogenous and it was concentrated to a volume of ~0.4 mL. Then with rapid stirring, anhydrous acetonitrile (6.0 mL) was added to form a thick slurry. With a positive pressure nitrogen line, the previously prepared solution of Intermediate 4D was added via cannula. The vial containing Intermediate 4D was rinsed with acetonitrile (1.0 mL) and added to the mixture for a quantitative transfer. Then the reaction was sonicated for 30 min. The mixture was then stirred at room for 2 h. Then (E)-N,N-dimethyl-N'-(3-thioxo-3H-1,2,4-dithiazol-5-yl)formimidamide (203 mg, 0.99 mmol) was added and the reaction was stirred for 10 minutes. The yellow solution was carefully concentrated in vacuo (120 mbar, 36° C. water bath). The resulting solid was washed with $Et_2O$. Then the solid was dissolved in of MeOH (2 mL) and filtered. To the filtrate was added of $Et_2O$ (15 mL) and the resulting solid was collected by filtration. The isolated material was then suspended in DCM (10 mL) and triethylsilane (1440 μl, 9.0 mmol) was added, followed by 2,2-dichloroacetic acid (232 mg, 1.80 mmol). After 1 h, the reaction was concentrated and the residue was triturated, collected by filtration and washed with $Et_2O$ (2 mL×3). The isolated solid was then purified on a reverse phase ISCO 50 g column eluting with a gradient of 0-90% B in 12 min, with an initial hold for 5 min, (A: water with 0.1% ammonia acetate, B: 95% acetonitrile/5% water with 0.1% ammonia acetate) to give Intermediate 4E (170 mg, 0.19 mmol, 21% yield). MS (ES): m/z=880.5[M+H]$^+$.

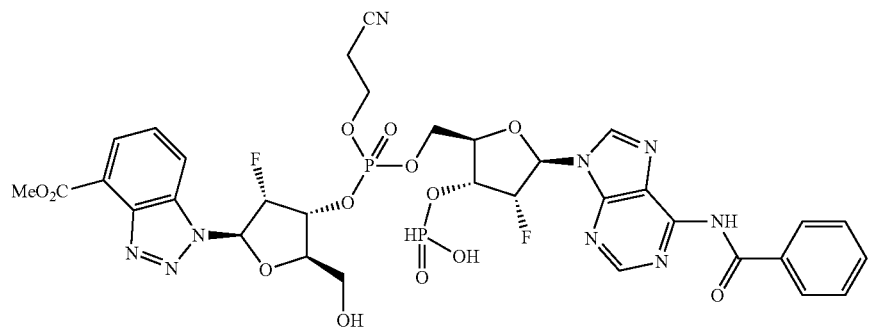

4E

Preparation of Intermediate 4F

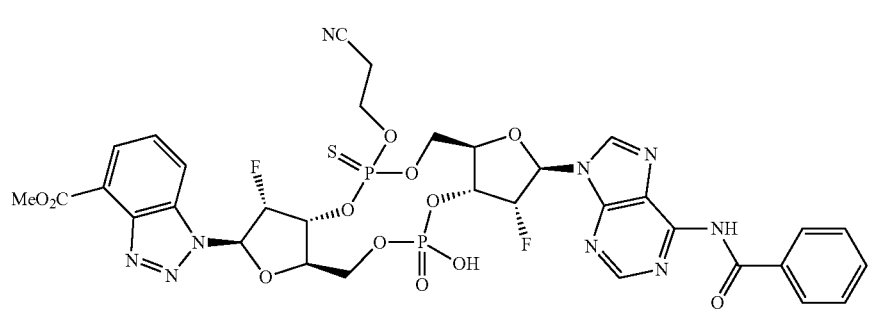

Intermediate 4E (170 mg, 0.19 mmol) was azeotroped with pyridine (2 mL) two times, and then the residue was dissolved in pyridine (5 mL). This solution was then added dropwise to a solution of 2-chloro-5,5-dimethyl-1,3,2-dioxaphosphinane 2-oxide (107 mg, 0.58 mmol) in DCM (20 mL) with vigorous stirring. After 20 min, (E)-N,N-dimethyl-N'-(3-thioxo-3H-1,2,4-dithiazol-5-yl)formimidamide (44 mg, 0.21 mmol) was added, followed by water (0.1 mL) and the mixture was stirred for an additional 30 min. The resulting mixture was diluted with DCM (20 mL) and washed with brine. The organic layer was dried ($Na_2SO_4$), filtered and concentrated. The residue was purified on a reverse phase ISCO 50 g column, eluting with 0-90% B in 12 min with an initial hold for 5 min (A: water with 0.1% ammonia acetate, B: 95% acetonitrile/5% water with 0.1% ammonia acetate) to give Intermediate 4F (42 mg, 0.05 mmol, 24% yield). MS (ES): m/z=894.5[M+H]+.

Example 4

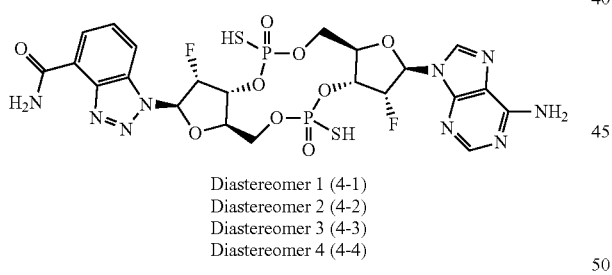

Diastereomer 1 (4-1)
Diastereomer 2 (4-2)
Diastereomer 3 (4-3)
Diastereomer 4 (4-4)

Intermediate 4F (41 mg, 0.05 mmol) was dissolved in 7 N ammonia/MeOH (3 mL) and stirred at 50° C. for 3 h. The reaction was then concentrated in vacuo. The residue was dissolved in 3 mL of water and purified on a chiral preparative HPLC (Column: Xselect RP Prep C18 OBD Column, 5 μm, 19×150 mm; Flow rate: 20.0 mL/min; Mobile Phase: A: 100 mM $NH_4OAc$ (pH 7); B: Acetonitrile.) to give the 4 diastereomers of Example 4.

Example 4-1: (2.2 mg) $^1H$ NMR (400 MHz, METHANOL-$d_4$) δ 8.92 (s, 1H), 8.37 (d, J=8.3 Hz, 1H), 8.25 (s, 1H), 8.10 (d, J=7.3 Hz, 1H), 7.75-7.66 (m, 1H), 6.86 (d, J=19.0 Hz, 1H), 6.42 (d, J=15.5 Hz, 1H), 6.19-5.93 (m, 1H), 5.76-5.52 (m, 1H), 5.51-5.29 (m, 1H), 5.25-5.06 (m, 1H), 4.61-4.46 (m, 2H), 4.46-4.36 (m, 1H), 4.28-4.18 (m, 1H), 4.18-4.10 (m, 1H), 4.10-3.99 (m, 1H). MS (ES): m/z=722.2[M+H]+.

Example 4-2: (2.7 mg) $^1H$ NMR (400 MHz, METHANOL-$d_4$) δ 8.57 (s, 1H), 8.41 (d, J=8.3 Hz, 1H), 8.25 (s, 1H), 8.09 (d, J=7.1 Hz, 1H), 7.73 (dd, J=8.3, 7.5 Hz, 1H), 6.87 (d, J=18.8 Hz, 1H), 6.40 (d, J=17.0 Hz, 1H), 5.79 (dd, J=8.5, 4.3 Hz, 1H), 5.66 (dd, J=9.2, 4.2 Hz, 1H), 5.42 (br d, J=17.9 Hz, 1H), 5.25-5.07 (m, 1H), 4.65 (br d, J=12.0 Hz, 1H), 4.52-4.38 (m, 2H), 4.25 (br d, J=11.2 Hz, 1H), 4.15-3.99 (m, 2H). MS (ES): m/z=722.3[M+H]+.

Example 4-3: (6.2 mg) $^1H$ NMR (400 MHz, METHANOL-$d_4$) δ 8.98 (s, 1H), 8.31-8.18 (m, 2H), 8.11 (d, J=7.2 Hz, 1H), 7.70 (dd, J=8.3, 7.5 Hz, 1H), 6.80 (d, J=19.6 Hz, 1H), 6.42 (d, J=15.8 Hz, 1H), 6.38-6.18 (m, 1H), 5.54-5.39 (m, 1H), 5.37-5.21 (m, 1H), 5.19-5.08 (m, 1H), 4.60-4.47 (m, 2H), 4.45-4.35 (m, 2H), 4.25-4.09 (m, 1H), 4.00 (br d, J=10.8 Hz, 1H). MS (ES): m/z=722.2[M+H]+.

Example 4-4: (5.5 mg) $^1H$ NMR (400 MHz, METHANOL-$d_4$) δ 8.62 (s, 1H), 8.27-8.22 (m, 2H), 8.10 (d, J=7.3 Hz, 1H), 7.70 (dd, J=8.3, 7.5 Hz, 1H), 6.84-6.80 (d, 1H), 6.43-6.38 (d, 1H), 6.01-5.88 (d, J=4.4 Hz, 1H), 5.56-5.38 (m, 2H), 5.21-5.07 (m, 1H), 4.65-4.59 (m, 1H), 4.48-4.34 (m, 3H), 4.10-3.99 (m, 2H). MS (ES): m/z=722.3[M+H]+.

Example 5

(1S,6R,8R,9R,10R,15R,17R,18R)-8-(6-amino-9H-purin-9-yl)-9-fluoro-18-hydroxy-17-{4-oxo-1H,4H,5H-imidazo[2,1-b]purin-1-yl}-3,12-disulfanyl-2,4,7,11,13,16-hexaoxa-3$\lambda^5$,12$\lambda^5$-diphosphatricyclo[13.3.0.0$^{6,10}$]octadecane-3,12-dione

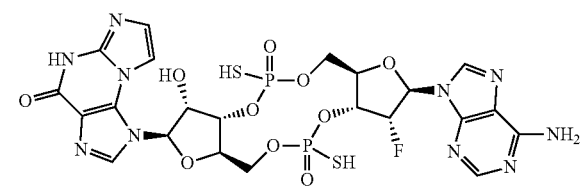

Preparation of Intermediate 5A

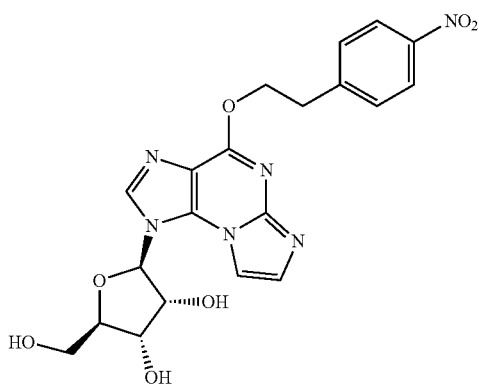

To a solution containing (2R,3R,4S,5R)-2-(2-amino-6-(4-nitrophenethoxy)-9H-purin-9-yl)-5-(hydroxymethyl)tetrahydrofuran-3,4-diol (*J Org. Chem.* 2014, 79, 3311) (5.5 g, 12.7 mmol) in EtOH (50 mL) was added NH$_4$OAC/AcOH buffer (pH 4.5) (50 mL, 12.72 mmol) and the mixture was heated for 24 h at 35° C. About ⅔ of the solvent was removed in vacuo and the reaction was neutralized with solid ammonium bicarbonate to pH 7. Acetonitrile (~200 mL) was added, resulting in the precipitation of the product as a while solid. The solid was filtered and rinsed with acetonitrile and dried to give ~2 g of product. The filtrate was re-concentrated to give a slurry. The slurry was diluted with additional acetonitrile (100 mL) and a small amount of MeOH (10 mL), filtered and rinsed with acetonitrile. The solids were combined to give Intermediate 5A (3.4 g, 7.45 mmol, 59% yield), m/z (557, M+H).

Preparation of Intermediate 5B

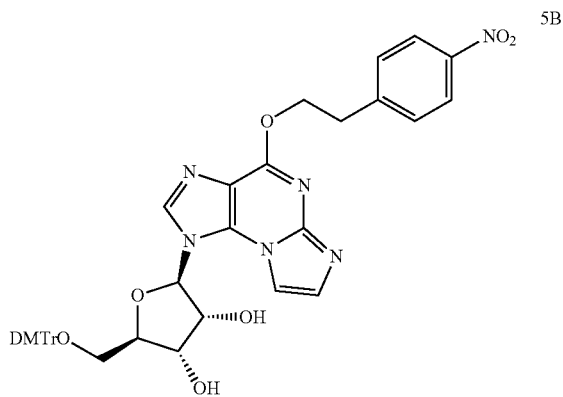

A solution containing Intermediate 5A (2.4 g, 5.26 mmol) in pyridine (40 mL) was azeotroped (2×) using the rotary evaporator and then re-dissolved in pyridine (40 mL) under a nitrogen atmosphere and treated with 4,4'-chloro(phenyl)methylene) bis(methoxybenzene) (2.23 g, 6.57 mmol) in small portions. The reaction was stirred for 20 h, and then MeOH (2 mL) was added and the reaction was concentrated on the rotary evaporator (water bath temperature ~40° C.). The residue was taken up in DCM (100 mL) and washed with aqueous 1.5 M KHPO$_4$ solution and concentrated. The residue was purified on a 40 g ISCO column that was pre-treated with 1% TEA in DCM and eluted with 1% TEA in DCM/MeOH (2% to 20%) to give Intermediate 5B (3.1 g, 4.09 mmol, 78% yield), m/z (759, M+H).

Preparation of Intermediate 5C

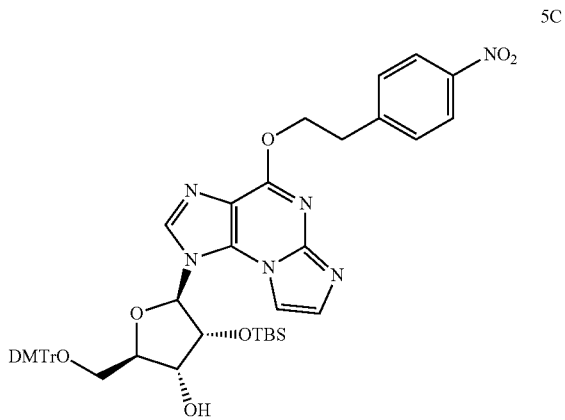

To a solution containing Intermediate 5B (3.8 g, 5.01 mmol) in DMF (15 mL) was added TBDMS-Cl (0.830 g, 5.51 mmol) followed by the addition of imidazole (1.36 g, 20.0 mmol). The reaction was stirred for 20 h, diluted with water and extracted with ethyl acetate (100 mL×2). The extracts were combined and washed with aq. 10% LiCl (2×50 mL) and sat. aq. NaCl solution, dried (Na$_2$SO$_4$), filtered and concentrated. The mixture was dissolved in a small amount of DCM and purified on an ISCO 330 g column which had been pre-equilibrated with DCM containing 0.25% TEA. A 2% to 45% DCM (0.25% TEA)/ethyl acetate gradient afforded Intermediate 5C (1 g), m/z (873, M+H).

Preparation of Intermediate 5D

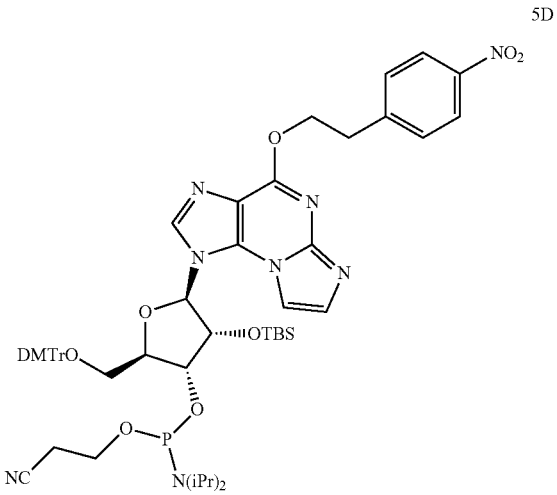

Intermediate 5C (470 mg, 0.54 mmol)) was dissolved in DCM (10 mL) and 1H-imidazole-4,5-dicarbonitrile (70 mg, 0.6 mmol) was added under a nitrogen atmosphere followed by the addition of 3-((bis(diisopropylamino)phosphanyl)oxy)propanenitrile (0.36 mL, 1.08 mmol). The reaction was stirred for 20 h, diluted with additional DCM (50 mL), poured into a separatory funnel and washed with a 10% NaHCO₃ aq. solution (25 mL). The aqueous layer was extracted with additional DCM (20 mL), combined with the other extract, dried (Na₂SO₄), filtered and concentrated. The crude product was dissolved in a small amount of DCM and purified on a 24 g ISCO silica gel column that had been equilibrated with 0.25% TEA in DCM and purified using the Teledyne ISCO system, eluting over a 15 min gradient with 0%-50% 0.25% TEA in DCM/ethylacetate to give Intermediate 5D (540 mg, 0.5 mmol, 92% yield), as a mixture of diastereomers, m/z (990/991, M+H).

Preparation of Intermediate 5E amino-methylidene)amino)-3H-1,2,4-dithiazoline-3-thione (130 mg, 0.63 mmol). The solution was stirred for 1 h and concentrated to almost dryness. The yellow residue was dissolved in a minimal amount of MeOH/DCM (5 mL, 1/1) and ~3 g of celite was added. The mixture was concentrated to dryness on the rotary evaporator to adsorb the crude product mixture and transferred to an empty ISCO cartridge and purified on the ISCO reverse phase chromatography system using a RediSep C18, 150 g Gold column using the following conditions: Flow Rate: 40 mL/min, solvent A: water (95%)/ACN (5%) with ammonium acetate (0.05%) as additive and solvent B Acetonitrile (95%)/water with 0.05% ammonium acetate as additive. Elution gradient of 0% B, hold for 2 column volumes to 100% B over 14 column volumes to afford (2R,3R,4R,5R)-5-(6-benzamido-9H-purin-9-yl)-2-((((((2R,3R,4R,5R)-2-((bis(4-methoxyphenyl)(phenyl)methoxy)methyl)-4-((tert-butyldimethylsilyl)oxy)-5-(4-(4-nitrophenethoxy)-1H-imidazo[2,1-b]purin-1-yl)

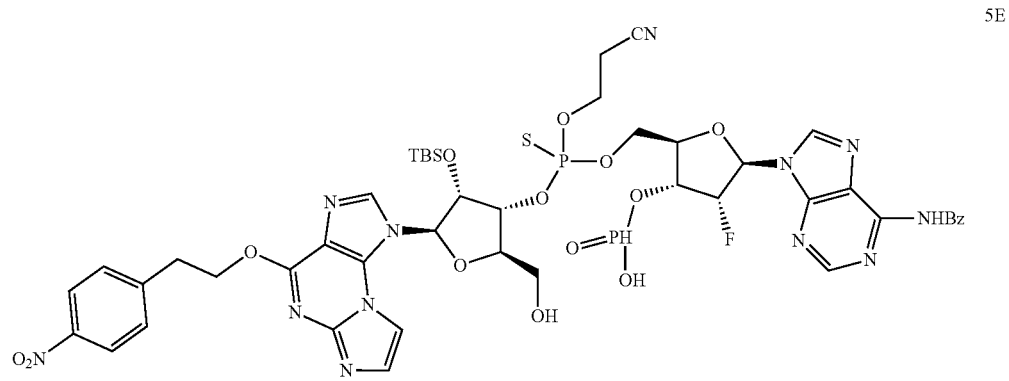

5E

A solution of Intermediate 5D (535 mg, 0.50 mmol) in acetonitrile (5 mL) was concentrated in vacuo (35° C. water bath) to afford a thick oil. The oil obtained was azeotroped a second time from acetonitrile (5 mL), and concentrated to a thick oil. To this oil was added a third portion of acetonitrile (5 mL). A solution of Intermediate I-1 (240 mg, 0.55 mmol) in pyridine (5 mL) was concentrated in vacuo (35° C. water bath). The procedure was repeated twice with additional portions of pyridine (5 mL). Pyridine trifluoroacetate (110 mg, 0.0.55 mmol) and a small stir bar were added, and the compound was azeotroped again with pyridine (5 mL). Acetonitrile (2.5 mL) was added to form a slightly cloudy solution. This was stirred as the previously prepared solution of Intermediate 5D in acetonitrile (5 mL) was added via syringe. The flask was rinsed with additional acetonitrile (0.5 mL) for a quantitative transfer. The mixture was stirred for 3 h and then quenched with the addition of ((dimethyltetrahydrofuran-3-yl)oxy)(2-cyanoethoxy)phosphorothioyl)oxy)methyl)-4-fluorotetrahydrofuran-3-yl hydrogen phosphonate (400 mg, 0.277 mmol, 55.7% yield). m/z (1442, M+H). To the intermediate was added dichloromethane (5 mL), then MeOH (0.5 mL) and finally 2,2-dichloroacetic acid (0.120 mL, 1.25 mmol) was added dropwise. The reaction was quenched with pyridine (160 µL, 2.0 mmol) and concentrated in vacuo (~40° C.). The resulting oil was azeotroped with ACN (2×20 mL) and then re-dissolved in ~2 mL of an ACN (95%)/H₂O (5%, 0.1% NH₄OAc) mixture. The solution was loaded onto a ISCO Gold C-18 150 g Reverse Phase column and eluted from 0% B to 100% B (Solvent A (90% water, 10% CH₃CN, 5 mmol NH₄OAc), Solvent B (10% water, 90% CH₃CN, 5 mmol NH₄OAc). The fractions containing the desired pair of diastereomers were collected concentrated to afford Intermediate 5E (220 mg, 0.19 mmol, 70% yield), m/z (1140, M+H).

Preparation of Intermediate 5F

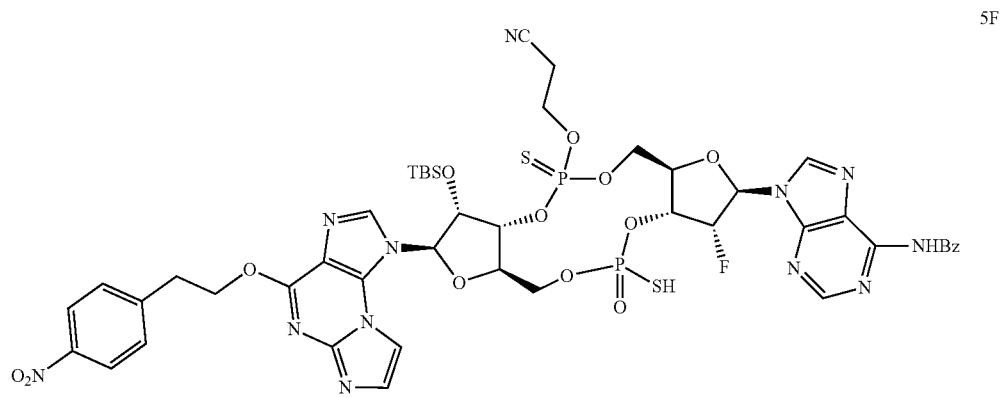

Intermediate 5E (465 mg, 0.41 mmol) was dissolved in anhydrous pyridine (10 mL) and concentrated on the rotary evaporator. The oil was re-dissolved in additional anhydrous pyridine (10 mL) and again concentrated to an oil. The procedure was repeated one more time and the resulting oil was re-dissolved in anhydrous pyridine (10 mL) and kept under a nitrogen atmosphere. 2-Chloro-5,5-dimethyl-1,3,2-dioxaphosphinane 2-oxide (225 mg, 1.2 mmol) in pyridine (15 mL) under a nitrogen atmosphere was cooled to −5° C. in an ice/NaCl slush bath. To this cooled solution was added the pyridine solution of Intermediate 5F via syringe over 30 min (dropwise slow addition). The reaction was stirred for an additional 30 min, warmed to room temperature (20 min) and (E)-N,N-dimethyl-N'-(3-thioxo-3H-1,2,4-dithiazol-5-yl)formimidamide (105 mg, 0.5 mmol) was added and the mixture was stirred for 30 min. The reaction was then treated with water (0.10 mL), stirred for 30 min. and then concentrated in vacuo. The residue was dissolved in ACN (3 mL) and purified on a reverse phase C-18, 50 g Gold ISCO column. Solvent A 95% water/5% ACN/0.01 mM NH$_4$OAc; solvent B 95% ACN/5% water/0.01 mM NH$_4$OAc. Gradient: 0% B hold for 3 column volumes and 0% B to 50% B over 10 column volumes. Fractions containing all four diastereomers were collected, combined and lyophilized to give Intermediate 5F (400 mg, 85% yield), m/z (1154, M+H) as mixture of diasteromers.

Preparation of Intermediate 5G

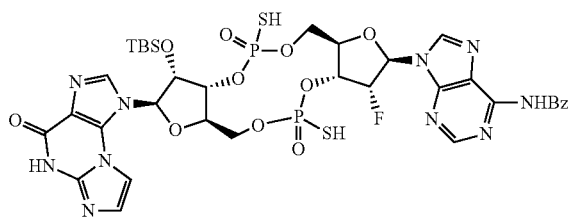

A vial containing nitromethane (400 µl, 7.42 mmol) in pyridine (1 mL) was treated with DBU (784 µl, 5.20 mmol) and stirred for 10 min. To this DBU solution was added a solution of Intermediate 5F (400 mg, 0.347 mmol) dissolved in pyridine (1 mL). The reaction was stirred for 10 h at 30° C. and then concentrated to a viscus oil. The oil was dissolved in a 7 N ammonia in MeOH solution (2 mL, 14 mmol) and heated in a sealed vial at 35° C. for 12 h. The reaction was then concentrated to dryness. The residue was dissolved in a minimal amount of MeOH and purified on a reverse phase C-18, 50 g HP Gold ISCO column using solvent A (95% water/5% ACN (0.01 M NH$_4$OAc additive)) and solvent B (95% ACN/5% water (0.01M NH$_4$OAc additive)). Gradient: 0% B hold for 3 column volumes to 50% B over 10 column volumes. Fractions containing the desired compound were collected and concentrated to afford Intermediate 51G (150 mg, 0.177 mmol, 51.1% yield), m/z (847, M+H), as a mixture of diasteromers.

Example 5

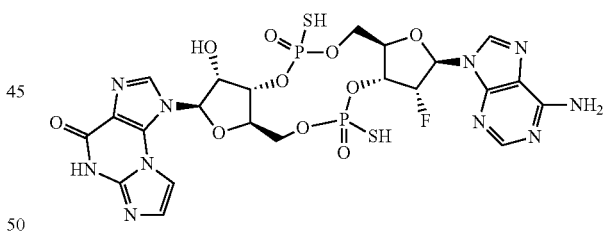

The mixture of diastereomers from Intermediate 5G (200 mg, 0.236 mmol) in pyridine (2 mL) was treated with triethylamine trihydrofluoride (0.385 mL, 2.362 mmol). The reaction was heated at 35° C. for 20 h and then filtered through a 0.45 micron nylon syringe filter and concentrated. The residue was dissolved in a minimal amount of MeOH and purified on a reverse phase C-18, 50 g HP Gold ISCO column using solvent A 95% water/5% ACN (0.01 M NH$_4$OAc additive) and solvent B 95% ACN/5% water (0.01M NH$_4$OAc additive). Gradient: 0% B hold for 3 column volumes to 50% B over 10 column volumes. Fractions containing the desired compound were collected and lyophilized to give crude Example 5 as one major diasteromer along with other minor isomers. The crude Example 5 was further purified via preparative LC/MS with the following conditions: Column: Agilent Bonus RP, 21.2×200 mm, 5-μm particles; Mobile Phase A: 5:95 acetonitrile:water with 20-mM ammonium acetate; Mobile Phase B: 95:5 acetonitrile:water with 20-mM ammonium acetate; Gradient: 0-60% B over 20 minutes, then a 4-minute hold at 100% B; Flow: 20 mL/min. Fractions containing the desired product were combined and dried via centrifugal evaporation to give Example 5 (60 mg, 0.078 mmol, 33% yield), m/z (733, M+H). Retention Time: 0.43 min (ACQUITY UPLC® BEH C18 1.7 μm; Mobile Phase A: water with 0.05% TFA; Mobile Phase B: acetonitrile with 0.05% TFA. Temperature: 50° C.; Gradient: 2% B to 98% B over 1.5 min, then 0.3 min hold at 98% B; Flow: 0.8 mL/min; Detection: MS and UV (220 nm). Observed Mass: 733.23. $^1$H NMR (400 MHz, DEUTERIUM OXIDE) δ 8.27-8.25 (m, 1H), 8.18-8.16 (m, 1H), 8.05-8.02 (m, 1H), 7.81-7.78 (m, 1H), 7.22-7.20 (m, 1H), 6.39-6.30 (m, 2H), 5.61-5.46 (m, 1H), 5.04-4.92 (m, 2H), 4.55-4.45 (m, 4H), 4.36-4.29 (m, 1H), 4.18-4.11 (m, 2H).

Example 6

5-[(1R,6R,8S,9S,10S,15R,17R,18R)-17-(6-amino-9H-purin-9-yl)-18-fluoro-9-hydroxy-3,12-dioxo-3,12-disulfanyl-2,4,7,11,13,16-hexaoxa-3λ$^5$,12λ$^5$-diphosphatricyclo[13.3.0.0$^{6,10}$]octadecan-8-yl]-1H-pyrazole-3-carboxamide

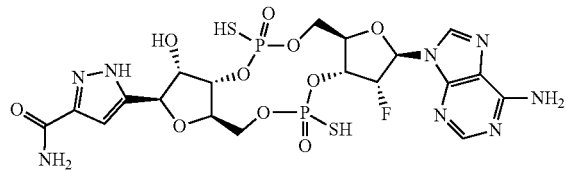

Diastereomer 1 (6-1)
Diastereomer 2 (6-2)
Diastereomer 3 (6-3)
Diastereomer 4 (6-4)

Preparation of Intermediate 6A

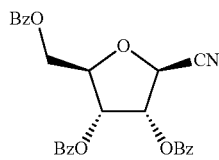

To a flask was added (2S,3R,4R,5R)-2-acetoxy-5-((benzoyloxy)methyl) tetrahydrofuran-3,4-diyl dibenzoate (40 g, 79 mmol) and anhydrous dichloromethane (80 mL). To the resulting clear solution was added trimethylsilyl cyanide (14.9 mL, 111 mmol) and the mixture was cooled in an ice water bath. To the cooled solution was added BF$_3$·OEt$_2$ (10.1 mL, 79 mmol) over a 30 minute period. The resulting dark solution was warmed to room temperature and stirred for 20 h. The reaction mixture was then carefully poured into an ice cold solution of sodium carbonate (6.7 g, 80 mmol) in water (500 mL). To the resulting emulsion was added EtOAc (400 mL), and the mixture was stirred and then filtered through a pad of Celite. The biphasic filtrate was transferred to a separatory funnel. The phases were separated. The aqueous layer was extracted with EtOAc (2×200 mL). The combined organics were washed with sat'd aq. sodium bicarbonate, then brine, and then dried over sodium sulfate and concentrated. The resulting brown oil was purified by silica gel chromatography using 0-50% EtOAc in hexanes. Intermediate 6A (29.9 g, 80% yield) was obtained as a colorless solid. LCMS: m/z 472.2 (M+H); Retention time: 1.11 min; LCMS Analytical Method A. $^1$H NMR (400 MHz, Chloroform-d) δ 8.17-8.11 (m, 2H), 8.00-7.91 (m, 4H), 7.65-7.53 (m, 3H), 7.51-7.35 (m, 6H), 6.02 (t, J=4.8 Hz, 1H), 5.87 (t, J=5.5 Hz, 1H), 4.99 (d, J=4.4 Hz, 1H), 4.80-4.69 (m, 2H), 4.67-4.56 (m, 1H).

Analytical LCMS Method A

Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm.

Preparation of Intermediate 6B

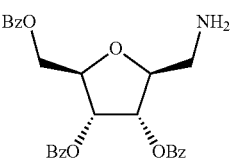

The following procedure was adapted from Schneller, Synthesis 1991, 747. To a flask was added sodium borohydride (3.60 g, 95 mmol) and anhydrous THF (25 mL) and the resulting suspension was cooled in an ice water bath. To the resulting chilled suspension was dropwise added TFA (6.84 mL, 89 mmol), followed by a solution of Intermediate 6A (29.9 g, 63.4 mmol) in THF (75 mL). The resulting reaction mixture was warmed to room temperature and stirred for 20 h. The reaction mixture was then cooled in an ice water bath and quenched by dropwise addition of water. The resulting mixture was concentrated to remove THF. To the resulting residue was added water (200 mL) and the mixture was extracted with DCM (2×250 mL). The combined organics were washed with water (2×250 mL), brine (1×100 mL), and then dried over sodium sulfate and concentrated. This crude Intermediate 6B (~30 g) was used as such in the next step. LCMS: m/z 476.2 (M+H), Retention time: 0.88 min; LCMS Analytical Method A.

Preparation of Intermediate 6C

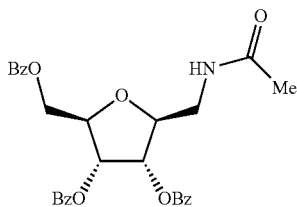

To crude Intermediate 6B (29.3 g, 61.6 mmol) was added anhydrous tetrahydrofuran (200 mL), triethylamine (15.46 mL, 111 mmol), and acetic anhydride (9.30 mL, 99 mmol) followed by DMAP (0.075 g, 0.616 mmol). The resulting reaction mixture was stirred at room temperature for 5 h. The reaction mixture was cooled in an ice-water bath, then quenched with methanol and concentrated. The residue was dissolved in toluene (750 mL), washed with 1 N HCl (2×200 mL), sat. sodium bicarbonate (2×200 mL) and brine (1×200 mL). The organic layer was dried over sodium sulfate and concentrated. The residue was purified by silica gel chromatography using 0-100% EtOAc in hexanes to afford Intermediate 6C (14.66 g, 46.0% yield). LCMS: m/z 518.2 (M+H). Retention time: 1.02 min; LCMS Analytical Method A. $^1$H NMR (499 MHz, chloroform-d) δ 8.14-8.10 (m, 2H), 8.00-7.93 (m, 4H), 7.63-7.46 (m, 5H), 7.41-7.35 (m, 4H), 6.04 (br t, J=5.4 Hz, 1H), 5.71 (dd, J=5.7, 4.1 Hz, 1H), 5.37 (dd, J=7.2, 5.9 Hz, 1H), 4.76 (dd, J=11.9, 2.9 Hz, 1H), 4.67-4.50 (m, 2H), 4.50-4.34 (m, 1H), 3.69-3.56 (m, 2H), 1.87 (s, 3H).

Preparation of Intermediate 6D

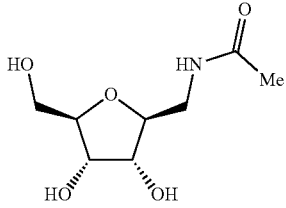

6D

To Intermediate 6C (4.64 g, 8.97 mmol) was added sodium methoxide (0.5 M in MeOH, 55.0 mL, 27.5 mmol) and the reaction mixture was stirred at room temperature for 1.5 h. The reaction mixture was neutralized to pH-6.5 with 1N HCl and then concentrated in vacuo. The crude material was re-dissolved in water (50 mL) and washed with DCM (25 mL×2). The aqueous phase was concentrated in vacuo and then dissolved in abs. EtOH to precipitate salts and then filtered. The filtrate was concentrated to a light yellow oil and then co-evaporated with toluene (3×20 mL) and dried under vacuum to yield Intermediate 6D (7.5 g) which was taken to the next step without further purification. LCMS: m/z 206.1 (M+H). Retention time: 0.27 min; LCMS Analytical Method A.

Preparation of Intermediate 6E

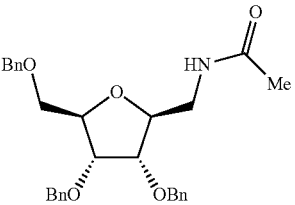

6E

Crude Intermediate 6D (4.5 g, 11.67 mmol) was suspended in DMSO (23.4 mL) under nitrogen and powdered KOH (0.786 g, 14.01 mmol) was added and the mixture was stirred at room temperature for 15 min. The reaction mixture was then cooled to 15° C. in an ice-water bath and (chloromethyl)benzene (1.61 mL, 14.0 mmol) was added dropwise. The reaction mixture was stirred in an ice/water bath overnight at 15° C. then poured over ice-water and stirred for 30 min. The mixture was extracted with toluene (100 mL×3) and the organic phase was dried with MgSO$_4$, filtered and concentrated to a light yellow oil. The crude material was purified on an ISCO column (80 g) and eluted with a 0-80% DCM-EtOAc gradient to yield Intermediate 6E (4.0 g, 8.41 mmol, 72.0% yield). LCMS: m/z 476.3 (M+H). Retention time: 1.07 min; LCMS Analytical Method A. $^1$H NMR (499 MHz, DMSO-d$_6$) δ 7.80 (t, J=5.8 Hz, 1H), 7.36-7.27 (m, 15H), 4.56-4.47 (m, 6H), 4.04 (br d, J=4.6 Hz, 2H), 3.95-3.88 (m, 2H), 3.84-3.77 (m, 1H), 3.57-3.42 (m, 2H), 3.28-3.22 (m, 1H), 3.12 (dt, J=13.8, 6.0 Hz, 1H), 1.76 (s, 3H).

Preparation of Intermediate 6F

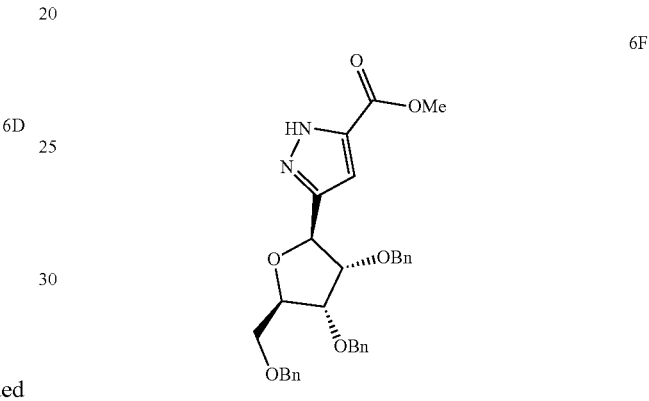

6F

A mixture of sodium acetate (6.90 g, 84 mmol) and Intermediate 6E (4 g, 8.41 mmol) in DCM (112 mL) was cooled to 0° C. Gaseous N$_2$O$_4$/NO$_2$ was bubbled into the reaction mixture for ~20 min. until the reaction mixture stayed consistently yellow. Stirring was continued for 2 h at 0° C. The reaction mixture was then poured into ice water (200 mL) and extracted with DCM (200 mL×2). The organic layer was then washed with iced sat. NaHCO$_3$ (200 mL), then with ice cold water (200 mL) and dried with MgSO$_4$. The mixture was filtered and the filtrate was concentrated. The material was dried under vacuum in an ice water bath for 1 h and then dissolved in cold diethyl ether (28 mL). A cold aqueous solution of KOH (9M, 15 mL, 135 mmol) was added and the reaction mixture stirred at 0° C. for 45 min. Then 10 mL of cold ether and 5 mL of cold water were added and stirring continued for 15 minutes. The reaction mixture was then diluted with cold ether (50 mL) and cold water (100 mL). The organic phase was separated and washed with cold water (50 mL). The organic phase was briefly vigorously swirled over KOH pellets and decanted over anhydrous MgSO$_4$ pre-wetted with dry ether and quickly filtered into a flask containing methyl propiolate (0.919 g, 10.93 mmol). The reaction mixture was stirred at room temperature for 30 min. The reaction mixture was then diluted with EtOAc (100 mL), washed with water then with brine and dried over Na$_2$SO$_4$, filtered and concentrated to give crude Intermediate 6F (4.3 g, 97% yield) which was taken to the next step without further purification. LCMS: m/z 529.1 (M+H). Retention time: 1.09 min; LCMS Analytical Method A. $^1$H NMR (499 MHz, CHLOROFORM-d) δ 7.39-7.28 (m, 13H), 7.25-7.21 (m, 2H), 6.59 (s, 1H), 5.22 (d, J=2.4 Hz, 1H), 4.69-4.62 (m, 3H), 4.61-4.54 (m, 1H), 4.48 (d, J=11.7

Hz, 2H), 4.34 (d, J=11.7 Hz, 1H), 4.28 (dt, J=7.6, 2.2 Hz, 1H), 4.13 (dd, J=7.5, 4.4 Hz, 1H), 3.93 (s, 3H), 3.92 (d, J=2.6 Hz, 1H), 3.87 (dd, J=10.7, 2.7 Hz, 1H), 3.57 (dd, J=10.7, 1.8 Hz, 1H).

Preparation of Intermediates $6G_1$ and $6G_2$

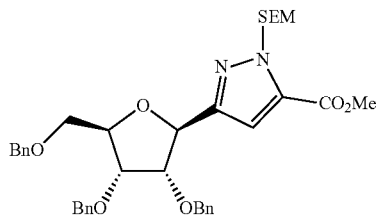

6G1

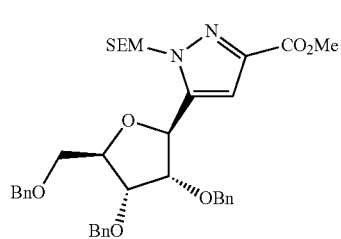

6G2

To a solution of Intermediate 6F (4.45 g, 8.41 mmol) in THF (34 mL) cooled to 15° C. was added NaH (0.51 g, 12.62 mmol). After 10 min, SEM-Cl (2.24 mL, 12.62 mmol) was added dropwise and the reaction mixture was allowed to warm to room temperature for 1 hour. The reaction mixture was then treated with water and then concentrated. The crude material was diluted with DCM and washed with NH$_4$Cl and then with brine. The organic phase was dried over MgSO$_4$, filtered and concentrated in vacuo, giving a colorless oil which was purified on an ISCO 80 g GOLD column eluted with 0-40% EtOAc-Hexane to give Intermediate 6G1 (0.52 g, 0.789 mmol, 9.38% yield). LCMS: m/z 659.3 (M+H). Retention time: 1.31 min; LCMS Analytical Method A. $^1$H NMR (499 MHz, CHLOROFORM-d) δ 7.35-7.24 (m, 15H), 6.88 (s, 1H), 5.86-5.71 (m, 2H), 5.15 (d, J=5.0 Hz, 1H), 4.65-4.49 (m, 6H), 4.32 (dt, J=5.7, 4.0 Hz, 1H), 4.13 (t, J=5.1 Hz, 1H), 4.05-4.00 (m, 1H), 3.84 (s, 3H), 3.71-3.64 (m, 1H), 3.62-3.54 (m, 3H), 0.88 (ddd, J=9.0, 7.3, 0.8 Hz, 2H), −0.06 (s, 8H) and Intermediate 6G2 (3.2 g, 4.86 mmol, 57.8% yield). LCMS: m/z 659.3 (M+H), Retention time: 1.29 min; LCMS Analytical Method A. $^1$H NMR (499 MHz, CHLOROFORM-d) δ 7.35-7.24 (m, 13H), 7.24-7.20 (m, 2H), 6.75 (s, 1H), 5.61 (d, J=11.0 Hz, 1H), 5.51 (d, J=10.8 Hz, 1H), 5.23 (d, J=6.4 Hz, 1H), 4.64-4.51 (m, 4H), 4.51-4.44 (m, 2H), 4.30 (q, J=4.0 Hz, 1H), 4.12-4.02 (m, 2H), 3.62-3.49 (m, 3H), 0.86-0.80 (m, 2H), −0.05 (s, 7H).

Preparation of Intermediate 6H

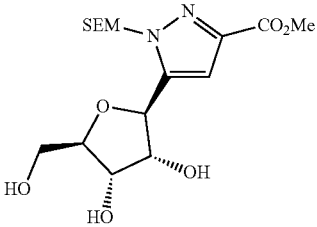

6H

A solution of Intermediate 6G2 (2.9 g, 4.40 mmol) in ethanol (58.7 mL) and cyclohexene (29.3 mL) was purged with nitrogen. PdOH$_2$ (0.618 g, 0.880 mmol) was added to the reaction mixture. The reaction mixture was heated at reflux (80° C.) for 3 h, and then Celite was added to the reaction mixture and the mixture was filtered. The filter cake was washed with EtOH and the filtrate was concentrated. The crude product was purified on a 12 g ISCO column and flushed with a 0-100% gradient; Solvent A=DCM and Solvent B=20% MeOH in DCM to afford Intermediate 6H (1.32 g, 3.40 mmol, 77% yield). LCMS: m/z 389.1 (M+H), retention time: 0.77 min; LCMS Analytical Method A. $^1$H NMR (499 MHz, CHLOROFORM-d) δ 6.88 (s, 1H), 5.75 (d, J=11.1 Hz, 1H), 5.55 (d, J=11.1 Hz, 1H), 4.98 (d, J=7.0 Hz, 1H), 4.38-4.24 (m, 1H), 4.15-4.07 (m, 2H), 3.94 (s, 3H), 3.93-3.89 (m, 1H), 3.76 (ddd, J=12.1, 8.3, 3.5 Hz, 1H), 3.70-3.61 (m, 1H), 3.59 (d, J=5.0 Hz, 1H), 2.87 (d, J=3.8 Hz, 1H), 2.58 (dd, J=8.3, 4.5 Hz, 1H), 0.99-0.83 (m, 2H), −0.01 (s, 9H).

Preparation of Intermediate 6I

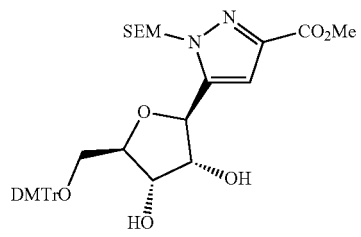

6I

Intermediate 6H (1.32 g, 3.40 mmol) was dissolved in pyridine and concentrated to dryness on a rotary evaporator (5 mL×3). DMTr-Cl (1.900 g, 5.61 mmol), DMAP (0.062 g, 0.510 mmol) and pyridine (68.0 mL) were added and the reaction mixture was allowed to stir at room temperature overnight. The reaction mixture was then treated with methanol (1 mL) and then concentrated to dryness. The residue was taken up in DCM and washed with sat aq. sodium bicarbonate solution. The organic layer was dried with Na$_2$SO$_4$, filtered and concentrated under reduced pressure to give the crude product which was purified on an ISCO column (40 g) eluting with a gradient of 0-100% EtOAc-Hex (with 0.5% TEA) to afford Intermediate 6I (1.75 g, 2.53 mmol, 74.6% yield). LCMS: m/z 691.3 (M+H). Retention time: 1.13 min; LCMS Analytical Method A. $^1$H NMR (499 MHz, CHLOROFORM-d) δ 7.49-7.43 (m, 2H), 7.39-7.33 (m, 4H), 7.33-7.29 (m, 2H), 7.27-7.20 (m, 1H), 6.97 (s, 1H), 6.88-6.83 (m, 4H), 5.62 (s, 2H), 4.99 (d, J=6.5 Hz, 1H), 4.25 (dd, J=5.6, 3.8 Hz, 1H), 4.21-4.15 (m, 2H), 3.95 (s, 3H), 3.82 (s, 6H), 3.72-3.62 (m, 2H), 3.42-3.32 (m, 2H), 1.03-0.94 (m, 1H), 0.92-0.82 (m, 2H), 0.02 (s, 9H).

Preparation of Intermediates 6J1 and 6J2

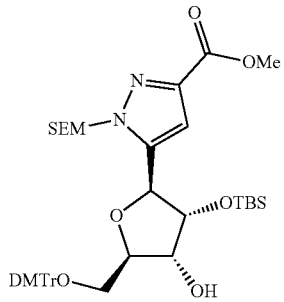

6J1

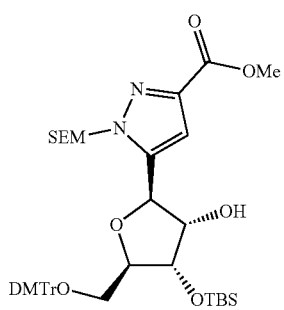

6J2

To a stirring solution of Intermediate 6I (1.75 g, 2.53 mmol) and 1H-imidazole (0.517 g, 7.60 mmol) in anhydrous DMF (30 mL) was added tert-butylchlorodimethylsilane (0.458 g, 3.04 mmol) in anhydrous DMF (30 mL) dropwise. The reaction mixture was stirred at room temperature overnight. The reaction mixture was then diluted with DCM (200 mL) and washed with water, then with 10% LiCl followed sat NaHCO$_3$ and sat/aq. NaCl and dried over Na$_2$SO$_4$. The reaction mixture was filtered and the filtrate was concentrated. The crude material was purified on an ISCO 24 g Gold column eluting with a 0-50% gradient; Solvent A=0.5% TEA in Hexanes; Solvent B=0.5% TEA in Ethyl Acetate with hold at 20% for 8 min. Eluting first was Intermediate 6J1 (0.34 g, 24% yield). $^1$H NMR (499 MHz, CHLOROFORM-d) δ 7.44 (d, J=7.3 Hz, 2H), 7.32 (dd, J=9.0, 2.1 Hz, 4H), 7.29-7.24 (m, 2H), 7.24-7.15 (m, 1H), 6.89 (s, 1H), 6.84-6.80 (m, 4H), 5.72 (d, J=10.8 Hz, 1H), 5.55 (d, J=11.0 Hz, 1H), 5.03 (d, J=6.8 Hz, 1H), 4.44 (dd, J=6.8, 5.3 Hz, 1H), 4.21-4.05 (m, 2H), 3.93 (s, 3H), 3.80 (d, J=0.9 Hz, 6H), 3.65-3.55 (m, 2H), 3.40 (dd, J=10.4, 3.1 Hz, 1H), 3.26 (dd, J=10.3, 4.0 Hz, 1H), 2.65 (d, J=3.8 Hz, 1H), 0.89 (s, 2H), −0.02 (s, 9H). Eluting second was Intermediate 6J2 (0.75 g, 24% yield). $^1$H NMR (499 MHz, CHLOROFORM-d) δ 7.44 (dd, J=8.6, 1.3 Hz, 2H), 7.34 (dd, J=9.1, 2.0 Hz, 4H), 7.31-7.26 (m, 2H), 7.26-7.20 (m, 1H), 6.96 (s, 1H), 6.84 (dd, J=8.9, 0.7 Hz, 4H), 5.74 (d, J=11.0 Hz, 1H), 5.66 (d, J=11.0 Hz, 1H), 5.03 (d, J=6.2 Hz, 1H), 4.28-4.23 (m, 1H), 4.23-4.17 (m, 1H), 4.06 (q, J=3.4 Hz, 1H), 3.94 (s, 3H), 3.81 (d, J=0.8 Hz, 6H), 3.63 (td, J=8.2, 1.5 Hz, 2H), 3.39 (dd, J=10.7, 3.3 Hz, 1H), 3.19 (dd, J=10.7, 4.3 Hz, 1H), 2.85 (d, J=7.3 Hz, 1H), 0.89 (s, 2H), 0.01--0.01 (m, 9H).

Preparation of Intermediate 6K

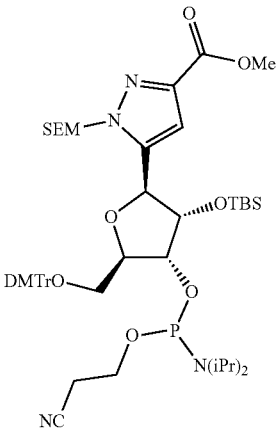

6K

Intermediate 6J1 (0.92 g, 1.143 mmol) was co-evaporated twice with CH$_3$CN (2 5×5 mL) and dissolved in CH$_2$Cl$_2$ (23 mL). 1H-imidazole-4,5-dicarbonitrile (0.135 g, 1.14 mmol) was added as a solution in CH$_3$CN (5 mL), and then under nitrogen, 3-((bis(diisopropylamino)phosphanyl)oxy)propanenitrile (0.726 mL, 2.285 mmol) was added dropwise via syringe. The reaction was stirred at room temperature under a nitrogen atmosphere overnight. The reaction mixture was diluted with EtOAc (100 mL), washed with sat'd aq. NaHCO$_3$ (25 mL), brine (25 mL), dried (Na$_2$SO$_4$), filtered, and concentrated in vacuo. The crude product was dissolved in a small amount of 20% Ethylacetate/Hexanes and purified on an ISCO 24 g column, eluted with a 0-30% gradient: Solvent A=0.5% TEA in Hexanes; Solvent B=0.5% TEA in ethyl acetate to afford Intermediate 6K (1.0 g, 87% yield) as a white solid.

Preparation of Intermediate 6L

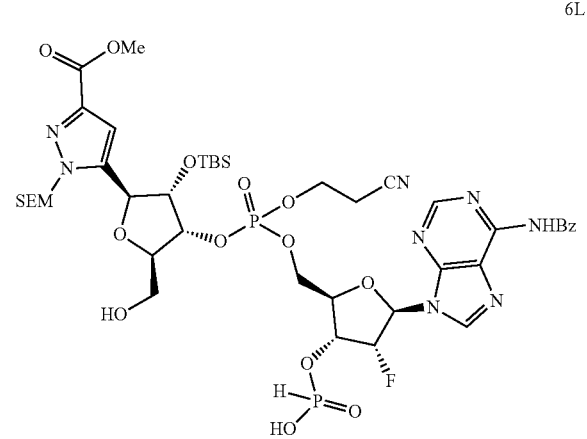

6L

Intermediate I-1 (16.95 mg, 0.030 mmol) was azeotroped with pyridine (2×3 mL), then azeotroped with MeCN (2×3 mL). The mixture was dissolved in DMF (0.5 mL) and acetonitrile (4 mL). To this solution was added Intermediate 6K (30 mg, 0.030 mmol) which was pre-azeotroped with MeCN and dried under vacuum overnight, as a solid in one portion, followed by the addition of pyridine 2,2,2-trifluoroacetate (5.76 mg, 0.030 mmol). The reaction mixture was stirred under a nitrogen atmosphere at room temperature for 1 h. (E)-N,N-dimethyl-N'-(3-thioxo-3H-1,2,4-dithiazol-5-yl)formimidamide (6.43 mg, 0.031 mmol) was added and the reaction mixture was stirred at room temperature under a nitrogen atmosphere for 20 min. The reaction mixture was filtered through a small pad of Celite and the filter cake was washed with EtOAc. The filtrate was concentrated and then re-dissolved in EtOAc, washed with 10% aq. LiCl solution (3×10 mL), and then with brine. The organic phase was dried ($Na_2SO_4$) and evaporated in vacuo to a yellow residue. The residue was azeotroped several times with MeCN and then re-dissolved in DCM and concentrated. The crude material was dissolved in DCM (4 mL) and treated with 2,2-dichloroacetic acid (0.012 mL, 0.149 mmol) dropwise. The reaction mixture was stirred for 30 min and then quenched with excess pyridine, and then concentrated in vacuo. The residue was azeotroped with MeCN to a pale yellow solid which was washed with ether several times and dried overnight to give Intermediate 6L (20 mg, 62.6%) as a mixture of two diastereomers. LCMS, $[M+H]^+=1071$.

Preparation of Intermediate 6M

6M

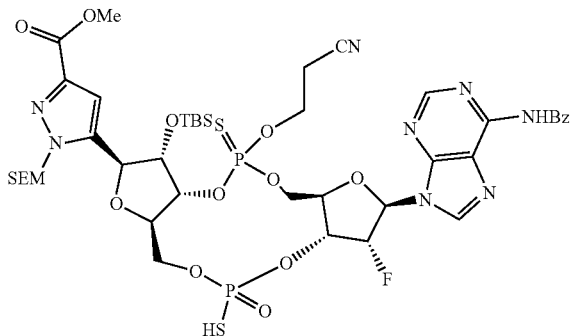

Intermediate 6L (55 mg, 0.051 mmol) was azeotroped with anhydrous pyridine (5 mL×2) and then dissolved in anhydrous pyridine (10 mL) and THF (40.0 mL). To this solution was added 2-chloro-5,5-dimethyl-1,3,2-dioxaphosphinane 2-oxide (28.4 mg, 0.154 mmol) in one portion with rapid stirring and the solution was allowed to stir for 30 minutes. The reaction was treated with (E)-N,N-dimethyl-N'-(3-thioxo-3H-1,2,4-dithiazol-5-yl)formimidamide (12.65 mg, 0.062 mmol) and then stirred for 20 minutes at room temperature. The mixture was then filtered and treated with water (0.050 mL, 2.76 mmol), and stirred for 30 minutes at room temperature. The mixture was filtered and quenched with saturated aqueous sodium bicarbonate, and then concentrated. The resulting residue was re-dissolved in EtOAc and washed with saturated aqueous sodium bicarbonate. The aqueous solution was extracted three times with ethyl acetate (3×5 mL). The combined organic layers were concentrated in vacuo to a yellow solid which was purified on an ISCO 4 g silica gel column: Solvent A=DCM; Solvent B=20% MeOH in DCM to afford Intermediate 6M (50 mg, 90%) as a mixture of four diastereomers.

Example 6

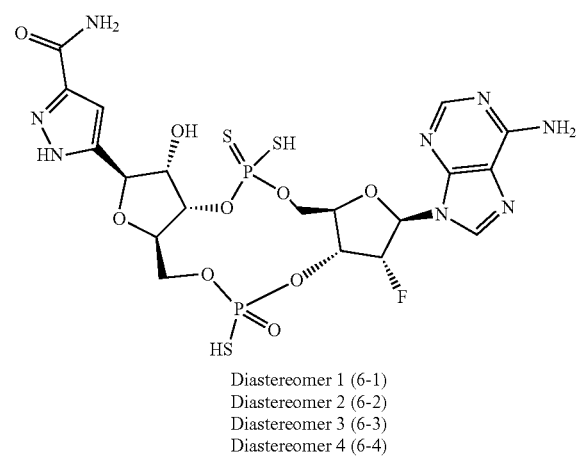 [SMILES: NC(=O)c1cc([C@@H]2O[C@@H]3COP(=O)(S)O[C@H]4[C@@H](F)[C@H](n5cnc6c(N)ncnc65)O[C@@H]4COP(=S)(S)O[C@H]3[C@H]2O)[nH]n1]

Diastereomer 1 (6-1)
Diastereomer 2 (6-2)
Diastereomer 3 (6-3)
Diastereomer 4 (6-4)

The mixture of diastereomers, Intermediate 6M (50 mg, 90%), was suspended in MeOH (2 mL) and 27% $NH_4OH$ (2 mL) and stirred at 55° C. for 2 h. The reaction mixture was then concentrated and azeotroped with toluene to an off white solid, which was washed with ether (4×4 mL). The solid was dried overnight in-vacuo and then treated with 20% TFA in DCM and stirred at room temperature for 45 min. The reaction mixture was concentrated to dryness and then azeotroped with MeOH (4×4 mL) and then with ether (2×5 mL) to form a light yellow solid. The solid was collected, washed with ether (4×2 mL) and then dissolved in MeCN and concentration to dryness. Triethylamine trihydrofluoride (0.4 mL, 2.46 mmol) was added and the reaction mixture was heated at 45° C. for 1 h. The reaction mixture was then neutralized with ammonium acetate buffer (2M~10 mL) to ~ pH 6.5 and then lyophilized to dryness. The crude material was purified via preparative LC/MS with the following conditions: Column: Agilent Bonus RP, 200 mm×21.2 mm, 5-µm particles; Mobile Phase A: 5:95 acetonitrile:water with 20-mM ammonium acetate; Mobile Phase B: 95:5 acetonitrile:water with 20-mM ammonium acetate; Gradient: a 6-minute hold at 0% B, 0-25% B over 20 minutes, then a 4-minute hold at 100% B; Flow Rate: 20 mL/min; Column Temperature: 25 C. Fraction collection was triggered by MS signals. Fractions containing the desired products were combined and dried via centrifugal evaporation to afford four diastereomers: Examples 6-1, 6-2, 6-3 and 6-4.

Example 6-1: 0.7 mg. Analytical LCMS method B: Observed Mass: 667.9; Retention Time: 1.92 min.

Example 6-2: 2.6 mg. Analytical LCMS method B: Observed Mass: 668.88; Retention Time: 1.96 min.

Example 6-3: 2.2 mg. Analytical LCMS method B: Observed Mass: 668.93; Retention Time: 2.09 min.

Example 6-4: 1 mg. Analytical LCMS method B: Observed Mass: 668.88; Retention Time: 2.2 min.

Analytical LCMS Method B

Column: Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm).

Example 7

1-[(1R,6R,8R,9R,10R,15R,17R,18R)-17-(6-amino-9H-purin-9-yl)-9,18-difluoro-3,12-dihydroxy-3,12-dioxo-2,4,7,11,13,16-hexaoxa-3λ⁵,12λ⁵-diphosphatricyclo[13.3.0.0⁶,¹⁰]octadecan-8-yl]-1H-1,2,3-benzotriazole-4-carboxamide

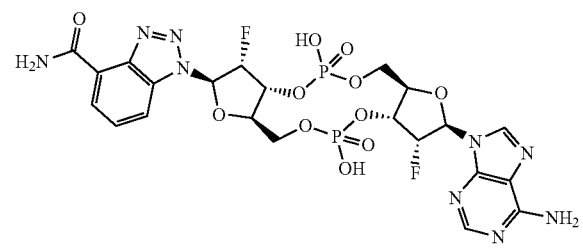

Preparation of Intermediate 7A

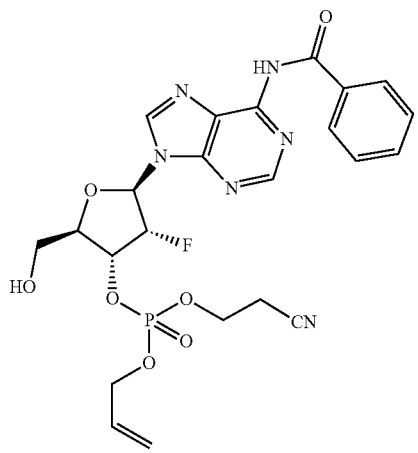

(2R,3R,4R,5R)-5-(6-benzamido-9H-purin-9-yl)-2-((bis (4-methoxyphenyl)(phenyl)methoxy)methyl)-4-fluorotetrahydrofuran-3-yl (2-cyanoethyl) diisopropylphosphoramidite (Sigma-Aldrich, 5 g, 5.71 mmol), was azeotroped with 5 mL of dry acetonitrile. Then 0.2 g of 4 Å molecular sieves and acetonitrile (15 mL) were added. To this mixture was added prop-2-en-1-ol (0.663 g, 11.42 mmol) and the mixture was stirred at room temperature for 30 min. To the reaction mixture was added 1H-tetrazole (0.800 g, 11.42 mmol) and the reaction was stirred at room temperature for an additional 30 min. To the reaction was then added 2-hydroperoxy-2-((2-hydroperoxybutan-2-yl)peroxy)butane (2.40 g, 11.42 mmol) and stirring was continued for 30 min. The reaction was then filtered through celite and the filtrate was concentrated. The residue was dissolved in DCM (15 mL) and 2,2-dichloroacetic acid (4.42 g, 34.2 mmol) was added dropwise. After stirring for 30 min, the reaction mixture was treated with sat. aq. NaHCO₃, and then extracted with DCM (30 mL×3). The combined organic layers were dried over Na₂SO₄ and concentrated in vacuo. The residue was purified on silica gel (0-10% MeOH/DCM) to give Intermediate 7A (2.86 g, 5.23 mmol, 92% yield). MS (ES): m/z=547.15[M+H]⁺.

Preparation of Intermediate 7B and Intermediate 8A

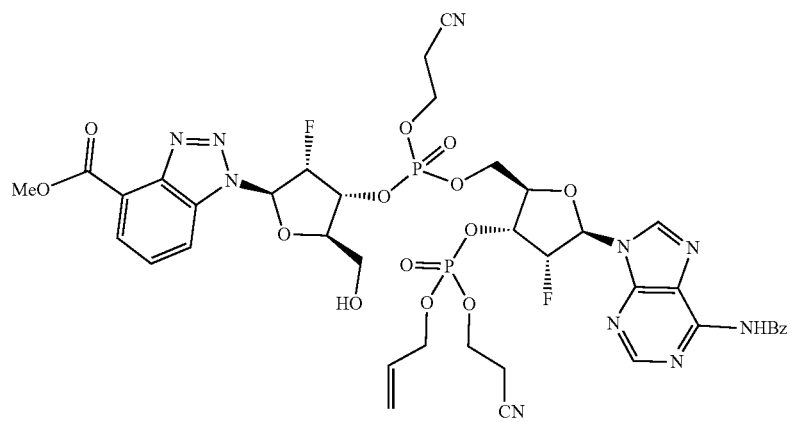

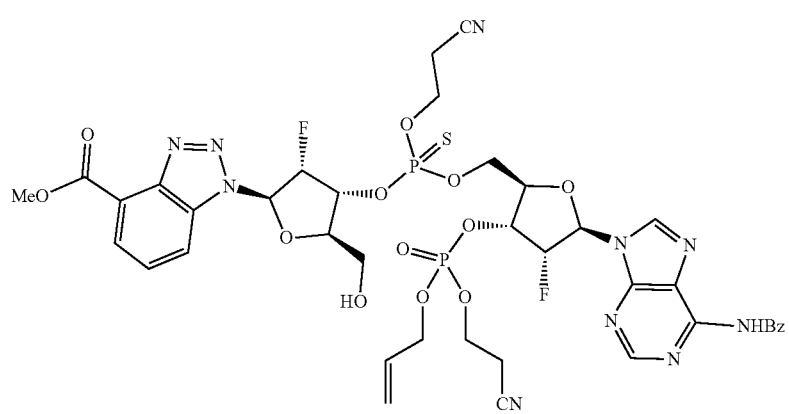

8A

Intermediate 7A (376 mg, 0.688 mmol) and 1H-tetrazole (96 mg, 1.376 mmol) were mixed together in a small flask and azeotroped with 5 mL of dry acetonitrile 3 times. Then 4 Å molecular sieves (300 mg) and acetonitrile (10 mL) were added under nitrogen and this mixture (I) was stirred at room temperature for 30 min. Intermediate 4D (560 mg, 0.688 mmol) in a vial was azeotroped with 2 mL of acetonitrile 3 times, then 100 mg of 4 Å molecular sieves and acetonitrile (2 mL) were added and this mixture (II) was stirred at room temperature for 30 min. With positive $N_2$ pressure, mixture II was added dropwise to mixture I. To achieve a complete transfer, the vial containing II was rinsed with 1 mL of ACN and added to mixture I. The reaction was stirred at room temperature for 60 min. Half of the reaction mixture (6.5 mL) was transferred by a syringe to a 20 mL vial with a stir bar and 2-hydroperoxy-2-((2-hydroperoxybutan-2-yl)peroxy)butane (145 mg, 0.688 mmol) was added and the resulting mixture was left stirring at room temperature for 30 min. Then it was filtered through celite and the filtrate was concentrated. The residue was dissolved in DCM (5 mL) and 2,2-dichloroacetic acid (266 mg, 2.064 mmol) was added dropwise. After stirring 30 min, the reaction mixture was made basic with sat. aq. $NaHCO_3$, then extracted with DCM (30 mL×3). The combined organic layers were dried over $Na_2SO_4$ and concentrated in vacuo. The residue was purified on silica gel (40 g) eluting with 0-10% MeOH/DCM to give Intermediate 7B (204 mg, 0.206 mmol, 29.9% yield). MS (ES): m/z=973.7[M+H]$^+$. To the other half of the mixture was added (E)-N,N-dimethyl-N'-(3-thioxo-3H-1,2,4-dithiazol-5-yl)formimidamide (85 mg, 0.413 mmol) and it was stirred at room temperature for 30 min. Then the reaction mixture was filtered through celite and the filtrate was concentrated. The residue was dissolved in DCM (5 mL) and 2,2-dichloroacetic acid (266 mg, 2.064 mmol) was added dropwise. After stirring 30 min, the reaction mixture was made basic with sat. aq. $NaHCO_3$, then extracted with DCM (30 mL×3). The combined organic layers were dried over $Na_2SO_4$ and concentrated in vacuo. The residue was purified on silica gel (40 g) eluting with 0-10% MeOH/DCM to give Intermediate 8A (178 mg, 0.171 mmol, 25% yield). MS (ES): m/z=989.3[M+H]$^+$.

Preparation of Intermediate 7C

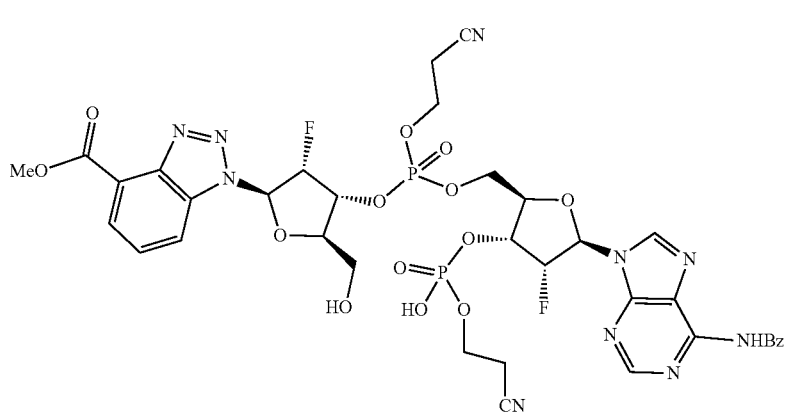

7C

To a solution of Intermediate 7B (204 mg, 0.210 mmol) in acetone (5 mL) was added sodium iodide (314 mg, 2.10 mmol). The resulting yellow solution was heated to 50° C. for 3 h. The solvent was then removed and the residue was purified on a silica gel column (24 g) eluting with 0-20% MeOH/DCM to give Intermediate 7C (130 mg, 0.139 mmol, 67% yield). MS (ES): m/z=933.5[M+H]$^+$.

Preparation of Intermediate 7D

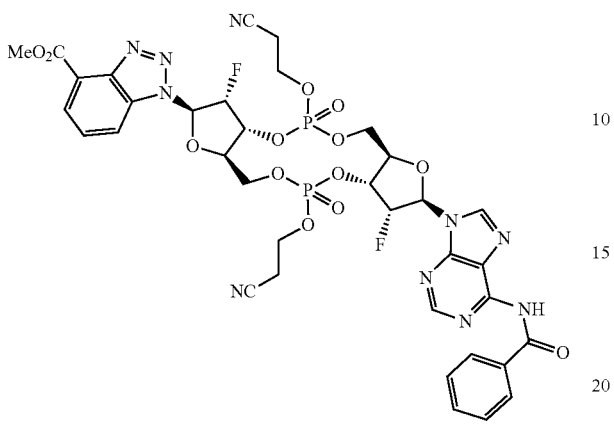

Intermediate 7C (130 mg, 0.139 mmol) was azeotroped with 2 mL of pyridine. Then it was dissolved in dry pyridine (100 mL) and 1-(mesitylsulfonyl)-3-nitro-1H-1,2,4-triazole (206 mg, 0.697 mmol) was added under a $N_2$ atmosphere. The reaction was stirred at room temperature for 60 h and then the solvent was removed in vacuo. To the residue was added 10 mL of water and it was extracted with DCM (15 mL×3). The combined organic layers were dried, and then concentrated. The residue was purified on a silica column (24 g) eluting with 0-10% MeOH/DCM to give Intermediate 7D (82 mg, 0.090 mmol, 65%). MS (ES): m/z=915.4[M+H]$^+$.

Example 7

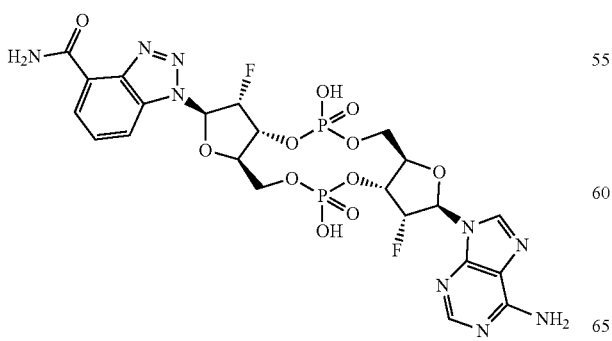

Intermediate 7D (82 mg, 0.090 mmol) was dissolved in 4 mL of 3.5 N MeOH and heated to 50° C. for 2 h. The reaction was then continued at 37° C. overnight, and then concentrated. The residue was dissolved in 3 mL of water and purified by preparative HPLC (Column: Xselect RP Prep C18 OBD Column, 5 μm, 19×150 mm; Flow rate: 20.0 mL/min; Mobile Phase: A: 100 mM NH$_4$OAc (pH 7); B: Acetonitrile.) to give Example 7 (27 mg). $^1$H NMR (499 MHz, METHANOL-d$_4$) δ 8.59 (s, 1H), 8.28-8.21 (m, 2H), 8.12 (dd, J=7.2, 0.7 Hz, 1H), 7.71 (dd, J=8.4, 7.3 Hz, 1H), 6.85 (d, 1H), 6.43 (d, 1H), 6.06-5.96 (d, J=4.3 Hz, 1H), 5.49-5.32 (m, 2H), 5.14-4.98 (m, 1H), 4.51-4.43 (m, 2H), 4.38 (br d, J=9.4 Hz, 1H), 4.30-4.23 (m, 1H), 4.19-4.13 (m, 1H), 4.11-4.06 (m, 1H). MS (ES): m/z=690.3[M+H]$^+$.

Example 8

1-[(1R,6R,8R,9R,10R,15R,17R,18R)-17-(6-amino-9H-purin-9-yl)-9,18-difluoro-3,12-dihydroxy-3-oxo-12-sulfanylidene-2,4,7,11,13,16-hexaoxa-3λ$^5$,12λ$^5$-diphosphatricyclo[13.3.0.0$^{6,10}$]octadecan-8-yl]-1H-1,2,3-benzotriazole-4-carboxamide

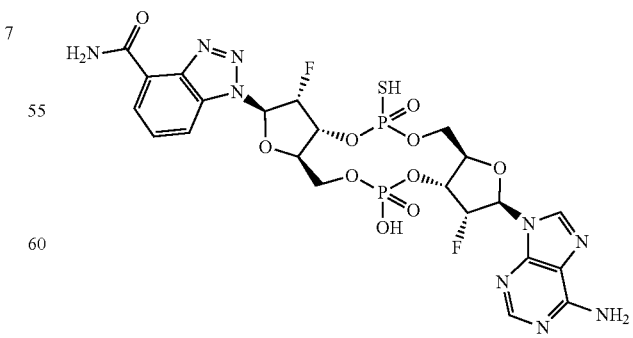

Diastereomer 1 (8-1)
Diastereomer 2 (8-2)

Preparation of Intermediate 8B

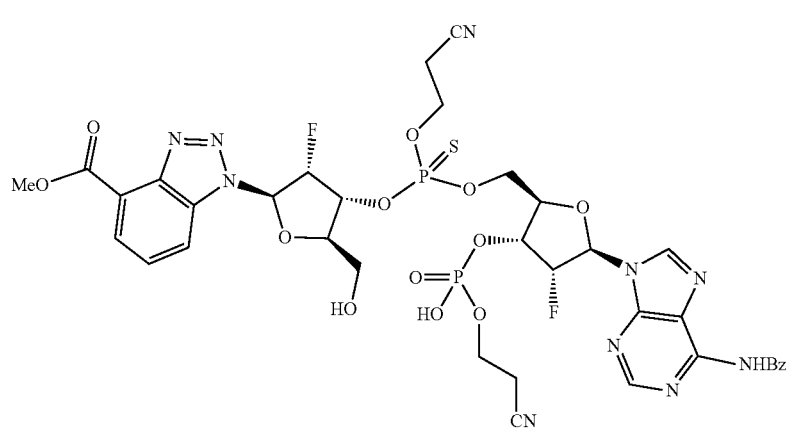

8B

Following the procedures described in the preparation of Intermediate 7C, Intermediate 8A (178 mg, 0.180 mmol) gave Intermediate 8B (92 mg, 0.097 mmol, 54% yield). MS (ES): m/z=949.4[M+H]$^+$.

Preparation of Intermediate 8C

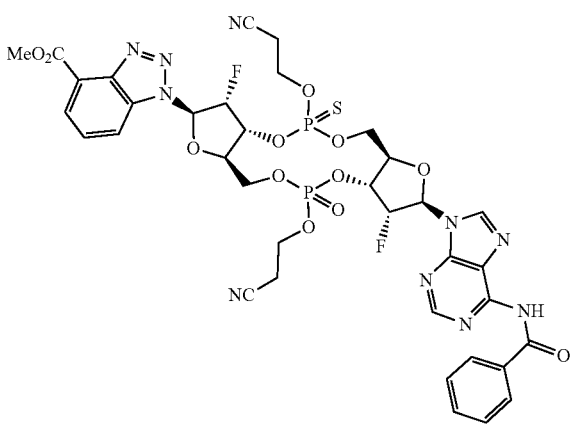

8C

Following the procedures described in the preparation of Intermediate 7D, Intermediate 8B (92 mg, 0.097 mmol) gave Intermediate 8C (42 mg, 0.045 mmol, 46% yield). MS (ES): m/z=931.4[M+H]$^+$.

Example 8

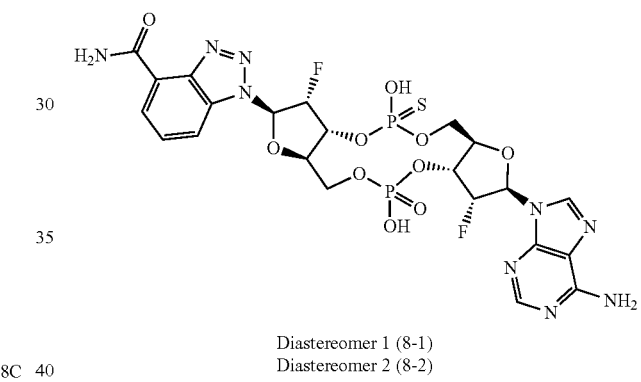

Diastereomer 1 (8-1)
Diastereomer 2 (8-2)

Intermediate 8C (42 mg, 0.045 mmol) was dissolved in 2 mL of 7 N MeOH and heated to 50° C. for 5 h. Then the reaction mixture was concentrated. The residue was dissolved in 3 mL of water and was purified by preparative HPLC (Column: Xselect RP Prep C18 OBD Column, 5 μm, 19×$_{150}$ mm; Flow rate: 20.0 mL/min; Mobile Phase: A: 100 mM NH$_4$OAc (pH 7); B: Acetonitrile) to give Example 8-1 (4.2 mg)$^1$H NMR (499 MHz, METHANOL-d$_4$) δ 8.95 (s, 1H), 8.24 (s, 1H), 8.20-8.18 (m, 1H) 8.11 (dd, J=7.3, 0.7 Hz, 1H), 7.80-7.62 (m, 1H), 6.80 (d, J=19.8 Hz, 1H), 6.43 (d, 1H), 40-6.23 (m, 1H), 5.55-5.37 (m, 1H), 5.37-5.17 (m, 1H), 5.10-4.98 (m, 1H), 4.56-4.51 (m, 1H), 4.51-4.43 (m, 1H), 4.43-4.39 (m, 1H), 4.35-4.25 (m, 1H), 4.19-4.10 (m, 1H), 4.10-3.98 (m, 1H). MS (ES): m/z=706.2[M+H]$^+$ and Example 8-2 (6.1 mg)$^1$H NMR (499 MHz, METHANOL-d$_4$) δ 8.62 (s, 1H), 8.30-8.22 (s, 1H), 8.22-8.17 (m, 1H), 8.11 (d, J=7.1 Hz, 1H), 7.76-7.65 (m, 1H), 6.83 (d, J=19.2 Hz, 1H), 6.41 (d, J=17.2 Hz, 1H), 6.12-5.91 (m, 1H), 5.61-5.32 (m, 2H), 5.10-4.98 (m, 1H), 4.67-4.57 (m, 1H), 4.49-4.35 (m, 2H), 4.29-4.19 (m, 1H), 4.14-3.99 (m, 2H). MS (ES): m/z=706.2[M+H]$^+$.

Example 9

1-[(1R,6R,8R,9R,10R,15R,17R,18R)-9,18-difluoro-3,12-dihydroxy-17-{3H-imidazo[2,1-f]purin-3-yl}-3,12-dioxo-2,4,7,11,13,16-hexaoxa-3λ⁵,12λ⁵-diphosphatricyclo[13.3.0.0⁶,¹⁰]octadecan-8-yl]-1H-1,2,3-benzotriazole-4-carboxamide

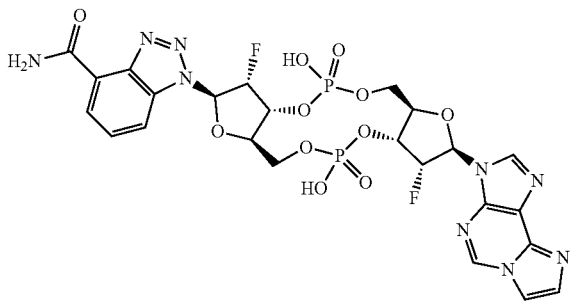

Example 7 (10 mg, 0.015 mmol) was dissolved in 2 mL of NaOAc/HOAc buffer (pH 4-4.5), and then 2-chloroacetaldehyde (5.25 mg, 0.044 mmol, 65% by weight in water) was added. The mixture was heated to 30° C. for 48 h. The mixture was filtered and then purified by preparative HPLC (Column: Agilent Bonus RP 21.2×100 mm, 5-μm; Flow rate: 20.0 mL/min; Mobile Phase: A: 20 mM NH₄OAc; B: Acetonitrile) to give Example 9 (8.1 mg). MS (ES): m/z=714.0[M+H]⁺. Retention time 2.04 min. (Column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min).

Example 10

(1S,6R,8R,9R,10R,15R,17R,18R)-8-(6-amino-9H-purin-9-yl)-9-fluoro-12,18-dihydroxy-3-sulfanyl-17-{3H-[1,2,4]triazolo[3,2-f]purin-3-yl}-2,4,7,11,13,16-hexaoxa-3λ⁵,12λ⁵-diphosphatricyclo[13.3.0.0⁶,¹⁰]octadecane-3,12-dione

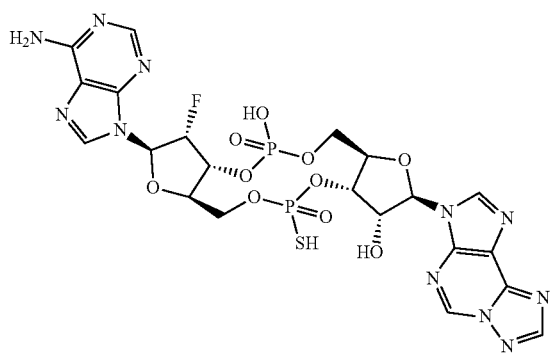

Diastereomer 1 (10-1)
Diastereomer 2 (10-2)

Preparation of Intermediate 10A

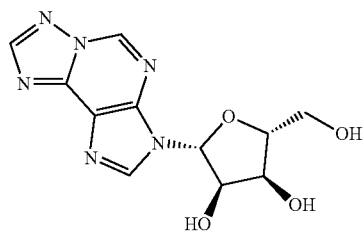

10A

To (2R,3R,4S,5R)-2-(6-chloro-9H-purin-9-yl)-5-(hydroxymethyl)tetrahydrofuran-3,4-diol (Sigma Aldrich, 2 g, 6.98 mmol) in 5 mL of MeOH was added 2 mL of hydrazine hydrate (65% aq. by weight). The reaction was stirred at room temperature for 2 h. The white solid that precipitated was collected and washed with MeOH (2 mL×2), then was dried under vacuum. The dried solid was suspended in 10 mL of trimethoxy orthoformate and heated at 100° C. overnight. The solvent was removed in vacuo. The residue was dissolved in 10 mL of MeOH and 2 mL of 1 N HCl and heated at 50° C. for 3 h. The mixture was then concentrated and the solid was washed with NaHCO₃ aq (5 mL) and water (2 mL×3), and then dried to give Intermediate 10A (1.4 g, 69% yield) as a white solid. ¹H NMR (499 MHz, METHANOL-d₄) δ 9.50 (s, 1H), 8.75 (s, 1H), 8.53 (s, 1H), 6.27 (d, J=5.0 Hz, 1H), 4.72 (m, 1H), 4.46-4.36 (m, 1H), 4.19 (d, J=4.1 Hz, 1H), 3.92 (d, J=3.2 Hz, 1H), 3.84 (d, J=3.6 Hz, 1H). MS (ES): m/z=293.0[M+H]⁺.

Preparation of Intermediate 10B

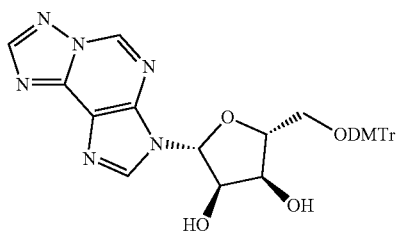

10B

To Intermediate 10A (1.4 g, 4.79 mmol) in 10 mL of pyridine and 2 mL of DMF was added 4,4'-(chloro(phenyl)methylene)bis(methoxybenzene) (1.8 g, 5.27 mmol). After 2 h, additional 4,4'-(chloro(phenyl)methylene)bis(methoxybenzene) (1.8 g, 5.27 mmol) was added and the mixture was stirred for an additional 1 h. To the reaction was then added 2 mL of MeOH and it was stirred for an additional 10 min. Then the mixture was concentrated and re-dissolved in 50 mL of EtOAc, washed with aq. NaHCO₃, brine, and then concentrated. The residue was purified on silica (40 g) eluting with 0-100% EtOAc/hexane (w 0.5% TEA) to give Intermediate 10B (1.9 g, 68% yield). ¹H NMR (499 MHz, CHLOROFORM-d) δ 9.09 (s, 1H), 8.44 (s, 1H), 8.31 (s, 1H), 7.41 (dd, J=8.3, 1.3 Hz, 2H), 7.32-7.29 (m, 4H), 7.27-7.22 (m, 2H), 7.21-7.18 (m, 1H), 6.79 (dd, J=9.1, 1.1 Hz, 4H), 6.19 (d, J=5.1 Hz, 1H), 4.86 (m, 1H), 4.51 (m, 1H), 4.37 (d, J=3.8 Hz, 1H), 3.78 (s, 6H), 3.56-3.50 (m, 1H), 3.42 (dd, J=10.6, 4.2 Hz, 1H). MS (ES): m/z=595.2[M+H]⁺.

Preparation of Intermediates 10C and 10D

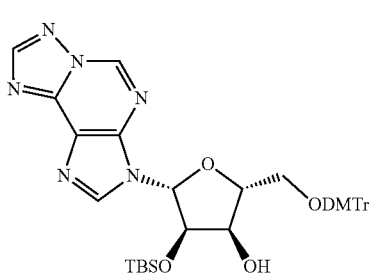
10C

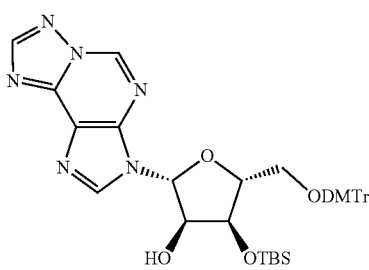
10D

To Intermediate 10B (1.9 g, 3.20 mmol) in 20 mL of DCM was added 1H-imidazole (0.65 g, 9.59 mmol) and tert-butylchlorodimethylsilane (0.53 g, 3.51 mmol). The reaction was stirred at room temperature for 6 h, and then it was diluted with 50 mL of DCM, washed with aq. NaHCO$_3$, brine, dried over Na$_2$SO$_4$ and concentrated. The residue was purified on silica (40 g) eluting with 0-100% EtOAc/hexane (w/ 0.5% TEA) to give Intermediate 10C (0.4 g, 0.56 mmol, 18% yield). $^1$H NMR (499 MHz, CHLOROFORM-d) δ 9.10 (s, 1H), 8.47 (s, 1H), 8.34 (s, 1H), 7.48 (d, J=7.2 Hz, 2H), 7.36 (d, J=8.2 Hz, 5H), 7.27-7.17 (m, 1H), 6.90-6.76 (m, 5H), 6.19 (d, J=5.5 Hz, 1H), 5.02 (t, J=5.2 Hz, 1H), 4.45-4.37 (m, 1H), 4.34 (d, J=3.2 Hz, 1H), 3.56 (d, J=3.0 Hz, 1H), 3.46 (d, J=3.8 Hz, 1H), 2.73 (br s, 1H). MS (ES): m/z=709.4[M+H]$^+$ and Intermediate 10D (0.8 g, 1.13 mmol, 35% yield). $^1$H NMR (499 MHz, CHLOROFORM-d) δ 9.17 (s, 1H), 8.47 (s, 1H), 8.36 (s, 1H), 7.47-7.39 (m, 2H), 7.37-7.30 (m, 5H), 7.27-7.18 (m, 1H), 6.91-6.74 (m, 5H), 6.15 (d, J=5.0 Hz, 1H), 4.75 (d, J=6.6 Hz, 1H), 4.58 (dd, J=5.4, 4.2 Hz, 1H), 4.25 (d, J=3.8 Hz, 1H), 3.57 (dd, J=10.7, 3.5 Hz, 1H), 3.33 (dd, J=10.7, 4.1 Hz, 1H), 3.03 (d, J=7.0 Hz, 1H). MS (ES): m/z=709.4[M+H]$^+$.

Preparation of Intermediate 10E

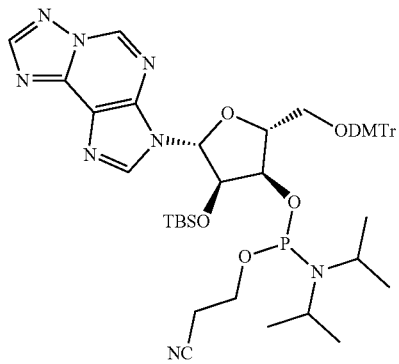
10E

To Intermediate 10C (0.4 g, 0.56 mmol) in 10 mL of DCM was added a 1 M solution of 1H-imidazole-4,5-dicarbonitrile (0.395 mL, 0.395 mmol) in acetonitrile, followed by the addition of 3-((bis(diisopropylamino)phosphanyl)oxy)propanenitrile (0.20 g, 0.68 mmol). The reaction was stirred at room temperature for 16 h, and then it was diluted with 30 mL of DCM, washed with NaHCO$_3$ aq., dried over Na$_2$SO$_4$, and then concentrated to dryness. The residue was purified on silica (12 g) eluting with 0-100% EtOAc/hexane (with 0.5% TEA and the column was primed with hexane with 0.5% TEA) to give Intermediate 10E (0.41 g, 0.45 mmol, 80% yield). MS (ES): m/z=826.5[M+H]$^+$ (with TFA in mobile phase). MS (ES): m/z=909.2[M+H]$^+$ (with ammonium acetate in mobile phase).

Preparation of Intermediate 10F

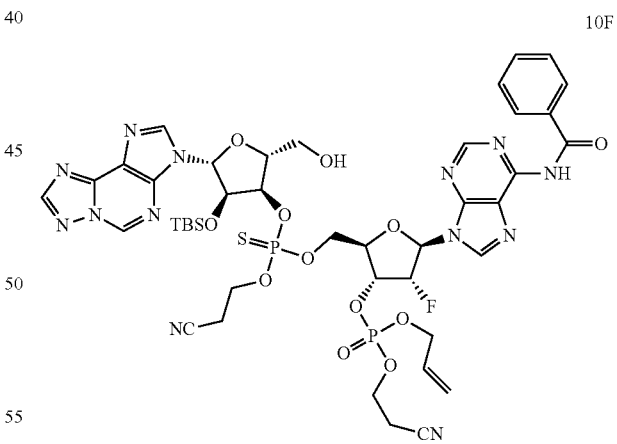
10F

Intermediate 7A (120 mg, 0.220 mmol) and 1H-tetrazole (30.8 mg, 0.440 mmol) in a 50 mL flask with a stir bar were azeotroped with ACN (2 mL×3). Then, 100 mg of 4 Å molecular sieves and 4 mL of ACN were added and this mixture (I) was stirred at room temperature for 30 min. Intermediate 10E (200 mg, 0.220 mmol) in a 20 mL vial was azeotroped with ACN (2 mL×2). Then, 100 mg of 4 Å molecular sieves and 1 mL of ACN were added and this mixture (II) was stirred at room temperature for 30 min. With positive N$_2$ pressure, mixture II was added to mixture I. To achieve a complete transfer, the vial containing (II) was rinsed with 1 mL of ACN and added to the mixture I. The reaction was stirred at room temperature for 2 h. (E)-N,N-dimethyl-N'-(3-thioxo-3H-1,2,4-dithiazol-5-yl)formimidamide (49.7 mg, 0.242 mmol) was added, and the reaction was stirred for an additional 30 min. The reaction was then filtered and the filtrate was concentrated. The residue was dissolved in 10 mL of DCM and 2,2-dichloroacetic acid (170 mg, 1.320 mmol) was added dropwise. After stirring for 30 min, the reaction was diluted with 30 mL of DCM, washed with NaHCO₃, dried over Na₂SO₄, and then concentrated. The residue was purified on silica (24 g) eluting with 0-10% MeOH/DCM to give Intermediate 10F (120 mg, 0.111 mmol, 50% yield). MS (ES): m/z=1084.5 [M+H]⁺.

Preparation of Intermediate 10G

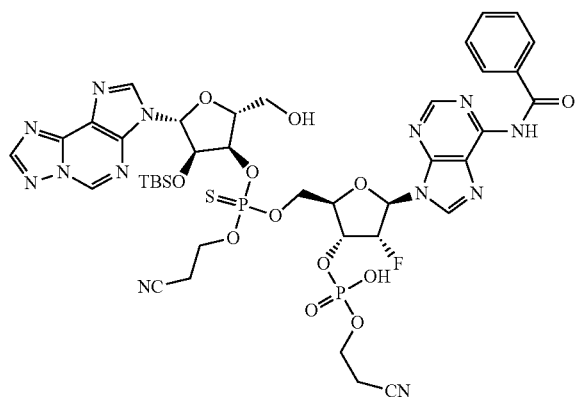

10G

Following the procedures described in the preparation of Intermediate 7C, Intermediate 10F (120 mg, 0.111 mmol) gave Intermediate 10G (74 mg, 0.071 mmol, 64% yield). MS (ES): m/z=1044.5[M+H]⁺.

Preparation of Intermediate 10H

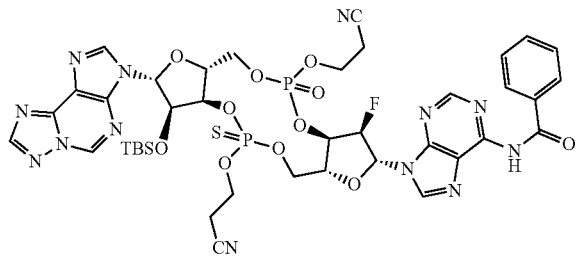

10H

Following the procedures described in the preparation of Intermediate 7C, Intermediate 10G (74 mg, 0.071 mmol) gave Intermediate 10H (46 mg, 0.045 mmol, 63% yield). MS (ES): m/z=1026.4[M+H]⁺.

Example 10

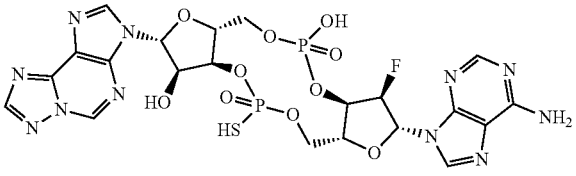

Diastereomer 1 (10-1)
Diastereomer 2 (10-2)

Intermediate 10H (46 mg, 0.045 mmol) was dissolved in 2 mL of 7 N NH₃/MeOH and heated to 50° C. for 5 h. Then the reaction was concentrated and the residue was suspended in neat trihydrogenfluoride triethylamine (0.4 mL) and stirred at 37° C. for 14 h. The mixture was quenched with 2 mL of a 2 N ammonium acetate solution and stirred for 10 min. Then it was filtered and purified by preparative HPLC (Column: Xselect RP Prep C18 OBD Column, 5 μm, 19×150 mm; Flow rate: 20.0 mL/min; Mobile Phase: A: 100 mM NH₄OAc (pH 7); B: Acetonitrile.) to give a pair of diastereomers Example 10-1 (6.4 mg)¹H NMR (499 MHz, METHANOL-d₄)¹H NMR (499 MHz, METHANOL-d₄) δ 9.45 (s, 1H), 8.85 (s, 1H), 8.73 (s, 1H), 8.48 (s, 1H), 8.21 (s, 1H), 6.42 (d, J=15.6 Hz, 1H), 6.32 (d, J=1.4 Hz, 1H), 5.46-5.28 (m, 1H), 5.25-5.17 (m, 1H), 5.10-4.98 (m, 1H), 4.52 (br d, J=11.8 Hz, 1H), 4.44 (br d, J=9.7 Hz, 3H), 4.21-4.10 (m, 2H), 3.73 (dt, J=13.2, 6.6 Hz, 1H). MS (ES): m/z=702.2[M+H]⁺ and Example 10-2 (5.3 mg)¹H NMR (499 MHz, METHANOL-d₄) δ 9.49 (s, 1H), 8.72 (s, 1H), 8.45 (s, 1H), 8.43 (s, 1H), 8.16 (s, 1H), 6.35 (d, J=16.8 Hz, 1H), 6.28 (d, 1H), 5.55-5.32 (m, 1H), 5.21 (td, J=9.0, 4.5 Hz, 1H), 5.15-5.00 (m, 1H), 4.60 (br d, J=12.0 Hz, 1H), 4.50-4.38 (m, 3H), 4.21-4.00 (m, 2H), 3.74 (m, 1H) MS (ES): m/z=702.2[M+H]⁺.

Example 11

(1S,6R,8R,9R,10R,15R,17R,18R)-8-(6-amino-9H-purin-9-yl)-9-fluoro-3,12,18-trihydroxy-17-{3H-[1,2,4]triazolo[3,2-f]purin-3-yl}-2,4,7,11,13,16-hexaoxa-3λ⁵,12λ⁵-diphosphatricyclo[13.3.0.0⁶,¹⁰]octadecane-3,12-dione

11

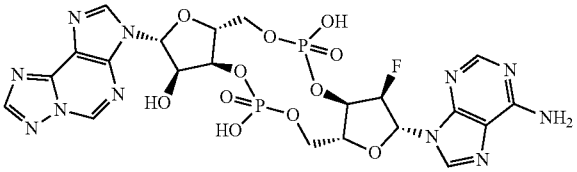

Preparation of Intermediate 11A

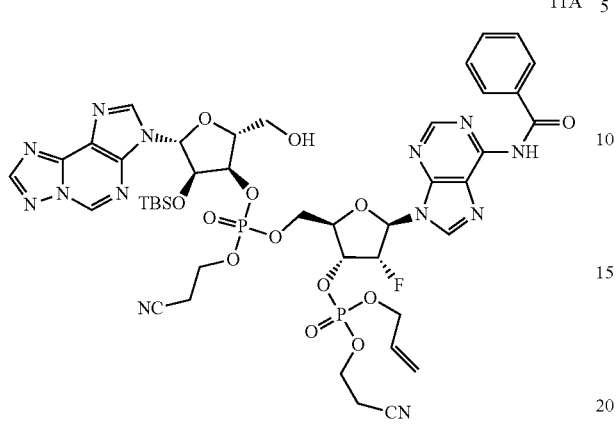

11A

Intermediate 7A (72 mg, 0.13 mmol) and 1H-tetrazole (18.49 mg, 0.264 mmol) in a 50 mL flask with a stir bar were azeotroped with ACN (2 mL×3). Then, 100 mg of 4 Å molecular sieves and 4 mL of ACN were added and this mixture (I) was stirred at room temperature for 30 min. Intermediate 10E (120 mg, 0.13 mmol) in a 20 mL vial was azeotroped with ACN (2 mL×2). Then, 100 mg of 4 Å molecular sieves and 1 mL of ACN were added and this mixture (II) was stirred at room temperature for 30 min. With positive $N_2$ pressure, mixture II was added to mixture I. To achieve a complete transfer, the vial containing (II) was rinsed with 1 mL of ACN and added to the mixture (I). The reaction was stirred at room temperature for 2 h. 2-hydroperoxy-2-((2-hydroperoxybutan-2-yl)peroxy)butane (41.6 mg, 0.198 mmol) was then added, and the reaction was stirred for an additional 30 min. The mixture was then filtered and the filtrate was concentrated. The residue was dissolved in 10 mL of DCM and 2,2-dichloroacetic acid (102 mg, 0.79 mmol) was added dropwise. After stirring for 30 min, the reaction was diluted with 30 mL of DCM, washed with $NaHCO_3$, dried over $Na_2SO_4$, and then concentrated. The residue was purified on silica (24 g) eluting with 0-10% MeOH/DCM to give Intermediate 11A (50 mg, 0.047 mmol, 36% yield). MS (ES): m/z=1068.4[M+H]$^+$.

Preparation of Intermediate 11B

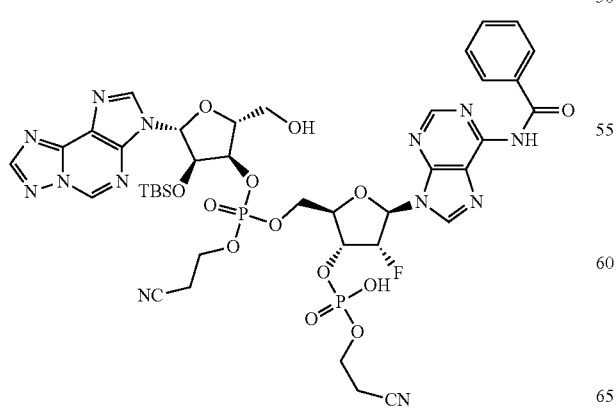

11B

Following the procedures described in the preparation of Intermediate 7C, Intermediate 11A (50 mg, 0.047 mmol) gave Intermediate 11B (46 mg, 0.045 mmol, 96% yield). MS (ES): m/z=1028.6[M+H]$^+$.

Preparation of Intermediate 11C

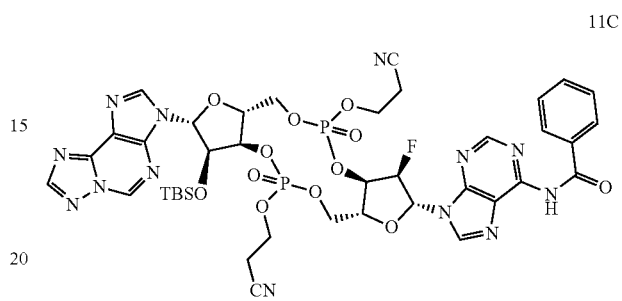

11C

Following the procedures described in the preparation of Intermediate 7D, Intermediate 11B (46 mg, 0.045 mmol) gave Intermediate 11C (46 mg, 0.046 mmol, 100% yield). MS (ES): m/z=1010.3[M+H]$^+$.

Example 11

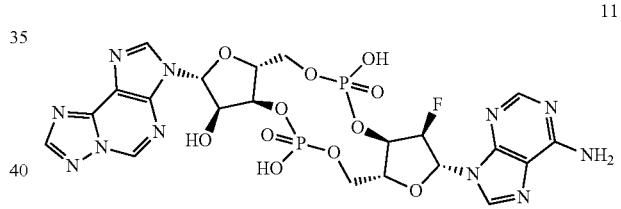

11

Following the procedures described in the preparation of Example 10-1 and Example 10-2, Intermediate 11C (46 mg, 0.046 mmol) gave Example 11 (10.6 mg) $^1$H NMR (499 MHz, METHANOL-$d_4$) δ 9.49 (s, 1H), 8.72 (s, 1H), 8.46 (s, 1H), 8.43 (s, 1H), 8.17 (s, 1H), 6.36 (d, J=17.0 Hz, 1H), 6.29 (d, J=1.1 Hz, 1H), 5.61-5.37 (m, 1H), 5.21-5.02 (m, 2H), δ 4.87 (br d, J=4.6 Hz, 1H) 4.52-4.34 (m, 4H), 4.21-4.09 (m, 2H). MS (ES): m/z=686.2[M+H]$^+$.

Preparation of Phosphorus (V) Reagents

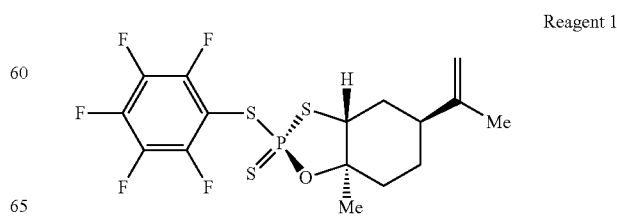

Reagent 1

139
-continued

Reagent 2

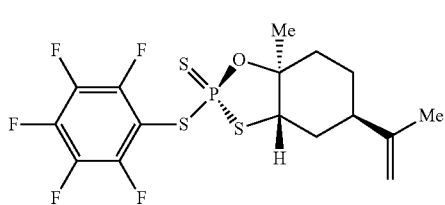

The phosphorus (V) reagents (Reagents 1-2) used in the preparation of Example 12 were prepared according to the procedures provided in U.S. Ser. No. 62/657,551 filed Apr. 13, 2018.

Example 12

(1R,6R,8R,9R,10R,15R,17R,18R)-8-(6-amino-9H-purin-9-yl)-9,18-difluoro-3,12-disulfanyl-17-{3H-[1,2,4]triazolo[3,2-f]purin-3-yl}-2,4,7,11,13,16-hexaoxa-3$\lambda^5$,12$\lambda^5$-diphosphatricyclo[13.3.0.0$^{6,10}$]octadecane-3,12-dione

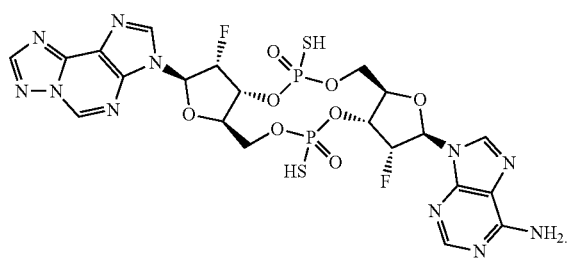

Diastereomer 1 (12-1)
Diastereomer 2 (12-2)
Diastereomer 3 (12-3)
Diastereomer 4 (12-4)

Preparation of Intermediate 12A

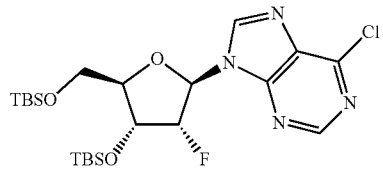

12A

To (2R,3R,4R,5R)-5-(6-amino-9H-purin-9-yl)-4-fluoro-2-(hydroxymethyl) tetrahydrofuran-3-ol (0.6 g, 2.23 mmol) in 10 mL of DCM was added 1H-imidazole (0.455 g, 6.69 mmol) and tert-butylchlorodimethylsilane (1.0 g, 6.69 mmol). The reaction was stirred at room temperature for 5 h. Then, the mixture was diluted with 30 mL of DCM, washed with aq. NaHCO$_3$, water, and brine, and then dried over Na$_2$SO$_4$, and was then concentrated. The crude material was dissolved in 30 mL of DCM, cooled to 0° C. under N$_2$, and chlorotrimethylsilane (2.26 mL, 17.8 mmol) was added dropwise. After 20 min., tert-butyl nitrite (2.47 mL, 18.7 mmol) was added dropwise. The reaction was warmed slowly and then stirred at room temperature for 16 h. The mixture was quenched with aq. NaHCO$_3$, washed with water, brine, dried over Na$_2$SO$_4$, and was them concentrated to give crude Intermediate 12A ~1.1 g. MS (ES): m/z=517.2 [M+H]$^+$.

Preparation of Intermediate 12B

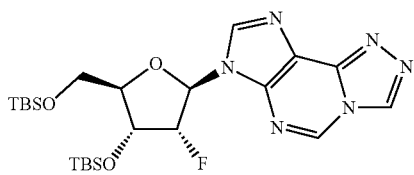

21B

The crude Intermediate 12A (~1.1 g) was dissolved in 2 mL of MeOH, hydrazine hydrate (1 mL, 65% aq by weight) was added and the mixture was stirred at room temperature for 1 h. Then the mixture was diluted with 20 mL of DCM, washed with water (10 mL×2), brine, dried over Na$_2$SO$_4$, and then concentrated. The residue was dissolved in 10 mL of trimethoxy orthoformate and heated at 100° C. for 2 h. The solvent was removed in vacuo and the crude was purified on silica (24 g) eluting with 0-5% MeOH/DCM to give Intermediate 12B (0.7 g, 1.34 mmol, 60.1% yield). $^1$H NMR (499 MHz, CHLOROFORM-d) δ 9.02 (s, 1H), 8.91 (s, 1H), 8.44 (s, 1H), 6.44 (dd, J=14.8, 2.7 Hz, 1H), 5.29-5.13 (m, 1H), 4.65 (ddd, J=16.1, 6.1, 4.4 Hz, 1H), 4.26-4.20 (m, 1H), 4.07 (dd, J=11.7, 2.5 Hz, 1H), 3.85 (dd, J=11.7, 2.3 Hz, 1H), 0.95 (d, J=8.3 Hz, 18H), 0.19-0.11 (m, 12H). MS (ES): m/z=523.2[M+H]$^+$.

Preparation of Intermediate 12C

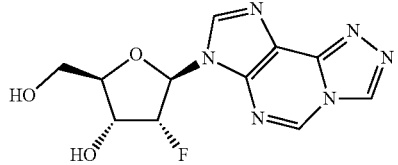

21B

To Intermediate 12B (0.7 g, 1.34 mmol) in 10 mL of THF was added tetrabutyl ammonium fluoride (1 M in THF, 0.67 mL, 0.67 mmol). The reaction was stirred at room temperature for 20 h. The mixture was co-evaporated with 5 g of silica, and then it was purified on a 24 g silica column eluting with 0-10% MeOH/DCM (w/ 0.25% TEA) to give Intermediate 12C (0.31 g, 1.054 mmol, 79% yield). $^1$H NMR (499 MHz, METHANOL-d$_4$) δ 9.49 (s, 1H), 8.76 (s, 1H), 8.51 (s, 1H), 6.61-6.43 (m, 1H), 5.51 (m, 1H), 4.78-4.59 (m, 1H), 4.25-4.10 (m, 1H), 4.03-3.94 (m, 1H), 3.88-3.75 (m, 1H). MS (ES): m/z=295.0[M+H]$^+$.

Preparation of Intermediate 12D

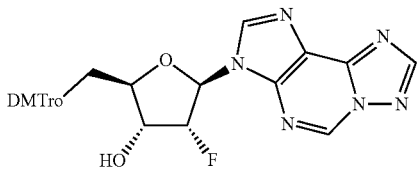

To Intermediate 12C (0.8 g, 2.72 mmol) in 5 mL of pyridine was added 4,4'-(chloro(phenyl)methylene)bis(methoxybenzene) (1.20 g, 3.53 mmol) and the mixture was stirred at room temperature for 16 h. Then, 1 mL of MeOH was added and the reaction was stirred for an additional 10 min. The solvent was removed and the residue was purified on silica (24 g) eluting with 0-5% MeOH/DCM (with 0.25% TEA) to give Intermediate 12D (1.1 g, 1.84 mmol, 68% yield). MS (ES): m/z=597.2[M+H]$^+$.

Preparation of Intermediate 12E

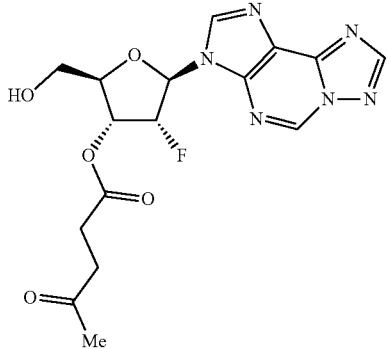

To Intermediate 12D (0.72 g, 1.207 mmol) in DCM (20 mL) was added 4-oxopentanoic anhydride (0.388 g, 1.810 mmol), followed by a catalytic amount of DMAP (20 mg). The reaction was stirred at room temperature for 2 h. The mixture was then diluted with 20 mL of DCM, washed with aq. NaHCO$_3$ and brine, dried over Na$_2$SO$_4$, and then concentrated. The residue was dissolved in 20 mL of DCM and triethylsilane (0.702 g, 6.03 mmol) was added, followed by 2,2-dichloroacetic acid (0.47 g, 3.62 mmol). The reaction was stirred at room temperature for 1 h. The mixture was then washed with sat. aq. NaHCO$_3$, brine, and then dried over Na$_2$SO$_4$, and concentrated to dryness. The residue was purified on silica (24 g) eluting with 0-10% MeOH/DCM to give Intermediate 12E (0.47 g, 1.20 mmol, 99% yield). $^1$H NMR (499 MHz, CHLOROFORM-d) δ 9.31 (s, 1H), 8.51 (s, 1H), 8.35 (s, 1H), 6.46-6.25 (m, 1H), 5.94-5.65 (m, 2H), 4.47 (dd, J=3.2, 1.7 Hz, 1H), 4.15 (br d, J=7.2 Hz, 1H), 4.05 (br d, J=12.9 Hz, 1H), 3.97-3.84 (m, 1H), 3.02-2.57 (m, 4H), 2.25 (s, 3H). MS (ES): m/z=393.1[M+H]$^+$.

Preparation of Intermediate 12F

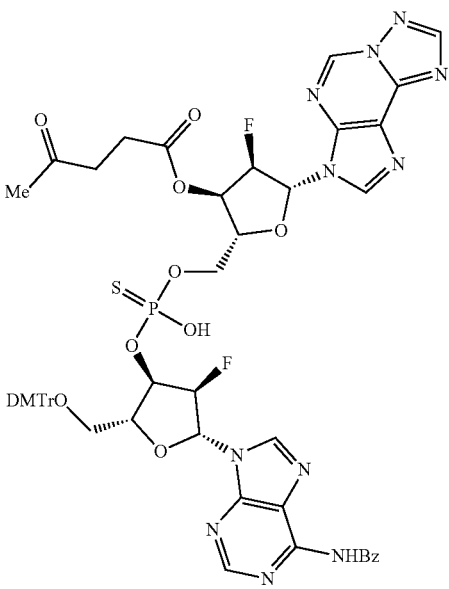

Intermediate 12E (0.47 g, 1.2 mmol) and 5-(ethylthio)-1H-tetrazole (0.32 g, 2.45 mmol) in a 50 mL flask with a stir bar was azeotroped with 4 mL of acetonitrile three times. Then, 100 mg of 4 Å molecular sieves and 4 mL of dry acetonitrile were added under a N$_2$ atmosphere. This mixture (I) was stirred at room temperature for 30 min. (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl)diisopropylphosphoramidite (Sigma Aldrich, 1.50 g, 1.71 mmol) in a 20 mL vial was azeotroped with 2 mL of acetonitrile two times. Then, 100 mg of 4 Å molecular sieves and 2 mL of ACN were added. This mixture (II) was stirred at room temperature for 30 min. With positive N$_2$ pressure, mixture II was added to mixture I. To achieve a complete transfer, the vial containing (II) was rinsed with 1 mL of ACN and added to the mixture (I). The reaction was then stirred at room temperature for 16 h. Then, (E)-N,N-dimethyl-N'-(3-thioxo-3H-1,2,4-dithiazol-5-yl)formimidamide (0.28 g, 1.35 mmol) was added and the reaction was stirred for an additional 10 minutes. The yellow solution was then filtered and the filtrated was diluted with 30 mL of EtOAc, washed with aq. NaHCO$_3$, dried over Na$_2$SO$_4$ and concentrated. The residue was purified on silica (24 g) eluting with 0-100% EtOAc/hexane (with 0.5% TEA) to give Intermediate 12F (1.02 g, 0.89 mmol, 74% yield) as a pair of diastereomers. MS (ES): m/z=1146.2[M+H]$^+$.

Preparation of Intermediate 12G

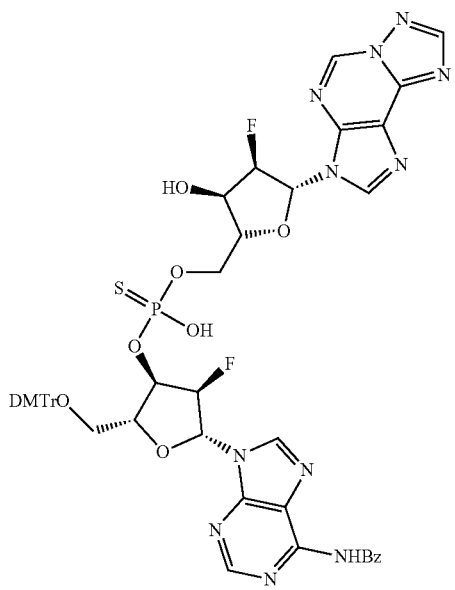

12G

Intermediate 12F (1.02 g, 0.89 mmol) in AcOH (6 mL) and pyridine (4 mL) was treated with hydrazine hydrate (0.13 mL, 2.67 mmol, 65% aq. by wt). After stirring at room temperature for 15 min, the reaction was complete. Pentane-2,4-dione (0.27 g, 2.67 mmol) was added and the mixture was stirred for an additional 10 min. The reaction was then diluted with DCM (20 mL), washed with aq. NaHCO$_3$, dried over Na$_2$SO$_4$, and then concentrated. The crude was purified on silica (24 g) eluting with 0-10% MeOH/DCM to give Intermediate 12G (0.7 g, 0.67 mmol, 75% yield). MS (ES): m/z=1048.1[M+H]$^+$.

Preparation of Intermediate 12H

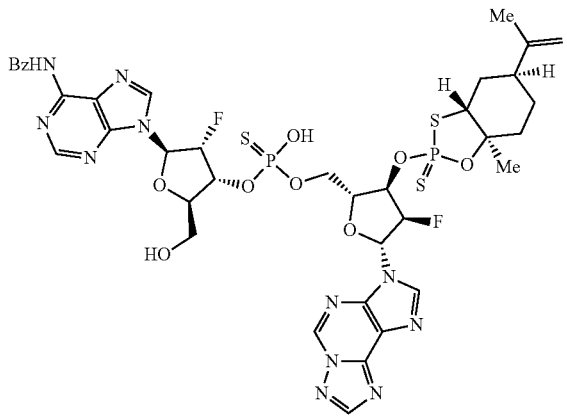

12H

To a solution of Intermediate 12G (175 mg, 0.167 mmol) and Reagent 1 (149 mg, 0.334 mmol) in acetonitrile (4 mL) was added DBU (0.050 mL, 0.334 mmol). The reaction was stirred at room temperature for 20 min. Then, 2,2-dichloroacetic acid (215 mg, 1.670 mmol) was added and the mixture was subsequently stirred at room temperature for 30 min. Then the mixture was concentrated and the residue was purified by silica flash column chromatography (24 g) eluting with 0-30% MeOH/DCM to give Intermediate 12H (90 mg, 0.091 mmol, 54% yield). MS (ES): m/z=992.1 [M+H]$^+$.

Preparation of Intermediate 12I

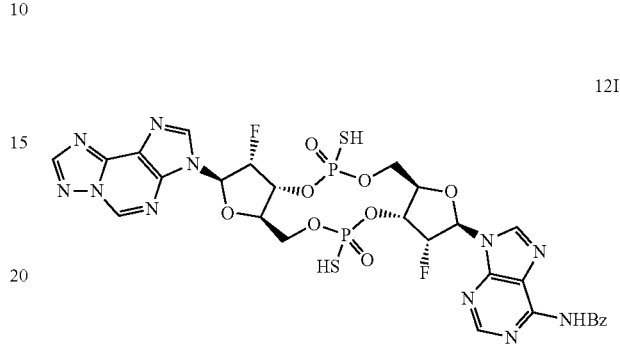

12I

Intermediate 12H (90 mg, 0.091 mmol) was suspended in acetonitrile (4 mL). DBU (0.045 mL, 0.18 mmol) was added and the reaction mixture became homogeneous. The reaction was stirred at room temperature for 1 h. The reaction was then concentrated and the residue was triturated with ether (10 mL×2). The crude material was purified on a reverse phase ISCO column (100 g gold C18 column, A: 0.01 nM NH$_4$OAc; B: 0.01 nM NH$_4$OAc in 95% ACN and 5% H$_2$O) to give Intermediate 12I (55 mg, 0.067 mmol, 74% yield). MS (ES): m/z=823.8[M+H]$^+$.

Example 12

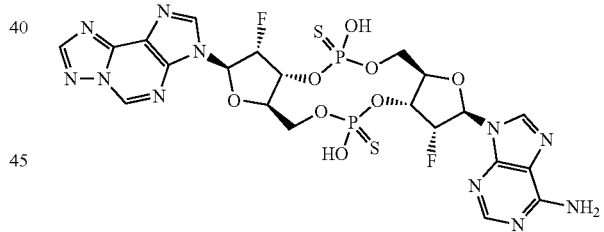

Diastereomer 1 (12-1)
Diastereomer 2 (12-2)

Following the procedures described in the preparation of Examples 10-1 and 10-2, Intermediate 12I (55 mg, 0.067 mmol) gave two diastereomers of Example 12.

Example 12-1: (8.5 mg) $^1$H NMR (499 MHz, METHANOL-d$_4$) δ 9.40 (s, 1H), 8.93 (s, 1H), 8.84 (s, 1H), 8.47 (s, 1H), 8.21 (s, 1H), 6.59 (d, J=16.6 Hz, 1H), 6.39 (d, J=15.5 Hz, 1H), 6.02-5.86 (m, 1H), 5.80-5.63 (m, 1H), 5.41-5.25 (m, 1H), 5.19-5.07 (m, 1H), 4.59-4.43 (m, 4H), 4.19-4.06 (m, 2H). MS (ES): m/z=720.3[M+H]$^+$.

Example 12-2: (6.0 mg) $^1$H NMR (499 MHz METHANOL-d$_4$) δ 9.57-9.42 (s, 1H), 8.81 (s, 1H), 8.68 (s, 1H), 8.48 (s, 1H), 8.14 (s, 1H), 6.54 (d, J=17.0 Hz, 1H), 6.35 (d, J=15.5 Hz, 1H), 6.21-6.01 (m, 1H), 5.44-5.26 (m, 2H), 5.23-5.10 (m, 1H), 4.65 (br d, J=12.3 Hz, 1H), 4.51 (br d, J=10.3 Hz, 2H), 4.43 (br d, J=9.2 Hz, 1H), 4.11 (dd, J=11.7, 3.9 Hz, 1H), 4.05 (dd, J=11.8, 4.1 Hz, 1H). MS (ES): m/z=720.3[M+H]$^+$.

Preparation of Intermediate 12J

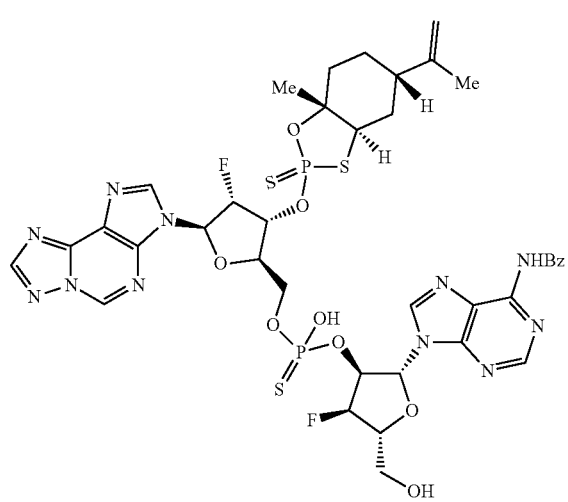
12J

Following the procedures described in the preparation of Intermediate 12H, Intermediate 12G (300 mg, 0.286 mmol) was reacted with Reagent 2 (256 mg, 0.573 mmol) to give Intermediate 12J (216 mg, 0.22 mmol, 76% yield). MS (ES): m/z=992.1[M+H]$^+$.

Preparation of Intermediate 12K

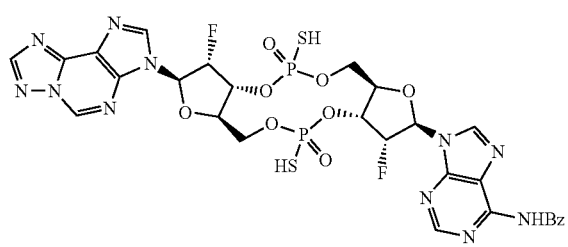
12K

Following the procedures described in the preparation of Intermediate 12I, Intermediate 12J (216 mg, 0.22 mmol) gave Intermediate 12K (152 mg, 0.19 mmol, 85% yield). MS (ES): m/z=823.8[M+H]$^+$.

Examples 12-3 and 12-4

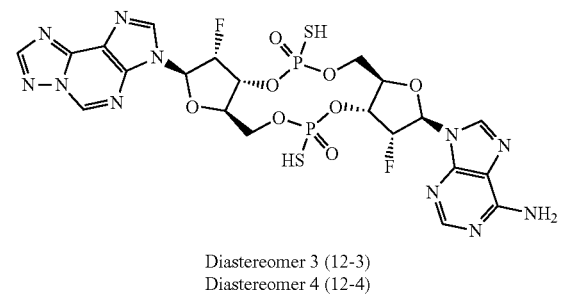 [SMILES: Nc1ncnc2c1ncn2[C@@H]1O[C@@H]2COP(=O)(S)O[C@H]3[C@@H](F)[C@H](n4cnc5c4ncn4ncnc54)O[C@@H]3COP(=O)(S)O[C@H]2[C@H]1F]

Diastereomer 3 (12-3)
Diastereomer 4 (12-4)

Following the procedures described in the preparation of Examples 12-1 and 12-2, Intermediate 12K (192 mg, 0.233 mmol) gave two other diastereomers of Example 12.

Example 12-3: (20 mg) $^1$H NMR (499 MHz, METHANOL-d$_4$) δ 9.48 (s, 1H), 8.91 (s, 1H), 8.46 (s, 1H), 8.41 (s, 1H), 8.17 (s, 1H), 6.55 (d, J=15.9 Hz, 1H), 6.31 (d, J=16.5 Hz, 1H), 5.96-5.74 (m, 1H), 5.68-5.50 (m, 1H), 5.40-5.27 (m, 1H), 5.22-5.03 (m, 1H), 4.66 (br d, J=12.2 Hz, 1H), 4.58-4.38 (m, 3H), 4.23-3.97 (m, 2H). MS (ES): m/z=720.3[M+H]$^+$.

Example 12-4: (13.6 mg) $^1$H NMR (499 MHz, METHANOL-d$_4$) δ 9.56-9.25 (s, 1H), 8.51 (s, 1H), 8.34 (s, 1H), 8.14 (s, 1H), 7.98 (s, 1H), 6.39 (d, J=15.3 Hz, 1H), 6.14 (d, J=15.6 Hz, 1H), 6.04-5.86 (m, 1H), 5.63-5.42 (m, 2H), 5.39-5.22 (m, 1H), 4.67-4.51 (m, 3H), 4.45 (br d, J=9.1 Hz, 1H), 4.04 (dt, J=12.7, 6.5 Hz, 2H). MS (ES): m/z=720.3[M+H]$^+$.

Example 13

(1S,6R,8R,9R,10R,15R,17R,18R)-8-(6-amino-9H-purin-9-yl)-9-fluoro-12,18-dihydroxy-17-(4-nitro-1H-1,2,3-benzotriazol-1-yl)-3-sulfanyl-2,4,7,11,13,16-hexaoxa-3λ$^5$,12λ$^5$-diphosphatricyclo[13.3.0.0$^{6,10}$]octadecane-3,12-dione

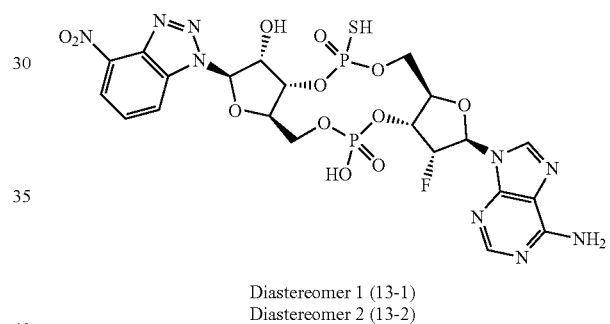

Diastereomer 1 (13-1)
Diastereomer 2 (13-2)

Preparation of Intermediate 13A

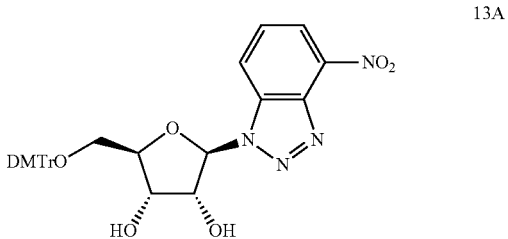
13A

Step 1:

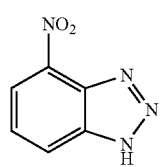

1H-benzo[d][1,2,3]triazole (5 g, 42.0 mmol) in conc. $H_2SO_4$ (150 mL) was cooled to 0° C. Potassium nitrate (8.49 g, 84 mmol) was added in small portions over 20 min. Then the reaction was heated to 60° C. for 1.5 h. The mixture was cooled to room temperature, and then poured onto 100 g of ice. After warming to room temperature, the solid was collected and washed with water (10 mL×3). The solid was treated with 50 mL of sat. aq.$NaHCO_3$, and stirred for 5 min. The resulting solid was collected and washed with water (10 mL×3), hexane (10 mL×3), and then dried under vacuum to provide the desired product (5.82 g, 84% yield) LCMS: M/Z 165.00 (M+H), $^1$H NMR (499 MHz, CHLOROFORM-d) δ 13.10 (br s, 1H), 8.55 (d, J=8.2 Hz, 1H), 8.49 (dd, J=7.8, 0.7 Hz, 1H), 7.62 (t, J=8.1 Hz, 1H).

Step 2:

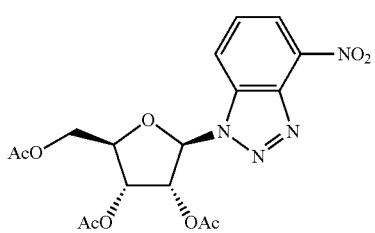 [SMILES: CC(=O)OC[C@H]1O[C@@H](n2nnc3c([N+](=O)[O-])cccc32)[C@H](OC(C)=O)[C@@H]1OC(C)=O]

To a solution of (2S,3R,4R,5R)-5-(acetoxymethyl)tetrahydrofuran-2,3,4-triyl triacetate (10 g, 31.4 mmol) and 4-nitro-1H-benzo[d][1,2,3]triazole (5.16 g, 31.4 mmol) in 50 mL of DCM, was added perchlorostannane (1.47 mL, 12.6 mmol) dropwise. The reaction mixture was stirred at room temperature for 16 h. To the reaction was slowly added 300 mL of sat. aq. $NaHCO_3$. The mixture was then extracted with DCM (300 mL×3). The combined organic layers were washed with brine, dried over $Na_2SO_4$ and concentrated. The residue was purified on silica eluting with 0-50% EtOAc/hexane to give the desired (2R,3R,4R,5R)-2-(acetoxymethyl)-5-(4-nitro-TH-benzo[d][1,2,3]triazol-1-yl)tetrahydrofuran-3,4-diyl diacetate (5.7 g, 43%). LCMS: M/Z 422.85 (M+H), $^1$H NMR (499 MHz, DMSO-$d_6$) δ 8.52 (d, J=8.4 Hz, 1H), 8.39 (d, J=7.6 Hz, 1H), 7.89 (t, J=7.9 Hz, 1H), 6.97 (d, J=3.0 Hz, 1H), 6.15 (dd, J=5.4, 3.0 Hz, 1H), 5.76-5.71 (m, 1H), 4.59-4.55 (m, 1H), 4.34 (dd, J=12.3, 3.2 Hz, 1H), 4.13 (dd, J=12.5, 4.6 Hz, 1H), 2.14 (s, 6H), 1.86 (s, 3H).

Step 3:

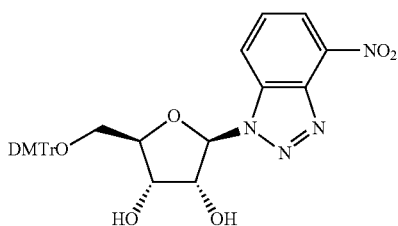

Ammonia was bubbled through a solution of (2R,3R,4R,5R)-2-(acetoxymethyl)-5-(4-nitro-TH-benzo[d][1,2,3]triazol-1-yl)tetrahydrofuran-3,4-diyl diacetate (4 g, 9.5 mmol) in 30 mL of MeOH for 15 min, and then the mixture was stirred at room temperature for 16 h. The reaction mixture was then concentrated. The residue was azeotroped with 5 mL of pyridine, and then dissolved in 20 mL of pyridine. 4,4'-(Chloro(phenyl)methylene)bis(methoxybenzene) (3.85 g, 11.36 mmol) was added and the reaction was stirred at room temperature for 6 h. The reaction was then quenched with 1 mL of MeOH and stirred for an additional 10 minutes. The mixture was then concentrated in vacuo and the residue was purified on silica eluting with 0-100% EtOAc/Hexane to give Intermediate 13A (3.7 g, 5.56 mmol, 59% yield).

Preparation of Intermediate 13B

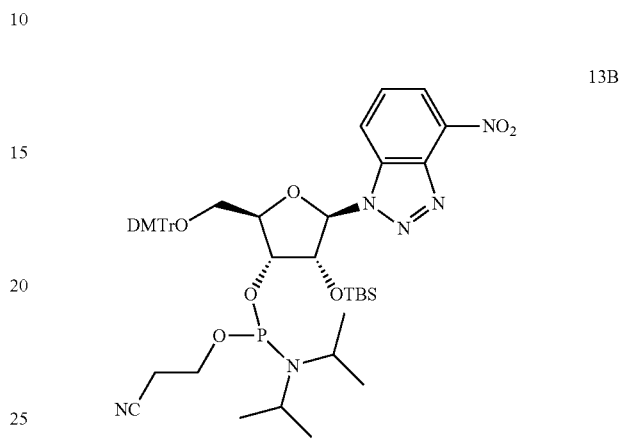

Step 1:

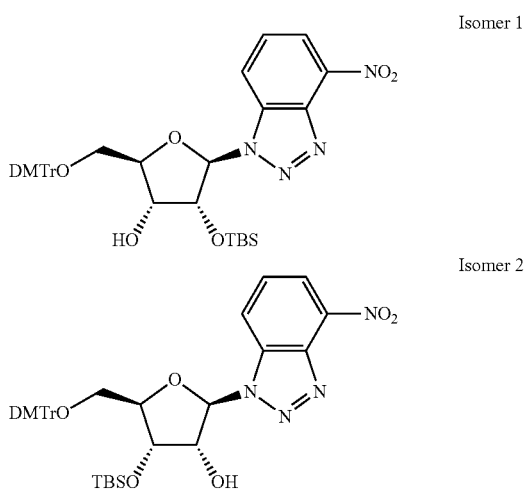

To a solution of Intermediate 13A (3.7 g, 6.18 mmol) in 25 mL of dry pyridine was added 1H-imidazole (1.262 g, 18.54 mmol), followed by the dropwise addition of tert-butylchlorodimethylsilane (0.978 g, 6.49 mmol). The reaction was stirred at room temperature for 6 h, and then quenched with 1 mL of MeOH, and stirring was continued for an additional 10 min. The reaction mixture was then concentrated and the residue was purified on silica gel (eluting with 0-60% EtOAc/Hexane) to give two isomers: (2R,3R,4R,5R)-2-((bis(4-methoxyphenyl)(phenyl) methoxy)methyl)-4-((tert-butyldimethylsilyl)oxy)-5-(4-nitro-1H-benzo[d][1,2,3]triazol-1-yl)tetrahydrofuran-3-ol (Isomer 1) (1.6 g, 2.24 mmol, 36% yield), $^1$H NMR (499 MHz, CHLOROFORM-d) δ 9.26-9.18 (m, 1H), 8.28 (s, 1H), 7.48 (d, J=7.3 Hz, 2H), 7.39-7.29 (m, 6H), 7.27-7.22 (m, 1H), 7.09-7.05 (m, 1H), 6.88-6.83 (m, 4H), 6.74 (d, J=7.0 Hz, 1H), 6.67 (d, J=4.9 Hz, 1H), 4.67 (t, J=5.0 Hz, 1H), 4.34-4.31 (m, 1H), 4.27-4.22 (m, 1H), 3.81 (d, J=0.9 Hz, 6H), 3.57-3.47 (m, 2H), 2.70 (d, J=5.0 Hz, 1H), 0.92-0.87 (m, 9H), 0.07-0.04 (m, 3H), 0.02--0.02 (m, 3H) and (2R,3R,4S,5R)-5-((bis(4-methoxyphenyl)(phenyl)methoxy)methyl)-4-((tert-butyldimethylsilyl)oxy)-2-(4-nitro-1H-benzo[d][1,2,3]triazol-1-yl)tetrahydrofuran-3-ol (Isomer 2) (2.1 g, 2.95 mmol, 48% yield)$^1$H NMR (499 MHz, CHLOROFORM-d) δ 8.28 (d, J=7.5 Hz, 1H), 8.23 (d, J=8.2 Hz, 1H), 7.58 (t, J=7.8 Hz, 1H), 7.20-7.09 (m, 9H), 6.73-6.68 (m, 4H), 6.43 (d, J=2.4 Hz, 1H), 5.15-5.11 (m, 1H), 4.91-4.87 (m, 1H), 4.33-4.29 (m, 1H), 3.78 (d, J=2.6 Hz, 6H), 3.41 (dd, J=10.8, 2.7 Hz, 1H), 3.12-3.07 (m, 2H), 2.07 (s, 1H), 1.55 (s, 12H), 1.29 (t, J=7.2 Hz, 1H), 0.91 (s, 9H), 0.12 (s, 3H), 0.02--0.04 (m, 3H).

Step 2:

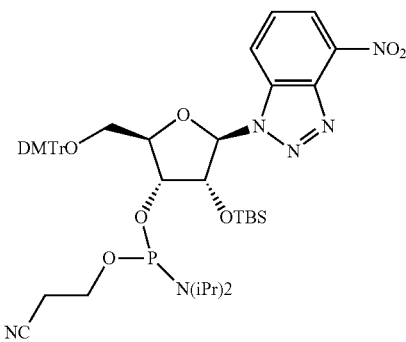

To a solution of (2R,3R,4R,5R)-2-((bis(4 methoxyphenyl) (phenyl)methoxy) methyl)-4-((tert-butyldimethylsilyl)oxy)-5-(4-nitro-1H-benzo[d][1,2,3]triazol-1-yl) tetrahydrofuran-3-ol (Isomer 1, step 1) (1.3 g, 1.824 mmol) in anhydrous DCM (15 mL) was added a 1.0 M solution of 1H-imidazole-4,5-dicarbonitrile (1.459 mL, 1.824 mmol) in acetonitrile, followed by the dropwise addition of 3-((bis (diisopropylamino)phosphanyl)oxy) propanenitrile (0.82 g, 2.74 mmol). After the addition was complete, the mixture was stirred at room temperature for 10 h. The mixture was then quenched with MeOH (2 mL) and then diluted with 100 mL of DCM, washed with sat aq NaHCO₃, dried over MgSO₄, and then concentrated to dryness. The residue was purified by silica gel column chromatography (40 g column, eluting with 0-80% EtOAc/hexane/with 0.5% Et₃N) to afford Intermediate 13B (1.4 g, 1.533 mmol, 84% yield). m/z 830.0 (M+H), (hydrolyzed on LCMS with TFA in the mobile phase).

Preparation of Intermediate 13C

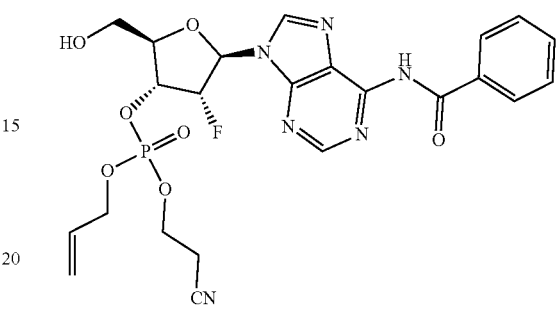

Intermediate 13B (5 g, 5.71 mmol) was azeotroped with 5 mL of dry acetonitrile. Then 0.2 g of 4 Å molecular sieves and acetonitrile (15 mL) were added. To this mixture was added prop-2-en-1-ol (0.663 g, 11.42 mmol) and the mixture was stirred at room temperature for 30 min. To the reaction mixture was added 1H-tetrazole (0.800 g, 11.42 mmol) and the reaction was stirred at room temperature for an additional 30 min. To the reaction was then added 2-hydroperoxy-2-((2-hydroperoxybutan-2-yl)peroxy)butane (2.40 g, 11.4 mmol) and stirring was continued for 30 min. The reaction was then filtered through celite and the filtrate was concentrated. The residue was dissolved in DCM (15 mL) and 2,2-dichloroacetic acid (4.42 g, 34.2 mmol) was added dropwise. After stirring for 30 min, the reaction mixture was treated with sat. aq. NaHCO₃, and then extracted with DCM (30 mL×3). The combined organic layers were dried over Na₂SO₄ and concentrated in vacuo. The residue was purified on silica gel (eluting with 0-10% MeOH/DCM) to give Intermediate 13C (2.86 g, 5.23 mmol, 92% yield) m/z 547.2 (M+H).

Preparation of Intermediate 13D

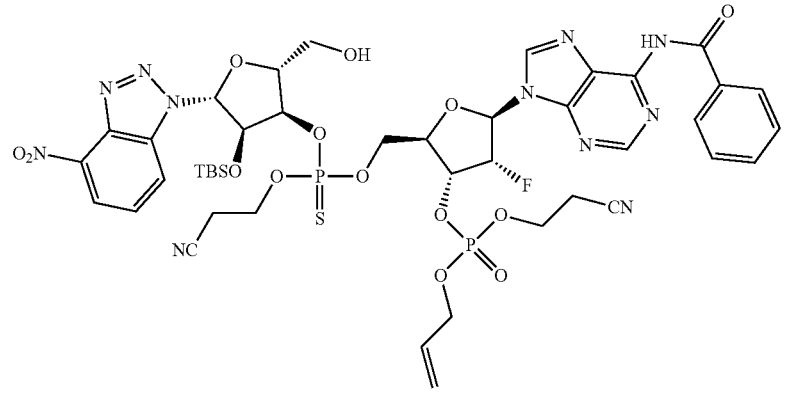

A mixture of Intermediate 13C (182 mg, 0.33 mmol) and 1H-tetrazole (78 mg, 1.11 mmol) in dry ACN (5 mL) was concentrated to dryness (repeated two times). Intermediate 13B (250 mg, 0.278 mmol) was dissolved in ACN (5 mL) and concentrated to dryness (repeated two times). Then 3A molecular sieves (0.5 g) and acetonitrile (10 mL) were added to Intermediate 13B, and this solution was then added to Intermediate 13C in dry ACN (2 mL). The reaction was stirred at room temperature for 90 minutes and then (E)-N,N-dimethyl-N'-(3-thioxo-3H-1,2,4-dithiazol-5-yl)formimidamide (114 mg, 0.56 mmol) was added. The reaction was left stirring for 30 min. The reaction was then filtered through celite and concentrated under reduced pressure. The residue was dissolved in DCM (5 mL) and then 2,2-dichloroacetic acid (0.138 mL, 1.66 mmol) was added dropwise. The reaction mixture was concentrated and then azeotroped with MeOH a few times. The crude product, Intermediate 13D, was used directly for next step. m/z 1088.6 (M+H).

Preparation of Example 13E solution of Intermediate 13E (200 mg, 0.19 mmol) in pyridine (2 mL), dropwise. The mixture was stirred at room temperature overnight. The mixture was concentrated under reduced pressure and the residue was then purified by silica gel column chromatography eluting with 0-15% MeOH in DCM to give the product, Intermediate 13F (146 mg, 74%). LCMS (ES, m/z): 1030.4 [M+H]+.

Example 13

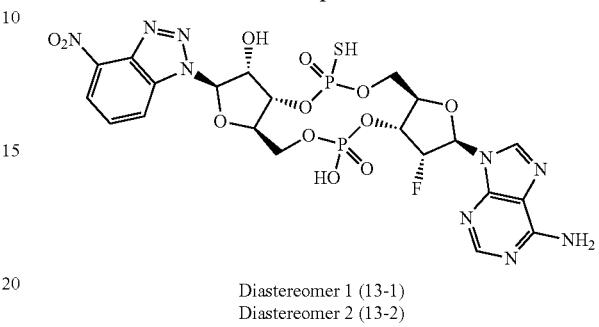

Diastereomer 1 (13-1)
Diastereomer 2 (13-2)

13E

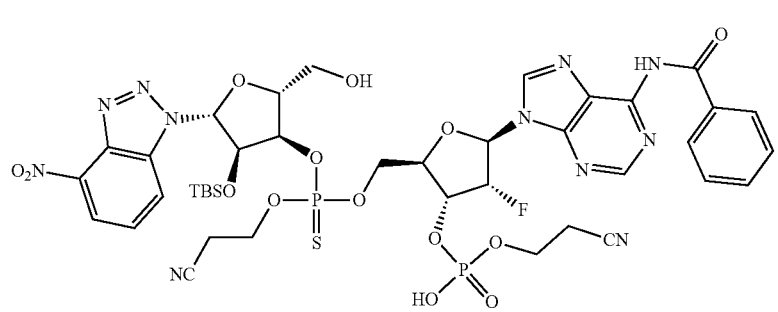

To a solution of crude Intermediate 13D in acetone (2 mL) was added sodium iodide (0.21 g, 1.39 mmol). The mixture was stirred at 50° C. for 2 hrs. The mixture was then concentrated to dryness and the residue was purified by silica gel column chromatography, eluting with 0-40% MeOH in DCM to give Intermediate 13E (200 mg, 69% yield, three steps). LCMS (ES, m/z): 1048.4 [M+H]+.

Preparation of Intermediate 13F

13F

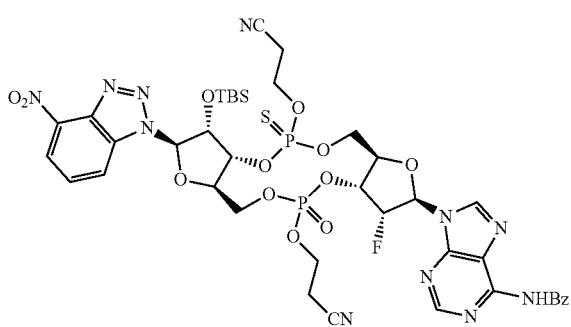

To a solution of 1-(mesitylsulfonyl)-3-nitro-1H-1,2,4-triazole (283 mg, 0.95 mmol) in pyridine (5 mL) was added a Intermediate 13F (146 mg) was dissolved in 7 N ammonia/MeOH (3 mL) and then heated at 50° C. for 10 h. The mixture was concentrated to dryness under a stream of nitrogen. The resulting solid was suspended in triethylamine trihydrofluoride (0.5 mL) and heated at 37° C. for 2 h. To the reaction was added 2M ammonia acetate solution (2 mL) and stirring was continued for 20 min. The mixture was then filtered and purified by Preparative HPLC chromatography (Conditions: Column: Xselect RP Prep C18 OBD, Column, 5 μm, 19×150 mm, Flow rate: 20.0 mL/min, Mobile Phase: A: 100 mM NH4OAc (pH 4.7); B: Acetonitrile) to provide two stereoisomers: Example 13-1 (9.3 mg, 14.7% yield). m/z: 706.1 (M+H). $^1$H NMR (499 MHz, METHANOL-$d_4$) δ 8.85 (s, 1H), 8.54 (d, J=8.34 Hz, 1H), 8.32 (d, J=7.63 Hz, 1H), 8.26 (s, 1H), 7.75 (t, J=8.11 Hz, 1H), 6.55 (d, J=2.27 Hz, 1H), 6.42 (dd, J=16.47 Hz, 1H), 5.42 (br d, J=3.22 Hz, 1H), 5.28-5.36 (m, 6H), 5.13-5.25 (m, 1H), 5.01-5.12 (m, 2H), 4.39-4.59 (m, 3H), 4.32 (br d, J=11.56 Hz, 1H), 4.06-4.21 (m, 2H). Example 13-2 (8 mg, 12.0% yield). $^1$H NMR (499 MHz, METHANOL-$d_4$) δ 8.57 d, 1H), 8.51 (d, 1H), 8.31 (d, J=7.75 Hz, 1H), 8.22 (s, 1H), 7.74 (t, J=8.05 Hz, 1H), 6.55 (s, 1H), 6.43 (d, 1H), 5.51 (s, 2H), 5.46 (br s, 2H), 5.36 (br s, 3H), 5.20 (br s, 6H), 5.00-5.11 (m, 10H), 4.61 (br d, J=11.68 Hz, 20H), 4.42 (br d, J=10.61 Hz, 10H), 4.30 (br d, J=11.32 Hz, 5H), 4.01-4.18 (m, 9H). m/z: 706.1 (M+H).

Example 14

4-[(1R,6R,8S,9S,10S,15R,17R,18R)-17-(6-amino-9H-purin-9-yl)-18-fluoro-3,9-dihydroxy-3,12-dioxo-12-sulfanyl-2,4,7,11,13,16-hexaoxa-3λ⁵,12λ⁵-diphosphatricyclo[13.3.0.0⁶,¹⁰]octadecan-8-yl]pyridine-2-carboxamide

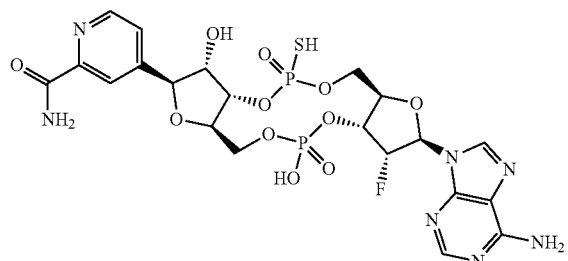

Preparation of Intermediate 14A

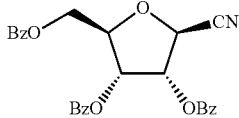

To a solution of (2S,3R,4R,5R)-2-acetoxy-5-((benzoyloxy)methyl) tetrahydrofuran-3,4-diyl dibenzoate (10 g, 19.82 mmol) in 30 mL of DCM under a nitrogen atmosphere, was added trimethylsilanecarbonitrile (3.47 mL, 27.8 mmol), followed by boron trifluoride diethyl etherate (2.45 mL, 19.82 mmol). The reaction mixture was stirred at room temperature for 14 hours. To this reaction mixture was added 100 mL of saturated aq. NaHCO₃ and stirring was continued at room temperature for 30 min. The mixture was extracted with EtOAc (100 mL×3). The combined organic layers were washed with brine, then dried over Na₂SO₄. The mixture was then concentrated in vacuo and the residue was purified on silica gel chromatography (80 g column, 0-50% EtOAc/Hexane) to give Intermediate 14A (7.56 g, 81% yield). ¹H NMR (499 MHz, CHLOROFORM-d) δ 8.17-8.09 (m, 2H), 8.04-7.90 (m, 4H), 7.63-7.55 (m, 3H), 7.51-7.34 (m, 6H), 6.03 (dd, J=5.3, 4.5 Hz, 1H), 5.88 (t, J=5.5 Hz, 1H), 5.00 (d, J=4.4 Hz, 1H), 4.81-4.72 (m, 2H), 4.64 (d, J=8.4 Hz, 1H).

Preparation of Intermediate 14B

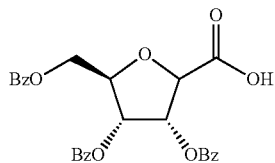

To a solution of Intermediate 14A (15 g, 31.8 mmol) in AcOH (40 mL) was added hydrogen chloride (5.30 mL, 63.6 mmol). The reaction mixture was heated to 120° C. for 40 min. The mixture was then concentrated to dryness and then purified by silica gel chromatography (120 g column, 0-60% EtOAc/hexane) to give Intermediate 14B (12.6 g, 25.7 mmol, 81% yield). Retention Time=0.73 min (H₂O/MeOH with 0.05% TFA, Shimadzu HPLC Xterra-S5-C18 4.6×50 mm, gradient=4 min, wavelength=220 nm); MS (ES): m/z=490 [M+H]⁺.

Preparation of Intermediate 14C

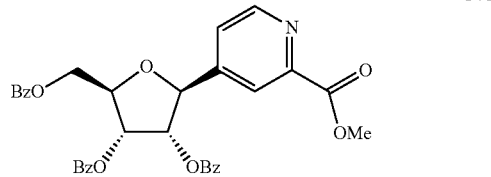

(4,4'-Di-t-butyl-2,2'-bipyridine)bis[3,5-difluoro-2-[5-trifluoromethyl-2-pyridinyl-kappaN)phenyl-kappaC]iridium (III) hexafluorophosphate (0.24 g, 0.24 mmol), nickel (II) chloride ethylene glycol dimethylether complex (0.260 g, 1.19 mmol), and 4,4'-di-tert-butyl-2,2'-bipyridine (0.32 g, 1.19 mmol) were added to a 50 mL vial equipped with a magnetic stir bar. Then, Intermediate 14B (5.81 g, 11.85 mmol) was added, followed by methyl 4-bromopicolinate (3.07 g, 14.22 mmol), and Cs₂CO₃ (6.18 g, 18.95 mmol). The vial was then placed under nitrogen and dry DMA (118 mL) was added. The solution was then degassed for 15 minutes with nitrogen. The vial was then sealed and the cap was wrapped in parafilm. The vial was placed approximately 8 cm from a 34 W Blue LED, with the LED shining directly at the side of the vial. The reaction was then stirred for 72 hours. The crude reaction mixture was then poured into a mixture of water (100 mL) and ethyl acetate (100 mL). The water layer was extracted 3 times with ethyl acetate, and then the combined organic layers were washed with water, dried with Na₂SO₄, and concentrated. The product was then purified by column chromatography (120 g column, 0-80% EtOAc/Hex, 40 min) to provide Intermediate 14C (2.8 g, 4.81 mmol, 41% yield). ¹H NMR (499 MHz, CHLOROFORM-d) δ 8.66 (dd, J=0.61, 5.02 Hz, 1H), 8.29 (s, 1H), 7.93-8.07 (m, 6H), 7.65 (d, J=5.13 Hz, 1H), 7.49-7.56 (m, 3H), 7.28-7.41 (m, 6H), 5.74 (t, J=5.33 Hz, 1H), 5.54 (t, J=5.71 Hz, 1H), 5.38 (d, J=5.94 Hz, 1H), 4.91 (dd, J=3.04, 12.17 Hz, 1H), 4.79 (td, J=3.39, 5.10 Hz, 1H), 4.70 (dd, J=3.65, 12.17 Hz, 1H), 1.21 (t, J=7.15 Hz, 1H).

Preparation of Intermediate 14D

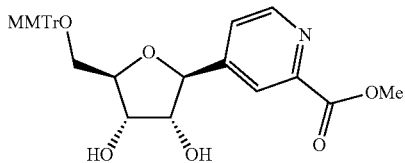

To Intermediate 14C (2.7 g, 4.59 mmol) was added 20 mL of dry MeOH and 6 mL of sodium methoxide (5.96 mL, 2.98 mmol). The mixture was stirred for 14 hours and then neutralized with Dowex 50W-X$_8$ H+ resin. The mixture was filtrated and washed with MeOH and then the filtrate was concentrated to dryness. To a solution of the crude intermediate in pyridine (20 mL) was added (chloro(4-methoxyphenyl)methylene) dibenzene (1.67 g, 4.70 mmol) in DCM (5 mL) slowly at 0° C. The mixture was then stirred at room temperature overnight. The solvent was then removed and the residue was poured into a mixture of water (100 mL) and ethyl acetate (100 mL). The water layer was extracted 3 times with ethyl acetate, and then the combined organic layers were washed with brine, dried with Na$_2$SO$_4$, and concentrated. The crude reaction was then purified by column chromatography (40 g column, 0-10% MeOH/DCM) to provide Intermediate 14D. (1.1 g, 45% yield). $^1$H NMR (499 MHz, CHLOROFORM-d) δ 8.69 (d, J=4.71 Hz, 1H), 8.32 (s, 1H), 7.67 (d, J=4.93 Hz, 1H), 7.41-7.51 (m, 3H), 7.22-7.38 (m, 9H), 6.87 (s, 1H), 6.85 (s, 1H), 4.87 (d, J=6.79 Hz, 1H), 4.07-4.27 (m, 3H), 4.02 (s, 1H), 3.93 (s, 2H), 3.80-3.84 (m, 3H), 3.55 (t, J=1.00 Hz, 1H), 3.52 (d, J=3.34 Hz, 1H), 3.38 (br d, J=3.55 Hz, 1H).

Preparation of Intermediates 14E and 14F

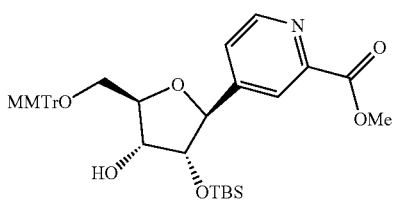

14E

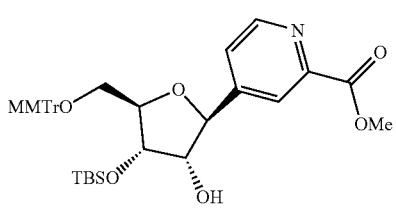

14F

To a solution of Intermediate 14D (1.1 g, 2.03 mmol) and imidazole (0.42 g, 6.09 mmol) in DCM was slowly added TBS-Cl (0.337 g, 2.234 mmol). The mixture was stirred for 5 hours and then 5 mL of MeOH was added into the reaction mixture. The mixture was stirred for 1 hour and then evaporated to dryness. The crude material was directly purified by silica chromatography (40 g column, 0-100% EtOAc/Hexane) to provide Intermediate 14E (445 mg, 0.678 mmol, 33.4% yield). $^1$H NMR (499 MHz, METHANOL-d$_4$) δ 8.67 (d, J=5.02 Hz, 1H), 8.49 (s, 1H), 7.75 (dd, J=1.05, 5.02 Hz, 1H), 7.42-7.55 (m, 4H), 7.22-7.40 (m, 8H), 6.86-6.93 (m, 2H), 4.90-4.92 (m, 1H), 4.25 (dd, J=5.02, 8.05 Hz, 1H), 4.19 (br d, J=2.19 Hz, 1H), 4.05-4.14 (m, 1H), 4.00 (s, 1H), 3.80-3.81 (m, 3H), 3.74-3.75 (m, 3H), 3.58 (dd, J=2.72, 10.56 Hz, 1H), 3.14-3.32 (m, 2H), 0.83-0.93 (m, 9H), −0.05--0.02 (m, 3H), −0.12--0.10 (m, 3H) and Intermediate 14F (418 mg, 0.637 mmol, 31.4% yield). $^1$H NMR (499 MHz, METHANOL-d$_4$) δ 8.66 (dd, J=0.63, 5.02 Hz, 1H), 8.49 (s, 1H), 7.78 (d, J=5.19 Hz, 1H), 7.43-7.54 (m, 4H), 7.22-7.39 (m, 8H), 6.89 (s, 1H), 6.88 (s, 1H), 4.89-4.92 (m, 1H), 4.07-4.21 (m, 3H), 3.90-4.05 (m, 1H), 3.79-3.81 (m, 3H), 3.75-3.78 (m, 2H), 3.58 (dd, J=2.87, 10.61 Hz, 1H), 3.13-3.32 (m, 1H), 0.88-0.88 (m, 1H), 0.86-0.88 (m, 8H), 0.17 (br d, J=11.50 Hz, 1H), 0.06-0.08 (m, 3H), −0.02-0.00 (m, 3H).

Preparation of Intermediate 14G

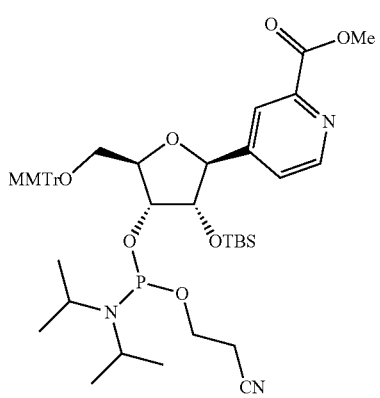

14G

To a solution of Intermediate 14E (445 mg, 0.68 mmol) in anhydrous DCM (10 mL) was added a 1.0 M solution of 1H-imidazole-4,5-dicarbonitrile (0.543 mL, 0.543 mmol) in acetonitrile, followed by the dropwise addition of 3-((bis (diisopropylamino) phosphanyl) oxy)propanenitrile (0.409 g, 1.36 mmol). After the addition was complete, the mixture was stirred at room temperature for 10 h. The mixture was quenched with MeOH (2 mL) and then diluted with 100 mL of DCM, washed with sat. aq. NaHCO$_3$, dried over MgSO$_4$, and then concentrated to dryness. The residue was purified by silica gel column chromatography (40 g column, 0-50% EtOAc/DCM/with 0.5% Et$_3$N) to afford Intermediate 14G (449 mg, 0.52 mmol, 77% yield).

Preparation of Intermediate 14H

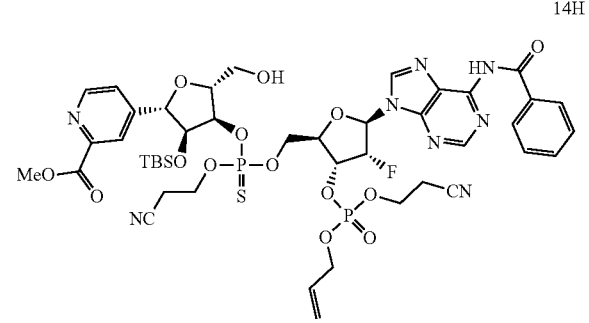 [SMILES: C=CCOP(=O)(OCCC#N)O[C@H]1[C@@H](F)[C@H](n2cnc3c(NC(=O)c4ccccc4)ncnc32)O[C@@H]1COP(=S)(OCCC#N)O[C@H]1[C@@H](O[Si](C)(C)C(C)(C)C)[C@H](c2ccnc(C(=O)OC)c2)O[C@@H]1CO]

14H

A mixture of Intermediate 13C (158 mg, 0.29 mmol) and 1H-tetrazole (92 mg, 1.31 mmol) in dry ACN (5 mL) was concentrated to dryness (repeated two times). Intermediate 14G (225 mg, 0.263 mmol) was dissolved in ACN (5 mL) and concentrated to dryness (repeated two times). Then, 3A molecular sieves (0.5 g) and acetonitrile (10 mL) were added to Intermediate 14B, and this solution was then added to Intermediate 13C in dry ACN (2 mL). The reaction was stirred at room temperature for 90 minutes and then (E)-N, N-dimethyl-N'-(3-thioxo-3H-1,2,4-dithiazol-5-yl)formimidamide (108 mg, 0.53 mmol) was added. The reaction was left stirring for 10 hours. The reaction was then filtered through celite and concentrated under reduced pressure. The residue was dissolved in DCM (5 mL) and then 2,2-dichloroacetic acid (0.130 mL, 1.58 mmol) was added dropwise. The reaction mixture was concentrated and then azeotroped with MeOH a few times. The crude product was purified by silica gel chromatography (12 g column, 0-20% MeOH/DCM, 15 min) to provide Intermediate 14H (70 mg, 25% yield), which was used directly in the next step. m/z 1061.4 (M+H).

Preparation of Intermediate 14I

14I

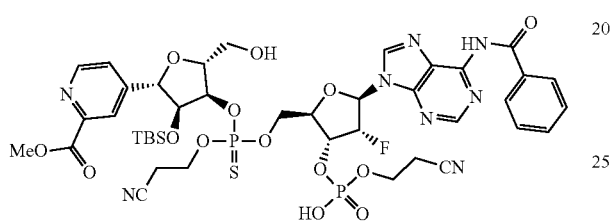

To a solution of Intermediate 14H (70 mg) in acetone (2 mL) was added sodium iodide (0.118 g, 0.79 mmol). The mixture was stirred at 50° C. for 2 hrs. The mixture was then concentrated to dryness and the residue was purified by silica gel column chromatography, eluting with 0-40% MeOH in DCM to give Intermediate 14I (30 mg, 44% yield). LCMS (ES, m/z): 1021.4 [M+H]+.

Preparation of Intermediate 14J

14J

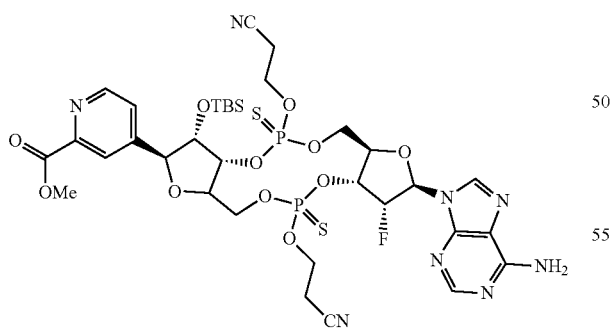

To a solution of 1-(mesitylsulfonyl)-3-nitro-1H-1,2,4-triazole (87 mg, 0.29 mmol) in pyridine (3 mL) was added a solution of Intermediate 14I (30 mg, 0.029 mmol) in pyridine (2 mL) dropwise. The mixture was stirred at room temperature overnight. The mixture was concentrated under reduced pressure and the residue was then purified by silica gel column chromatography eluting with 0-15% MeOH in DCM to give the product, Intermediate 14J (25 mg, 85%). LCMS (ES, m/z): 1003.4 [M+H]+.

Example 14

14

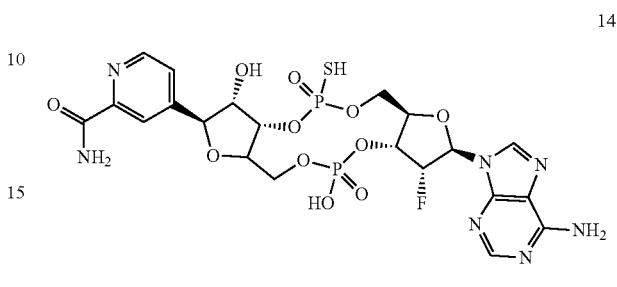

Intermediate 14J (25 mg) was dissolved in 7 N ammonia/MeOH (2 mL) and then heated at 50° C. for 10 h. The mixture was then concentrated to dryness under a stream of nitrogen. The resulting solid was suspended in triethylamine trihydrofluoride (0.5 mL) and heated at 37° C. for 2 h. To the reaction was then added 2M ammonium acetate solution (2 mL) and stirring was continued for 20 min. The mixture was then filtered and purified by Preparative HPLC chromatography (Conditions: Agilent Zorbax Eclipse Plus C18 Prep column, 5 μm, 21.2×250 mm, Flow rate: 20 mL/min, Mobile Phase: A: 100 mM NH4OAc (pH 6.5); B: Acetonitrile) to provide Example 14 (0.7 mg). m/z: 664.4 (M+H). $^1$H NMR (499 MHz, METHANOL-$d_4$) δ 8.59-8.62 (m, 1H), 8.47-8.52 (m, 1H), 8.24-8.30 (m, 1H), 8.06-8.11 (m, 1H), 7.85-7.90 (m, 1H), 6.36-6.42 (m, 1H), 5.30-5.46 (m, 1H), 4.96-5.00 (m, 3H), 4.56-4.64 (m, 2H), 4.31-4.43 (m, 2H), 4.18-4.28 (m, 2H), 4.03-4.13 (m, 2H).

Example 15

(1S,8R,9R,10S,15R,17R,18R)-8-(2-amino-6-oxo-6,9-dihydro-1H-purin-9-yl)-17-(6-amino-9H-purin-9-yl)-3,9,18-trihydroxy-12-sulfanyl-2,4,7,11,13,16-hexaoxa-3λ$^5$,12λ$^5$-diphosphatricyclo[13.3.0.0$^{6,10}$]octadecane-3,12-dione

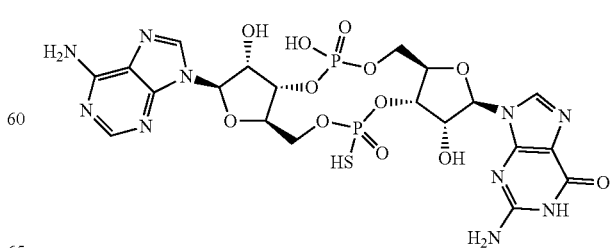

Step 1:

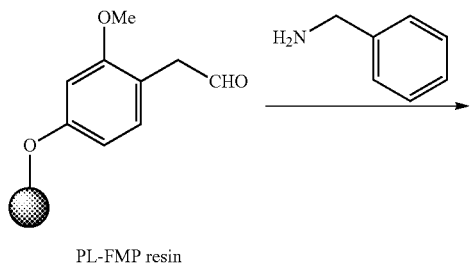

PL-FMP resin

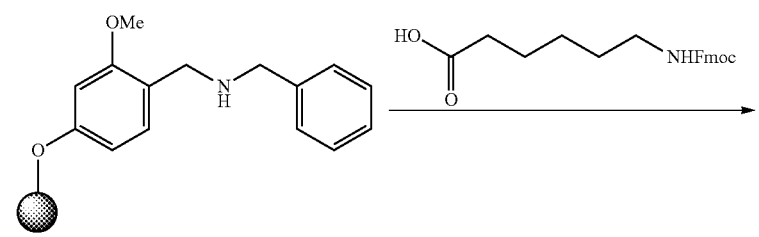

15A

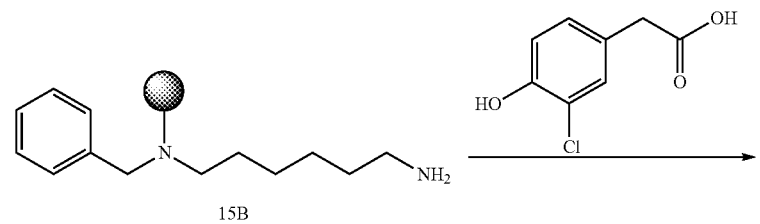

15B

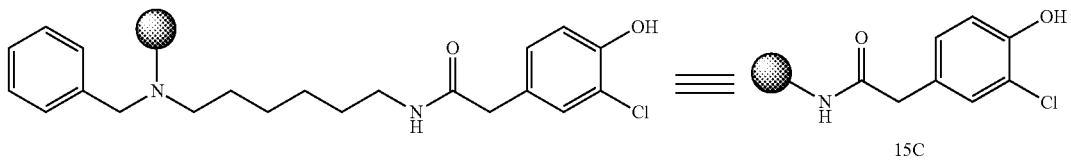

15C

PL-FMP resin (2-(4-Formyl-3-methoxyphenoxy)ethyl polystyrene, 85 g, 1.00 mmol/g loading, ~85 mmol, 100-200 mesh, Novabiochem) was swollen with ~600 mL DMF (N,N-dimethylformamide) at room temperature and then excess solvent was drained off. After an additional 400 mL of DMF was added, phenylmethanamine (21.43 g, 200 mmol), and acetic acid (18 mL, 9.43 mmol) (3%×600 mL=18.5 mL) were added into the reaction vessel. After 10 min of agitation, sodium triacetoxyborohydride (33.9 g, 160 mmol) was added. The reaction was allowed to agitate overnight. The resin was then washed with the following washing sequence: DMF (1×), then with THF/H$_2$O/AcOH (6:3:1), DMF, DCM (3×/each), three times with 5% Et$_3$N in DCM, and finally with MeOH before drying under vacuum at room temperature overnight to afford resin 15A (Loading: 0.87 mmol/g).

To a solution of 6-((((9H-fluoren-9-yl)methoxy)carbonyl) amino)hexanoic acid (14.40 g, 40.8 mmol) and HATU (15.49 g, 40.8 mmol) in DMF (60 mL) was added preswollen resin 15A (Loading: 0.87 mmol/g, 23.3 g of resin) and then DIEA (11.39 mL, 65.2 mmol). The mixture was stirred for 10 h. The resin batch was washed with the following washing sequence: DMF, DCM, DMF, MeOH, DCM, DMF (2× each). The resin was then treated with 20% piperidine in DMF (3×, 5 min/each). The resin was washed with DMF and then DCM (2×) and dried to give resin 15B. (0.76 mmol/g loading).

Resin 15B (16 mmol, 25 g, 0.76 mmol/g loading) was swollen with dry DMF (2×) under nitrogen, suspended in additional dry DMF (100 mL) and 2-(3-chloro-4-hydroxyphenyl)acetic acid (8956 mg, 48.0 mmol) and DIEA (13.97 mL, 80 mmol) were added. The mixture was stirred for a few minutes and then HATU (18.3 g, 48.0 mmol) was added and stirring was continued for 10 h. The resin batch was washed with the following washing sequence: DMF, DCM, THF, MeOH and THF. Then, the resin was treated with 20/40/40 mL of 1 N NaOH/MeOH/THF overnight. The resin was then washed with MeOH/water (2×), THF/water (2×), THF (2×), DCM (4×), Et$_2$O and then dried to afford resin 15C. (Loading: ~0.70 mmol/g).

Step 2

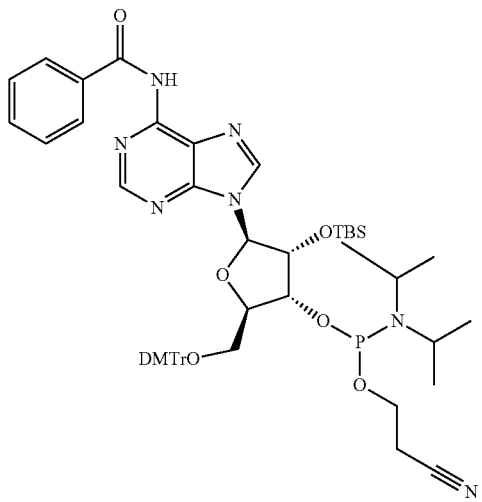

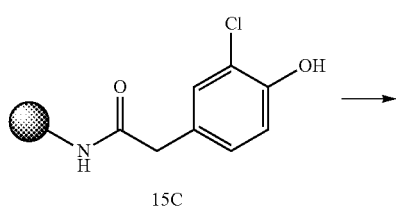

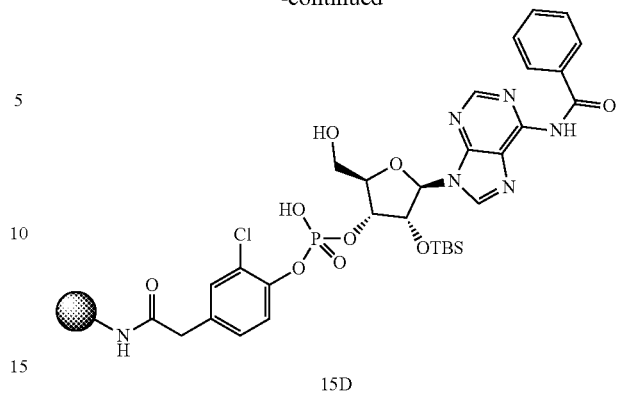

(2R,3R,4R,5R)-5-(6-benzamido-9H-purin-9-yl)-2-((bis (4-methoxyphenyl) (phenyl)methoxy)methyl)-4-((tert-butyldimethylsilyl)oxy)tetrahydrofuran-3-yl (2-cyanoethyl) diisopropylphosphoramidite (4.5 g, 4.55 mmol) was co-evaporated with dry actonitrile several times and then dissolved in DCM (23 mL). Under anhydrous conditions, resin 15C (3.5 mmol, 5 g resin, loading: 0.7 mmol/g) was swollen with dry acetonitrile (2×30 mL) under nitrogen, then the above solution of the phosphoramidite and 1H-tetrazole (1.23 g, 17.50 mmol) in dry acetonitrile (30 mL) were added. The reaction mixture was stirred at room temperature for 2 h, washed with dry DCM (3×) under nitrogen and anhydrous DCM (20 mL) was added. 2-Butanone peroxide (4.41 g, 21.00 mmol) was added and the mixture was stirred for 40 min. The resin was then washed with DCM (4×) and dried. The resin was capped by treatment with 1:1 Ac₂O/pyridine (10 mL) in DCM (20 mL) containing N-Me-imidazole (3 equivalents) for 30 min. The resin was then treated with 3% 2,2-dichloroacetic acid in DCM (3×5 min/each) to remove the DMTr group. The resin was washed with DCM (3×), MeCN (2×), DCM (2×) and anhydrous MeCN (2×). The resin was finally treated with Et₃N/pyridine. The support resin was then washed with DCM (3×), MeCN (2×), DCM (2×) and anhydrous MeCN (2×), and then dried under vacuum to provide resin 15D.

Step 3:

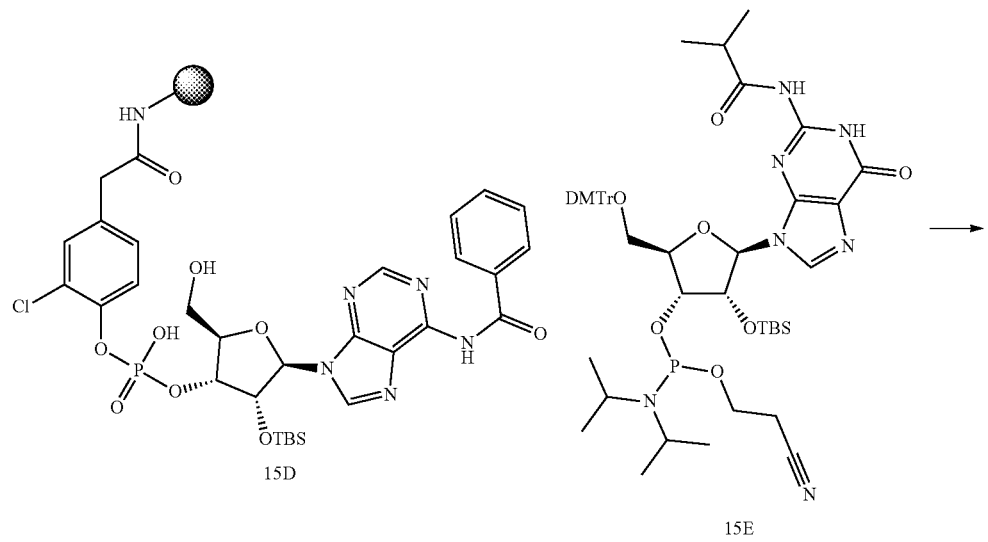

-continued

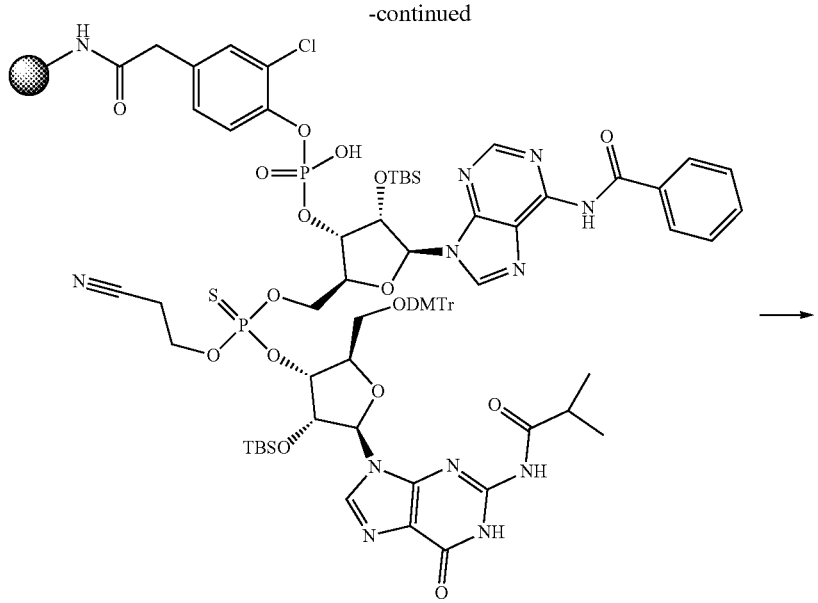

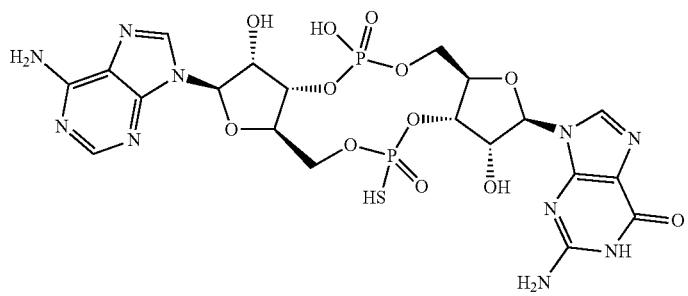

Example 15

Intermediate 15E (ARKPHARMINC, WO 02/18405 A2, 0.34 g, 0.35 mmol) was co-evaporated with dry acetonitrile several times and then dissolved in dry DCM (25 mL). Under anhydrous conditions, resin 15D (0.175 mmol) was swollen with dry acetonitrile (6 mL) twice under nitrogen. To the resin was added a solution of 1H-tetrazole (1.05 mmol) in anhydrous $CH_3CN$ (3 mL) and then the above solution of Intermediate 15E was added. The reaction mixture was stirred at room temperature for 3 h. The resin was washed with dry DCM (3×) under nitrogen, suspended in dry DCM (10 mL), and DDTT (0.52 mmol) was added. The reaction was stirred at RT for 40 min. The resin was then washed with DCM (2×), $CH_3CN$ (2×), DCM (3×) and $Et_2O$ (2×) and then dried under vacuum. The resin was then treated with a 1:1 $Ac_2O$/DIEA mixture (20 eq.) in DCM for 20 min, then washed with DCM (3×) and $CH_3CN$ (3×) and then treated with 3% 2,2-dichloroacetic acid in DCM (3×, each 10 min) to remove the DMTr group. The resin was then washed with DCM, DMF, DCM, $CH_3CN$ (3× each) and then dried under vacuum. The resin was then treated with a 0.1 M solution of MSNT (2×4 h, 1×12 h). The resin was then washed with DCM, pyridine, DCM, $CH_3CN$ (2× each) and then treated with TEA/pyridine (1:1) (3× for 1 h). Finally, the resin was washed with DCM, DMF, DCM, ACN (3× each) and then dried. The resin was then treated with $NH_4OH$ (33%)/MeOH (1:1 ratio, 8 mL) at 55° C. for 10 h. The solvent was removed and the residue was treated with triethylamine trihydrofluoride (0.35 mL, 2.15 mmol) at 37° C. for 3 h. The mixture was quenched with ammonium acetate (1.0 M, 2 mL), and the mixture was then stirred vigorously at 35° C. for 30 min. After cooling to room temperature, the solution was filtered, and the filtrate was purified via preparative LC/MS with the following conditions: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-25% B over 16 minutes, then a 4-minute hold at 100% B; Flow: 20 mL/min. Fractions containing the desired product were combined and dried via centrifugal evaporation to afford Example 15. LCMS, $[M+H]^-=691.1$. Retention time=1.9 min. (Column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min).

Example 16

(1S,6R,8R,9R,10S,15R,17R,18R)-8-(2-amino-6-oxo-6,9-dihydro-1H-purin-9-yl)-3,9,18-trihydroxy-17-{3H-imidazo[2,1-f]purin-3-yl}-12-sulfanyl-2,4,7,11,13,16-hexaoxa-3λ$^5$,12λ$^5$-diphosphatricyclo[13.3.0.0$^{6,10}$]octadecane-3,12-dione

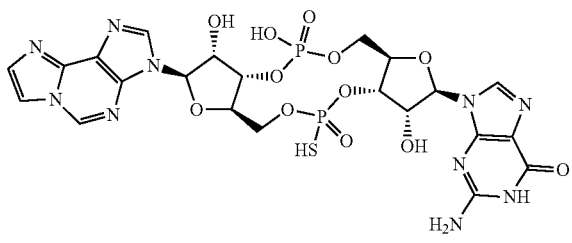 [SMILES: Nc1nc2c(ncn2[C@@H]2O[C@@H]3COP(=O)(O)O[C@H]4[C@@H](O)[C@H](n5cnc6c5ncn5ccnc65)O[C@@H]4COP(=O)(S)O[C@H]3[C@H]2O)c(=O)[nH]1]

Example 17

(1S,6R,8R,9R,10S,15R,17R,18R)-3,9,18-trihydroxy-17-{3H-imidazo[2,1-f]purin-3-yl}-8-{9-oxo-3H,4aH,5H,9H,9aH-imidazo[1,2-a]purin-3-yl}-12-sulfanyl-2,4,7,11,13,16-hexaoxa-3λ$^5$,12λ$^5$-diphosphatricyclo[13.3.0.0$^{6,10}$]octadecane-3,12-dione

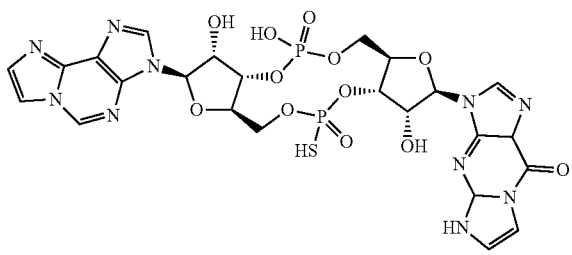 [SMILES: O=C1C2N=CN([C@@H]3O[C@@H]4COP(=O)(O)O[C@H]5[C@@H](O)[C@H](n6cnc7c6ncn6ccnc76)O[C@@H]5COP(=O)(S)O[C@H]4[C@H]3O)C2=NC2NC=CN12]

Example 15 (14.79 mg, 0.021 mmol) was dissolved in NaOAc/HOAc buffer (1 mL, pH=4.5) and 2-chloroacetaldehyde (50% in water, 0.321 mmol) was added and the mixture was stirred at room temperature for 48 hours. The crude material was purified via preparative LC/MS with the following conditions: Column: Agilent Bonus RP, 200 mm×21.2 mm, 5-µm particles; Mobile Phase A: 5:95 acetonitrile:water with 20-mM ammonium acetate; Mobile Phase B: 95:5 acetonitrile:water with 20-mM ammonium acetate; Gradient: a 6-minute hold at 0% B, 0-25% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford Example 16 (1.6 mg). LC/MS, m/z 714.9 (M+1). Retention time: 2.07 min, LC/MS (Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection). Also isolated was Example 17 (0.8 mg). LC/MS, m/z 738.0 (M+1). Retention time: 1.96 min. (Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection)

Example 18

(1S,6R,8R,9R,10S,15R,17R,18R)-3,9,12,18-tetrahydroxy-8-{3H-imidazo[2,1-f]purin-3-yl}-17-(6-oxo-6,9-dihydro-1H-purin-9-yl)-2,4,7,11,13,16-hexaoxa-3λ$^5$,12λ$^5$-diphosphatricyclo[13.3.0.0$^{6,10}$]octadecane-3,12-dione

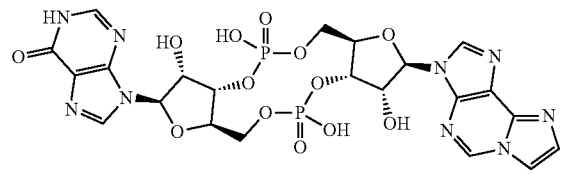 [SMILES: O=c1[nH]cnc2c1ncn2[C@@H]1O[C@@H]2COP(=O)(O)O[C@H]3[C@@H](O)[C@H](n4cnc5c4ncn4ccnc54)O[C@@H]3COP(=O)(O)O[C@H]2[C@H]1O]

(1S,6R,8R,9R,10S,15R,17R,18R)-8-(6-amino-9H-purin-9-yl)-3,9,12,18-tetrahydroxy-17-(6-oxo-6,9-dihydro-1H-purin-9-yl)-2,4,7,11,13,16-hexaoxa-3λ$^5$,12λ$^5$-diphosphatricyclo[13.3.0.0$^{6,10}$]octadecane-3,12-dione (J. Med Chem., 2016, 59, 10253) (8.3 mg, 0.013 mmol) was dissolved in NaOAc buffer (0.4 mL, pH=4.5). A 50% 2-chloroacetaldehyde solution in water (40 µL, 0.013 mmol) was added and the mixture was stirred at room temperature overnight. The crude material was purified via preparative LC/MS with the following conditions: Column: Agilent Bonus RP, 200 mm×21.2 mm, 5-µm particles; Mobile Phase A: 5:95 acetonitrile:water with 20-mM ammonium acetate; Mobile Phase B: 95:5 acetonitrile:water with 20-mM ammonium acetate; Gradient: a 6-minute hold at 0% B, 0-40% B over 20 minutes, then a 4-minute hold at 100% B; Flow Rate: 20 mL/min; Fractions containing the desired product were combined and dried to give Example 18. HPLC retention time=1.89 min (Agilent Bonus RP, 2.1 mm×50 mm, 1.8 µm particles; Mobile Phase A: water with 20 mM ammonium acetate; Mobile Phase B: acetonitrile. Gradient: 0% B hold 1 min, then 0% B to 100% B over 4 min, then a 0.75 min hold at 100% B; Flow: 1 mL/min; Detection: MS and UV (220 nm)), MS (ES): m/z=684[M+H]$^+$.

Example 19

(1S,6R,8R,9R,10S,15R,17R,18R)-3,9,12,18-tetrahydroxy-8,17-bis({3H-imidazo[2,1-f]purin-3-yl})-2,4,7,11,13,16-hexaoxa-3λ$^5$,12λ$^5$-diphosphatricyclo[13.3.0.0$^{6,10}$]octadecane-3,12-dione

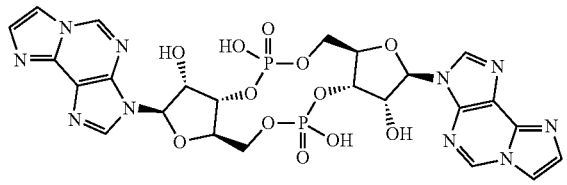 [SMILES: O=P1(O)OC[C@H]2O[C@@H](n3cnc4c3ncn3ccnc43)[C@H](O)[C@@H]2OP(=O)(O)OC[C@H]2O[C@@H](n3cnc4c3ncn3ccnc43)[C@H](O)[C@@H]2O1]

(1S,6R,8R,9R,10S,15R,17R,18R)-8,17-bis(6-amino-9H-purin-9-yl)-3,9,12,18-tetrahydroxy-2,4,7,11,13,16-hexaoxa-3lambda5,12lambda5-diphosphatricyclo[13.3.0.0$^{6,10}$]octadecane-3,12-dione (*Synthesis*, 2006, 24, 4230) (15 mg, 0.023 mmol) was dissolved in NaOAc buffer (1.5 mL, pH=4.5). A 50% 2-chloroacetaldehyde solution in water (0.5 mL, 0.58 mmol) was added and the mixture was stirred at room temperature overnight. The crude material was purified via preparative LC/MS with the following conditions: Column: Agilent Bonus RP, 200 mm×21.2 mm, 5-μm particles; Mobile Phase A: 5:95 acetonitrile:water with 20-mM ammonium acetate; Mobile Phase B: 95:5 acetonitrile:water with 20-mM ammonium acetate; Gradient: a 6-minute hold at 0% B, 0-40% B over 20 minutes, then a 4-minute hold at 100% B; Flow Rate: 20 mL/min; Fractions containing the desired product were combined and dried to give Example 19. HPLC retention time=1.98 min (Agilent Bonus RP, 2.1 mm×50 mm, 1.8 μm particles; Mobile Phase A: water with 20 mM ammonium acetate; Mobile Phase B: acetonitrile. Gradient: 0% B hold 1 min, then 0% B to 100% B over 4 min, then a 0.75 min hold at 100% B; Flow: 1 mL/min; Detection: MS and UV (220 nm)), MS (ES): m/z=707[M+H]⁺.

Example 20

(1R,6R,8R,9R,10S,15R,17R,18R)-8-(6-amino-9H-purin-9-yl)-18-fluoro-3,9,12-trihydroxy-17-{3H-imidazo[2,1-f]purin-3-yl}-2,4,7,11,13,16-hexaoxa-3λ⁵,12λ⁵-diphosphatricyclo[13.3.0.0⁶,¹⁰]octadecane-3,12-dione

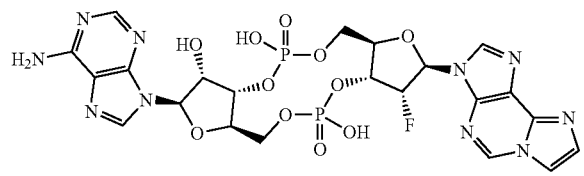 [SMILES: Nc1ncnc2c1ncn2[C@@H]1O[C@@H]2COP(=O)(O)O[C@H]3[C@@H](F)[C@H](n4cnc5c4ncn4ccnc54)O[C@@H]3COP(=O)(O)O[C@H]2[C@H]1O]

Preparation of Intermediate 20A

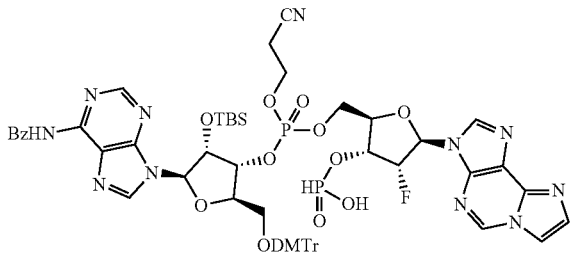

20A (2R,3R,4R,5R)-5-(6-benzamido-9H-purin-9-yl)-2-((bis(4-methoxyphenyl) (phenyl)methoxy)methyl)-4-((tert-butyldimethylsilyl)oxy)tetrahydrofuran-3-yl (2-cyanoethyl) diisopropylphosphoramidite (Organic Process Research & Development 2000, 4, 175-181) (360 mg, 0.364 mmol) was co-evaporated with acetonitrile (10 mL) three times, the last time approximately 3 mL of solvent was left. To the solution was added 4 Å molecular sieves (10 pieces). Intermediate 3D (100 mg, 0.28 mmol) was dissolved in DMF (4 mL) and ACN (4 mL) was added. The mixture was concentrated to remove most of the ACN. Then, 4 Å molecular sieves (100 mg) was added and the mixture was stirred for 10 min. To the mixture was added the above dried (2R,3R,4R,5R)-5-(6-benzamido-9H-purin-9-yl)-2-((bis(4-methoxyphenyl) (phenyl) methoxy)methyl)-4-((tert-butyldimethylsilyl)oxy) tetrahydrofuran-3-yl (2-cyanoethyl) diisopropylphosphoramidite via cannula, and the mixture was stirred for 30 min. 1H-tetrazole (58.8 mg, 0.84 mmol) was added, and the mixture was sonicated and stirred for 1 h, then 2-butanone peroxide (111 μL, 0.560 mmol) was added and stirring was continued for 30 min. The reaction mixture was filtered and the filtrate was concentrated to a volume of ~5 mL. The solution was directly loaded onto a C18 column (50 g, ISCO Gold, eluted with 0-95% ACN in aqueous NH₄OAc) to give Intermediate 20A (105 mg, 30% yield). HPLC retention time=0.93 min (H₂O/ACN with 0.05% TFA, Waters Acquity HPLC BEH C18, 2.1×50 mm, 1.7-μm particles, gradient=2 min, wavelength=220 nm); MS (ES): m/z=1260 [M+H]⁺.

Preparation of Intermediate 20B

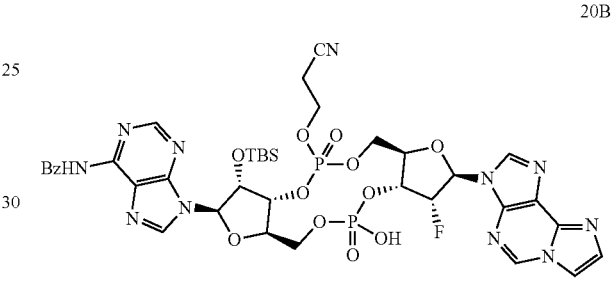

20B

To a solution of Intermediate 20A (105 mg, 0.083 mmol) in DCM (2 mL) was added triethylsilane (0.080 mL, 0.500 mmol), followed by 2,2-dichloroacetic acid (0.021 mL, 0.25 mmol). The mixture was stirred at room temperature for 1 h, and then pyridine (3 mL) was added and the mixture was concentrated. The residue was co-evaporated with pyridine (3×20 mL), the last time leaving approximately 15 mL of the solvent. To this solution was added 2-chloro-5,5-dimethyl-1,3,2-dioxaphosphorinane 2-oxide (76 mg, 0.410 mmol), and the reaction was stirred for 8 min, and then water (0.052 mL, 2.87 mmol) was added, immediately followed by iodine (62.4 mg, 0.246 mmol). The reaction was stirred for 30 min, and then quenched with a solution of sodium bisulfite (42.6 mg, 0.410 mmol) in water (3 mL) and then concentrated. The residue was purified by reverse phase (C18) chromatography and eluted with 5-95% ACN in aq. 10 mM NH₄OAc to give Intermediate 20B (47 mg, 60%). HPLC retention time=0.75 min (H₂O/ACN with 0.05% TFA, Waters Acquity HPLC BEH C18, 2.1×50 mm, 1.7-μm particles, gradient=2 min, wavelength=220 nm); MS (ES): m/z=956 [M+H]⁺.

Example 20

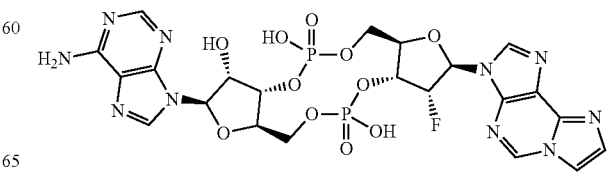

Intermediate 20B (47 mg, 0.049 mmol) was treated with 33% MeNH₂ in EtOH (3 mL) and stirred for 3 h. The reaction mixture was concentrated to dryness, and the residue was treated with TEA·3HF (1 mL), heated to 50° C. for 3.5 h and then cooled to room temperature. The reaction was neutralized with 1M NH₄HCO₃. The solution was purified by preparative LC/MS with the following conditions: Column: Agilent Bonus RP 21.2×100 mm, 5-µm particles; Mobile Phase A: water with 20-mM ammonium acetate; Mobile Phase B: acetonitrile; Gradient: 0% B hold 0-6 minute. 0%-25% B over 16 minutes, then a 4-minute hold at 100% B; Flow: 20 mL/min. Fractions containing the desired product were combined and dried to give Example 20. HPLC retention time=1.96 min (Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm)) MS (ES): m/z=685[M+H]⁺.

Example 21

(1R,6R,8R,9R,10R,15R,17R,18R)-8-(6-amino-9H-purin-9-yl)-9,18-difluoro-17-{3H-imidazo[2,1-f]purin-3-yl}-3,12-disulfanyl-2,4,7,11,13,16-hexaoxa-3λ⁵,12λ⁵-diphosphatricyclo[13.3.0.0⁶,¹⁰]octadecane-3,12-dione

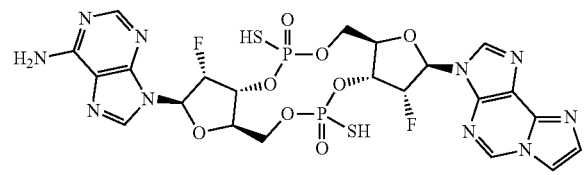 [SMILES: Nc1ncnc2c1ncn2[C@@H]1O[C@@H]2COP(=O)(O)O[C@H]3[C@@H](F)[C@H](n4cnc5c4ncn4ccnc54)O[C@@H]3COP(=O)(O)O[C@H]2[C@H]1O]

Diastereomer 1 (21-1)
Diastereomer 2 (21-2)
Diastereomer 3 (21-3)
Diastereomer 4 (21-4)

Preparation of Intermediate 21A

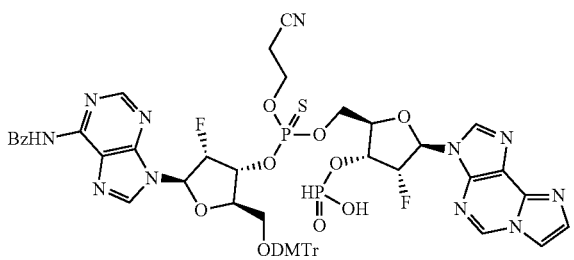

21

(2R,3R,4R,5R)-5-(6-benzamido-9H-purin-9-yl)-2-((bis(4-methoxyphenyl) (phenyl)methoxy)methyl)-4-fluorotetrahydrofuran-3-yl (2-cyanoethyl) diisopropylphosphoramidite (956 mg, 1.09 mmol) was co-evaporated with ACN (2×10 mL), and then dissolved in acetonitrile (10 mL) and concentrated to approximately 4 mL. Molecular sieves (4A) were added to the solution. In a separate flask, Intermediate 3D (300 mg, 0.84 mmol) was co-evaporated with ACN (2×10 mL). The residue was again taken up in acetonitrile (10 mL) and concentrated to approximately 4 mL. The above dried solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite was added via cannula to the mixture of Intermediate 3D. The resulting solution was sonicated and stirred for about 30 min, then (E)-N,N-dimethyl-N'-(3-thioxo-3H-1,2,4-dithiazol-5-yl)formimidamide (345 mg, 1.68 mmol) was added and stirring continued for 30 min. The mixture was then concentrated, and then treated with MeOH. The resulting solids were removed by filtration, and the filtrate was purified by C18 reverse phase chromatography (50 g Gold column, eluted with 5-95% ACN in aqueous NH₄OAc). The desired fractions were combined and lyophilized to give Intermediate 21A (280 mg, 28.6%). HPLC retention time=0.86 min and 0.88 min (H₂O/ACN with 0.05% TFA, Waters Acquity HPLC BEH C18, 2.1×50 mm, 1.7-µm particles, gradient=2 min, wavelength=220 nm); MS (ES): m/z=1164 [M+H]⁺.

Preparation of Intermediate 21B

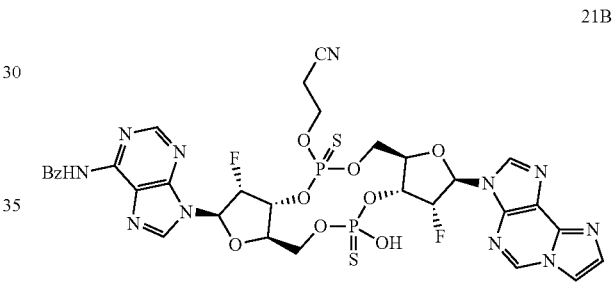

21B

To a solution of Intermediate 21A (280 mg, 0.241 mmol) in DCM (4 mL) was added two drops of water and triethylsilane (0.19 mL, 1.20 mmol), followed by 2,2-dichloroacetic acid (0.199 mL, 2.41 mmol), and the mixture was stirred at room temperature for 1.5 h. The reaction was then quenched with pyridine (3 mL), and then concentrated. The residue was co-evaporated with pyridine one time. The residue was then dissolved in 30 mL of pyridine and concentrated to a volume of about 20 mL. To the solution was then added 2-chloro-5,5-dimethyl-1,3,2-dioxaphosphinane 2-oxide (222 mg, 1.20 mmol). The mixture was stirred for 8 min, and then H₂O (0.15 mL, 8.42 mmol) was added followed immediately by (E)-N,N-dimethyl-N'-(3-thioxo-3H-1,2,4-dithiazol-5-yl)formimidamide (148 mg, 0.722 mmol). The mixture was stirred for 1 h, and then concentrated, and azeotroped with toluene to remove excess pyridine. The residue was purified by silica gel column chromatography (24 g, MeOH/DCM=0-30%, hold on 30% for 10 min) to give Intermediate 21B. HPLC retention time=0.66 min and 0.68 min (H₂O/ACN with 0.05% TFA, Waters Acquity HPLC BEH C18, 2.1×50 mm, 1.7-µm particles, gradient=2 min, wavelength=220 nm); MS (ES): m/z=876 [M+H]⁺.

Example 21

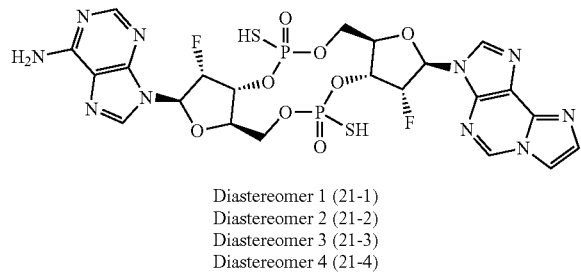 [SMILES: Nc1ncnc2c1ncn2[C@@H]1O[C@@H]2COP(=O)(S)O[C@H]3[C@@H](F)[C@H](n4cnc5c4ncn4ccnc54)O[C@@H]3COP(=O)(S)O[C@H]2[C@H]1F]

Diastereomer 1 (21-1)
Diastereomer 2 (21-2)
Diastereomer 3 (21-3)
Diastereomer 4 (21-4)

Intermediate 21B was treated with MeOH (10 mL) and conc. NH$_4$OH (15 mL). The solution was stirred at room temperature for 5 h and then concentrated. The crude material was purified via preparative LC/MS with the following conditions: Column: Agilent Bonus RP 21.2×100 mm, 5-µm particles; Mobile Phase A: water with 20-mM ammonium acetate; Mobile Phase B: acetonitrile; Gradient: 0% B hold 0-6 minute. 0%-40% B over 20 minutes, then a 4-minute hold at 100% B; Flow: 20 mL/min. Fractions containing the desired product were combined and dried. Four isomers were obtained.

Example 21-1: 2.4 mg, HPLC Retention time=2.61 min (Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm)) MS (ES): m/z=719[M+H]$^+$.

Example 21-2: 32.4 mg, HPLC Retention time=2.73 min (Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm)) MS (ES): m/z=719[M+H]$^+$.

Example 21-3: 3.9 mg, HPLC Retention time=2.77 min (Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm)) MS (ES): m/z=719[M+H]$^+$.

Example 21-4: 27.5 mg, HPLC Retention time=2.97 min (Agilent Bonus RP, 2.1 mm×50 mm, 1.8 µm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm)) MS (ES): m/z=719[M+H]$^+$.

Evaluation of Biological Activity

STING THP1 Reporter Assay Protocol

THP1-Dual™ cells were derived from the human THP-1 monocyte cell line by stable integration of two inducible reporter constructs. To this end, THP1-Dual™ cells allow the simultaneous study of the NF-κB pathway, by monitoring the activity of SEAP, and the IRF pathway by assessing the activity of a secreted luciferase (Lucia). Both reporter proteins are readily measurable in the cell culture supernatant when using QUANTI-Blue™, a SEAP detection reagent, and QUANTI-Luc™, a luciferase detection reagent.

THP1-Dual™ cells induce the activation of NF-κB in response to STING agonists. They also trigger the IRF pathway upon stimulation with STING agonists, such as cGAMP. Here, the THP-1-Dual cells were used to assess STING binders for function on the cellular level.

Serial dilutions of compounds in DMSO were added to low volume 384 well plates at 100 nl/well using an ECHO acoustic dispenser (Labcyte, model 550) to achieve final starting concentration of 100 µM in cell suspension. THP-1 Dual™ STING reporter cells (Invivogen, Dual cells cat #THPD-nfis) were added to the plates with compounds at 15,000 cells in 10 µL per well in RPMI media (Gibco, cat #11875) containing 10% human plasma in a low volume 384-well black wall clear bottom tissue culture plate (Corning, cat #3542) for SEAP assay and low volume solid white plate (Corning, cat #3826) for luciferase assay. One column of the plate was reserved for treatment with cGAMP at 100 µM for 100% activation calculation and one column for no treatment (DMSO only) for baseline activation. Plates were then incubated in 37° C. incubator at 5% CO$_2$ for 20 hours.

In the SEAP assay, 5 µl of 2× QuantiBlue (Invivogen, cat #Rep-qb2) is added to 384 well black plates seeded with THP1 cells and incubated at 37° C. for 2 hours. Plates were read on the Envision (Perkin Elmer) at 620 nm wavelength (OD620). In the luciferase assay, 5 µl of Quantiluc (Invivogen, Rep-qlc2) is added to white 384 well plates seeded with THP1 cells and read at 5 minutes on the Envision (Perkin Elmer) using a luminescence protocol (RLU). For both cell lines, 100% activation was determined by value (RLU) of THP-1 Dual STING cells stimulated with 100 µM cGAMP (Invivogen, cat #TLRL-NACGA23-5).

STING HTRF Binding Assays

A time resolved FRET-based competition binding assay was used to assess test article binding to STING WT and STING AQ. His-tagged STING cytoplasmic domain (WT or AQ) at a concentration of 20 nM was incubated with 2.5 nM Tb-labeled anti-His antibody, test compound, and fluorescein-labeled cGAMP analog probe (BioLog cat. no. C195) at a concentration of 200 nM (STING WT) or 40 nM (STING AQ) in PBS containing 0.005% Tween-20 and 0.1% BSA for one hour. Fluorescence at 495 nm and 520 nm was measured using an EnVision microplate reader to quantify FRET between Tb-labeled anti-His antibody and fluorescein-labeled probe. Background was defined as the signal obtained in the absence of STING protein, and background subtracted FRET ratios were normalized to the maximum signal obtained in the absence of test compound. These values were converted to a percent inhibition. Percent inhibition was determined for test compounds at 11 concentrations. The IC$_{50}$, defined as the concentration of competing test compound needed to reduce specific binding of the probe by 50%, was calculated using the 4 parameter logistic equation to fit the data

```
STING WT: His-TVMV-S-hSTING(155-341)-H232R
                                    (SEQ ID NO: 1)
MGSSHHHHHHSSGETVRFQGHMSVAHGLAWSYYIGYLRLILPELQARIRTY

NQHYNNLLRGAVSQRLYILLPLDCGVPDNLSMADPNIRFLDKLPQQTGDRA

GIKDRVYSNSIYELLENGQRAGTCVLEYATPLQTLFAMSQYSQAGFSREDR
```

LEQAKLFCRTLEDILADAPESQNNCRLIAYQEPADDSSFSLSQEVLRHLRQ
EEKEEV

STING AQ: His-TVMV-S-hSTING(155-341)-G230A-R293Q
(SEQ ID NO: 2)
MGSSHHHHHHSSGETVRFQGHMSVAHGLAWSYYIGYLRLILPELQARIRTY

NQHYNNLLRGAVSQRLYILLPLDCGVPDNLSMADPNIRFLDKLPQQTADRA

GIKDRVYSNSIYELLENGQRAGTCVLEYATPLQTLFAMSQYSQAGFSREDR

LEQAKLFCQTLEDILADAPESQNNCRLIAYQEPADDSSFSLSQEVLRHLRQ

EEKEEV

| Example # | THP1 Reporter Assays EC$_{50}$ (μM) | | HTRF Binding Assays IC$_{50}$ (μM) | |
|---|---|---|---|---|
| | IRF3 | NFkB | STING WT | STING AQ |
| Example 1-1 | 0.38 | 0.94 | 0.02 | 0.01 |
| Example 1-2 | 2.69 | 5.35 | 0.07 | 0.01 |
| Example 2 | 2.36 | 4.38 | 0.04 | 0.01 |
| Example 3 | 5.76 | 24.38 | 0.04 | 0.02 |
| Example 4-1 | >100 | >100 | >100 | 17.75 |
| Example 4-2 | >100 | >100 | 8.10 | 0.24 |
| Example 4-3 | >100 | >100 | 11.97 | 0.39 |
| Example 4-4 | 81.08 | 92.38 | 0.78 | 0.02 |
| Example 5 | 0.49 | 1.35 | 0.004 | 0.001 |
| Example 6-1 | >100 | >100 | 5.58 | 1.32 |
| Example 6-2 | >100 | >100 | 88.56 | 5.75 |
| Example 6-3 | >100 | >100 | >100 | 16.16 |
| Example 6-4 | >100 | >100 | 3.03 | 0.19 |
| Example 7 | >100 | >100 | 11.94 | 0.31 |
| Example 8-1 | >100 | >100 | 64.63 | 1.75 |
| Example 8-2 | >100 | >100 | 2.23 | 0.07 |
| Example 9 | >100 | >100 | 84.14 | 0.42 |
| Example 10-1 | >100 | >100 | 2.50 | 0.04 |
| Example 10-2 | 3.69 | 8.99 | 0.05 | 0.00 |
| Example 11 | 8.35 | 15.95 | 0.23 | 0.00 |
| Example 12-1 | 8.20 | 65.88 | 0.56 | 0.04 |
| Example 12-2 | 0.20 | 2.64 | 0.01 | 0.002 |
| Example 12-3 | 0.27 | 2.65 | 0.02 | 0.003 |
| Example 12-4 | 0.06 | 1.09 | 0.002 | 0.005 |
| Example 13-1 | >100 | >100 | 8.45 | 1.44 |
| Example 13-2 | >100 | >100 | 5.49 | 0.45 |
| Example 14 | >100 | >100 | >100 | 1.14 |
| Example 15 | >100 | >100 | 9.55 | 0.83 |
| Example 16 | >100 | >100 | 96.01 | 5.65 |
| Example 17 | >100 | >100 | >100 | 31.71 |
| Example 18 | >100 | >100 | 25.30 | 0.49 |
| Example 19 | >100 | >100 | 28.57 | 0.65 |
| Example 20 | 3.71 | 13.58 | 0.04 | 0.01 |
| Example 21-1 | 28.17 | 34.56 | 0.32 | 0.01 |
| Example 21-2 | 0.13 | 0.56 | 0.02 | 0.01 |
| Example 21-3 | 0.14 | 0.53 | 0.02 | 0.01 |
| Example 21-4 | 0.28 | 0.67 | 0.01 | 0.01 |

We claim:

1. A compound of the formula

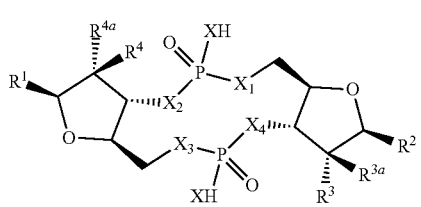

wherein

X is S;

$X_1$, $X_2$, $X_3$ and $X_4$ are each independently O or NH;

$R^1$ and $R^2$ are independently

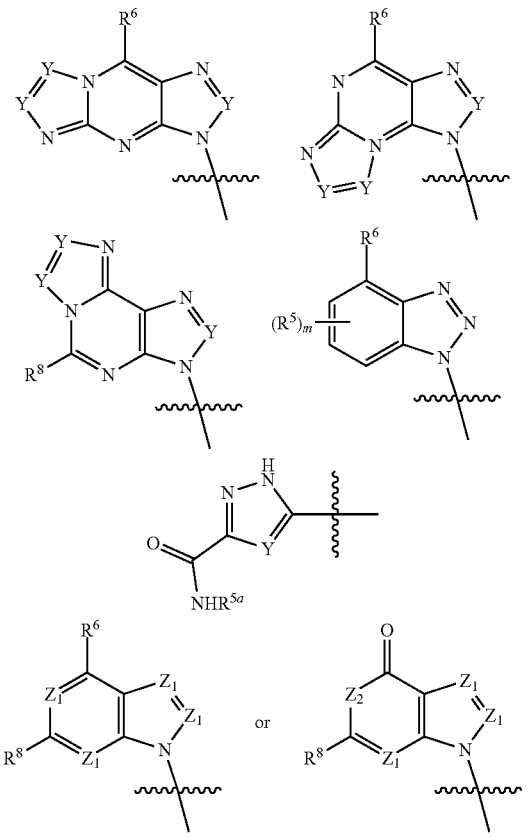

with the proviso that one of $R^1$ and $R^2$ must be

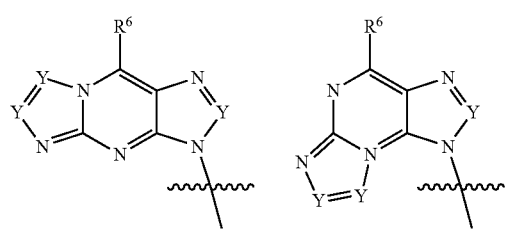

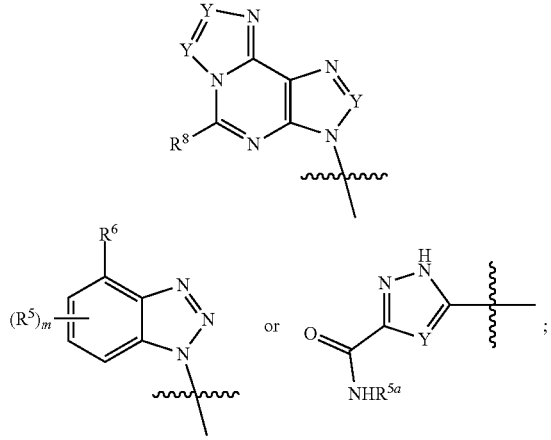

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=$CH_2$ substituent;

$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

or a pharmaceutically acceptable salt, tautomer or stereoisomer thereof.

2. The compound according to claim 1 of the formula

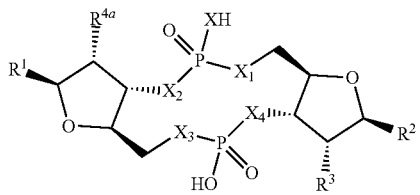

wherein

X is S;

$X^1$, $X^2$, $X^3$ and $X^4$ are each independently O or NH;

$R^1$ and $R^2$ are independently

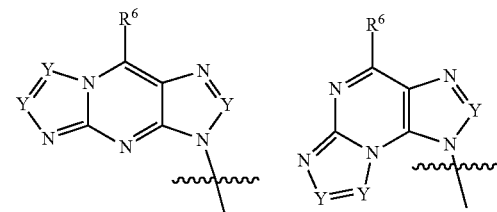

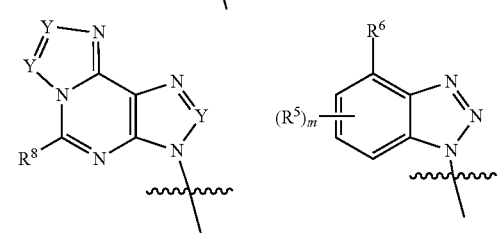

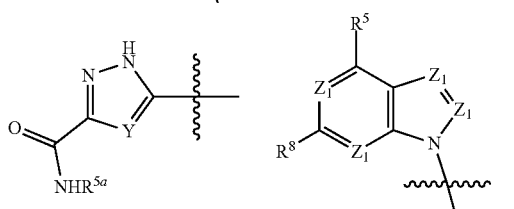

with the proviso that one of $R^1$ and $R^2$ must be

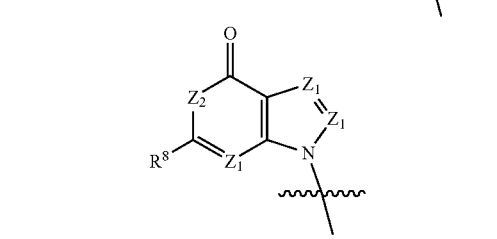

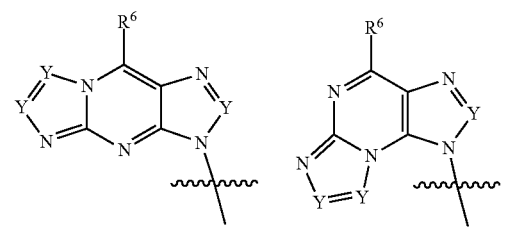

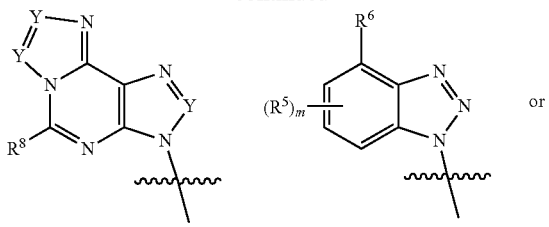

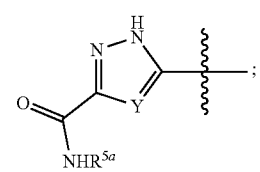

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl substituted with 0-6 $R^5$;

$R^3$ and $R^{4a}$ are independently H, $CH_3$, halogen, $NH_2$ or OH;

$R^5$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

or a pharmaceutically acceptable salt, tautomer or stereoisomer thereof.

3. The compound according to claim 1 of the formula

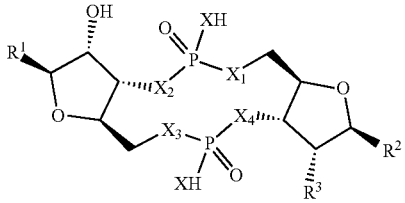
(I)

wherein
X is S;
$X^1$, $X^2$, $X^3$ and $X^4$ are each independently O or NH;
$R^1$ and $R^2$ are independently

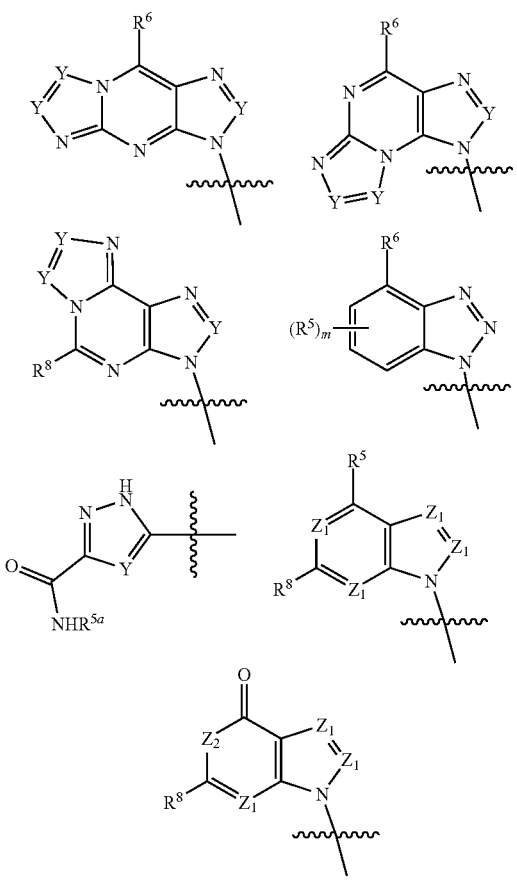

with the proviso that one of $R^1$ and $R^2$ must be

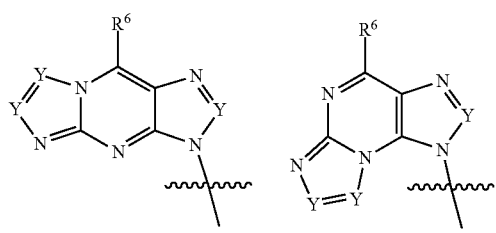

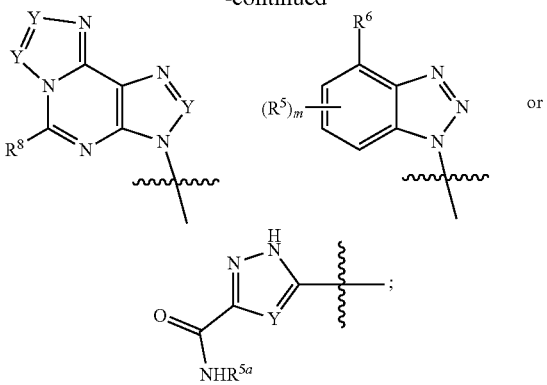

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H or $C_{1-3}$ alkyl substituted with 0-6 $R^5$;
$R^5$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl substituted with 0-6 $R^5$;
$R^6$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
Y is $CR^5$ or N;
or a pharmaceutically acceptable salt, tautomer or stereoisomer thereof.

4. A compound of the formula

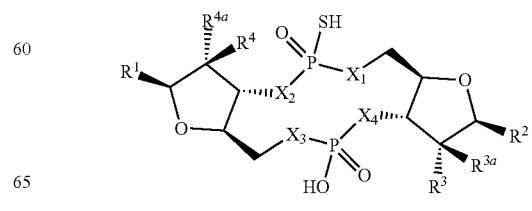

wherein

X₁, X₂, X₃ and X₄ are each independently O or NH;

R¹ and R² are independently

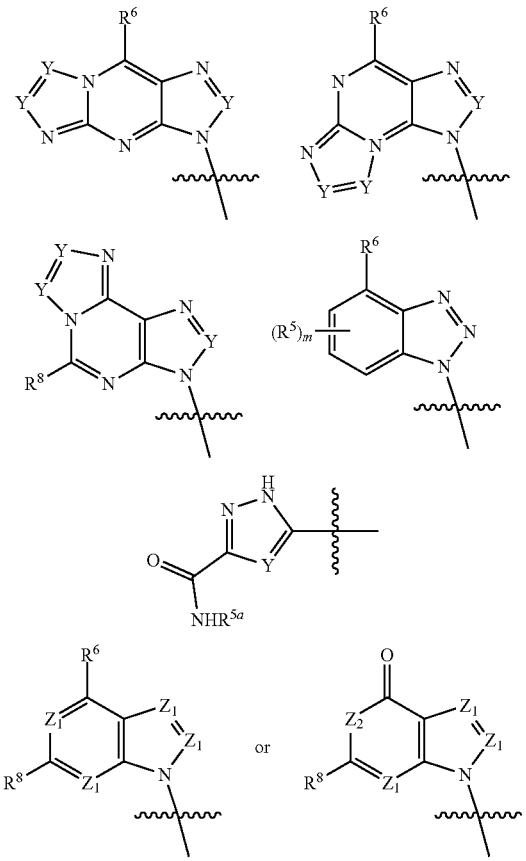

with the proviso that one of R¹ and R² must be

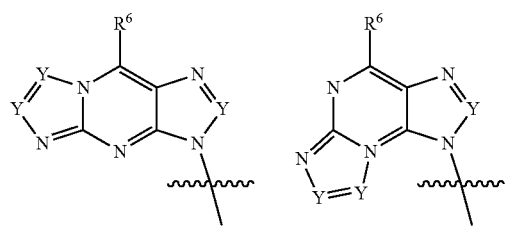

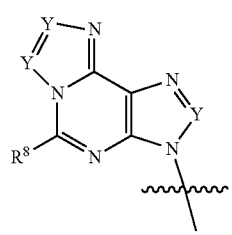

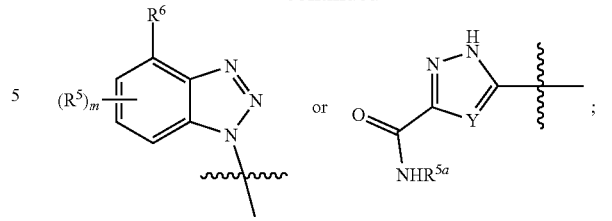

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $—C(O)R^{a1}$, $—C(O)NR^{a1}R^{a1}$, $—S(O)_2R^{a1}$ or $S(O)_2NR^{a1}R^{a1}$;

$R^{a1}$ is H or $C_{1-3}$ alkyl substituted with 0-6 $R^5$;

$R^3$ and $R^4$ are independently H, $CH_3$, halogen, $NH_2$ or OH;

$R^{3a}$ and $R^{4a}$ are independently H, $CH_3$, halogen, $NH_2$ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a $C=CH_2$ substituent;

$R^5$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

$R^8$ is H, halogen, $C_{1-3}$ alkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;

Y is $CR^5$ or N;

or a pharmaceutically acceptable salt, tautomer or stereoisomer thereof.

5. A compound of the formula

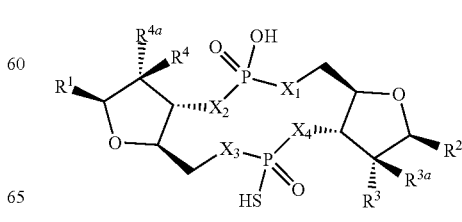

wherein

X₁, X₂, X₃ and X₄ are each independently O or NH;

R¹ and R² are independently

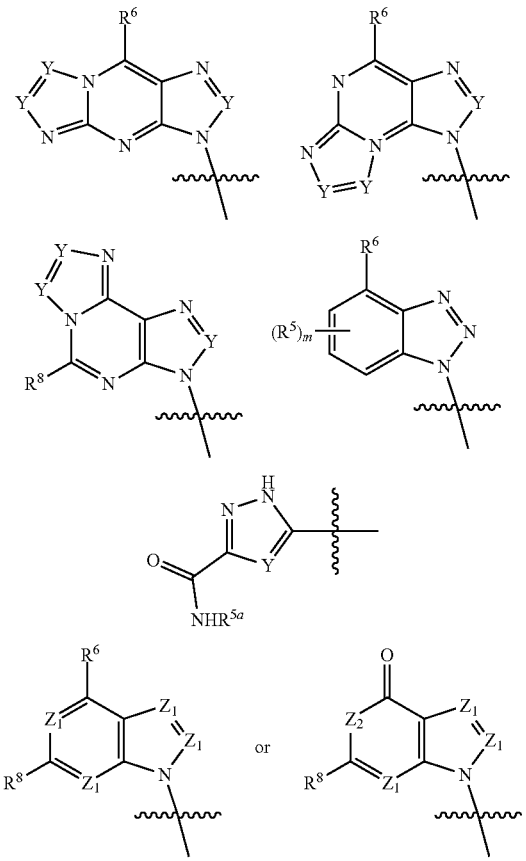

with the proviso that one of R¹ and R² must be

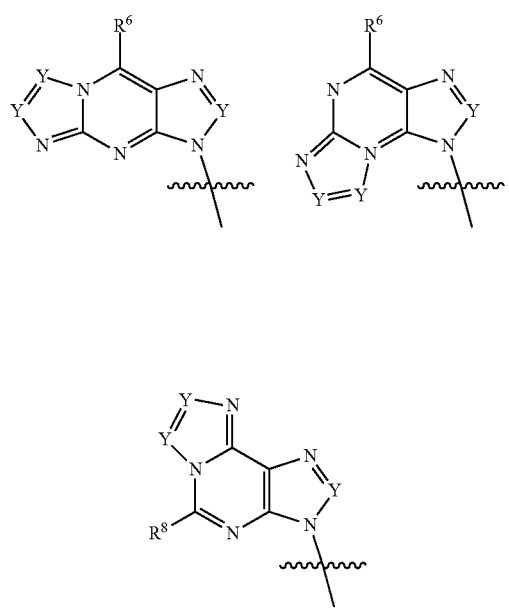

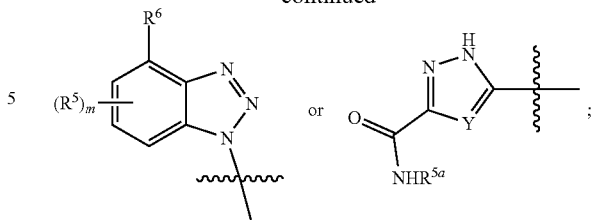

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, NO₂, OH, $OR^{a1}$, $SR^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)₂R$^{a1}$ or S(O)₂NR$^{a1}$R$^{a1}$;

$R^{a1}$ is H or $C_{1-3}$ alkyl substituted with 0-6 $R^5$;

$R^3$ and $R^4$ are independently H, CH₃, halogen, NH₂ or OH;

$R^{3a}$ and $R^{4a}$ are independently H, CH₃, halogen, NH₂ or OH; or $R^3$ and $R^{3a}$ or $R^4$ and $R^{4a}$ may independently be taken together to form a 3-4 membered carbocycle; or $R^3$ and $R^{3a}$ or $R^4$ and $R^{4a}$ may independently be taken together to form a C=CH₂ substituent;

$R^5$ is H, halogen, $C_{1-3}$ alkyl substituted with 0-6 $R^5$, CN, NO₂, OH, $OR^{a1}$, $SR^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

$R^{5a}$ is H or $C_{1-3}$ alkyl substituted with 0-6 $R^5$;

$R^6$ is H, halogen, $C_{1-3}$ alkyl substituted with 0-6 $R^5$, CN, NO₂, OH, $OR^{a1}$, $SR^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

$R^8$ is H, halogen, $C_{1-3}$ alkyl substituted with 0-6 $R^5$, CN, NO₂, OH, $OR^{a1}$, $SR^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

Y is $CR^5$ or N;

or a pharmaceutically acceptable salt, tautomer or stereoisomer thereof.

6. The compound that is

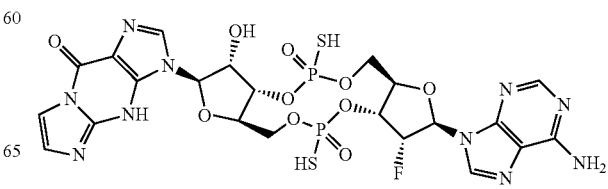

187
-continued
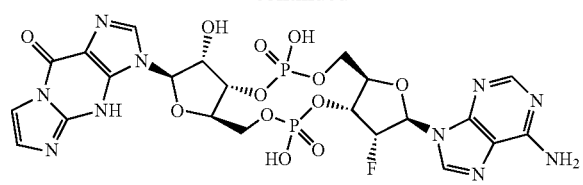
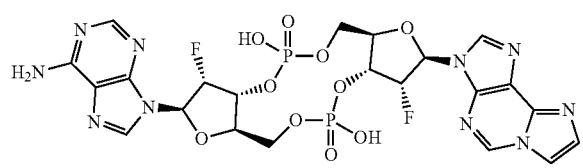
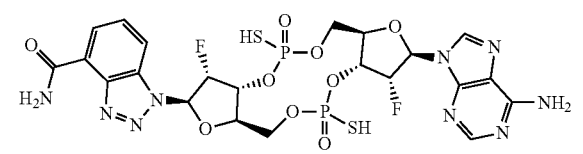
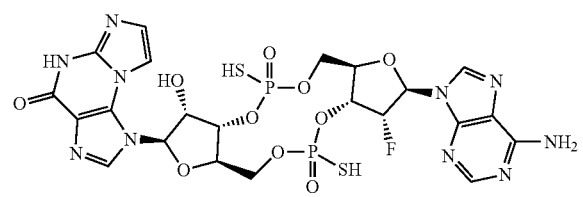
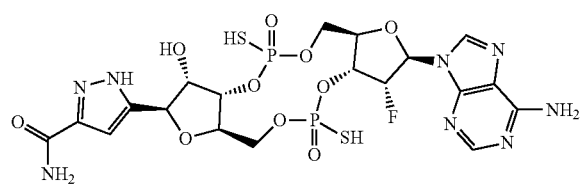
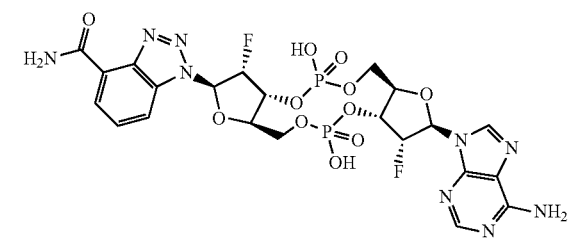
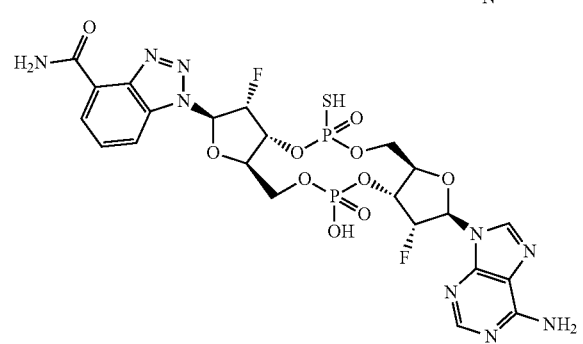
188
-continued
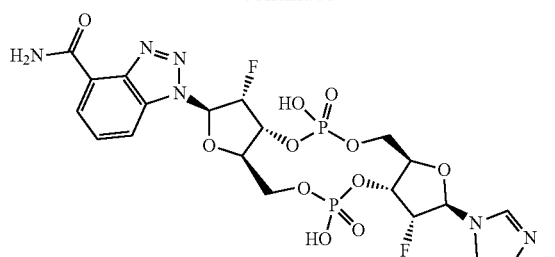
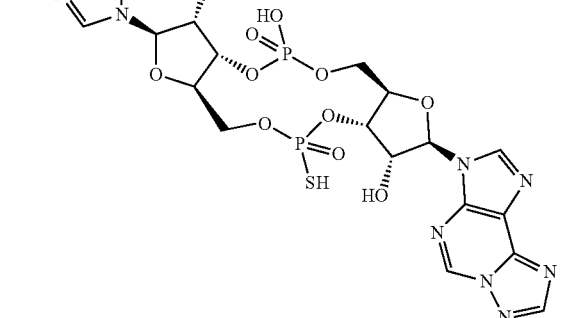
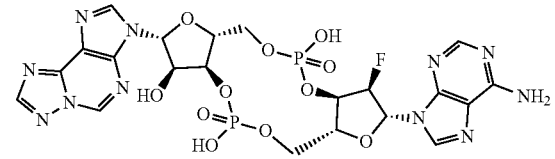
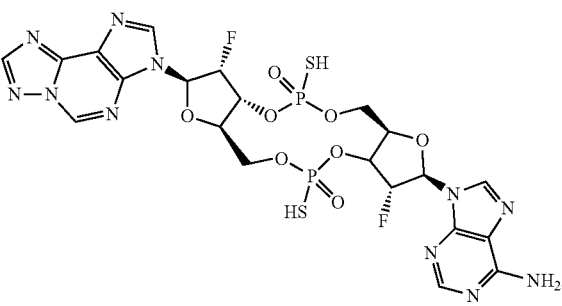
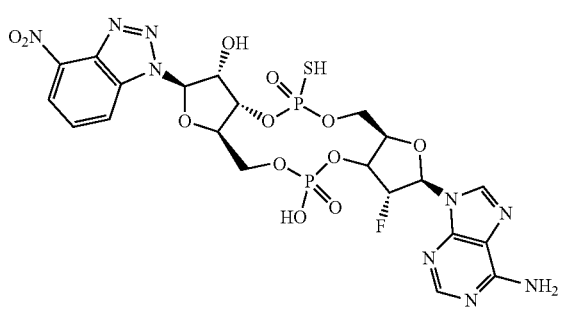

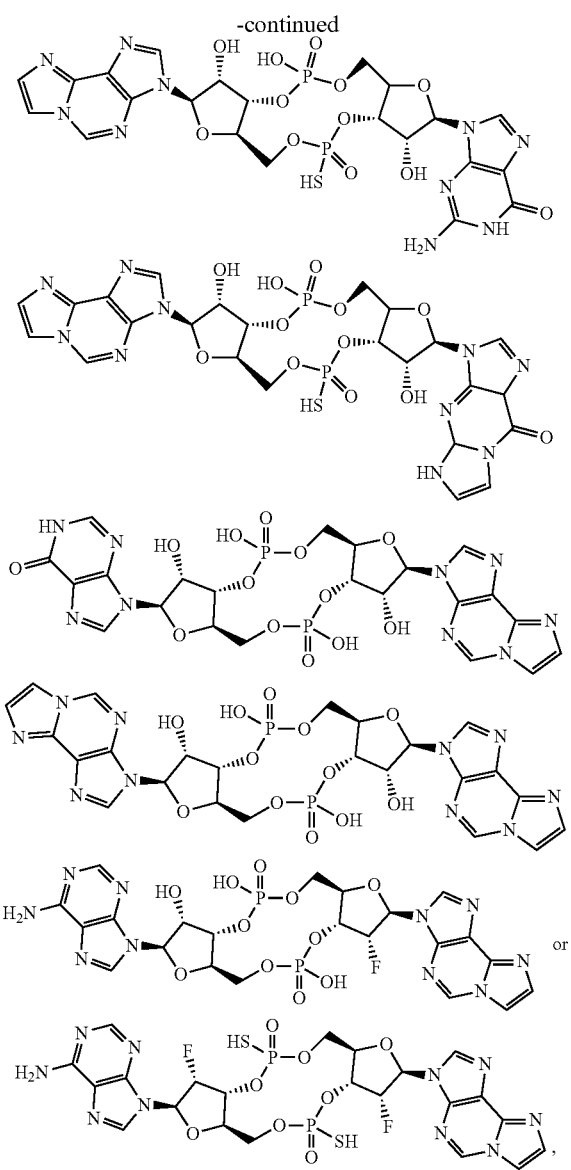

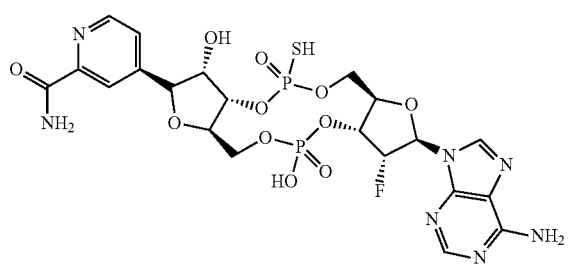

or a pharmaceutically acceptable salt, tautomer or stereoisomer thereof.

7. A compound which is

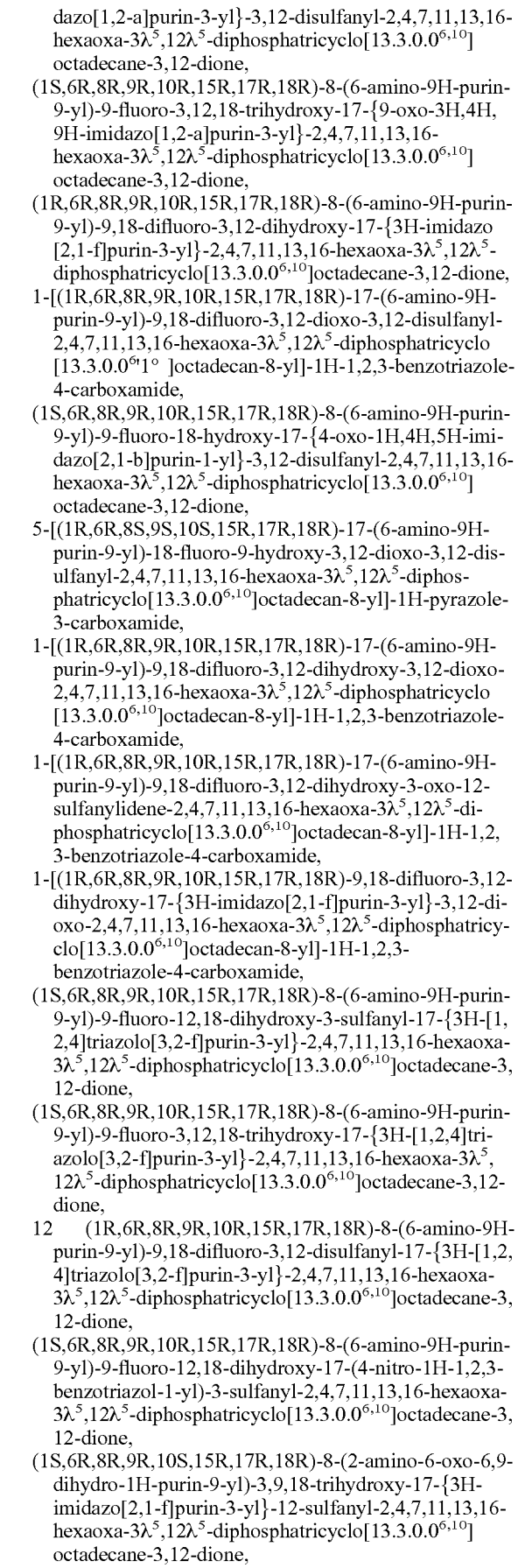

or a pharmaceutically acceptable salt, tautomer or stereoisomer thereof.

8. The compound which is
(1S,6R,8R,9R,10R,15R,17R,18R)-8-(6-amino-9H-purin-9-yl)-9-fluoro-18-hydroxy-17-{9-oxo-3H,4H,9H-imidazo[1,2-a]purin-3-yl}-3,12-disulfanyl-2,4,7,11,13,16-hexaoxa-3λ$^5$,12λ$^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-3,12,18-trihydroxy-17-{9-oxo-3H,4H,9H-imidazo[1,2-a]purin-3-yl}-2,4,7,11,13,16-hexaoxa-3λ$^5$,12λ$^5$-diphosphatricyclo[13.3.0.0$^{6,10}$]octadecane-3,12-dione, (1R,6R,8R,9R,10R,15R,17R,18R)-8-(6-amino-9H-purin-9-yl)-9,18-difluoro-3,12-dihydroxy-17-{3H-imidazo[2,1-f]purin-3-yl}-2,4,7,11,13,16-hexaoxa-3λ$^5$,12λ$^5$-diphosphatricyclo[13.3.0.0$^{6,10}$]octadecane-3,12-dione, 1-[(1R,6R,8R,9R,10R,15R,17R,18R)-17-(6-amino-9H-purin-9-yl)-9,18-difluoro-3,12-dioxo-3,12-disulfanyl-2,4,7,11,13,16-hexaoxa-3λ$^5$,12λ$^5$-diphosphatricyclo[13.3.0.0$^{6,1°}$]octadecan-8-yl]-1H-1,2,3-benzotriazole-4-carboxamide, (1S,6R,8R,9R,10R,15R,17R,18R)-8-(6-amino-9H-purin-9-yl)-9-fluoro-18-hydroxy-17-{4-oxo-1H,4H,5H-imidazo[2,1-b]purin-1-yl}-3,12-disulfanyl-2,4,7,11,13,16-hexaoxa-3λ$^5$,12λ$^5$-diphosphatricyclo[13.3.0.0$^{6,10}$]octadecane-3,12-dione, 5-[(1R,6R,8S,9S,10S,15R,17R,18R)-17-(6-amino-9H-purin-9-yl)-18-fluoro-9-hydroxy-3,12-dioxo-3,12-disulfanyl-2,4,7,11,13,16-hexaoxa-3λ$^5$,12λ$^5$-diphosphatricyclo[13.3.0.0$^{6,10}$]octadecan-8-yl]-1H-pyrazole-3-carboxamide, 1-[(1R,6R,8R,9R,10R,15R,17R,18R)-17-(6-amino-9H-purin-9-yl)-9,18-difluoro-3,12-dihydroxy-3,12-dioxo-2,4,7,11,13,16-hexaoxa-3λ$^5$,12λ$^5$-diphosphatricyclo[13.3.0.0$^{6,10}$]octadecan-8-yl]-1H-1,2,3-benzotriazole-4-carboxamide, 1-[(1R,6R,8R,9R,10R,15R,17R,18R)-17-(6-amino-9H-purin-9-yl)-9,18-difluoro-3,12-dihydroxy-3-oxo-12-sulfanylidene-2,4,7,11,13,16-hexaoxa-3λ$^5$,12λ$^5$-diphosphatricyclo[13.3.0.0$^{6,10}$]octadecan-8-yl]-1H-1,2,3-benzotriazole-4-carboxamide, 1-[(1R,6R,8R,9R,10R,15R,17R,18R)-9,18-difluoro-3,12-dihydroxy-17-{3H-imidazo[2,1-f]purin-3-yl}-3,12-dioxo-2,4,7,11,13,16-hexaoxa-3λ$^5$,12λ$^5$-diphosphatricyclo[13.3.0.0$^{6,10}$]octadecan-8-yl]-1H-1,2,3-benzotriazole-4-carboxamide, (1S,6R,8R,9R,10R,15R,17R,18R)-8-(6-amino-9H-purin-9-yl)-9-fluoro-12,18-dihydroxy-3-sulfanyl-17-{3H-[1,2,4]triazolo[3,2-f]purin-3-yl}-2,4,7,11,13,16-hexaoxa-3λ$^5$,12λ$^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-3,12,18-trihydroxy-17-{3H-[1,2,4]triazolo[3,2-f]purin-3-yl}-2,4,7,11,13,16-hexaoxa-3λ$^5$,12λ$^5$-diphosphatricyclo[13.3.0.0$^{6,10}$]octadecane-3,12-dione, 12 (1R,6R,8R,9R,10R,15R,17R,18R)-8-(6-amino-9H-purin-9-yl)-9,18-difluoro-3,12-disulfanyl-17-{3H-[1,2,4]triazolo[3,2-f]purin-3-yl}-2,4,7,11,13,16-hexaoxa-3λ$^5$,12λ$^5$-diphosphatricyclo[13.3.0.0$^{6,10}$]octadecane-3,12-dione, (1S,6R,8R,9R,10R,15R,17R,18R)-8-(6-amino-9H-purin-9-yl)-9-fluoro-12,18-dihydroxy-17-(4-nitro-1H-1,2,3-benzotriazol-1-yl)-3-sulfanyl-2,4,7,11,13,16-hexaoxa-3λ$^5$,12λ$^5$-diphosphatricyclo[13.3.0.0$^{6,10}$]octadecane-3,12-dione, (1S,6R,8R,9R,10S,15R,17R,18R)-8-(2-amino-6-oxo-6,9-dihydro-1H-purin-9-yl)-3,9,18-trihydroxy-17-{3H-imidazo[2,1-f]purin-3-yl}-12-sulfanyl-2,4,7,11,13,16-hexaoxa-3λ$^5$,12λ$^5$-diphosphatricyclo[13.3.0.0$^{6,10}$]octadecane-3,12-dione, (1S,6R,8R,9R,10S,15R,17R,18R)-3,9,18-trihydroxy-17-{3H-imidazo[2,1-f]purin-3-yl}-8-{9-oxo-3H,4aH,5H,9H,9aH-imidazo[1,2-a]purin-3-yl}-12-sulfanyl-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10S,15R,17R,18R)-3,9,12,18-tetrahydroxy-8-{3H-imidazo[2,1-f]purin-3-yl}-17-(6-oxo-6,9-dihydro-1H-purin-9-yl)-2,4,7,11,13,16-hexaoxa-3$\lambda^5$,12$\lambda^5$-diphosphatricyclo[13.3.0.0$^{6,10}$]octadecane-3,12-dione, (1S,6R,8R,9R,10S,15R,17R,18R)-3,9,12,18-tetrahydroxy-8,17-bis({3H-imidazo[2,1-f]purin-3-yl})-2,4,7,11,13,16-hexaoxa-3$\lambda^5$,12$\lambda^5$-diphosphatricyclo[13.3.0.0$^{6,10}$]octadecane-3,12-dione, (1R,6R,8R,9R,10S,15R,17R,18R)-8-(6-amino-9H-purin-9-yl)-18-fluoro-3,9,12-trihydroxy-17-{3H-imidazo[2,1-f]purin-3-yl}-2,4,7,11,13,16-hexaoxa-3$\lambda^5$,12$\lambda^5$-diphosphatricyclo[13.3.0.0$^{6,10}$]octadecane-3,12-dione, or (1R,6R,8R,9R,10R,15R,17R,18R)-8-(6-amino-9H-purin-9-yl)-9,18-difluoro-17-{3H-imidazo[2,1-f]purin-3-yl}-3,12-disulfanyl-2,4,7,11,13,16-hexaoxa-3$\lambda^5$,12$\lambda^5$-diphosphatricyclo[13.3.0.0$^{6,10}$]octadecane-3,12-dione, or a pharmaceutically acceptable salt thereof.

9. A pharmaceutical composition comprising a compound according to claim 6 or a pharmaceutically acceptable salt thereof and one or more pharmaceutically acceptable carriers, diluents or excipients.

10. A method of treating diseases and conditions in which the modulation of STING is indicated in a subject which comprises administering a compound according to claim 6 or a pharmaceutically acceptable salt thereof.

11. A method of treating cancer comprising administering one or more compounds according to claim 6 or a pharmaceutically acceptable salt thereof.

12. The method of claim 11 wherein the cancer is small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers.

13. The method of claim 12 wherein the cancer is small cell lung cancer, non-small cell lung cancer, colorectal cancer, melanoma, renal cell carcinoma, head and neck cancer, Hodgkin's lymphoma or bladder cancer.

14. A method for treating cancer in a subject, comprising administering a compound according to claim 6, or a pharmaceutically acceptable salt thereof, in combination with the administration of one or more immuno-oncology agents.

15. A method for treating a subject afflicted with cancer comprising administering to the subject
 a) a compound according to claim 6, or a pharmaceutically acceptable salt thereof, and
 b) an anti-cancer agent which is an antibody or an antigen-binding portion thereof that binds specifically to a Programmed Death-1 (PD-1) receptor and inhibits PD-1 activity.

16. The method of claim 15, wherein the anti-PD-1 antibody is nivolumab or pembrolizumab.

17. The method of claim 16, wherein the anti-PD-1 antibody is nivolumab.

* * * * *